US011857620B2

(12) United States Patent
Soon-Shiong et al.

(10) Patent No.: US 11,857,620 B2
(45) Date of Patent: *Jan. 2, 2024

(54) METHOD OF INDUCING IMMUNITY AGAINST SARS-COV-2 USING SPIKE (S) AND NUCLEOCAPSID (N)-ETSD IMMUNOGENS DELIVERED BY A REPLICATION-DEFECTIVE ADENOVIRUS

(71) Applicant: ImmunityBio, Inc., Culver City, CA (US)

(72) Inventors: Patrick Soon-Shiong, Culver City, CA (US); Peter Sieling, Culver City, CA (US); Kayvan Niazi, Culver City, CA (US); Shahrooz Rabizadeh, Culver City, CA (US); Lise Geissert, Culver City, CA (US); Annie Shin, Culver City, CA (US); Adrian Rice, Culver City, CA (US); Elizabeth Gabitzsch, Culver City, CA (US); Jeffrey Safrit, Culver City, CA (US); Leonard Sender, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/198,164

(22) Filed: Mar. 10, 2021

(65) Prior Publication Data

US 2023/0086390 A1 Mar. 23, 2023
US 2023/0338508 A9 Oct. 26, 2023

Related U.S. Application Data

(63) Continuation-in-part of application No. 17/082,994, filed on Oct. 28, 2020, now abandoned, and a (Continued)

(51) Int. Cl.

*A61K 39/215* (2006.01)
*A61K 39/39* (2006.01)

(Continued)

(52) U.S. Cl.

CPC ........... *A61K 39/215* (2013.01); *A61K 39/39* (2013.01); *C12N 15/86* (2013.01);

(Continued)

(58) Field of Classification Search

CPC ................ A61K 39/215; C12N 15/861; C12N 2710/10343; C12N 2770/20022; C12N 2770/20034; C07K 2319/06

See application file for complete search history.

(56) References Cited

U.S. PATENT DOCUMENTS 6,133,036 A 10/2000 Putcha et al.
6,716,392 B1 4/2004 Putcha et al.

(Continued)

FOREIGN PATENT DOCUMENTS

EP 1 508 615 A1 2/2005
KR 10-1453923 B1 10/2014

(Continued)

OTHER PUBLICATIONS

Bhatti, J. S., et al., Nov. 2020, Therapeutic Strategies in the Development of Anti-viral Drugs and Vaccines Against SARS-CoV-2 Infection, Mol. Neurobiol., DOI: 10.1007/s12035-020-02074-2, published online Aug. 18, 2020, pp. 1-22.*

(Continued)

*Primary Examiner* — Jeffrey S Parkin

(74) *Attorney, Agent, or Firm* — Martin Fessenmaier; Umberg Zipser LLP

(57) ABSTRACT

Disclosed herein are methods for inducing immunity against a virus such as a coronavirus in the mucosal tissue of a patient, include administering a vaccine composition to the (Continued)

patient by oral administration (e.g., nasal injection, nasal inhalation, oral inhalation, and/or oral ingestion). Also disclosed are compositions for assaying the presence of antiviral antibodies induced by the administered vaccine or the presence of viral proteins in a saliva sample include a stabilizing solution and may also include the use of aragonite particle beads. Compositions and methods are presented for prevention and/or treatment of a coronavirus disease wherein the composition comprises comprises a recombinant entity. The recombinant entity is bivalent, comprising a nucleic acid encoding a coronavirus 2 nucleocapsid protein CoV2 nucleocapsid protein fused to an endosomal targeting sequence, and a nucleic acid encoding a CoV2 spike protein sequence optimized for cell surface expression.

11 Claims, 26 Drawing Sheets

Specification includes a Sequence Listing.

Related U.S. Application Data continuation-in-part of application No. 16/883,263, filed on May 26, 2020, now Pat. No. 11,684,668, and a continuation-in-part of application No. 16/880,804, filed on May 21, 2020, now abandoned.

(60) Provisional application No. 63/135,380, filed on Jan. 8, 2021, provisional application No. 63/121,102, filed on Dec. 3, 2020, provisional application No. 63/118,697, filed on Nov. 26, 2020, provisional application No. 63/117,922, filed on Nov. 24, 2020, provisional application No. 63/117,460, filed on Nov. 24, 2020, provisional application No. 63/117,847, filed on Nov. 24, 2020, provisional application No. 63/115,127, filed on Nov. 18, 2020, provisional application No. 63/082,145, filed on Sep. 23, 2020, provisional application No. 63/080,887, filed on Sep. 21, 2020, provisional application No. 63/069,598, filed on Aug. 24, 2020, provisional application No. 63/067,033, filed on Aug. 18, 2020, provisional application No. 63/064,157, filed on Aug. 11, 2020, provisional application No. 63/059,975, filed on Aug. 1, 2020, provisional application No. 63/053,691, filed on Jul. 19, 2020, provisional application No. 63/036,445, filed on Jun. 9, 2020, provisional application No. 63/022,146, filed on May 8, 2020, provisional application No. 63/016,048, filed on Apr. 27, 2020, provisional application No. 63/016,241, filed on Apr. 27, 2020, provisional application No. 63/009,960, filed on Apr. 14, 2020, provisional application No. 63/010,010, filed on Apr. 14, 2020, provisional application No. 62/991,504, filed on Mar. 18, 2020, provisional application No. 62/988,328, filed on Mar. 11, 2020.

(51) Int. Cl.

| | |
|---|---|
| ***C12N 15/86*** | (2006.01) |
| *A61P 31/14* | (2006.01) |
| *A61K 39/00* | (2006.01) |

(52) U.S. Cl.

CPC .................. *A61K 2039/545* (2013.01); *A61K 2039/55505* (2013.01); *A61P 31/14* (2018.01); *C12N 2710/10343* (2013.01); *C12N 2770/20022* (2013.01); *C12N 2770/20034* (2013.01)

(56) References Cited

U.S. PATENT DOCUMENTS

| | | | |
|---|---|---|---|
| 7,618,817 B2 | 11/2009 | Campbell | |
| 7,750,123 B2 | 7/2010 | Marasco et al. | |
| 8,034,332 B2 | 10/2011 | Klingemann | |
| 8,313,943 B2 | 11/2012 | Campbell | |
| 9,150,636 B2 | 10/2015 | Campbell | |
| 9,181,322 B2 | 11/2015 | Campbell | |
| 10,695,417 B2 | 6/2020 | Jones et al. | |
| 10,953,089 B1 | 3/2021 | Smith et al. | |
| 11,104,916 B2 * | 8/2021 | Jones | C07K 14/005 |
| 2004/0161388 A1 | 8/2004 | Liu et al. | |
| 2005/0003548 A1 | 1/2005 | Korokhov et al. | |
| 2010/0150923 A1 | 6/2010 | Jiang et al. | |
| 2010/0196411 A1 | 8/2010 | Duke et al. | |
| 2012/0076820 A1 | 3/2012 | Amara et al. | |
| 2012/0107347 A1 | 5/2012 | Todge et al. | |
| 2012/0288502 A1 | 11/2012 | Diskin et al. | |
| 2016/0076053 A1 | 3/2016 | Jones et al. | |
| 2017/0224794 A1 | 8/2017 | Franzusoff et al. | |
| 2017/0246276 A1 | 8/2017 | Palena et al. | |
| 2018/0244756 A1 | 8/2018 | Graham et al. | |
| 2018/0296663 A1 | 10/2018 | Hipp et al. | |
| 2018/0306814 A1 | 10/2018 | Kulshrestha et al. | |
| 2019/0307819 A1 | 10/2019 | Drew et al. | |
| 2020/0054730 A1 | 2/2020 | Niazi | |
| 2020/0164058 A1 | 5/2020 | Hashem | |
| 2021/0283245 A1 | 9/2021 | Niazi et al. | |
| 2021/0284713 A1 | 9/2021 | Niazi et al. | |
| 2021/0284716 A1 | 9/2021 | Niazi et al. | |
| 2021/0371822 A1 | 12/2021 | Chaudhary | |
| 2022/0016234 A1 | 1/2022 | Rice et al. | |

FOREIGN PATENT DOCUMENTS

| | | |
|---|---|---|
| WO | 2005/120565 A2 | 12/2005 |
| WO | 2009006479 A3 | 3/2009 |
| WO | 2012109404 A1 | 8/2012 |
| WO | 2014031178 A1 | 2/2014 |
| WO | 2018/140456 A1 | 8/2018 |
| WO | 2019/143606 A1 | 7/2019 |
| WO | 2020086745 A1 | 4/2020 |
| WO | 2021/183665 A1 | 9/2021 |
| WO | 2021183717 A1 | 9/2021 |
| WO | 2021188599 A1 | 9/2021 |
| WO | 2021212021 A2 | 10/2021 |
| WO | 2021/250467 A2 | 12/2021 |

OTHER PUBLICATIONS

Lin, H.-X., et al., 2008, Identification of Residues in the Receptor-Binding Domain (RBD) of the Spike Protein of Human Coronavirus NL63 That Are Critical for the RBD-ACE2 Receptor Interaction, J. Gen. Virol. 89:1015-1024.*

Liniger, M., et al., 2008, Induction of Neutralising Antibodies and Cellular Immune Responses Against SARS Coronavirus by Recombinant Measles Viruses, Vaccine 26:2164-2174.*

Wu, F., et al., Mar. 2020, A New Coronavirus Associated with Human Respiratory Disease in China, Nature 579:265-284, published online Feb. 3, 2020.*

Non Final Office Action received for U.S. Appl. No. 17/726,427 dated Aug. 2, 2022, 10 pages.

Lei et al., "Potent neutralization of 2019 novel coronavirus by recombinant ACE2-Ig", bioRxiv, 2020, 11 pages.

Amalfitano et al., "Production and Characterization of Improved Adenovirus Vectors with the E1, E2b, and E3 Genes Deleted", Journal of Virology, 1998, vol. 72, No. 2, pp. 926-933.

Yan et al., "Structural basis for the recognition of the SARS-CoV-2 by full-length human ACE2", Science, 2020, pp. 1-9.

Zhang et al., "Angiotensin-converting enzyme 2(ACE2) as a SARS-CoV-2 receptor: molecular mechanisms and potential therapeutic target", Intensive Care Med, 2020, 5 pages.

(56) References Cited

OTHER PUBLICATIONS

Zhonghua Yi Xue Za Zhi, "Dynamic Changes of T-lymphocytes and Immunoglobulins in Patients With Severe Acute Respiratory Syndrome", Natl Med J China, Jun. 25, 2003, vol. 83, No. 12, pp. 1014-1017.
"The Involvement of Natural Killer Cells in the Pathogenesis of Severe Acute Respiratory Syndrome", National Research Project for SARS, Beijing Group, American Journal of Clinical Pathology, 2004, vol. 121, pp. 507-511.
Bergamaschi et al., "Intracellular Interaction of Interleukin-15 with Its Receptor alpha during Production Leads to Mutual Stabilization andIncreased Bioactivity", The Journal of Biological Chemistry, 2008, vol. 283, No. 7, pp. 4189-4199.
Bessard et al., "High Antitumor Activity of RLI, an interleukin-15 (IL-15)-IL-15 Receptor Alpha Fusion Protein, in Metastatic Melanoma and Colorectal Cancer", Mol Cancer Ther, 2009, vol. 8, No. 9, pp. 2736-2745.
Chan et al., "A familial cluster of pneumonia associated with the 2019 novel coronavirus indicating person-to-person transmission: a study of a family cluster", lancet, vol. 395, pp. 514-523.
Clay et al., "Severe Acute Respiratory Syndrome Coronavirus Infection in Aged Nonhuman Primates Is Associated With Modulated Pulmonary and Systemic Immune Responses", Immunity & Ageing, 2014, vol. 11, No. 4, pp. 1-16.
Dubois et al., "Preassociation of IL-15 With IL-15R alpha-IgG1-Fc Enhances Its Activity on Proliferation of NK and CD8+/CD44high T Cells and Its Antitumor Action", The Journal of Immunology, 2008, vol. 180, pp. 2099-2106.
Duitman et al., "How a Cytokine Is Chaperoned Through the Secretory Pathway by Complexing With Its Own Receptor: Lessons From interleukin-15 (IL-15)/IL-15 Receptor Alpha", molecular and Cellular Biology, Aug. 2008, vol. 28, No. 15, pp. 4851-4861.
Ellis-Connell et al., "ALT-803 Transiently Reduces Simian Immunodeficiency Virus Replication in the Absence of Antiretroviral Treatment", Journal of Virology, 2018, vol. 92, No. 3, pp. 1-21.
Epardaud et al., "Interleukin-15/interleukin-15R Alpha Complexes Promote Destruction of Established Tumors by Reviving Tumor-Resident CD8+ T Cells", Cancer Research, 2008, vol. 68, No. 8, pp. 2972-2983.
Fehniger et al., "Interleukin-2 and interleukin-15: Immunotherapy for Cancer", Cytokine Growth Factor Rev, 2002, vol. 13, No. 2, pp. 169-183.
Furuya et al., "Effectiveness of two different dose administration regimens of an IL-15 superagonist complex (ALT-803) in an orthotopic bladder cancer mouse model", Journal of translational Medicine, 2019, vol. 17, No. 29, pp. 1-12.
Gomes-Giacoia et al., "Intravesical ALT-803 and BCG Treatment Reduces Tumor Burden in a Carcinogen Induced Bladder Cancer Rat Model; A Role for Cytokine Production and NK Cell Expansion", Plos One, 2014, vol. 9, No. 6, pp. 1-11.
Guan et al., "Clinical Characteristics of Coronavirus Disease 2019 in China", The New England Journal of Medicine, 2020, 13, pages.
Guilliams et al., "The function of Fc gamma receptors in dendritic cells and macrophages", Nature Reviews Immunology, 2014, vol. 14, pp. 94-108.
Huang et al., "Clinical features of patients infected with 2019 novel coronavirus in Wuhan, China", Lancet, 2020, vol. 395, No. 10223, pp. 1-10.
Huntington et al., "IL-15 transpresentation promotes both human T-cell reconstitution and T-cell-dependent antibody responses in vivo", Proceedings of the National Academy of Sciences, 2011, vol. 108, No. 15, pp. 6217-6222.
Jones et al., "A Subset of Latency-Reversing Agents Expose HIV-Infected Resting CD4+ T-Cells to Recognition by Cytotoxic T-Lymphocytes", Plos Pathogens, 2016, pp. 1-25.
Kim et al., "IL-15 superagonist/IL-15RαSushi-Fc Fusion Complex (IL-15SA/IL-15RαSu-Fc; ALT-803) Markedly Enhances Specific Subpopulations of NK and Memory CD8+ T Cells, and Mediates Potent Anti-Tumor Activity Against Murine Breast and Colon Carcinomas", Oncotarget, 2016, vol. 7, No. 13, 16130-16145.
Law et al., "Chemokine Up-Regulation in SARS-coronavirus-infected, Monocyte-Derived Human Dendritic Cells", Blood, 2005, vol. 106, No. 7, pp. 2366-2374.
Mah et al., "Glycolytic Requirement for NK Cell Cytotoxicity and Cytomegalovirus Control", JCI Insight, 2017, vol. 2, No. 23, 18 pages.
Margolin et al., "Phase I Trial of ALT-803, A Novel Recombinant IL 15 Complex, in Patients With Advanced Solid Tumors", Clinical Cancer Research, 2018, vol. 24, No. 22, pp. 555-5561.
Mathios et al., "Therapeutic Administration of IL-15 Superagonist Complex ALT-803 Leads to Long-Term Survival and Durable Antitumor Immune Response in a Murine Glioblastoma Model", International Journal of Cancer, 2016, vol. 138, pp. 187-194.
McBrien et al., "Robust and persistent reactivation of SIV and HIV by N-803 and depletion of CD8+ cells", Nature, Feb. 6, 2020, vol. 578, pp. 154-159.
Mortier et al., "Soluble Interleukin-15 Receptor α (IL-15Rα)-sushi as a Selective and Potent Agonist of IL-15 Action through IL-15Rβ/γ Hyperagonist IL-15-IL-15Rα Fusion Proteins", Journal of Biological Chemistry, 2006, vol. 281, No. 3, pp. 1612-1619.
Rhode et al., "Comparison of the Superagonist Complex, ALT-803, to IL 15 as Cancer Immunotherapeutics in Animal Models", Cancer Immunol Res, 2016, vol. 4, pp. 1-12.
Romee et al., "First-in-human Phase 1 Clinical Study of the IL-15 Superagonist Complex ALT-803 to Treat Relapse After Transplantation", Blood, 2018, vol. 131, No. 23, pp. 2515-2527.
Rosario et al., "The IL-15-Based ALT-803 Complex Enhances FcγRIIIa-Triggered NK Cell Responses and In Vivo Clearance of B Cell Lymphomas", Clinical Cancer Research, 2016, vol. 22, No. 3, pp. 596-608.
Seay et al., "In Vivo Activation of Human NK Cells by Treatment With an Interleukin-15 Superagonist Potently Inhibits Acute In Vivo HIV-1 Infection in Humanized Mice", Journal of Virology, 2015, 46 pages.
Spiegel et al., "Inhibition of Beta Interferon Induction by Severe Acute Respiratory Syndrome Coronavirus Suggests a Two-Step Model for Activation of Interferon Regulatory Factor 3", Journal of Virology, 2005, vol. 79, No. 4, pp. 2079-2086.
Waldmann Thomas A., "The biology of interleukin-2 and interleukin-15: implications for cancer therapy and vaccine design", Nature Reviews Immunology volume, 2006, vol. 6, pp. 595-601.
Webb et al., "The human IL-15 superagonist ALT-803 directs SIV-specific CD8+ T cells into B-cell follicles", Blood Advances, 2018, vol. 2, No. 2, pp. 76-84.
Weiss et al., "Coronavirus Pathogenesis and the Emerging Pathogen Severe Acute Respiratory Syndrome Coronavirus", Microbiology and molecular Biology Reviews, 2005, vol. 69, No. 4, 31 pages.
Wrangle et al., "ALT-803, an IL-15 Superagonist, in Combination With Nivolumab in Patients With Metastatic Non-Small Cell Lung Cancer: A Non-Randomised, Open-Label, Phase 1b Trial", Lancet Oncol, 2018, vol. 19, No. 5, pp. 1-11.
Xu et al., "Efficacy and Mechanism-Of-Action of a Novel Superagonist interleukin-15: Interleukin-15 Receptor αSu/Fc Fusion Complex in Syngeneic Murine Models of Multiple Myeloma", Cancer Research, 2013, vol. 73, No. 10, pp. 3075-3086.
Zhu et al., "Novel Human Interleukin-15 Agonists", The Journal of Immunology, 2009, vol. 183, pp. 3598-3607.
Zhu et al., "MHC Class I-Related Neonatal Fc Receptor for IgG Is Functionally Expressed in Monocytes, Intestinal Macrophages, and Dendritic Cells", The Journal of immunology, 2001, vol. 166, pp. 3266-3276.
Saiki et al., "Induction of Humoral Responses Specific for Paraneoplastic Cerebellar Degeneration-Associated Antigen by Whole Recombinant Yeast Immunization", Journal of Autoimmunity, 2005, vol. 24, pp. 203-208.
Kim et al., "Oral Immunization With Whole Yeast Producing Viral Capsid Antigen Provokes a Stronger Humoral Immune Response Than Purified Viral Capsid Antigen", Letters in Applied Microbiology, 2013, vol. 58, pp. 285-291.
Safdari et al., "Use of Single-Chain Antibody Derivatives for Targeted Drug Delivery", Molecular Medicine, 2016, vol. 22, pp. 258-270.

(56) References Cited

OTHER PUBLICATIONS

"Sorrento Develops STI-4398 (Covidtrap™ Protein) for Potential Prevention and Treatment of SARS-COV-2 Coronavirus Disease (COVID-19)", Sorrento Therapeutics, 2020, 4 pages.
Batlle et al., "Soluble angiotensin-converting enzyme 2: a potential approach for coronavirus infection therapy?", Clinical Science, 2020, vol. 134, pp. 543-545.
Kruse Robert L., "Therapeutic strategies in an outbreak scenario to treat the novel coronavirus originating in Wuhan, China [version 2; peerreview: 2 approved]", F1000 Research, 2020, vol. 9, No. 7, 14 pages.
Lu et al., "Arg15-Lys17-Arg18 Turkey Ovomucoid Third Domain Inhibits Human Furin", The Journal of Biological Chemistry, 1993, vol. 268, No. 20, pp. 14583-14585.
Non-Final Office Action received in U.S. Appl. No. 16/883,263 dated Oct. 5, 2021, 40 pages.
Liniger et al., "Induction of neutralising antibodies and cellular immune responses against SARS coronavirus by recombinant measles virus", Vaccine, 2008, vol. 26, pp. 2164-2174.
Wu et al., "A new coronavirus associated with human respiratory disease in China", Nature, 2020, vol. 579, pp. 265-271.
Gen Bank MN908947.3, Severe acute respiratory syndrome coronavirus 2 isolate Wuhan-Hu-1, complete genome, Mar. 2020, 12 pages.
Non Final Office Action received for U.S. Appl. No. 16/883,263 dated Sep. 2, 2022, 62 pages.
Tan et al., "Amino acid residues critical for RNA-binding in the N-terminal domain of the nucleocapsid protein are essential determinants for the infectivity of coronavirus in cultured cells", Nucleic Acids Research, vol. 34, No. 17, Sep. 13, 2006, pp. 4816-4825.
Lin et al., "Identification of residues in the receptor-binding domain (RBD) of the spike protein of human coronavirus NL63 that are critical for the RBD-ACE2 receptor interaction", Journal of General Virology, vol. 89, 2008, pp. 1015-1024.
Lu et al., "Importance of SARS-CoV spike protein Trp-rich region in viral infectivity", Science Direct, Biochemical Biophysical Research Communications, vol. 371, 2008, pp. 356-360.
Guo et al., "Identification of a new region of SARS-CoV S protein critical for viral entry", Science Direct, J. Mol. Biol., vol. 394, 2009, pp. 600-605.
Final Office Action received for U.S. Appl. No. 16/883,263 dated Apr. 14, 2022, 40 pages.
International Search Report and Written Opinion received for PCT Application Serial No. PCT/IB2021/054887 dated Sep. 6, 2021, 13 pages.
Khodaei et al., "Covalent Immobilization of Protein A on Chitosan and Aldehyde Double-Branched Chitosan as Biocompatible Carriers for Immunoglobulin G (Igg) Purification", Journal of Chromatographic Science, 2018, pp. 1-8.
Byrnes et al., "A SARS-CoV-2 serological assay to determine the presence of blocking antibodies that compete for human ACE2 binding", medRxiv, 2020, 23 pages.
Wang et al., "A human monoclonal antibody blocking SARS-CoV-2 infection", NatureCommunications, 2020, vol. 11, No. 2251, pp. 1-6.
International Search Report and Written Opinion received for PCT Application Serial No. PCT/US2021/021737 dated Jun. 25, 2021, 11 pages.
Zhao et al., "Identification and characterization of dominant helper T-cell epitopes in the nucleocapsid protein of severe acute respiratory syndrome coronavirus", Journal of Virology, 2007, vol. 81, No. 11, pp. 6079-6088.
Gabitzsch et al., "Anti-tumor immunotherapy despite immunity to adenovirus using a novel adenoviral vector Ad5 [E1-,E2b-]-CEA", Cancer Immunology Immunotherapy, 2010, vol. 59, pp. 1131-1135.
Fan et al., "The nucleocapsid protein of coronavirus infectious bronchitis virus: crystal structure of its N-terminal domain and multimerization properties", Structure, 2005, vol. 13, pp. 1859-1868.
International Search Report and Written Opinion received for PCT Application Serial No. PCT/US2021/021819 dated Jun. 21, 2021, 20 pages.
Oi-Wing et al., "Substitution at Aspartic Acid 1128 in the SARSCoronavirus Spike Glycoprotein Mediates Escape from aS2 Domain-Targeting Neutralizing Monoclonal Antibody", Plos one, 2014, vol. 9, No. 7, pp. 1-11.
Pak et al., "Structural Insights into Immune Recognition of theSevere Acute Respiratory Syndrome Coronavirus SProtein Receptor Binding Domain", Journal of Molecular Biology, 2009, vol. 388, pp. 815-823.
Park et al., "Spike protein binding prediction with neutralizing antibodies of SARS-CoV-2", bioRxiv , 2020, 22 pages.
Tripp et al., "Monoclonal antibodies to SARS-associated coronavirus (SARS-CoV): Identification of neutralizing and antibodies reactive to S, N, M and E viral proteins", Journal of Virological Methods, 2005, vol. 128, pp. 21-28.
Zheng et al., "Monoclonal antibodies for the S2 subunit of spike of SARS-CoV-1 cross-react with the newly-emerged SARS-CoV-2", Eurosurveillance, 2020, vol. 25, No. 28, pp. 19-28.
Final Office Action received for U.S. Appl. No. 17/379,849 dated Mar. 24, 2022, 83 pages.
Non Final Office Action received for U.S. Appl. No. 17/379,849 dated Dec. 10, 2021, 30 pages.
Coutard et al., "The spike glycoprotein of the new coronavirus 2019-nCoV contains a furin-like cleavage site absent in CoV of the same clade", Antiviral Research, 2020, No. 176, 6 pages.
Yao et al., "Polyethyleneimine-coating enhances adenoviral transduction of mesenchymal stem cells", Biochemical and Biophysical Research Communications, 2014, vol. 447, No. 3, pp. 383-387.
Yin et al., "[Measurement of subsets of blood T lymphocyte in 93 patients with severe acute respiratory syndrome and its clinical significance]", Chinese Journal of Tuberculosis and Respiratory Diseases, 2003, vol. 26, No. 6, pp. 343-346.
Chen et al., "Fusion protein linkers: property, design and functionality", Adv Drug Deliv Rev, vol. 65, No. 10, pp. 1357-1369.
Non-Final Office Action received for U.S. Appl. No. 16/880,804 dated Jan. 1, 2021, 40 pages.
Levin et al., "Fc fusion as a platform technology: potential for modulating immunogenicity", Trends Biotechnol., 2015, vol. 33, No. 1, pp. 27-34.
Renegar et al., "Role of IgA versus IgG in the Control of Influenza Viral Infection in the Murine Respiratory Tract", J Immunol. 2004, vol. 173, pp. 1978-1986.
Raftery et al., "Chitosan for Gene Delivery and Orthopedic TissueEngineering Applications", Molecules, 2013, vol. 18, pp. 5611-5647.
Cunningham et al., "Effective Long-term Preservation of Biological Evidence", Bode Technology, 2014, 153 pages.
Roth et al., "Functionalized Calcium Carbonate Microparticles for theDelivery of Proteins", European Journal of Pharmaceutics and Biopharmaceutics, 2017, 38 pages.
Rogers et al., "Isolation of potent SARS-CoV-2 neutralizing antibodies and protection from disease in a small animal model", Science, 2020, 12 pages.
Wec et al., "Broad sarbecovirus neutralizing antibodies define a key site of vulnerability on the SARSCoV-2 spike protein", Version 2. bioRxiv., 2020, 18 pages.
Yuan et al., "A highly conserved cryptic epitope in the receptor binding domains of SARS-CoV-2 and SARS-CoV", Science, 2020,, vol. 368, pp. 1-4.
Glasgow et al., "Engineered ACE2 receptor traps potently neutralize SARS-CoV-2", PNAS, 2020, 25 pages.
Rice et al., "A Next Generation Bivalent Human Ad5 COVID-19 Vaccine Delivering Both Spike and Nucleocapsid Antigens Elicits Th1 Dominant CD4+, CD8+ T-cell and Neutralizing Antibody Responses", BioRxiv, 2020, 36 pages.
Final Office Action received for U.S. Appl. No. 16/880,804 dated Mar. 22, 2021, 40 pages.
UniProtKB—Q9BYF1 (ACE2_HUMAN), Aug. 2, 2005.

(56) References Cited

OTHER PUBLICATIONS

See et al., "Comparative evaluation of two severe acute respiratory syndrome (SARS) vaccine candidates in mice challenged with SARS coronavirus", Journal of General Virology, 2006, vol. 87, pp. 641-650.

Sieling et al., "Th1 Dominant Nucleocapsid and Spike Antigen-Specific CD4+ and CD8+ Memory T CellRecall Induced by hAd5 S-Fusion + N-ETSD Infection of Autologous Dendritic Cells fromPatients Previously Infected with SARS-CoV-2", Medrxiv the preprint server for health sciences, 2020, 44 pages.

Gabitzsch et al., "Complete Protection of Nasal and Lung Airways Against SARS-CoV-2 Challengeby Antibody Plus Th1 Dominant N- and S-Specific T-Cell Responses to SubcutaneousPrime and Thermally-Stable Oral Boost Bivalent hAd5 Vaccination in an NHP Study", Biorxiv the preprint server for biology, 2020, 31 pages.

Seif et al., "Yeast (*Saccharomyces cerevisiae*) Polarizes Both M-CSF- and GM-CSF-Differentiated Macrophages Toward an M1-Like Phenotype", Inflammation, 2016, 14 pages.

Biondo et al., "Recognition of yeast nucleic acids triggers a host-protective type I interferon response", Eur. J. Immunol., 2011, vol. 41, pp. 1969-1979.

Non Final Office Action received for U.S. Appl. No. 17/082,994 dated Mar. 3, 2022, 73 pages.

Pietravalle et al., "Cleavage of membrane-bound CD40 ligand is not required for inducing B cell proliferation and differentiation", Eur. J. Immunol, vol. 26, 1996, pp. 725-728.

Final Office Action received for U.S. Appl. No. 16/880,804 dated Oct. 25, 2021, 16 pages.

Rice et al., "Intranasal plus subcutaneous prime vaccination with a dual antigen COVID 19 vaccine elicits T cell and antibody responses in mice" Scientific Reports, (2021) 11:14917 p. 1-15.

* cited by examiner

Fig. 6

METHOD OF INDUCING IMMUNITY AGAINST SARS-COV-2 USING SPIKE (S) AND NUCLEOCAPSID (N)-ETSD IMMUNOGENS DELIVERED BY A REPLICATION-DEFECTIVE ADENOVIRUS

This application is a continuation-in-part of pending U.S. application Ser. No. 16/883,263. This application also claims the benefit of priority to the U.S. patent applications with the serial numbers 62/988,328; 62/991,504; 63/009,960; 63/010,010; 63/016,048; 63/016,241; 63/022,146; 63/036,445; 63/053,691; 63/059,975; 63/121,102; 63/080,887; 63/067,033; 63/115,127; 63/069,598; 63/082,145; 63/117,847; 63/118,697; 63/117,922; 16/880,804; 17/082,994; and PCT application number PCT/US21/21737. Each of the above applications are incorporated by reference in its entirety, including the drawings and the sequence listings.

INCORPORATION OF SEQUENCE LISTING

This application contains references to nucleic acid and polypeptide sequences which have been submitted concurrently herewith as the sequence listing text file "102538.0080US3_ST25", created on 8 Mar. 2020. The file is 182 kilobytes (kb) in size. The aforementioned sequence listing is hereby incorporated by reference in its entirety pursuant to 37 C.F.R. § 1.52(e).

FIELD

The present disclosure relates to composition and methods for administering a vaccine to a patient and monitoring induced immunity in the patient in a stabilized patient sample.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

After several noteworthy coronavirus outbreaks in the recent years, including SARS and MERS, Corona Virus Disease 2019 (COVID-19) is yet another example of a serious infectious disease precipitated by a member of the corona virus family. While diagnostic tests have become available in a relatively short time, testing is not efficient, and numerous attempts to treat the disease have so far not had significant success. Most typically, patients with severe symptoms are treated to maintain respiration/blood oxygenation, and supportive treatment is provided to reduce or prevent multi-organ damage or even failure. Despite such interventions, the mortality rate is significant, particularly in elderly, immune compromised individuals, and individuals with heart disease, lung disease, or diabetes.

Thus, even though various methods of addressing symptoms in patients with COVID-19 are known in the art, all or almost all of them suffer from various disadvantages. Consequently, there is a need to provide improved vaccine compositions and methods that render a therapeutic effect, reduce or prevent viral entry into a cell, reduce direct and indirect toxicity of the virus to the patient, and produce an immune response that is effective to clear the virus from the patient.

SUMMARY

The present disclosure is directed to various immune therapeutic compositions and methods suitable for treating and/or preventing a coronavirus disease. In one aspect, disclosed herein is a replication defective adenovirus, wherein the adenovirus comprises an E1 gene region deletion; an E2b gene region deletion; an E3 gene region deletion; a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S— Fusion). In a second aspect of this disclosure, provided herein is a recombinant yeast comprising a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S— Fusion). comprising a nucleic acid encoding a coronavirus 2 (CoV2) nucleocapsid protein CoV2 nucleocapsid protein fused to an endosomal targeting sequence (ETSD), and a nucleic acid encoding a CoV2 spike protein sequence optimized for cell surface expression (S—Fusion). Preferably, the recombinant yeast is *Saccharomyces cerevisiae*.

In one embodiment of each of the above two aspects, the CoV2 nucleocapsid protein has at least 85% identity to SEQ ID NO:1. It is further contemplated that the fusion protein contains a linker between the ETSD domain and the nucleocapsid protein. For example this linker may be a 16 amino acid linker having the sequence $(GGGS)_4$. In one embodiment, the fusion protein has at least 85% identity of SEQ ID NO:2. The CoV2 spike protein is contemplated to have at least 85% identity to SEQ ID NO:6. The nucleic acid encoding the CoV2 spike protein has at least 99% identity to SEQ ID NO:5 or SEQ ID NO:7.

In another embodiment of this disclosure, the adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition In another aspect, the method includes administering to the subject an immunotherapy composition comprising a recombinant entity, wherein the recombinant entity comprises a nucleic acid that encodes a nucleocapsid protein of coronavirus 2 (CoV2) and/or a spike protein of CoV2. In one embodiment, the nucleocapsid protein is ETSD.

Preferably, the nucleic acid that encodes a nucleocapsid protein of coronavirus 2 further encodes a trafficking sequence for the nucleocapsid protein. It is further contemplated that the recombinant entity may also comprise a sequence that encodes at least one of a co-stimulatory molecule and an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine is selected from the group consisting of IL-2, IL-12, IL-15, IL-15 super agonist (N803), IL-21, IPS1, and LMP1. In some preferred embodiments, the immune stimulatory cytokine is IL-15 super agonist N803.

The immunotherapy compositions disclosed herein to be administered subcutaneously or intravenously.

The recombinant entity contemplated herein may be a recombinant virus, such as a recombinant adenovirus. The recombinant entity may also be a recombinant yeast, such as *Saccharomyces cerevisiae*.

In some preferred embodiments, the coronavirus disease is COVID-19.

In yet another aspect of the present disclosure, disclosed herein is a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. As discussed throughout, the recombinant entity is preferably a recombinant adenovirus or *Saccharomyces cerevisiae*. The vaccine formulation may administered to a patient having a coronavirus disease for treatment and/or prevention of the coronavirus disease.

The present disclosure further provides methods and compositions for administering, monitoring, and assaying a vaccine. The contemplated methods include inducing immunity against a virus in a patient, administering a vaccine composition to the patient by administering a vaccine composition to the patient by delivery to the nasal mucosa, oral mucosa, and/or alimentary mucosa of the patient. Preferably, the vaccine targets severe acute respiratory syndrome (SARS)-like coronavirus (SARS-CoV2). The oral vaccine compositions described herein can serve as a booster vaccination to any initial prime vaccination against SARS-CoV2 S or N protein.

Notably, the disclosed methods also include obtaining a sample of saliva from the patient at a period of time after administering the vaccine. Typically, the sample of saliva is preserved in a stabilizing solution comprising glutaraldehyde, sodium benzoate, citric acid, propyl gallate, EDTA, zinc, actin, chitosan, parabens, sodium azide, or any combination thereof. More typically, the stabilizing solution comprises glutaraldehyde at 0.10 to 2.0% weight per volume (w/v), sodium benzoate at 0.10 to 1.0% w/v, and/or citric acid at 0.025 to 0.20% w/v. Additional embodiments include analyzing the sample of saliva for at least one selected from antibodies targeting the virus or a protein specific to the virus, wherein in the absence of antibodies in the sample saliva, the method further comprises administering a booster of the vaccine to the patient.

The oral vaccine compositions described herein can be used as a universal booster vaccine to any anti-SARS-CoV2 vaccine directed against the SARS-CoV2 spike (S) and/or nucleocapsid (N) proteins. This booster can work even in patients who were immunized with an anti-S or anti-N vaccine other than those described herein. In particular embodiments, the initial prime vaccine can be a lipid nanoparticle vaccine containing mRNA encoding the S protein, such as those vaccines currently being tested by Moderna and by Pfizer. In certain embodiments, the boost described herein is administered at least 7 days after the initial prime vaccination, for example at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 28 days, at least 35 days, or at least 42 days. The boost as described herein can effectively improve both antibody production against SARS-CoV2 and cell-mediate immunity against SARS-CoV2. The efficacy of the booster vaccine can be measured by any standard quantification of immune response (e.g., a QuantiFERON assay).

Additionally, the stabilizing solution further comprises aragonite particle beads having an average particle size of between 100 nm to 1 mm. The aragonite particle beads are capable of binding to immunoglobulin (Ig) proteins, anti-SARS-CoV2 antibodies, or a SAR-CoV2 viral protein. In exemplary embodiments, the aragonite particle beads are coupled to a recombinant ACE2 protein or a recombinant ACE2 alpha helix protein.

The contemplated subject matter also includes an aragonite composition formulated for binding an immunoglobulin (Ig) protein, an anti-SARS-CoV2 antibody protein, or a SARS-CoV2 viral protein. The aragonite composition includes a plurality of aragonite particle beads having an average particle size of between 100 nm to 1 mm, wherein the plurality of aragonite particle beads are functionalized with a moiety capable of binding to an immunoglobulin (Ig) protein, the anti-SARS-CoV2 antibody protein and/or the SARS-CoV2 viral protein.

In specific embodiments, the plurality of aragonite particle beads are functionalized with a moiety capable of binding to the anti-SARS-CoV2 comprises a recombinant ACE2 protein. For example, the moiety capable of binding to the anti-SARS-CoV2 may be selected from a recombinant ACE2 protein having at least 85% sequence identity to SEQ ID NO:1, a recombinant alpha-helix ACE2 protein of SEQ ID NO: 2, or the recombinant alpha-helix ACE2 protein having at least one mutation selected from T27F, T27W, T27Y, D30E, H34E, H34F, H34K, H34M, H34W, H34Y, D38E, D38M, D38W, Q24L, D30L, H34A, and/D355L.

Various objects, features, aspects, and advantages will become more apparent from the following detailed description of preferred embodiments, along with the accompanying drawing in which like numerals represent like components.

BRIEF DESCRIPTION OF THE DRAWING

Figure 6:
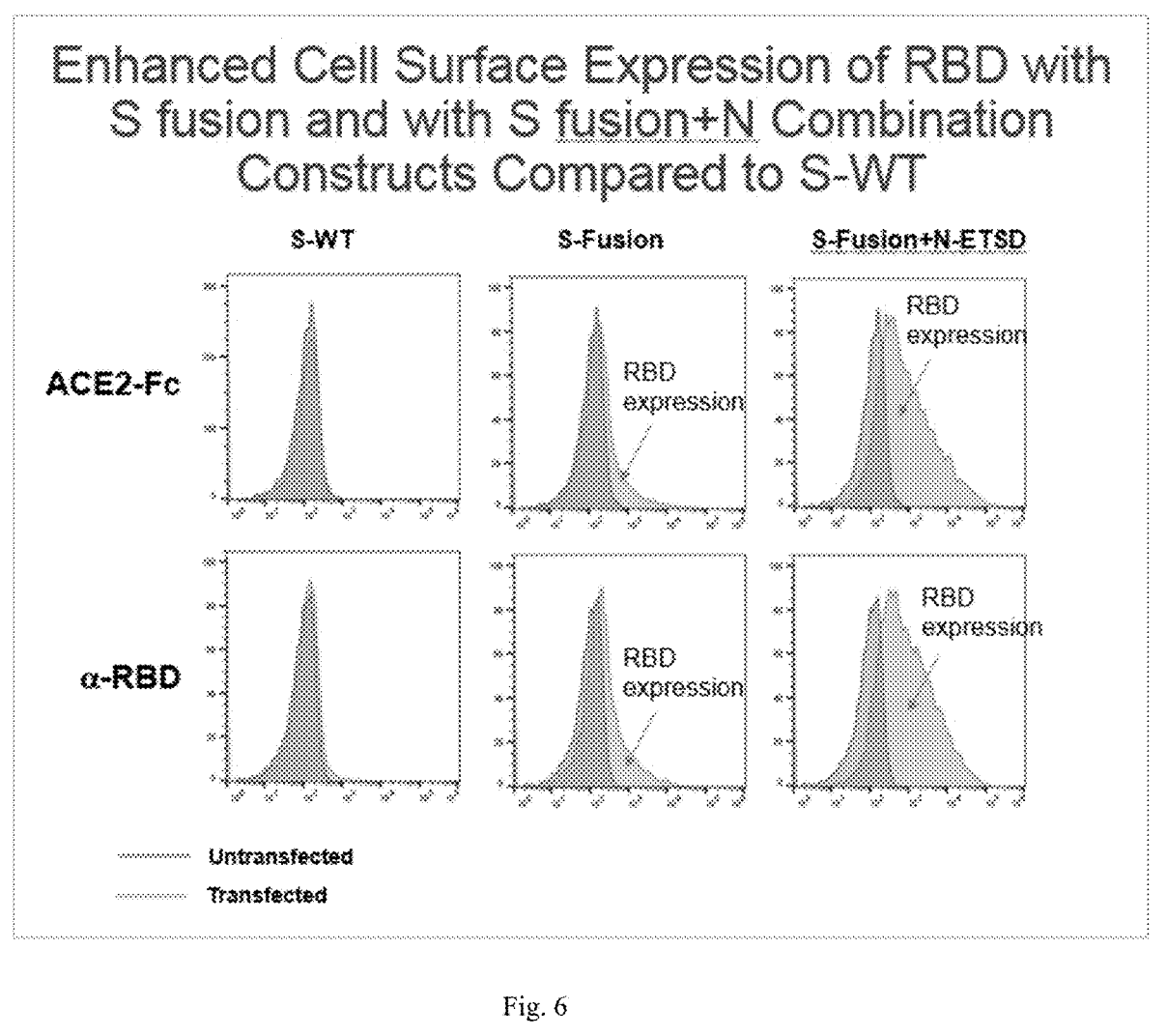

FIG. 6 exemplarily depicts enhanced cell surface expression of RBD with S Fusion and with S Fusion+N combination constructs compared to S-WT.

DETAILED DESCRIPTION

Figure 1:
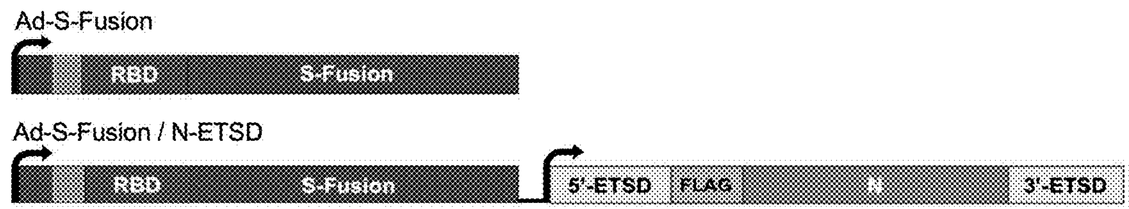
FIG. 1 exemplarily depicts vaccine constructs for Phase 1b clinical trials.

Disclosed herein are recombinant viruses and yeasts. The viruses and yeasts disclosed herein may be useful for a variety of purposes, such as treating and/or preventing a coronavirus disease. In one aspect, disclosed herein is a replication defective adenovirus, wherein the adenovirus comprises an E1 gene region deletion; an E2b gene region deletion; an E3 gene region deletion, a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S—Fusion).

In one embodiment, the N-ETSD may comprises a sequence with at least 80% identity to SEQ ID NO:2. In other embodiments, the identity value is at least 85%. In still other embodiments, the identity value is at least 90%. In some embodiments, the identity value is at least 95%. In some embodiments, the identity value is at least 99%. In some embodiments, the identity value is 100%. It is further contemplated that the fusion protein contains a linker between the N-ETSD domain and the nucleocapsid protein. For example this linker may be a 16 amino acid linker having the sequence $(GGGS)_4$. In certain embodiments, methods are disclosed herein for enhancing the immunogenicity of an intracellular antigen, the methods comprising tagging the antigen with ETSD and expressing the tagged antigen in an antigen-presenting cell (e.g., a dendritic cell).

In some embodiments, the fusion protein comprising N-ETSD and CoV2 nucleocapsid protein may be encoded by a nucleic acid sequence having at least 80% identity to SEQ ID NO:3. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

The CoV2 spike protein is contemplated to have at least 85% identity to SEQ ID NO:6. The nucleic acid encoding the CoV2 spike protein has at least 99% identity to SEQ ID NO:5 or SEQ ID NO:7.

In a second aspect of this disclosure, provided herein is a recombinant yeast comprising a nucleic acid encoding a protein selected from the group consisting of coronavirus 2 (CoV2) nucleocapsid protein, CoV2 spike protein, and a combination thereof. Preferably, the recombinant yeast is *Saccharomyces cerevisiae.*

In some embodiments of this second aspect, the CoV2 nucleocapsid protein comprises a sequence with at least 80% identity to SEQ ID NO:2 or SEQ ID NO:3. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiment of this second aspect, the CoV2 spike protein comprises a sequence with at least 80% identity to SEQ ID NO:5. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiments, the nucleic acid encoding the CoV2 spike protein comprises a sequence with at least 80% identity to SEQ ID NO:5 or SEQ ID NO:7. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

The adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1. Additionally or alternatively, the vaccines disclosed herein may also encode SARS-CoV-2 M protein, with or without an ETSD tag.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition Also disclosed herein are methods for preventing and/or treating coronavirus diseases, and especially COVID-19. Preferably, the method includes using a viral or yeast vector that encodes the nucleocapsid protein and/or spike protein of the coronavirus in an immunogenic composition that is administered to a subject individual. The virus and/or yeast vaccine, thus administered, would infect the individual with CoV2 nucleocapsid or spike protein. With that in place, the individual would have an immune response against it, and be vaccinated. Notably, as the nucleocapsid protein and the spike protein are relatively conserved polypeptides, immune responses can be elicited for a variety of members of the coronavirus family.

Where the recombinant vector is an adenovirus, the adenoviral vector may be modified to encode the nucleocapsid protein, and/or the spike protein. Similarly, in case of yeast, the yeast vector may also be modified to encode the nucleocapsid protein, and/or the spike protein. Positive responses were obtained on cell mediated immunity upon administration of immunogenic compositions comprising the viral and/or yeast vectors in patients in need thereof. Thus, in one embodiment, the present disclosure envision creating the coronaviral spikes to be expressed on the yeast surface. So, in this embodiment, the yeast is acting as an avatar coronavirus to stimulate the B cells. The stimulation of the B cells then results in humoral immunity.

In another embodiment, disclosed herein is a next generation bivalent human adenovirus serotype 5 (hAd5) vaccine capable of inducing immunity in patients with pre-existing adenovirus immunity, comprising both an S sequence optimized for cell surface expression (S— Fusion) and a conserved nucleocapsid (N) antigen designed to be transported to the endosomal subcellular compartment, with the potential to generate durable immune protection. As further described in this disclosure, this bivalent vaccine has been found to be is optimized for immunogenicity as evidenced by the following findings:

- The optimized S-Fusion displayed improved S receptor binding domain (RBD) cell surface expression compared to S-WT where little surface expression was detected;
- The expressed RBD from S-Fusion retained conformational integrity and recognition by ACE2-Fc;
- The viral N protein modified with an enhanced T-cell stimulation domain (ETSD) localized to endosomal/lysosomal subcellular compartments for MHC I/II presentation; and
- These optimizations to S and N (S-Fusion and N-ETSD) generated enhanced de novo antigen-specific B cell and CD4+ and CD8+ T-cell responses in antigen-naïve preclinical models.

Both the T-cell and antibody immune responses to S and N demonstrated a T-helper 1 (Th1) bias. The antibody responses were neutralizing as demonstrated by two independent SARS-CoV-2 neutralization assays. Thus, in one embodiment, this next generation bivalent hAd5 S-Fusion+N-ETSD vaccine provides robust, durable cell-mediated and humoral immunity against SARS-CoV-2 infection. This vaccine construct may be administered orally, intranasally or sublingually. Thus, in one embodiment, the instant disclosure provides vaccine construct in oral, intranasal, and sublingual formulations to induce mucosal immunity in addition to cell-mediated and humoral immunity. In one embodiment, the COVID-19 vaccine disclosed herein generates long-term T and B cell memory.

Coronaviruses and Vaccines Therefor

Coronaviruses are found in avian and mammalian species. They resemble each other in morphology and chemical structure: for example, the coronaviruses of humans and cattle are antigenically related. There is no evidence, however, that human coronaviruses can be transmitted by animals. In animals, various coronaviruses invade many different tissues and cause a variety of diseases in humans. One such disease was Severe acute respiratory syndrome (SARS) coronavirus disease that spread to several countries in Asia, Europe and North America in late 2002/early 2003. Another such disease is the novel Coronvirus Disease of 2019 (COVID 19) that has spread to several countries in the world. In December of 2019, reports emerged from Wuhan, China concerning a new infectious respiratory disease with high morbidity and mortality 1-3 that displayed human-to-human transmission.4 The causative agent was rapidly identified as a novel coronavirus and was designated SARS-coronavirus 2 (SARS-CoV-2). The disease it causes is referred to as COVID-19 and has rapidly become a world-wide pandemic that has disrupted socioeconomic life and resulted in more than 32 million infections and more than 1,100,000 deaths worldwide as of late October 2020.

COVID 19 usually begins with a fever greater than 38° C. Initial symptoms can also include cough, sore throat, malaise and mild respiratory symptoms. Within two days to a week, patients may have trouble breathing. Patients in more advanced stages of COVID 19 develop either pneumonia or respiratory distress syndrome. Public health interventions, such as surveillance, travel restrictions and quarantines, are being used to contain the spread of COVID 19. It is unknown, however, whether these draconian containment measures can be sustained with each appearance of the COVID 19 in humans. Furthermore, the potential of this new and sometimes lethal CoV as a bio-terrorism threat is obvious.

Coronavirus virions are spherical to pleomorphic enveloped particles. The envelope is studded with projecting glycoproteins, and surrounds a core consisting of matrix protein enclosed within which is a single strand of positive-sense RNA (Mr $6\times10^6$) associated with nucleocapsid protein. In that regard, it should be noted that the terms "nucleocapsid protein," "nucleoprotein," and "nucleocapsid" are used interchangeably throughout this disclosure. The coronavirus nucleocapsid (N) is a structural protein found in all coronaviruses, including COVID 19. The nucleocapsid protein forms complexes with genomic RNA, interacts with the viral membrane protein during virion assembly and plays a critical role in enhancing the efficiency of virus transcription and assembly.

Another protein found throughout all coronavirus virions is the viral spike(S) protein. Coronaviruses are large positive-stranded RNA viruses typically with a broad host range. Like other enveloped viruses, CoV enter target cells by fusion between the viral and cellular membranes, and that process is mediated by the viral spike (S) protein.

Figure 8:
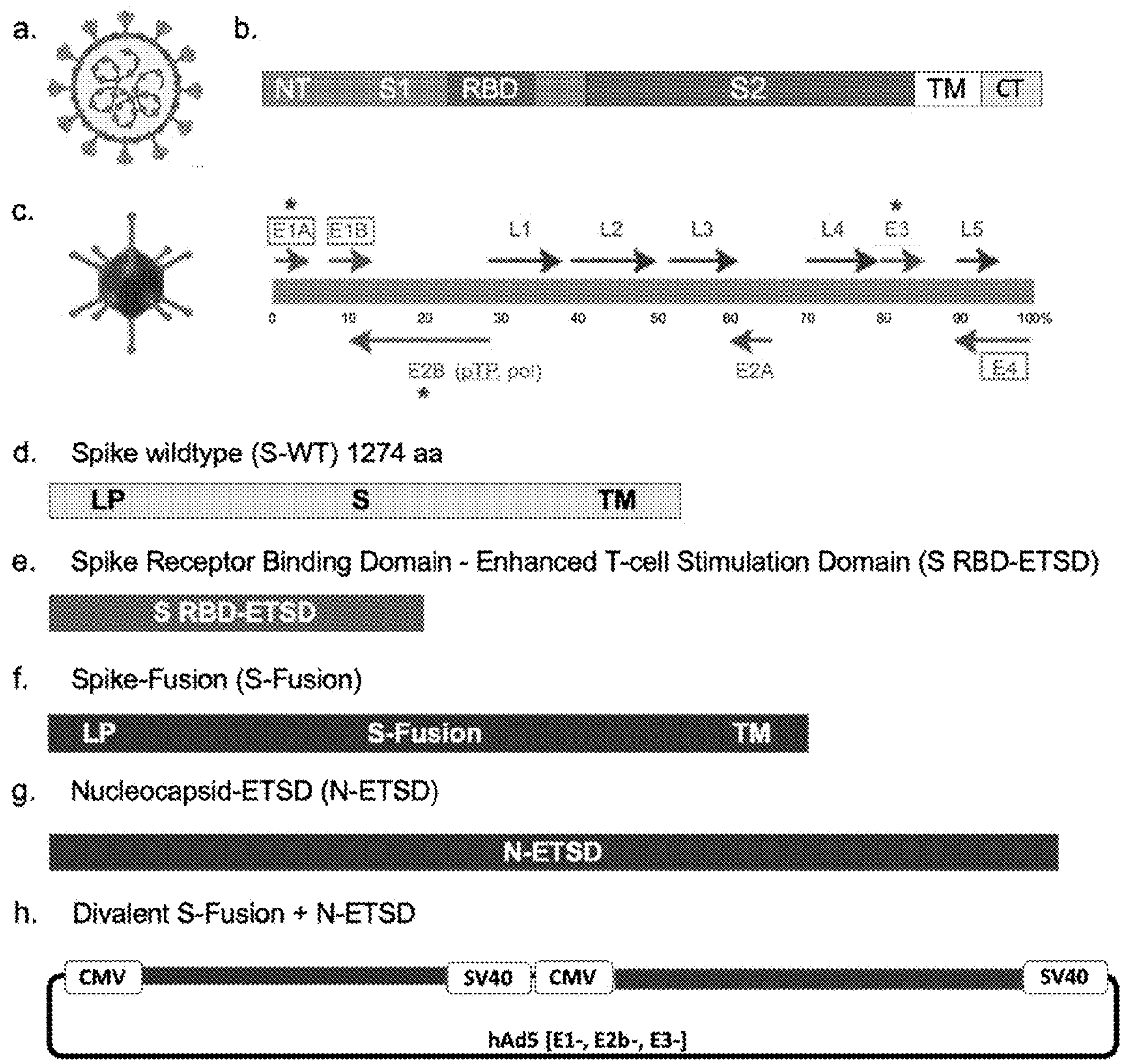
FIG. 8 exemplarily depicts the SARS-CoV-2 virus, spike, the hAd5 [E1-, E2b-, E3-] vector and vaccine candidate constructs. (a) Trimeric spike (S) protein (orange triangle) is displayed on the viral surface; the nucleocapsid (N) protein (blue circle) is associated with the viral RNA. (b) The Receptor Binding Domain (RBD) is within the S1 region, followed by other functional regions, the transmembrane domain (TM) and the C-terminus (CT), which is within the virus. (c) The second-generation human adenovirus serotype 5 (hAd5) vector used has the E1, E2b, and E3 regions deleted. Constructs are shown for (d) S wild type (S-WT), (e)S-RBD with the Enhanced T-cell Stimulation Domain (S RBD-ETSD), (f)S-Fusion, (g) N-ETSD, and (h) bivalent hAd5 S-Fusion+N-ETSD; LP— Leader peptide FIG. 9 exemplarily depicts transfection of HEK293T cells with hAd5 S-Fusion+ETSD results in enhanced surface expression of the spike receptor binding domain (RBD). Flow cytometric analysis of an anti-RBD antibody with construct-transfected cells reveals no detectable surface expression of RBD in either S-WT or (b)S-WT+N-ETSD transfected cells. Surface RBD expression was high for S RBD-ETSD and S RBD-ETSD+N-ETSD (c, d). Expression was low in (e)S-Fusion transfected cells. Cell surface expression of the RBD was high in (f)S-Fusion+N-ETSD transfected cells, particularly at day 1 and 2. (g) No expression was detected the N-ETSD negative control. Y-axis scale is normalized to mode (NM).

SARS-CoV-2 is an enveloped positive sense, single-strand RNA β coronavirus primarily composed of four structural proteins—spike (S), nucleocapsid (N), membrane (M), and envelope—as well as the viral membrane and genomic RNA. Of these, S is the largest and N the most prevalent. The S glycoprotein is displayed as a trimer on the viral surface (FIG. 8*a*), whereas N is located within the viral particle. A schematic of the S primary structure is shown in FIG. 8*b*. The sequence of SARS-CoV-2 was published8 and compared to that of previous coronaviruses. This was soon followed by reports on the crystal structure of the S protein. The virus uses S protein to enter host cells by interaction of the S receptor binding domain (S RBD) with angiotensin-converting enzyme 2 (ACE2), an enzyme expressed broadly on a variety of cell types in the nose, mouth, gut and lungs as well as other organs, and importantly on the alveolar epithelial cells of the lung where infection is predominantly manifested. As represented in FIG. 8*b*, the S RBD is found within the S1 region of spike.

The methods and compositions disclosed herein target the nucleoprotein and the spike protein that is conserved in all types of coronaviruses. In one embodiment, the present disclosure provides a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. The vaccine formulation may be useful for treating a disease, such as a coronavirus mediated disease or infection. Thus, in another embodiment, disclosed is a method for treating a coronavirus disease, in a patient in need thereof, comprising: administering to the subject an immunotherapy composition comprising a recombinant entity, wherein the recombinant entity comprises a nucleic acid that encodes a nucleocapsid protein of coronavirus 2 (CoV2). The coronavirus contemplated herein may be coronavirus disease 2019 (COVID-19) and/or severe acute respiratory syndrome coronavirus 2 (SARS-CoV2)

The instant disclosure also provides a method for treating coronavirus disease 2019 (COVID-19) and/or severe acute respiratory syndrome coronavirus 2 (SARS-CoV2), in a patient in need thereof, comprising: administering to the subject a first immunotherapy composition comprising a recombinant virus, wherein the recombinant virus comprises a nucleic acid that encodes a nucleocapsid protein of coronavirus 2 (CoV2), administering to the subject a second immunotherapy composition comprising a recombinant yeast, wherein the recombinant yeast comprises a nucleic acid that encodes a spike protein of CoV2. The first and second immunotherapy compositions may be administered concurrently or sequentially to the patient.

Viewed form a different perspective, contemplated herein is a viral vector (e.g., recombinant adenovirus genome, optionally with a deleted or non-functional E2b gene) that comprises a nucleic acid that encodes (a) at least a nucleocapsid protein; and (b) at least one spike protein. The viral vector may further comprise co-stimulatory molecule. Most typically, the nucleic acid will further include a trafficking signal to direct a peptide product encoded by the nucleic acid to the cytoplasm, the endosomal compartment, or the lysosomal compartment, and the peptide product will further comprise a sequence portion that enhances intracellular turnover of the peptide product.

The majority of current SARS-CoV-2 vaccines under development target S because of the potential to neutralize the ability of the virus to bind host cells by production of antibodies against the RBD. Support for RBD as a key antigen was recently confirmed, and it was reported that in 44 hospitalized COVID-19 patients, RBD-specific IgG responses and neutralizing antibody titers are detectable in all patients by 6 days post-PCR confirmation of infection, and that the two are correlated. See Suthar, M. S. et al. Rapid generation of neutralizing antibody responses in COVID-19 patients. Cell Reports Medicine, 2020, which is incorporated by reference herein. They confirmed this finding in an additional 231 PCR-confirmed COVID-19 patient samples. In addition to humoral responses, S epitopes are also frequent targets of COVID-19 recovered patient T cells, providing further justification for inclusion of S in prophylactic immunization strategies.

Despite the urgent need for rapid development of SARS-CoV-2 vaccines, reliance on any one antigen cargo or immunological pathway as occurring in the monovalent vaccines under development is not without risk. Evaluation of nearly 4000 SARS-CoV-2 genomic sequences has identified numerous mutations in S with the D614G variant emerging recently as a potentially more infectious strain six months after identification of the original virus.

In designing the vaccine disclosed herein, to overcome the risk of the emergence of new strains of the virus with mutations in S and to provide additional antigens against which responses can be elicited, an optimized N sequence was added. The N protein is a highly conserved and antigenic SARS-CoV-2-associated protein that has been studied previously as an antigen in coronavirus vaccine design for SARS-CoV. N associates with viral RNA within the virus and has a role in viral RNA replication, virus particle assembly, and release. SARS-CoV-2 N is a highly antigenic protein and recent studies have shown that nearly all patients infected with SARS-CoV-2 have antibody responses to N. Furthermore, another study reported that most, if not all, COVID-19 survivors tested were shown to have N-specific CD4+ T-cell responses.

Currently, there is keen focus on generation of humoral responses to vaccines with, arguably, less attention being paid to T-cell responses. The natural history of SARS-CoV-2 infection would suggest, however, that a robust T-cell response to vaccination is at least as important as the production of antibodies and should be a critical consideration for COVID-19 vaccine efficacy.

First, the humoral and T-cell responses are highly correlated, with titers of neutralizing antibodies being proportional to T-cell levels, suggesting the T response is necessary for an effective humoral response. It is well established that the activation of CD4+T helper cells enhances B-cell production of antibodies. Second, virus-specific CD4+ and CD8+ T cells are not only widely detected in COVID-19 patients, based on findings from patients recovered from the closely-related SARS-CoV, but such T cells persist for at least 6-17 years, suggesting that T cells may be an important part of long-term immunity. These T-cell responses were predominantly to N, and it has been reported that in all 36 convalescent COVID-19 patients in their study, the presence of CD4+ and CD8+ T cells recognizing multiple regions of the N protein could be demonstrated. Examination of blood from 23 individuals who had recovered from SARS-CoV and found that the memory T cells acquired 17 years ago also recognized multiple proteins of SARS-CoV-2. These findings emphasize the importance of designing a vaccine with the highly conserved nucleocapsid present in both SARS-CoV and SARS-CoV-2. Third, recovered patients exposed to SARS-CoV-2 have been found without seroconversion, but with evidence of T-cell responses. The T-cell based responses become even more critical given the finding in at least one study that neutralizing antibody titers decline in some COVID-19 patients after about 3 months.

In one embodiment, the vaccines disclosed herein results in the generation of T-cell in addition to humoral responses. A bivalent vaccine comprising many antigens— S RBD as displayed by inclusion of full-length S including SD1, S1 and S2 epitopes, along with N— would be more effective in eliciting both T-cell and antibody-based responses than a construct with either antigen alone by presenting both unique and conserved SARS-CoV-2 antigenic sites to the immune system. The importance of both S and N was highlighted by identifying that both S and N antigens as a priori potential B and T-cell epitopes for the SARS-CoV virus that shows close similarity to SARS-CoV-2 that are predicted to induce both T and B cell responses.

An additional consideration for design of an effective vaccine is the likelihood of antigen presentation on the surface of the vectored-protein-expressing cell and in a conformation that recapitulates natural virus infection. First, because wild type N does not have a signaling domain that directs it to endosomal processing and ultimately MEW class II complex presentation to CD4+ T cells, the wild type N sequence is not optimal for induction of a vigorous CD4+ T-cell responses, a necessity for both cell-mediated and B cell memory. To overcome this limitation, we have designed an Enhanced T-cell Stimulation Domain (ETSD) to N to allow the necessary processing and presentation. Second, to display the highly antigenic RBD region of S on the cell surface, we have optimized the wild type S protein "S Fusion sequence", to increase the likelihood of native folding, increased stability, and proper cell surface expression of RBD. Thus, in one embodiment, the vaccine construct design comprises an S-Fusion+N-ETSD sequence.

The vaccine platform utilized here is a next-generation recombinant human adenovirus serotype 5 (hAd5) vector with deletions in the E1, E2b, and E3 gene regions (hAd5 [E1-, E2b-, E3-]). This hAd5 [E1-, E2b-, E3-] vector (FIG. 8*c*) is primarily distinguished from other first-generation [E1-, E3-] recombinant Ad5 platforms by having additional deletions in the early gene 2b (E2b) region that remove the expression of the viral DNA polymerase (pol) and in pre terminal protein (pTP) genes, and its propagation in the E.C7 human cell line. Removal of these E2b regions confers advantageous immune properties by minimizing immune responses to Ad5 viral proteins such as viral fibers, 37 thereby eliciting potent immune responses to specific antigens in patients with pre-existing adenovirus (Ad) immunity. As a further benefit of these deletions, the vector has an expanded gene-carrying/cloning capacity compared to the first generation Ad5 [E1-, E3-] vectors. This next generation hAd5 [E1-, E2b-, E3-] vaccine platform, in contrast to Ad5 [E1-, E3-]-based platforms, does not promote activities that suppress innate immune signaling, thereby allowing for improved vaccine efficacy and a superior safety profile independent of previous Ad immunity. Since these deletions allow the hAd5 platform to be efficacious even in the presence of existing Ad immunity, this platform enables relatively long-term antigen expression without significant induction of anti-vector immunity. It is therefore also possible to use the same vector/construct for homologous prime-boost therapeutic regimens unlike first-generation Ad platforms which face the limitations of pre-existing and vaccine-induced Ad immunity. Importantly, this next generation Ad vector has demonstrated safety in over 125 patients with solid tumors. In these Phase I/II studies, CD4+ and CD8+antigen-specific T cells were successfully generated to multiple somatic antigens (CEA, MUC1, brachyury) even in the presence of pre-existing Ad immunity.

The instant disclosure provides findings of confirmed enhanced cell-surface expression and physiologically-relevant folding of the expressed S RBD from S-Fusion by ACE2-Fc binding. The N-ETSD protein was successfully localized to the endosomal/lysosomal subcellular compartment for MEW presentation and consequently generated both CD4+ and CD8+ T-cell responses. Immunization of CD-1 mice with the hAd5 S Fusion+N-ETSD vaccine elicited both humoral and cell-mediated immune responses to vaccine antigens. CD8+ and CD4+ T-cell responses were noted for both S and N. Statistically significant IgG responses were seen for antibody generation against S and N. Potent neutralization of SARS-CoV-2 by sera from hAd5 S Fusion+N-ETSD-immunized mice was confirmed by two independent SARS-CoV-2 neutralization assays: the cPass assay measuring competitive inhibition of RBD binding to ACE2,44 and in the live SARS-CoV-2 virus assay with infected Vero E6 cells. Analysis of T-cell responses as well as humoral responses to S and N were skewed toward a Th1-specific response.

Taken together, these findings illustrate that hAd5 S-Fusion+N-ETSD vaccine would be particularly effective against the SARS-CoV-2.

Recombinant Viruses

With respect to recombinant viruses it is contemplated that all known manners of making recombinant viruses are deemed suitable for use herein, however, especially preferred viruses are those already established in therapy, including adenoviruses, adeno-associated viruses, alphaviruses, herpes viruses, lentiviruses, etc. Among other appropriate choices, adenoviruses are particularly preferred.

Moreover, it is further generally preferred that the virus is a replication deficient and non-immunogenic virus. For example, suitable viruses include genetically modified alphaviruses, adenoviruses, adeno-associated viruses, herpes viruses, lentiviruses, etc. However, adenoviruses are particularly preferred. For example, genetically modified replication defective adenoviruses are preferred that are suitable not only for multiple vaccinations but also vaccinations in individuals with preexisting immunity to the adenovirus (see e.g., WO 2009/006479 and WO 2014/031178, which are incorporated by reference in its entirety). In some embodiments, the replication defective adenovirus vector comprises a replication defective adenovirus 5 vector. In some embodiments, the replication defective adenovirus vector comprises a deletion in the E2b region. In some embodiments, the replication defective adenovirus vector further comprises a deletion in the E1 region. In that regard, it should be noted that deletion of the E2b gene and other late proteins in the genetically modified replication defective adenovirus to reduce immunogenicity. Moreover, due to these specific deletions, such genetically modified viruses were replication deficient and allowed for relatively large recombinant cargo.

For example, WO 2014/031178 describes the use of such genetically modified viruses to express CEA (colorectal embryonic antigen) to provide an immune reaction against colon cancer. Moreover, relatively high titers of recombinant viruses can be achieved using genetically modified human 293 cells as has been reported (e.g., J Virol. 1998 February; 72(2): 926-933).

E1-deleted adenovirus vectors Ad5 [E1-] are constructed such that a trans gene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

One obstacle to the use of first generation (E1-deleted) Ad5-based vectors is the high frequency of pre-existing anti-adeno virus type 5 neutralizing antibodies. Attempts to overcome this immunity is described in WO 2014/031178, which is incorporated by reference herein. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. E2b deleted adenovirus vectors provide an improved Ad-based vector that is safer, more effective, and more versatile than First Generation adenovirus vectors.

In a further embodiment, the adenovirus vectors contemplated for use in the present disclosure include adenovirus vectors that have a deletion in the E2b region of the Ad genome and, optionally, deletions in the E1, E3 and, also optionally, partial or complete removal of the E4 regions. In a further embodiment, the adenovirus vectors for use herein have the E1 and/or the preterminal protein functions of the E2b region deleted. In some cases, such vectors have no other deletions. In another embodiment, the adenovirus vectors for use herein have the E1, DNA polymerase and/or the preterminal protein functions deleted.

The term "E2b deleted", as used herein, refers to a specific DNA sequence that is mutated in such a way so as to prevent expression and/or function of at least one E2b gene product. Thus, in certain embodiments, "E2b deleted" is used in relation to a specific DNA sequence that is deleted (removed) from the Ad genome. E2b deleted or "containing a deletion within the E2b region" refers to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As noted before, the desired nucleic acid sequences (for expression from virus infected cells) are under the control of appropriate regulatory elements well known in the art. In view of the above, it should be appreciated that compositions and methods presented are not only suitable for directing virally expressed antigens specifically to one or another (or both) MHC systems, but will also provide increased stimulatory effect on the CD8+ and/or CD4+ cells via inclusion of various co-stimulatory molecules (e.g., ICAM-1 (CD54), ICOS-L, LFA-3 (CD58), and at least one of B7.1 (CD80) and B7.2 (CD86)), and via secretion or membrane bound presentation of checkpoint inhibitors.

With respect to viral expression and vaccination systems it is contemplated that all therapeutic recombinant viral expression systems are deemed suitable for use herein so long as such viruses are capable to lead to expression of the recombinant payload in an infected cell.

Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patient's cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

As noted above, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

The replication defective adenovirus comprising an E1 gene region deletion, an E2b gene region deletion, and a nucleic acid encoding a coronavirus 2 (CoV2) nucleocapsid protein and/or a CoV2 spike protein, as disclosed herein may be administered to a patient in need for inducing immunity against CoV2. Routes and frequency of administration of the therapeutic compositions described herein, as well as dosage, may vary from individual to individual, and the severity of the disease, and may be readily established using standard techniques. In some embodiments, the administration comprises delivering $4.8\text{-}5.2\times10^{11}$ replication defective adenovirus particles, or $4.9\text{-}5.1\times10^{11}$ replication defective adenovirus particles, or $4.95\text{-}5.05\times10^{11}$replication defective adenovirus particles, or $4.99\text{-}5.01\times10^{11}$ replication defective adenovirus particles.

The administration of the virus particles can be through a variety of suitable paths for delivery. One preferred route contemplated herein is by injection, such as intracutaneous injection, intramuscular injection, intravenous injection or subcutaneous injection. In some embodiments, a subcutaneous delivery may be preferred.

Recombinant Yeasts

With respect to yeast expression and vaccination systems, it is contemplated that all known yeast strains are deemed suitable for use herein. However, it is preferred that the yeast is a recombinant *Saccharomyces* strain that is genetically modified with a nucleic acid construct encoding a protein selected from the group consisting of coronavirus 2 (CoV2) nucleocapsid protein, CoV2 spike protein, and a combination thereof, to thereby initiate an immune response against the CoV2 viral disease. In one aspect of any of the embodiments of the disclosure described above or elsewhere herein, the yeast vehicle is a whole yeast. The whole yeast, in one aspect is killed. In one aspect, the whole yeast is heat-inactivated. In one preferred embodiment, the yeast is a whole, heat-inactivated yeast from *Saccharomyces cerevisiae.*

The use of a yeast based therapeutic compositions are disclosed in the art. For example, WO 2012/109404 discloses yeast compositions for treatment of chronic hepatitis b infections.

It is noted that any yeast strain can be used to produce a yeast vehicle of the present disclosure. Yeasts are unicellular microorganisms that belong to one of three classes: Ascomycetes, Basidiomycetes and *Fungi Imperfecti*. One consideration for the selection of a type of yeast for use as an immune modulator is the pathogenicity of the yeast. In preferred embodiments, the yeast is a non-pathogenic strain such as *Saccharomyces cerevisiae* as non-pathogenic yeast strains minimize any adverse effects to the individual to whom the yeast vehicle is administered. However, pathogenic yeast may also be used if the pathogenicity of the yeast can be negated using pharmaceutical intervention.

For example, suitable genera of yeast strains include *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in a preferred aspect, *Saccharomyces* is used. Species of yeast strains that may be used include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*.

It should further be appreciated that a number of these species include a variety of subspecies, types, subtypes, etc. that are intended to be included within the aforementioned species. In one aspect, yeast species used in the instant disclosure include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). Therefore, particularly contemplated herein is a yeast strain that is capable of replicating plasmids to a particularly high copy number, such as a *S. cerevisiae* cir strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used, including those that exhibit reduced post-translational modifications of expressed target antigens or other proteins, such as mutations in the enzymes that extend N-linked glycosylation.

Expression of contemplated peptides/proteins in yeast can be accomplished using techniques known to those skilled in the art. Most typically, a nucleic acid molecule encoding at least one protein is inserted into an expression vector such manner that the nucleic acid molecule is operatively linked to a transcription control sequence to be capable of effecting either constitutive or regulated expression of the nucleic acid molecule when transformed into a host yeast cell. As will be readily appreciated, nucleic acid molecules encoding one or more proteins can be on one or more expression vectors operatively linked to one or more expression control sequences. Particularly important expression control sequences are those which control transcription initiation, such as promoter and upstream activation sequences.

Any suitable yeast promoter can be used in the methods and compositions of the present disclosure and a variety of such promoters are known to those skilled in the art and have generally be discussed above. Promoters for expression in *Saccharomyces cerevisiae* include promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GALT), UDP-galactose epimerase (GAL10), cytochrome cl (CYC1), Sec7 protein (SECT) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include the UASs of genes encoding the following proteins: PCK1, TPI, TDH3, CYC1, ADH1, ADH2, SUC2, GAL1, GALT and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the alpha-factor, GAPDH, and CYC1 genes. Transcription control sequences to express genes in methyltrophic yeast include the transcription control regions of the genes encoding alcohol oxidase and formate dehydrogenase.

Likewise, transfection of a nucleic acid molecule into a yeast cell according to the present disclosure can be accomplished by any method by which a nucleic acid molecule administered into the cell and includes diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins. Further exemplary yeast expression systems, methods, and conditions suitable for use herein are described in US20100196411A1, US2017/0246276, or US 2017/0224794, and US 2012/0107347.

So produced recombinant viruses and yeasts may then be individually or in combination used as a therapeutic vaccine in a pharmaceutical composition, typically formulated as a sterile injectable composition with a virus of between $10^4$-$10^{13}$ virus or yeast particles per dosage unit, or more preferably between $10^9$-$10^{12}$ virus or yeast particles per dosage unit. Alternatively, virus or yeast may be employed to infect patient cells ex vivo and the so infected cells are then transfused to the patient. However, alternative formulations are also deemed suitable for use herein, and all known routes and modes of administration are contemplated herein.

Second Generation hAd5 [E1-, E2b-, E3-] Based Vaccines Disclosed Herein Overcome Pre-Existing Anti-Ad5 Immunity To avoid the Ad immunization barrier and circumvent the adverse conditions for first generation Ad5 [E1-E3-] vectors, an advanced 2nd generation human adenoviral (hAd5) vector was constructed having two (2) additional deletions in the E2b region, removing the DNA polymerase and the preterminal protein genes [E1-, E2b-, E3-]. (Former names of our adenovirus vector were Ad5, ETBX in literature)

E2b-deleted hAd5 vectors have up to a 12-14 kb gene-carrying capacity as compared to the 7-kb capacity of first generation Ad5 [E1-] vectors, providing space for multiple genes if needed. hAd5 [E1-, E2b-, E3-] based recombinant vectors are produced using the human E.C7 cell line. Deletion of the E2b region also confers advantageous immune properties on these novel Ad vectors, eliciting potent immune responses to specific, non-viral antigens while minimizing the immune responses to Ad viral proteins.

hAd5 [E1-, E2b-, E3-] vectors induce a potent cell mediated immune (CMI) response, as well as Abs against the vectored antigens even in the presence of Ad immunity. hAd5 [E1-, E2b-, E3-] vectors also have reduced adverse reactions as compared to Ad5 [E1-] vectors, in particular the appearance of hepatotoxicity and tissue damage. In one embodiment, the reduced inflammatory response against hAd5 [E1-, E2b-, E3-] vector viral proteins and the resulting evasion of pre-existing Ad immunity increases the capability for the hAd5 [E1-, E2b-, E3-] vectors to infect dendritic cells (DC), resulting in greater immunization of the vaccine. In addition, increased infection of other cell types provides high levels of antigen presentation needed for a potent CD8+ and CD4+ T cell responses, leading to memory T cell development. In one embodiment, hAd5 [E1-, E2b-, E3-] vectors are superior to Ad5 [E1-] vectors in immunogenicity and safety and will be the best platform to develop a COVID-19 vaccine in a rapid and efficient manner. In one embodiment, a prophylactic vaccine is tested against COVID-19 by taking advantage of this new hAd5 vector system that overcomes barriers found with other Ad5 systems and permits the immunization of people who have previously been exposed to Ad5.

Track Record of Rapid Vaccine Development Utilizing Second Generation Human (hAd5) Adenovirus Platform During Pandemic Treats: H1N1 Experience in 2009

To address emerging pathogen threats, especially in times of pandemic, it is critical that modernized vaccine technologies be deployed. These technologies will utilize the power of genomic sequencing, rapid transfection in well-established vaccine vectors to rapidly identify constructs with high immunogenicity.

Vaccines against emerging pathogens such as the 2009 H1N1 pandemic virus can benefit from current technologies such as rapid genomic sequencing to construct the most biologically relevant vaccine. A novel platform (hAd5 [E1-, E2b-, E3-]) has been utilized to induce immune responses to various antigenic targets. This vector platform expressed hemagglutinin (HA) and neuraminidase (NA) genes from 2009 H1N1 pandemic viruses. Inserts were consensuses sequences designed from viral isolate sequences and the vaccine was rapidly constructed and produced. Vaccination induced H1N1 immune responses in mice, which afforded protection from lethal virus challenge. In ferrets, vaccination protected from disease development and significantly reduced viral titers in nasal washes. H1N1 cell mediated immunity as well as antibody induction correlated with the prevention of disease symptoms and reduction of virus replication. The hAd5 [E1-, E2b-, E3-] has thus demonstrated the capability for the rapid development of effective vaccines against infectious diseases.

hAd5 Vaccine Constructs and Results

Figure 2:
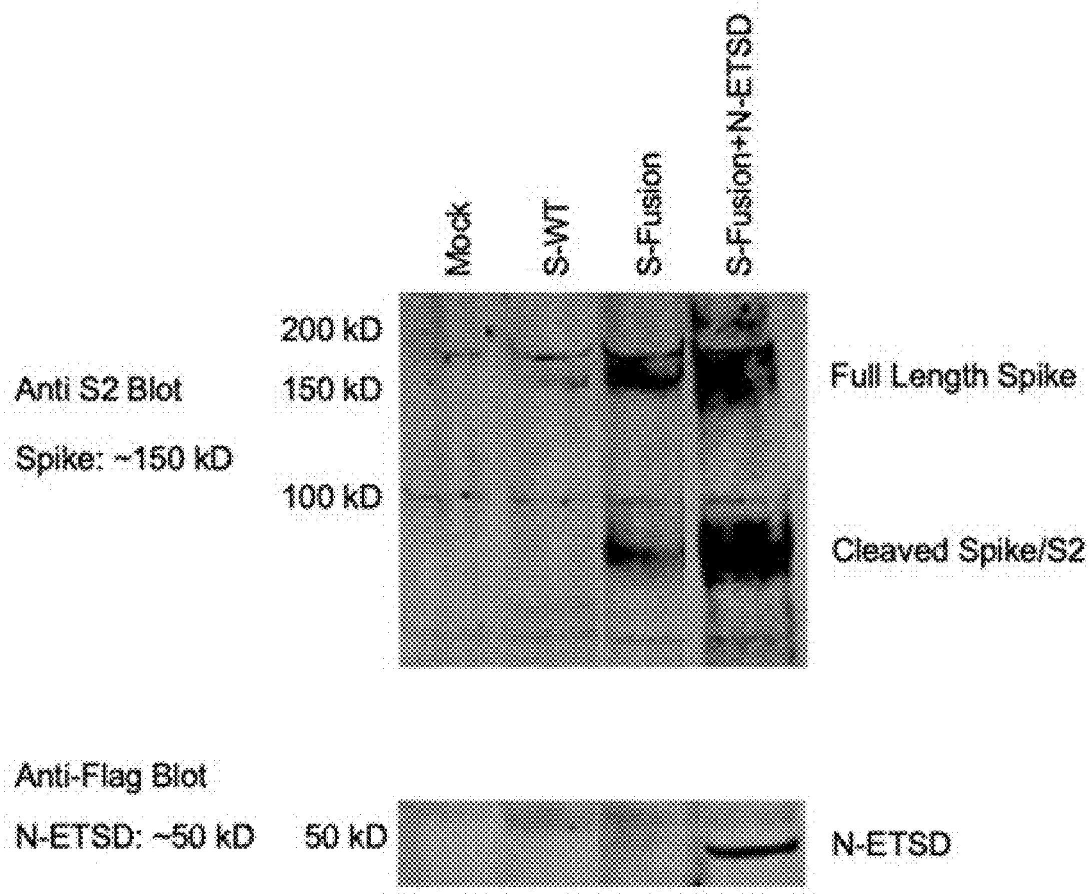
FIG. 2 exemplarily depicts in vitro Expression, Construct Expression via Western Blot, and detection of spike and nucleocapsid expression in by Western Blot.

Disclosed herein are constructs that have been constructed and tested, a hAd5-COVID-19 vaccine construct E1-, E2b-, E3-hAd5 vector with SARS-CoV-2 (S/N) protein insert (FIG. 1). This construct has been tested in preclinical experiments, including in vitro expression (FIG. 2) and small animal immunogenicity.

Figure 3:
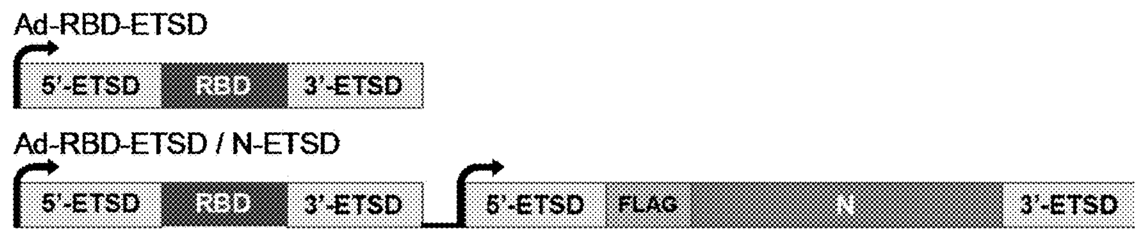
FIG. 3 exemplarily depicts COVID-19 vaccine constructs.

In addition, ImmunityBio has developed multiple COVID-19 constructs including RBD-alone, S1-alone, S1-fusion proteins, and combinations of RBD, S1 and S1 fusions with N. Preliminary in-vitro studies demonstrate that these constructs (FIG. 3) recognize convalescent serum antibodies and could serve as alternative vaccines following analysis of the two (2) constructs above (FIG. 1) which is intended to initiate in our first in human Phase 1b study.

Rationale for Inclusion of Nucleocapsid (N) in hAd5 Constucts for COVID-19

The nucleocapsid (N) protein of SARS-CoV-2 is highly conserved and highly expressed. Previous research with the related coronavirus that causes SARS demonstrated that N protein is immunogenic (Gupta, 2006), when integrated with intracellular trafficking constructs. To date, vaccine strategies in development all involve developing immunogenicity against spike (S) protein. However, very recent evidence in patients who recovered from COVID-19 demonstrates Th1 immunity generated against the nucleocapsid (N) (Grifoni, 2020). A second report by Grifoni et al. further confirmed that in the predictive bioinformatics model, T and B cell epitopes were highest for both spike glycoprotein and nucleoprotein (Grifoni, 2020). The present disclosure confirms the potential that combining S with N, that long-term cell-mediated immunity with a Th1 phenotype can be induced. The potential exists for this combination vaccine to serve as a long-term "universal" COVID-19 vaccine in light of mutations undergoing in S and the finding that the structural N protein is highly conserved in the coronavirus family. The clinical trial is designed to compare S alone versus S+N, to demonstrate safety and to better inform the immunogenicity of S and S+N. A single construct having S & N would be selected to induce potent humoral and cell mediated immunity.

Immunogenicity Studies (Small Animal Model):

Homologous prime-boost immunogenicity in BALB-c mice. Mice have been treated with 1, 2 or 3 doses of the hAd5 COVID-19 vaccine and serum and splenocyte samples are being tested for SARS-CoV-2 antigen-specific immune responses. Serum is tested for anti-spike and anti-nucleocapsid antibody responses by ELISA. Splenocytes is tested for spike- and nucleocapsid-specific cell mediated immune responses by ELISPOT and intracellular cytokine simulation assays.

The results show promising immunogenic activity. In one embodiment, hAd5 [E1-,E2b-, E3-] N-ETSD, a vaccine containing SARS-CoV-2 nucleocapsid plus an enhanced T cell stimulation domain (ETSD), alters T cell responses to nucleocapsid. Mice were immunized subcutaneously (SC) with a dose of 1010 VP twice at 7-day intervals. Blood was collected at several time points and spleen was collected upon sacrifice in order to perform immunogenicity experiments. Splenocytes were isolated and tested for cell mediated immune (CMI) responses. The results showed that SARS-CoV-2 nucleocapsid antigen specific CMI responses were detected by ELISpot and flow cytometry analyses in the spleens of all the mice immunized with hAd5 [E1-, E2b-, E3-] N-ETSD vaccine but not vector control (hAd5 [E1-, E2b-, E3-] null) immunized mice.

Figure 4:
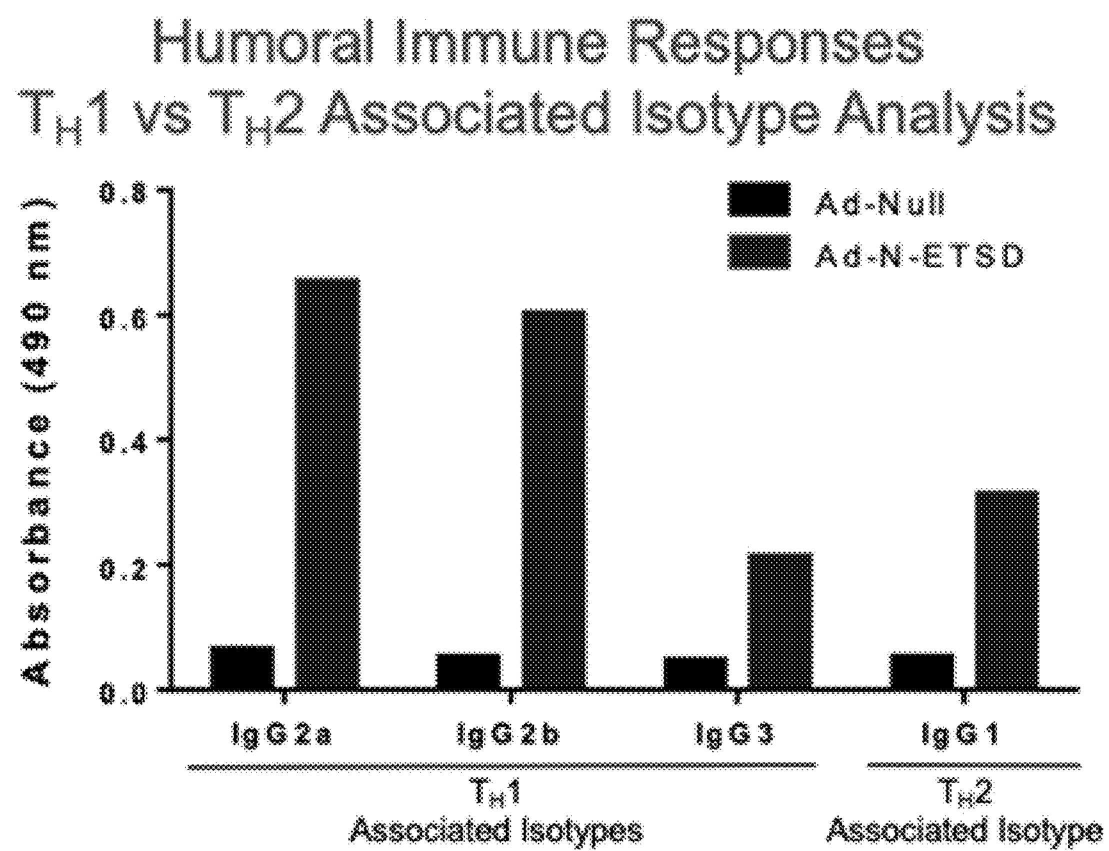
FIG. 4 exemplarily depicts antibody response to N with a Th1 phenotype. Humoral Immune Responses $T_H1$ vs $T_H2$ associated isotype analysis is shown.
Figure 5:
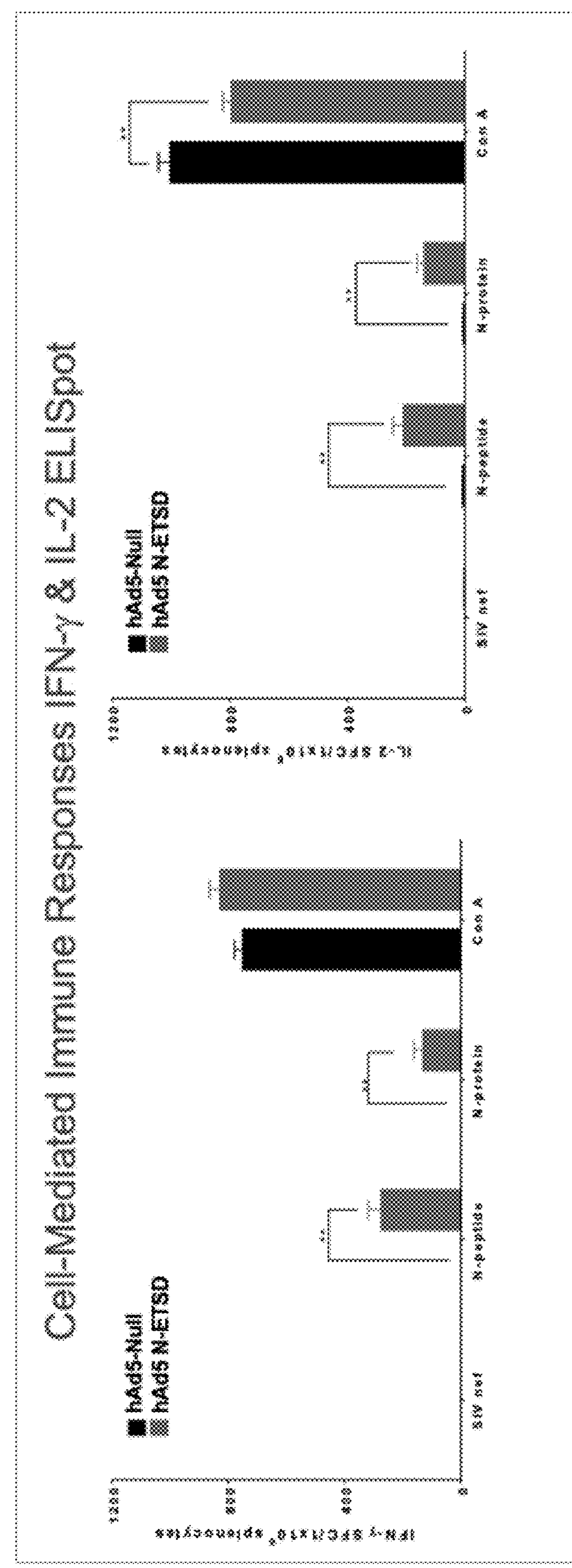
FIG. 5 exemplarily depicts cell mediated immunity (CMI) response to N focus phenotype— IFN-γ and IL-2 ELISpot.

In addition, antibody responses were detected in all the mice immunized with hAd5 [E1-, E2b-, E3-]-N-ETSD vaccine but not vector control (Ad5 [E1-, E2b-, E3-]-null) immunized mice (FIG. 4 & FIG. 5). Additional studies to confirm and extend these results are ongoing.

Enhanced RBD Cell Surface Expression:

Further evidence of the potential enhancing immunogenicity value of N when combined with S was the surprising finding of enhanced surface expression of the RBD protein in 293 cells transfected with the N-ETSD+S construct as seen in FIG. 6. Expression and presentation of RBD appears to be highly important as evidenced by the recent report by Robbiani et al who showed that rare but recurring RBD-specific antibodies with potent antiviral activity were found in all individuals tested who had recovered from COVID-19 infections (Robbiani 2020).

Figure 7:
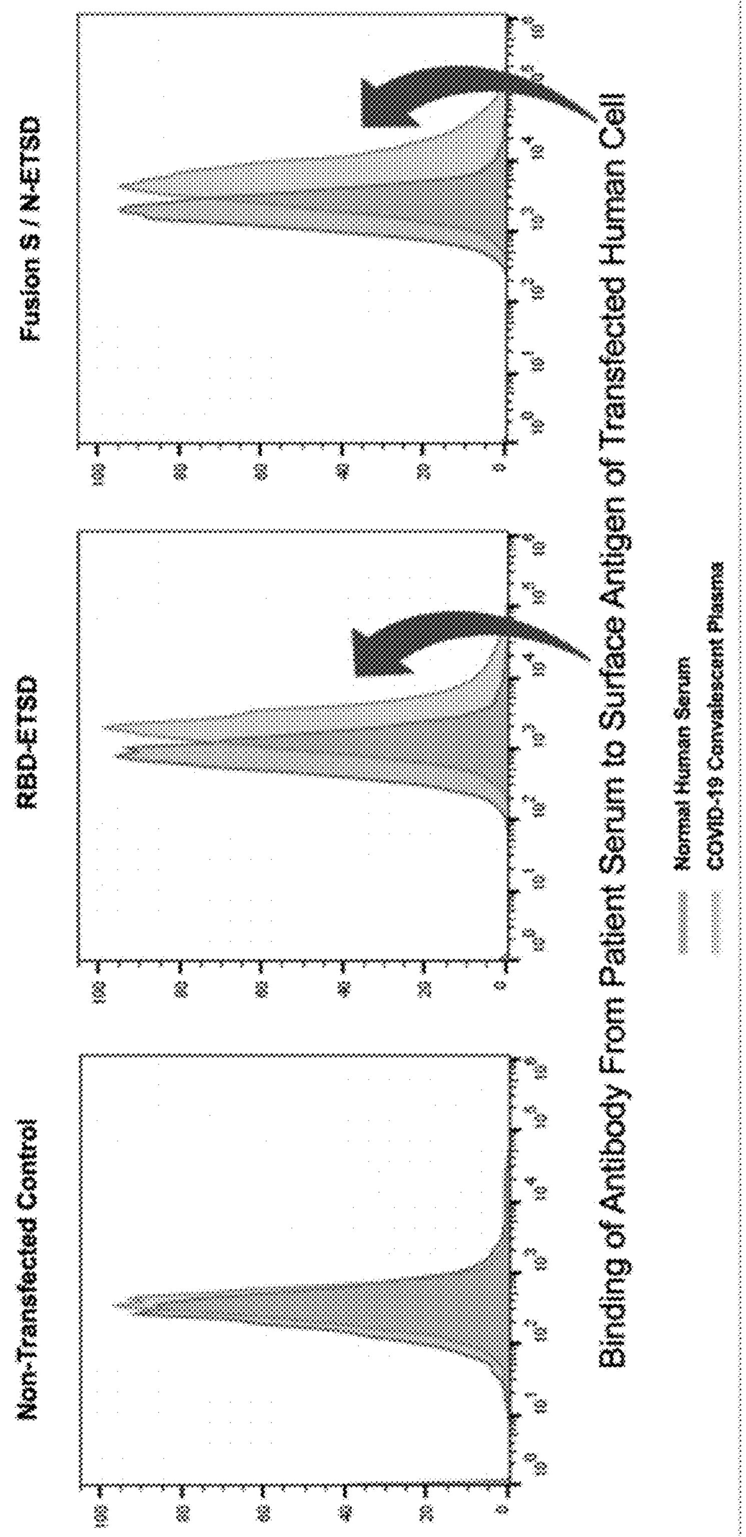
FIG. 7 exemplarily depicts that recovered COVID-19 patient plasma recognizes antigens expressed by NANT's RBD-ETSD and NANT fusion S/N-ETSD constructs.

This finding of enhanced expression of RBD when N is combined with S-Fusion was corroborated in studies using plasma from a patient recovered from COVID-19 infection (FIG. 7). The alternative construct of RBD-ETSD could serve as alternative vaccines following analysis of the two (2) constructs above (FIG. 1) which is intended to initiate in human Phase 1b studies.

In summary, on the basis of enhanced expression and exposure of the RBD protein with S Fusion and S Fusion+N construct, both were tested in the hAd5 vector. Furthermore, on the basis of recent clinical data from patients recovered from COVID-19, as well as the corroborating preclinical data that the N construct induces long lasting CD4+ and Th1 cell-mediated immunity, this combination of S Fusion+N construct could provide long-lasting immunity beyond short term neutralizing antibodies.

Immunogenicity Testing of Candidate COVID-19 Vaccine Constructs

Two (2) Adenovirus-based COVID-19 vaccine constructs will be tested in preclinical experiments, including in vitro expression; small animal immunogenicity, and non-human primate immunogenicity and efficacy.

Constructs description: ImmunityBio has generated two (2) second generation hAd5-based COVID-19 vaccine constructs for preclinical testing and clinical evaluation. First is a hAd5 vector with SARS-CoV-2 with spike protein insert (see FIG. 1). Second is E1-, E2b-, E3-hAd5 vector with SARS-CoV-2 wild type spike protein (S) insert and Nucleocapsid protein (N) insert containing an Endosomal-targeting domain sequence (ETSD) in the same vector backbone.

Immunogenicity Studies: Homologous prime-boost immunogenicity in mice was examined by treating Mice with 1, 2 or 3 doses of the ImmunityBio adenovirus vaccine candidates listed in FIG. 1 and serum and splenocyte samples will be tested for SARS-CoV-2 antigen-specific immune responses. Serum is being tested for anti-spike and anti-nucleocapsid antibody responses by ELISA. Splenocytes will be tested for spike- and nucleocapsid-specific cell mediated immune responses by ELISPOT and intracellular cytokine simulation assays. Data from these studies are disclosed throughout this disclosure.

SARS-CoV-2 Virus Neutralization Studies: Serum from the mice immunized during the course of the immunogenicity studies described above is used will be sent to a third-party subcontractor for SARS-CoV-2 neutralization studies to be performed in their ABSL-3 facility. Serum will be tested for COVID 19 virus neutralizing activity by mixing various dilutions of serum with COVID 19 virus, incubating the mixture, and then exposing the mixture to Vero cells to detect cytopathic effect (CPE). The last dilution that prevents CPE will be considered the endpoint neutralizing titer.

Immunogenicity and Efficacy Evaluation in Non-Human Primates (third-party subcontractor): Rhesus macaques will be treated with three doses of the ImmunityBio adenovirus vaccine candidates listed in FIG. 1. SARS-CoV-2 antigen-specific immune responses will be monitored in serum and PBMCs by ELISA, ELISPOT and ICS throughout the course of the therapy. Four weeks after the final vaccination, animals will be challenged with SARS-CoV-2 and monitored for disease hallmarks and virus shedding.

Phase 1b Clinical trial: ImmunityBio has submitted an IND for Phase 1b clinical trial testing of hAd5 [E1-, E2b-, E3-] CoV-2 vaccine.

Study Design: This is a Phase 1b open-label study in adult healthy subjects. This clinical trial is designed to assess the safety, reactogenicity, and immunogenicity of the hAd5-COVID-19-S and hAd5-COVID-19-S/N vaccines. The hAd5-COVID-19-S and hAd5-COVID-19-S/N vaccines are hAd5 [E1-, E2b-, E3-] vector-based targeting vaccines encoding the SARS-CoV-2 Spike (S) protein alone or together with the SARS-CoV-2 nucleocapsid (N) protein. The hAd5 [E1-, E2b-, E3-] vector is the platform technology for targeted vaccines that has demonstrated safety in over 125 patients with cancer to date at doses as high as 5×1011 virus particles per dose. Co-administration of three different hAd5 [E1-, E2b-, E3-] vector-based vaccines on the same day at 5×1011 virus particles per dose each (1.5×1012 total virus particles) has also been demonstrated to be safe.

COVID-19 infection causes significant morbidity and mortality in a worldwide population. The hAd5-COVID-19-S and hAd5-COVID-19-S/N vaccines are designed to induce both a humoral and cellular response even in individuals with pre-existing adenoviral immunity. Thus, the potential exists for the hAd5-COVID-19-S and hAd5-COVID-19-S/N to induce anti-COVID-19 immunity and prevent or lessen the health impact of COVID-19 infection in healthy subjects.

Phase 1b Safety Analysis: In the initial safety analysis of phase 1b, a total of 40 healthy subjects will be divided into 4 dosing cohorts (cohorts 1A, 1B, 2A, 2B; n=10 for each cohort):

Cohort 1A—hAd5-COVID-19-S at 5×1010 viral particles (VP) per dose (n=10),

Cohort 1B—hAd5-COVID-19-S at 1×1011 VP per dose (n=10),

Cohort 2A—hAd5-COVID-19-S/N at 5×1010 VP per dose (n=10),

Cohort 2B—hAd5-COVID-19-S/N at 1×1011 VP per dose (n=10).

Each subject will receive a subcutaneous (SC) injection of hAd5-COVID-19-S or hAd5-COVID-19-S/N on Day 1 and Day 22 (ie, 2 doses). This dosing schedule is consistent with hAd5 [E1-, E2b-, E3-] vector-based vaccines currently in clinical trials. Cohorts 1-2 will enroll in parallel and may be opened at the same time or in a staggered manner depending upon investigational product supply. Subjects in cohorts 1A and 2A will complete the low-dose vaccination regimen first. After all subjects in cohorts 1A and 2A have completed at least a single dose and follow-up assessments during the toxicity assessment period through study day 8, enrollment will proceed if ImmunityBio Safety Review Committee (SRC) and at least one qualified infectious disease physician, independent of the Sponsor and trial, confirms absence of safety concerns. Subjects will then be enrolled in higher-dose cohorts 1B and 2B, and vaccinated. For all subjects, follow-up study visits will occur at days 8, 22, 29, 52, and at months 3, 6, and 12 following the final vaccination. Additional follow up for safety information will occur via telephone contact as noted in the Schedule of Events. The primary objectives of the initial safety phase 1b are to evaluate preliminary safety and reactogenicity of the hAd5-COVID-19-S and hAd5-COVID-19-S/N vaccines. The secondary objectives are to evaluate the extended safety and immunogenicity of the hAd5-COVID-19-S and hAd5-COVID-19-S/N vaccines.

Expanded Phase 1b: Safety and Immunogenicity for Construct Selection

Phase 1b expansion will proceed if the SRC determines it is safe to do so based on a review of safety data from the phase 1b safety assessment. In phase 1b expansion, a total of 60 healthy subjects will be divided into 4 dosing cohorts (cohorts 1A, 1B, 2A, 2B; n=15 for each cohort):

Cohort 1A—hAd5-COVID-19-S at 5×1010 VP per dose (n=15)

Cohort 1B—hAd5-COVID-19-S at 1×1011 VP per dose (n=15)

Cohort 2A—hAd5-COVID-19-S/N at 5×1010 VP per dose (n=15)

Cohort 2B—hAd5-COVID-19-S/N at 1×1011 VP per dose (n=15)

Each subject will receive a SC injection of hAd5-COVID-19-S or hAd5-COVID-19-S/N on Day 1 and Day 22 (ie, 2 doses). For all subjects, follow-up study visits will occur at days 8, 22, 29, 52, and at months 3, 6, and 12 following the final vaccination. Additional follow up for safety information will occur via telephone contact as noted in the Schedule of Events. The primary objective of the expanded phase 1b is to select the most immunogenic construct between hAd5-COVID-19-S and hAd5-COVID-19-S/N and dose level as determined by changes in humoral and cellular immunogenicity indexes. The secondary objectives are to assess safety and reactogenicity of hAd5-COVID-19-S and hAd5-COVID-19-S/N.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient.

In one aspect of any of the embodiments described above or elsewhere herein, the composition is formulated in a pharmaceutically acceptable excipient suitable for administration to a subject.

It is still further contemplated that the recombinant viruses and yeasts contemplated herein may further comprises a sequence that encodes at least one of a co-stimulatory molecule, an immune stimulatory cytokine, and a protein that interferes with or down-regulates checkpoint inhibition. For example, suitable co-stimulatory molecules include CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and/or LFA3, while suitable immune stimulatory cytokine include IL-2, IL-12, IL-15, IL-15 super agonist (N803), IL-21, IPS1, and/or LMP1, and/or suitable proteins that interfere include antibodies against or antagonists of CTLA-4, PD-1, TIM1 receptor, 2B4, and/or CD160.

It should be appreciated that all of the above noted co-stimulatory genes are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

The immunotherapeutic compositions disclosed herein may be either "prophylactic" or "therapeutic". When provided prophylactically, the compositions of the present disclosure are provided in advance of the development of, or the detection of the development of, a coronavirus disease, with the goal of preventing, inhibiting or delaying the development of the coronavirus disease; and/or generally preventing or inhibiting progression of the coronavirus disease in an individual. Therefore, prophylactic compositions can be administered to individuals that appear to be coronavirus disease free (healthy, or normal, individuals), or to individuals who has not yet been detected of coronavirus. Individuals who are at high risk for developing a coronavirus disease, may be treated prophylactically with a composition of the instant disclosure.

When provided therapeutically, the immunotherapy compositions are provided to an individual who is diagnosed with a coronavirus disease, with the goal of ameliorating or curing the coronavirus disease; increasing survival of the individual; preventing, inhibiting, reversing or delaying development of coronavirus disease in the individual.

The contemplated subject matter further includes methods for administering a vaccine to a patient by more than one route of administration to induce both local and systemic immune responses to the vaccine. The contemplated subject matter also includes compositions and methods for assaying the presence or absence of the relevant antibodies (e.g., anti-SARS-CoV2 antibodies) in a patient sample (e.g., saliva, nasal mucosa, alimentary mucosa, or serum). The antibody status in the patient's sample may be used to assess the need for an additional vaccine dose (e.g., a booster dose/shot).

In addition to the coveted molecular epitopes presented in a vaccine, the route of administration of the vaccine as well as the regimen for administering additional (i.e., booster) doses of the vaccine, can also affect whether or not the patient's immune response is robust enough to establish protection.

For an emerging virus such as the severe acute respiratory syndrome (SARS)-like coronavirus (SARS-CoV2), the duration of immunity (both humoral and cell-mediated) in a patient recovered from a SARS-CoV2 infection is not yet completely known, and furthermore, a vaccine protocol has not yet been tested across a varied population. Considering the current SARS-CoV2 pandemic and the high rate of transmission for the SARS-CoV2 virus, there is a need for a robust vaccination protocol and effective testing for the virus or immunity to the virus (e.g., presence of anti-SARS-CoV2 antibodies).

Vaccine Administration. The presently disclosed contemplated methods for inducing immunity in a patient include administering a vaccine by at least oral administration, and preferably by oral administration and by injection to the blood supply. Many vaccines are given via the intramuscular (IM) route to optimize immunogenicity with the direct delivery of the vaccine to the blood supply in the muscle to induce systemic immunity. The IM administration is typically preferred over subcutaneous (SC) injection which is more likely to have adverse reactions at the injection site than IM injections.

In addition to IM injection, induction of mucosal immunity has been reported to be essential to stop person-to-person transmission of pathogenic microorganisms and to limit their multiplication within the mucosal tissue. Furthermore, for protective immunity against mucosal pathogens, (e.g., SARS coronaviruses) immune activation in mucosal tissues instead of the more common approach of tolerance to maintain mucosal homeostasis allows for enhanced mucosal immune responses and better local protection. For example, nasal vaccination (delivery of a vaccine by nasal administration) induces both mucosal immunity as well as systemic immunity. See, e.g., Fujkuyama et al., 2012, Expert Rev Vaccines, 11:367-379 and Birkhoff et al., 2009*, Indian J. Pharm. Sci.,* 71:729-731.

In order to induce both mucosal and systemic immunity in a patient, embodiments of the present disclosure include providing a vaccine to the patient by at least administration to the nasal mucosa, oral mucosa, and/or alimentary mucosa of the patient. In some embodiments, the routes of administration include administering the vaccine to the nasal mucosa, oral mucosa, and/or alimentary mucosa of the patient together with injection into the blood supply (e.g., intramuscular (IM), intravenous (IV), or subcutaneous (SC)). As used herein, oral administration of a vaccine composition includes nasal injection, nasal inhalation, ingestion by mouth, and administration (e.g., inhalation, ingestion, injection) to the alimentary mucosa. Preferably, the routes of administering the vaccine include oral administration selected from delivery to the alimentary mucosa, nasal injection, nasal inhalation, ingestion by mouth, or inhalation by mouth together with administration by intramuscular (IM) injection.

Notably, the vaccine administered for inducing immunity in the mucosal tissue of a patient is a vaccine against SARS-CoV2. In exemplary embodiments, the vaccine a replication defective adenovirus construct, comprising an E1 gene region deletion and an E2b gene region deletion. In certain embodiments the adenovirus comprises a sequence (e.g. SEQ ID NO:11) encoding a SARS-CoV2 spike protein antigen with at least 80% (e.g., at least 85%, at least 90%, at least 95%, at least 96%, at least 97%, at least 98%, at least 99%) primary sequence identity to SEQ ID NO:10. In certain embodiments the adenovirus comprises a sequence (e.g. SEQ ID NO:13) encoding a SARS-CoV2 spike protein antigen with at least 80% (e.g., at least 85%, at least 90%, at least 95%, at least 96%, at least 97%, at least 98%, at least 99%) primary sequence identity to SEQ ID NO:12. In certain embodiments, the adenovirus includes a sequence encoding a soluble ACE2 protein coupled to an immunoglobulin Fc portion, forming an ACE2-Fc hybrid construct that may also include a J-chain portion, as disclosed in U.S. Ser. No. 16/880,804 and U.S. 63/016,048, the entire contents of both of which are herein incorporated by reference. In other exemplary embodiments, the SARS-CoV2 vaccine (e.g., an adenovirus construct) includes a mutant variant of a recombinant soluble ACE2 protein (e.g., SEQ ID NO: 9), wherein the mutant variant has at least one mutated amino acid residue (e.g., by substitution) that imparts an increased binding affinity of the ACE2 protein for the RBD protein domain of the SARS-CoV2 spike protein as disclosed in U.S. 63/022,146, the entire content of which is herein incorporated by reference. In another exemplary embodiment, the SARS-CoV2 vaccine (e.g., an adenovirus construct) includes a CoV2 nucleocapsid protein or a CoV2 spike protein fused to an endosomal targeting sequence (N-ETSD), as disclosed in U.S. Ser. No. 16/883,263 and U.S. 63/009,960, the entire contents of both of which are herein incorporated by reference. Additionally or alternatively, the SARS-CoV2 vaccine includes modified yeast cells (e.g., *Saccharomyces cerevisiae*) genetically engineered to express coronaviral spike proteins on the yeast cell surface thereby creating yeast presenting cells to stimulate B cells (e.g., humoral immunity) as disclosed in U.S. 63/010,010.

In some embodiments, more than one vaccine composition as disclosed herein may be administered to a patient to induce immunity to SARS-CoV2. For example, a patient may be administered genetically modified yeast cells expressing corona viral spike proteins as a single type of vaccine, or the genetically modified yeast cells may be administered together or concurrently with one or more SARS-CoV2 adenovirus constructs as disclosed herein.

Monitoring presence of antibodies. The contemplated subject matter also includes monitoring or assessing a patient's immune response either to a vaccine administered as disclosed herein (e.g., by oral administration and injection into the blood supply), or to infection by the virus. In particular, disclosed herein are compositions and methods for assessing the continued presence of antibodies in a patient's respiratory and digestive mucosa following infection with SARS-CoV2 or following inoculation against SARS-CoV2 with administration of a SAR coronavirus vaccine.

For assaying a sample from a patient having received a vaccine against a pathogenic infection (e.g., targeting SARS-CoV2) and/or having been infected with a virus (e.g., SARS-CoV2), the presence of antibodies against the pathogen may be carried out using any one of many diagnostic tests. In some embodiments, the diagnostic test is a cell viability assay that allows for the detection of antibodies in the presence of antigen. Diagnostic tests using a cell viability assay for anti-SARS-CoV2 antibody detection are disclosed in U.S. 62/053,691, the entire contents of which are herein incorporated by reference. The cellular diagnostic assay relies on the expression of the target receptor for a given pathogen (e.g., ACE2 for SARS-CoV2 infection) on the surface of an immune effector cell line (e.g., killer T cells, natural killer cells, NK92® cells and derivatives thereof, etc.) and the expression of the pathogen ligand (e.g., Spike proteins for SARS-CoV2 infection) on the surface of a surrogate cell line (e.g., HEK293 cells or SUP-B15 cells).

Additional diagnostic tests using recombinant protein variants of the ACE2 protein (the human receptor targeted by SARS-CoV2 spike protein) are disclosed in U.S. Ser. No. 16/880,804, the entire contents of which are herein incorporated by reference.

Antibody testing in saliva samples. In order to more easily monitor a patient for the presence of anti-pathogen antibodies, assaying a saliva sample from the patient allows for expedited sample collection, increased patient participation, and may allow for the patient to obtain the sample themselves and either mail or transport the sample to the lab for testing. However, in order to assay saliva for the presence of neutralizing antibodies against SARS-CoV2, it may be necessary to stabilize proteins in the saliva against degradation during transport and storage after sample collection prior to testing.

Upon collection of the saliva sample, the saliva is placed into a preservative solution to stabilize the components (e.g., anti-SARS CoV2 antibody or viral spike protein) therein. Preservatives for biological samples are disclosed, for example, in Cunningham & al. (2018) report ("Effective Long-term Preservation of Biological Evidence," U.S. Department of Justice grant #2010-DN-BX-K193) and U.S.

Pat. No. 6,133,036 to Putcha et al. For example, a stabilizing preservative solution for a patient's saliva sample may include any one of glutaraldehyde, sodium benzoate, citric acid, propyl gallate, EDTA, zinc, actin, chitosan, parabens, sodium azide, and any combination thereof.

In specific embodiments, saliva samples may be mixed with stabilizing preservative solutions of glutaraldehyde to achieve a final glutaraldehyde concentration between 0.1% (w/v) and 2.0%(w/v), for example about 0.2%(w/v), about 0.3%(w/v), about 0.4%(w/v), about 0.5%(w/v), about 0.6% (w/v), about 0.7%(w/v), about 0.8%(w/v), about 1.0%(w/v), about 1.1%(w/v), about 1.2%(w/v), about 1.3%(w/v), about 1.4%(w/v), about 1.5%(w/v), about 1.6%(w/v), about 1.7% (w/v), about 1.8%(w/v), or about 1.9%(w/v).

In additionally or alternatively embodiments, saliva samples may be mixed with a stabilizing preservative solution of about 0.10% to about 1.00% sodium benzoate (weight/volume of sample) and/or about 0.025% to about 0.20% citric acid (weight/volume of sample). For example, the saliva sample may be mixed with 0.10%, 0.20%, 0.30%, 0.40%, 0.50%, 0.60%, 0.70%, 0.80%, 0.90%, or 1.00% w/v sodium benzoate. In additional embodiments, the saliva sample is mixed a stabilizing preservative solution of at least 0.5 mg/mL (for example, at least 0.6 mg/mL, at least 0.7 mg/mL, at least 0.8 mg/mL, at least 0.9 mg/mL, at least 1 mg/mL, at least 1.5 mg/mL, at least 2 mg/mL, at least 2.5 mg/mL, at least 3 mg/mL, at least 3.5 mg/mL, at least 4 mg/mL, at least 4.5 mg/mL, or even 5 mg/mL) of benzoic acid and/or at least 0.2 mg/mL (for example, at least 0.2 mg/mL, at least 0.25 mg/mL, at least 0.3 mg/mL, at least 0.35 mg/mL, at least 0.40 mg/mL, at least 0.50 mg/mL, at least 0.75 mg/mL, at least 1.0 mg/mL, at least 1.25 mg/mL, at least 1.5 mg/mL, at least 1.75 mg/mL, or even 2.0 mg/mL) of citric acid. As used herein, "benzoic acid" is interchangeable with benzoate salt (e.g., sodium benzoate) and "citric acid" is interchangeable with citrate salt (e.g., sodium citrate).

The saliva samples with preservatives as described above are stable for storage at temperatures between 15° C. and 40° C. for at least one hour (e.g., at least 5 hours, at least 10 hours, at least 12 hours, at least 24 hours, at least 48 hours, or even 36 hours). Therefore, disclosed herein is a method of preserving a saliva sample for neutralizing antibody testing, the method including mixing the saliva sample with the stabilizing solution made of one or more of glutaraldehyde, sodium benzoate, citric acid, propyl gallate, EDTA, zinc, actin, chitosan, parabens, and/or sodium azide and storing between 15° C. and 25° C. for at least one hour, and up to 2, 3, 4, 5, 6, 7, 8, 9, 10, 11, 12, 13, 14, 15, 16, 17, 18, 19, 20, 21, 22, 23, 24, 36, or 48 hours. In some embodiments, the saliva sample is mixed with a glutaraldehyde concentration between 0.1% (w/v) and 2.0% (w/v), and the glutaraldehyde-saliva is stored between 15° C. and 25° C. In certain embodiments, the glutaraldehyde-saliva may further comprise citric acid and/or benzoic acid at a concentration of as disclosed herein.

Aragonite. In some embodiments, any antibody proteins or any specific antibody protein may be captured from the saliva sample with oolitic aragonite particles. For example, the saliva preserving solution of glutaraldehyde, sodium benzoate and citric acid, propyl gallate, EDTA, zinc, actin, chitosan, parabens, sodium azide, and any combination thereof as disclosed herein, may also include oolitic aragonite (calcium carbonate, $CaCO_3$) particles. Use of aragonite particles for binding to proteins is disclosed, for example, in U.S. Ser. No. 16/858,548 and PCT/US20/29949, the entire contents of both of which are herein incorporated by reference. Accordingly, aragonite particles may be added to that have been modified to capture (e.g., bind to) any antibodies present in the saliva sample or specifically capture an antibody against a specific antigen. For example, aragonite may be functionalized with moieties capable of binding to an immunoglobulin (Ig) protein. Preferably, the Ig protein is an immunoglobulin A (IgA), immunoglobulin G (IgG), or immunoglobulin E (IgE) protein. More preferably, the aragonite is functionalized to bind to an IgA protein. Most preferably, the aragonite particles are functionalized with moieties capable of binding to specific antibodies. For example, the aragonite particles may be coupled with a moiety specific to anti-SARS-CoV2 antibodies. Preferably, the aragonite particle is coupled with a recombinant ACE2 protein as disclosed, for example, in U.S. Ser. No. 16/880,804, supra. In typical embodiments, the aragonite particle is coupled with a recombinant human ACE2 protein having at least 85%, at least 90%, or at least 95% sequence identity to SEQ ID NO: 8.

In additional or alternative embodiments, the aragonite particle is functionalized (e.g., coupled to) a recombinant soluble ACE2 protein (e.g., SEQ ID NO: 9). For more efficient capture or binding of an anti-SARS-CoV2 antibody or the spike protein of SARS CoV-2, the recombinant soluble ACE2 may be mutated to form ACE2 variants having higher binding affinities for SARS-CoV2 spike protein (e.g., the RBD domain of the spike protein). These ACE2 variant mutants of the recombinant soluble ACE2 protein include T27F, T27W, T27Y, D30E, H34E, H34F, H34K, H34M, H34W, H34Y, D38E, D38M, D38W, Q24L, D30L, H34A, and/or D355L.

As used herein, the term "functionalized" refers to coupling or binding of a moiety to the aragonite particle thereby imparting any function of the coupled moiety to the aragonite particle. For example, the aragonite particle may be functionalized with a protein moiety. Methods for preparing and using aragonite particle beads are disclosed in U.S. Ser. No. 16/858,548 and PCT/US20/29949. In some embodiments, the aragonite composition includes a plurality of aragonite particle beads. Preferably, the plurality of aragonite particle beads have an average particle size of between 100 nm to 1 mm, In some embodiments a protein moiety is coupled directly to the natural, untreated surface of aragonite particles. Aragonite particles approximately 2-3% amino acid content including aspartic acid and glutamic acid rendering the aragonite surface hydrophilic. Accordingly, in some embodiments, protein moieties may be directly coupled to the surface of the aragonite particles.

In alternative embodiments, the aragonite particle surface may be treated to modify the binding surface. For example, treatment with stearic acid (i.e., octadecanoic acid) provides for a hydrophobic surface, as disclosed in U.S. Ser. No. 16/858,548 and PCT/US20/29949. For protein loading, treatment of the aragonite with phosphoric acid forms lamellar structures. Additional conjugation techniques for coupling reactive groups to the amino acid surface of aragonite are known in the art as disclosed, for example, in *Bioconjugate Techniques, Third Edition*, Greg T. Hermanson, Academic Press, 2013.

Monitoring of Vaccine Protocol. Patients who do not show sufficient titers of (e.g., presence of) neutralizing antibody in their saliva may be sent oral dosages of the respective vaccine (e.g., a SARS-CoV2 vaccine as disclosed herein). The patients inhale or ingest these vaccine dosages, and then two weeks later send another saliva sample—prepared and stored in the same manner as above—to the test facility to confirm that the oral vaccine dose has restored their anti-SARS-CoV2 antibody (e.g., IgA) titers.

Accordingly, in additional embodiments, a kit for collecting a saliva sample from a patient includes a collection container with the saliva preservative solution as disclosed herein. For example, the kit includes a collection container with a solution of any of one or combination of glutaraldehyde, sodium benzoate and/or citric acid, propyl gallate, EDTA, zinc, actin, chitosan, parabens, and sodium azide. The kit may also include adhesive packaging and/or mailing supplies in order to secure the collection container with the saliva sample for transport or mailing. In some embodiments, the kit may also include at least one dose of the vaccine for oral administration.

Recited ranges of values herein are merely intended as a shorthand referring individually to each separate value falling within the range. Unless otherwise indicated herein, each individual value is incorporated into the specification as if it were individually recited herein.

EXAMPLES

The advantageous features of the compositions and methods described herein are further illustrated (but not limited) by the following examples.

Example 1. Two groups of Rhesus macaques (5 per group) were immunized subcutaneously on day 0 with an adenoviral anti-SARS-CoV2 vaccine as described above. Blood was drawn from each macaque before immunization. On day 14, one group of macaques (Group 1) received another subcutaneous booster injection of the same vaccine, while another group (Group 2) received an oral vaccine as described herein (E1-/E2b-Ad5 with SEQ ID NO:11 or SEQ ID NO:13). On day 28, both groups received an oral vaccine booster dose. Two macaques (Control) were vaccinated at the indicated time points with shams. Blood was drawn on days 14, 21, 28, 35, & 42.

Figure 19:
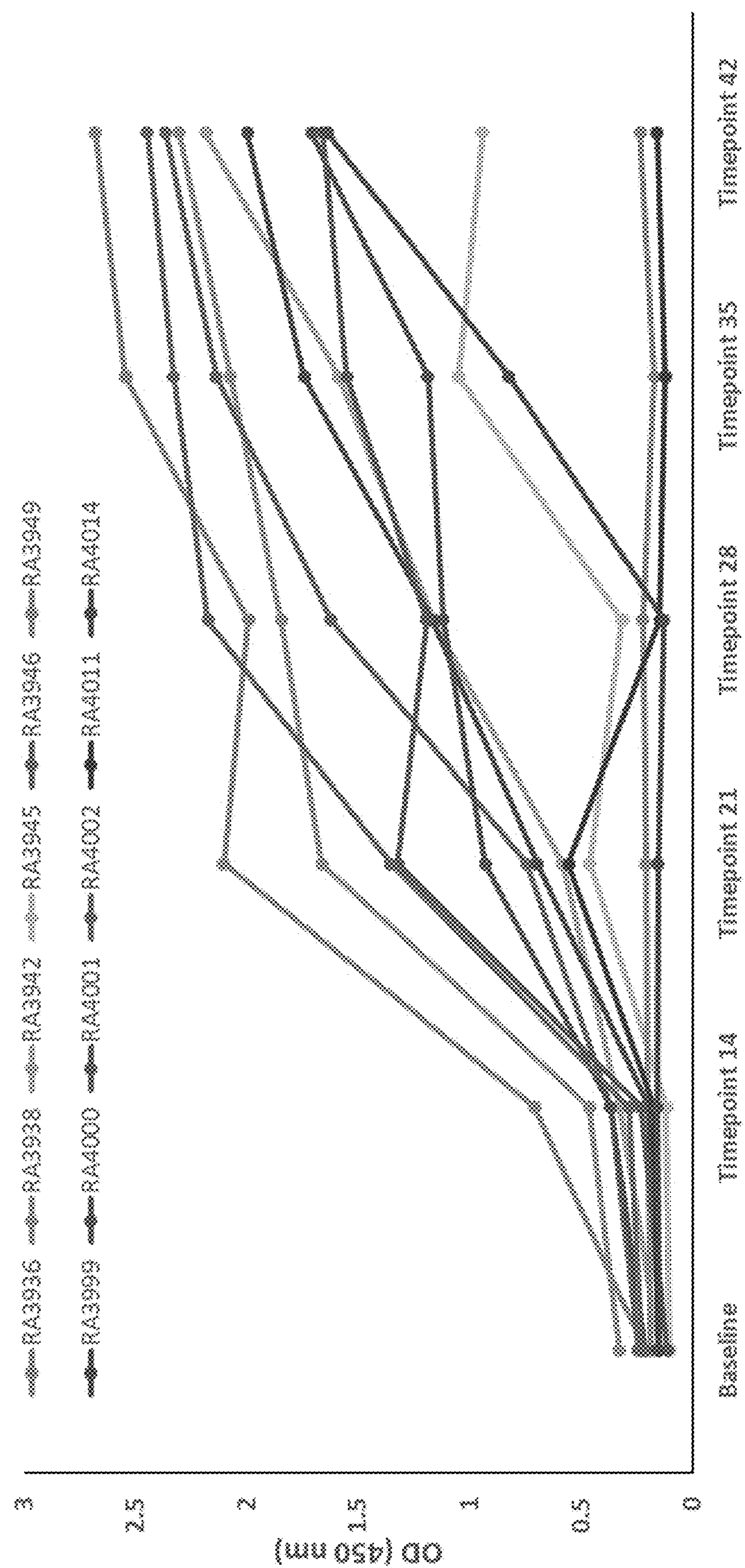
FIG. 19 shows ELISA results detecting IgG seroreactivity against SARS-CoV2 spike in sera samples drawn from immunized macaques.
Figure 20:
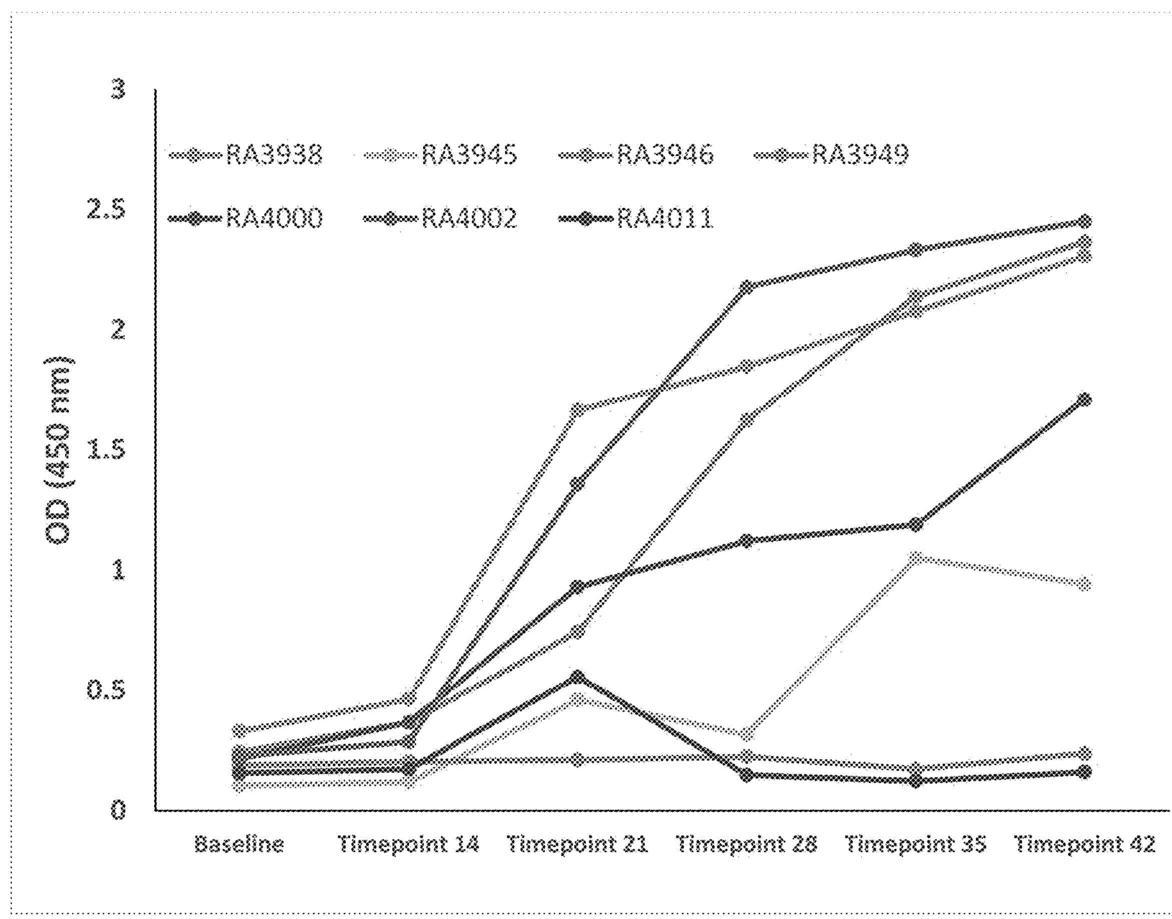
FIG. 20 breaks out the ELISA results in FIG. 1 for the Group 1 macaques.
Figure 21:
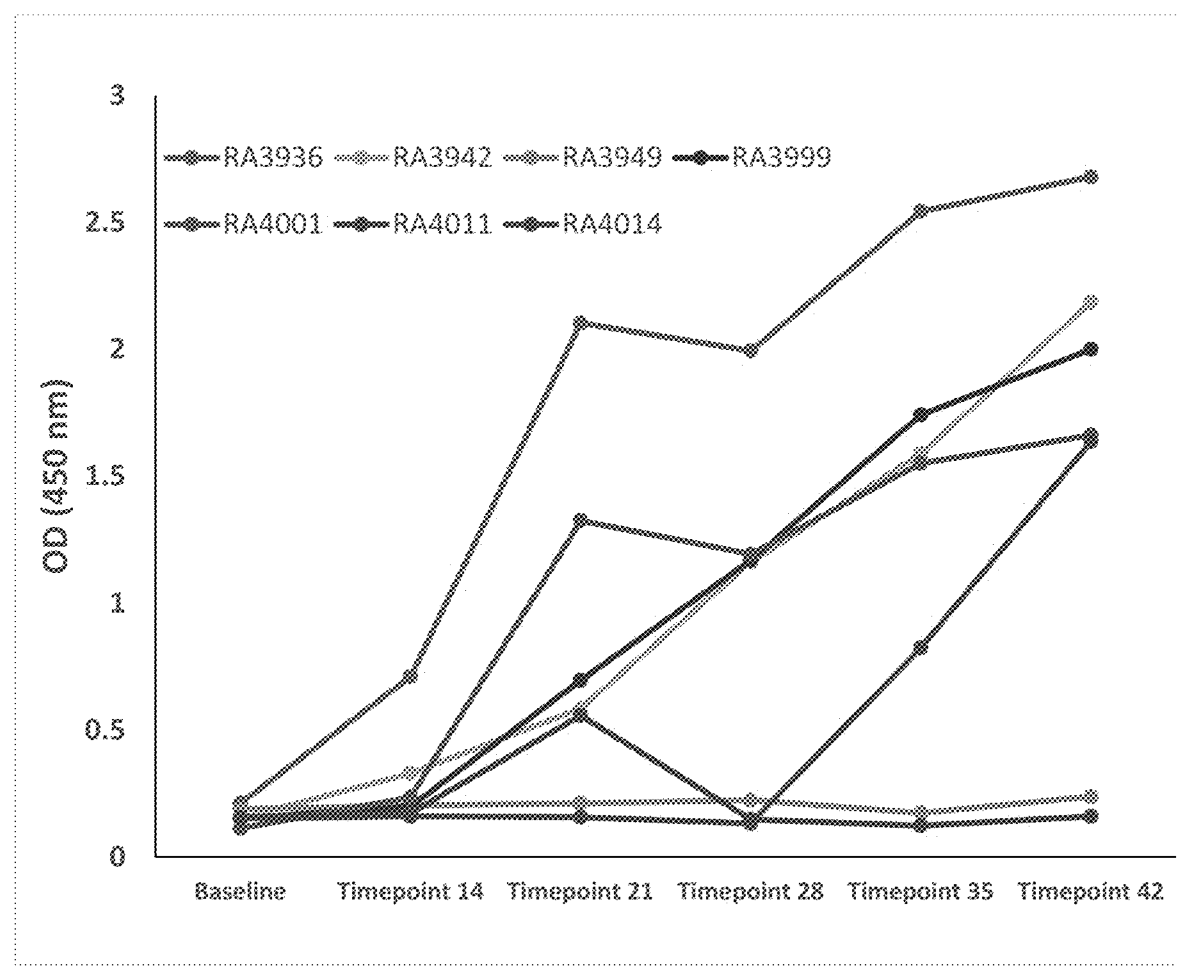
FIG. 21 breaks out the ELISA results in FIG. 1 for the Group 1 macaques.

Serum samples drawn at the indicated time points from these macaques was then assessed by ELISA for anti-spike protein IgG and IgM seroreactivity. Briefly, 96 well EIA/RIA plates (ThermoFisher, Cat #07-200-642) were coated with 50 μL/well of 1 μg/mL solution of purified recombinant SARS-CoV-2-derived Spike protein (S-Fusion. ImmunityBio, Inc.) suspended in coating buffer (0.05 M Carbonate-Bicarbonate, pH 9.6) and incubated overnight at 4° C. Individual 96 well plates were prepared for each immunoglobulins type (IgG or IgM) by washing three times each per well with 150 μL of TPBS solution (PBS+0.05% Tween 20). 100 μL/well of blocking solution (2% non-fat milk in TPBS) was then added and incubated for 1 hour at room temperature (RT). Plasma and serum samples were heat-inactivated at 56° C. for 1 hour before use. Serial dilutions of plasma, serum or antibody samples were prepared in 1% non-fat milk in TPBS. Plates were washed as described above and 50 μL/well of each serial dilution were added to the plate and incubated at RT for 1 hour. Plates were washed three times with 200 μL of TPBS. Dilutions (1:6000) of each goat anti-Human IgG (H+L) Cross-Adsorbed, HRP, Polyclonal; or Goat anti-Human IgM (Heavy chain) Cross-Adsorbed Secondary Antibody, HRP (ThermoFisher, Cat #62-842-0 or A18841 respectively) were 1 prepared in 1% non-fat milk/TPBS and 50 μL/well of these secondary antibodies were added in separate reactions/plates per immunoglobulin type (IgG or IgM) and incubated for 1 hour at RT. Plates were washed three times with 200 μL of TPBS. One component (3,3',5,5'-tetramethylbenzidine (TMB) substrate, 50 μL/well, VWR, Cat #100359-156) was added to each well and incubated at RT for 10 minutes and then the reaction was stopped by addition of 50 μL/well of IN Sulfuric acid (H2504). The optical density at 450 nm was measured with a Synergy 2 plate reader (BioTek Instruments, Inc). Data were analyzed using Prism 8 (GraphPad Software, LLC), and shown in FIG. 19.

Figure 22:
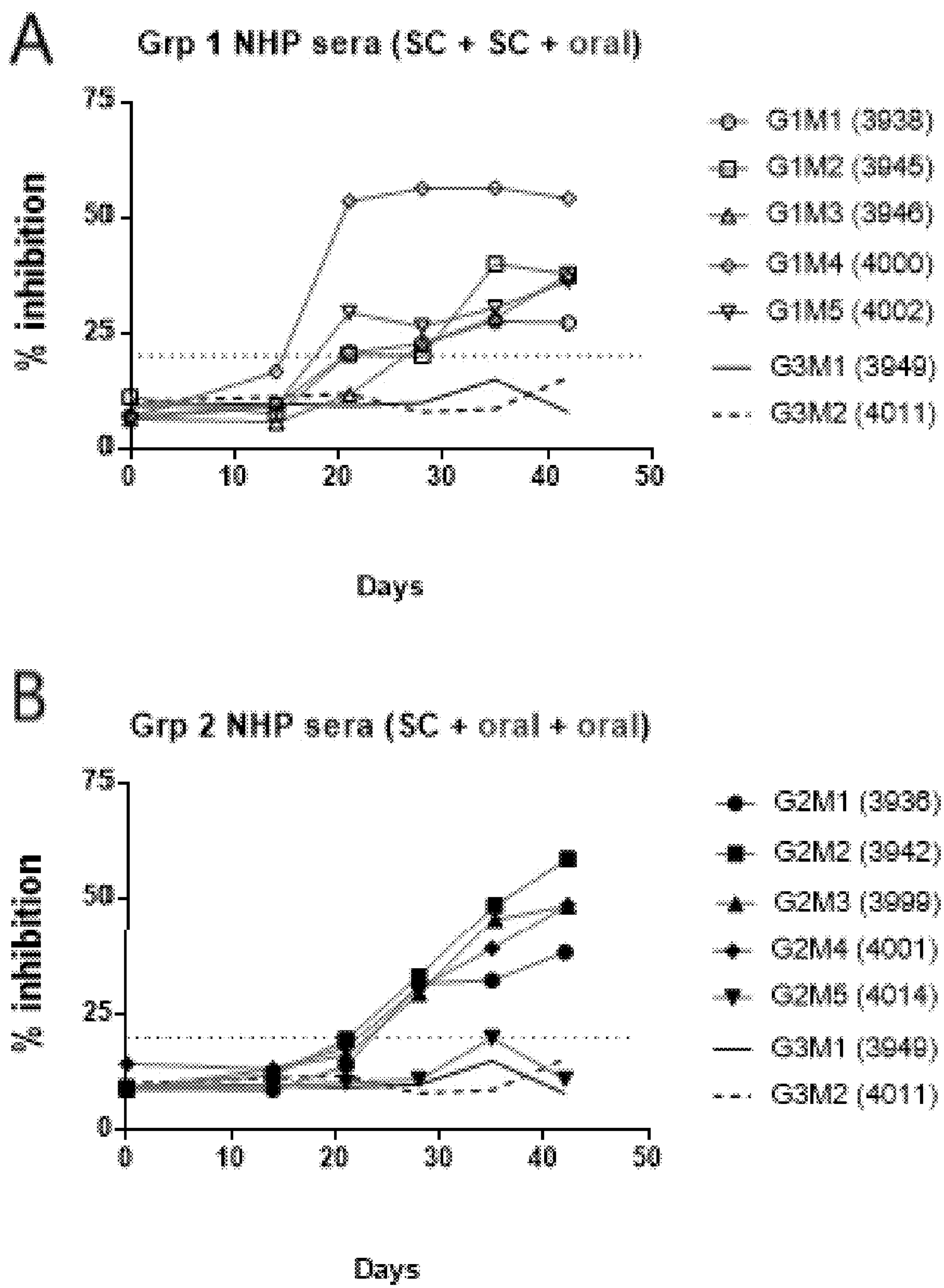
FIG. 22 illustrates one embodiment of the disclosure herein. (A) shows the ability of sera from vaccinated Group 1 macaques to inhibit SARS-CoV2 infectivity in vitro. (B) shows the ability of sera from vaccinated Group 2 macaques to inhibit SARS-CoV2 infectivity in vitro. The dotted line indicates 20% inhibition.
Figure 23:
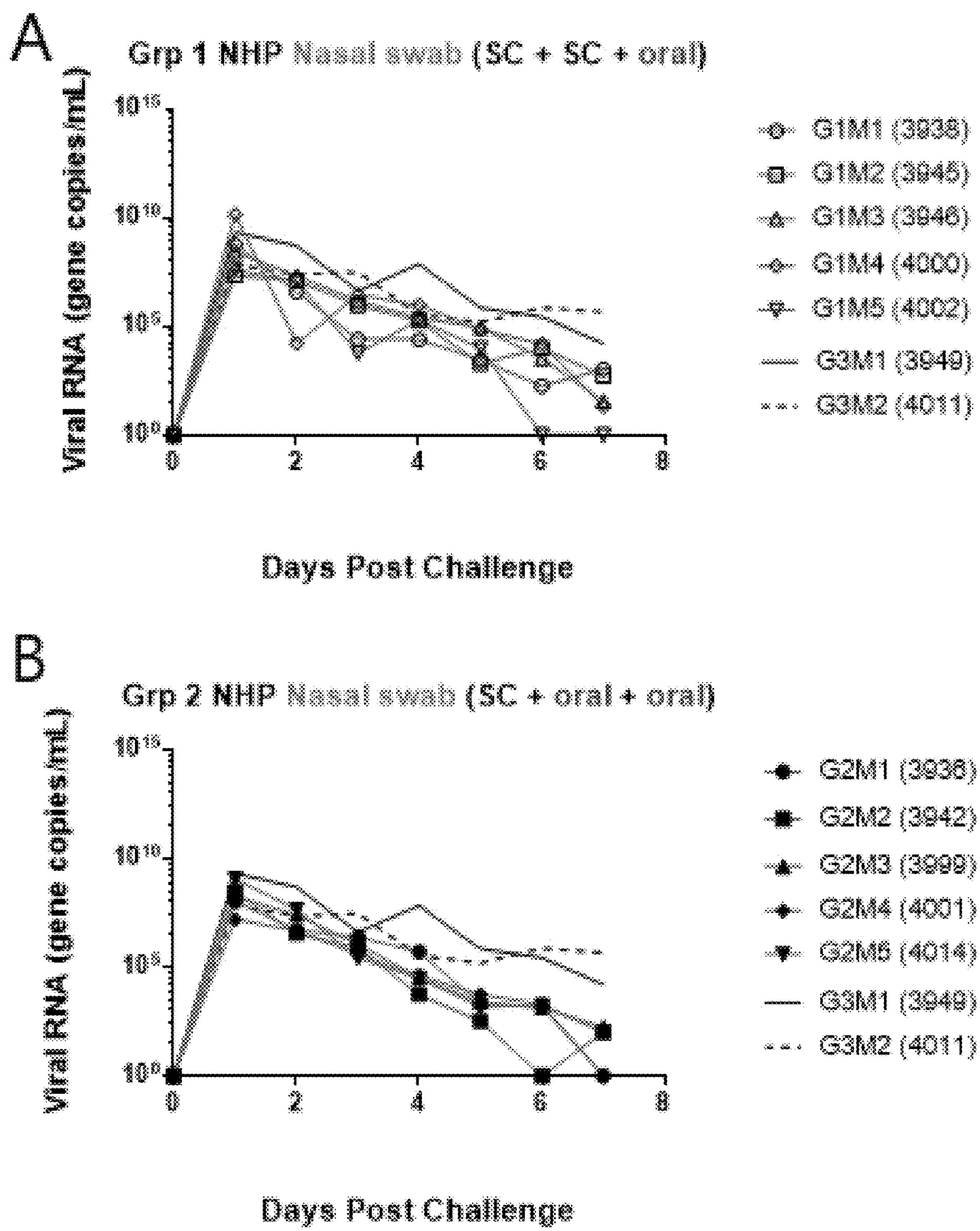
FIG. 23 illustrates one embodiment of the disclosure herein. (A) shows viral load (qPCR) in nasal swabs from Group 1 macaques. (B) shows viral load in nasal swabs from Group 2 macaques.
Figure 24:
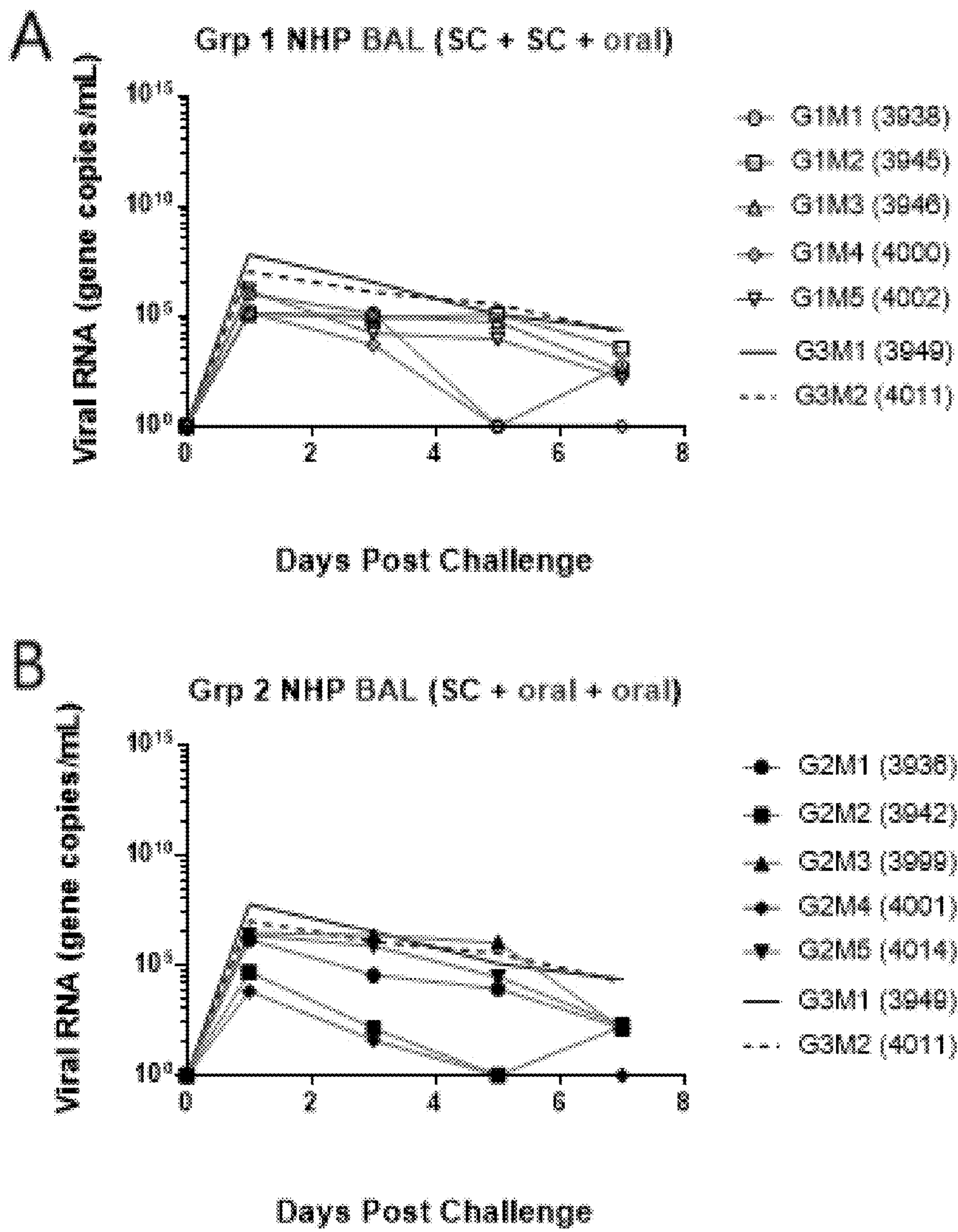
FIG. 24 illustrates one embodiment of the disclosure herein. (A) shows viral load (qPCR) in BAL from Group 1 macaques. (B) shows viral load in BAL from Group 2 macaques.

Example 2. On day 56, the macaques were challenged with respiratory exposure to the SARS-CoV2 virus. Nasal swabs were collected daily from these macaques on days 56-63. Bronchoalveolar lavage (BAL) fluid was collected on days 57, 59, 61, & 63. The ability of serum to inhibit SARS-CoV2 infectivity from the samples collected is shown in FIG. 22. As can be seen, the sera from both the Group 1 and Group 2 macaques inhibited infectivity, with later collected sera inhibited more powerfully than early collected sera. Sera from control macaques had no inhibitory effect at any time point tested. Viral load over time in the nasopharynx is shown in FIG. 23. Viral load over time in the lungs is shown in FIG. 24.

Figure 25:
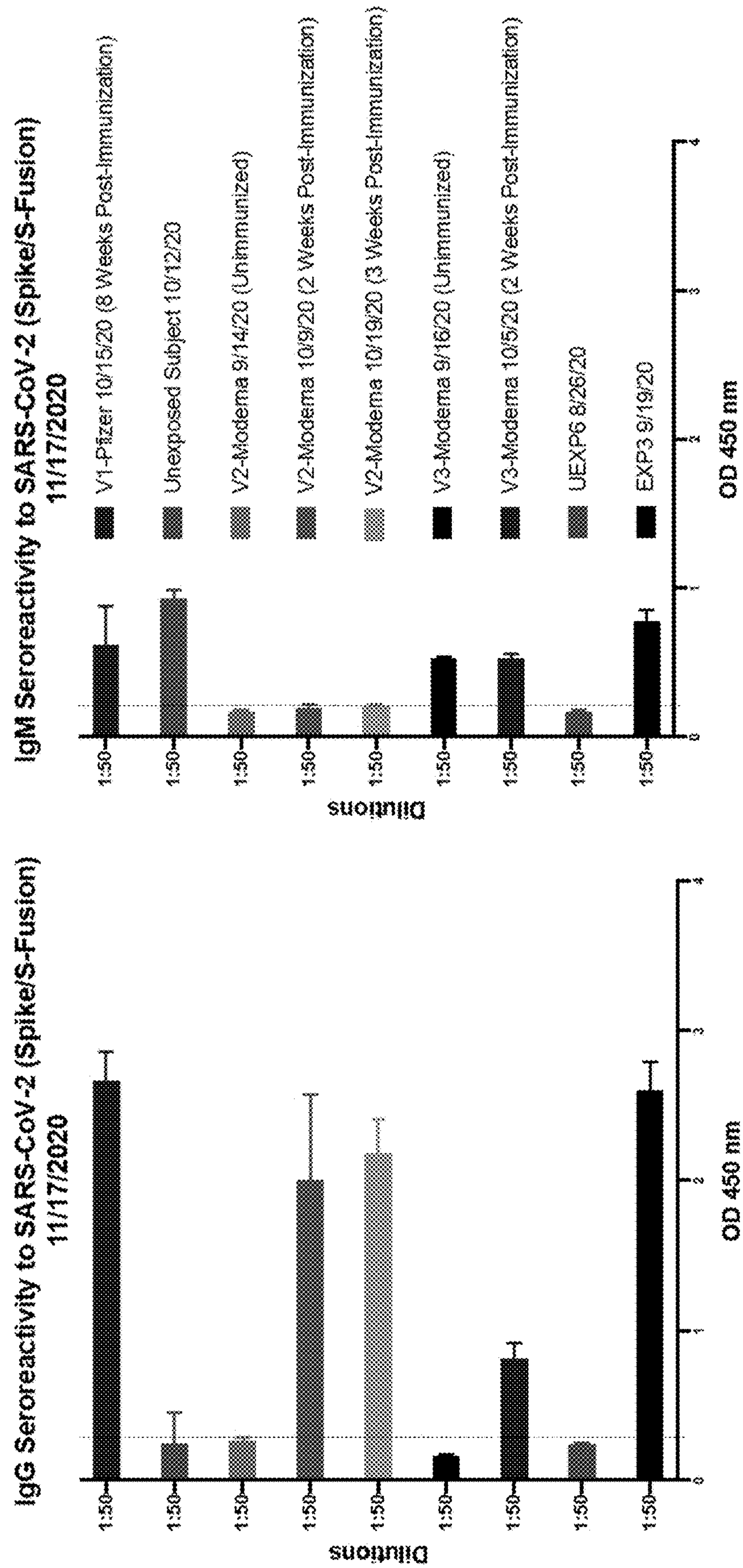
FIG. 25 shows ELISA results detecting IgG & IgM seroreactivity against SARS-CoV2 spike in sera samples drawn from human patients immunized with various experimental anti-SARS-CoV2 vaccines.

Example 3. Serum samples from various human volunteers who have received various experimental anti-SARS-CoV2 vaccines were collected and assayed by ELISA as described above for IgG and IgM seroreactivity against SARS-CoV2 S protein. The results are shown in FIG. 25.

Example 4. Human volunteers were divided into three cohorts. Cohort 1 (10 individuals) was immunized by subcutaneous injection with $5\times10^{10}$ viral particles of a vaccine as described herein (E1-/E2b-Ad5 containing SEQ ID NO:11 or SEQ ID NO:13). Cohort 2 (10 individuals) was immunized by subcutaneous injection with 1011 viral particles of a vaccine as described herein. Cohort 3 (15 individuals) was immunized by subcutaneous injection with $10^{11}$ viral particles of a vaccine as described herein (or $5\times10^{10}$ viral particles if safety concerns indicated a lower dose). Blood was drawn from each volunteer on the same day as the initial prime vaccination was administered. Blood was drawn again on days 8, 15, & 22. A booster injection of the same vaccine was administered on day 22.

ELISpot tests were run on the blood collected on days 1 & 15 to assess cell-mediated immunity against SARS-CoV2. 400,000 viable PBMCs from each blood draw per well (Cellometer K2 w/AO/PI viability stain) were stimulated with empty medium, SARS-CoV2 S, SARS-CoV2 N, SARS-CoV2 M, CD3/CD28/CD2, and CEFT. After 48 hrs of stimulation, supernatants were frozen (−80° C.) for later testing.

Figure 26:
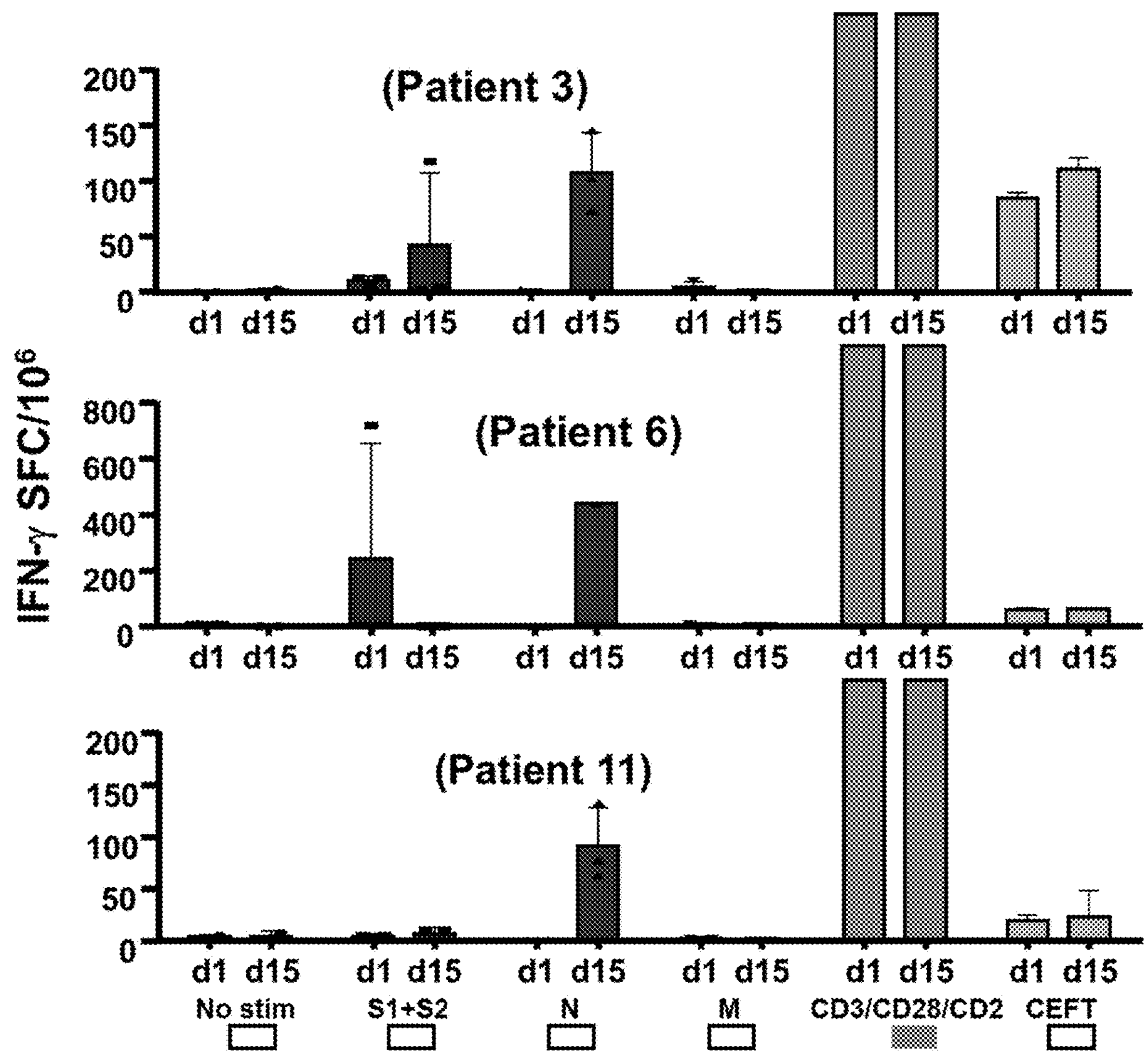
FIG. 26 shows Th1 ELISpot results from human patients 3, 6, & 11.
Figure 27:
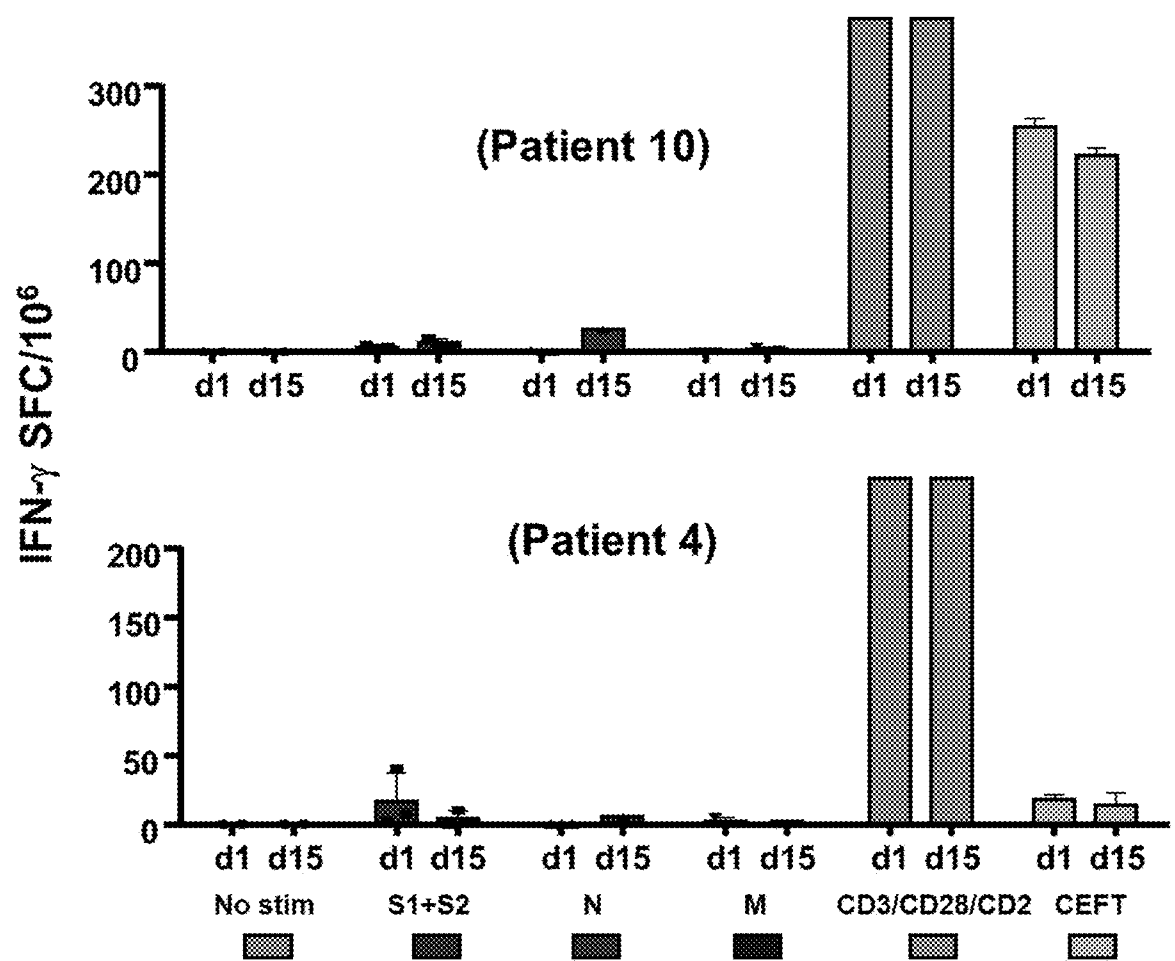
FIG. 27 shows Th1 ELISpot results from human patients 4 & 10.

FIG. 26 shows the results of this test from Th1 N-responsive patients 3, 6, & 11. FIG. 27 shows results from patient 4 (N-unresponsive) and patient 10 (weakly Th1 N-responsive). None of these patients showed a Th2 response to N.

Figure 28:
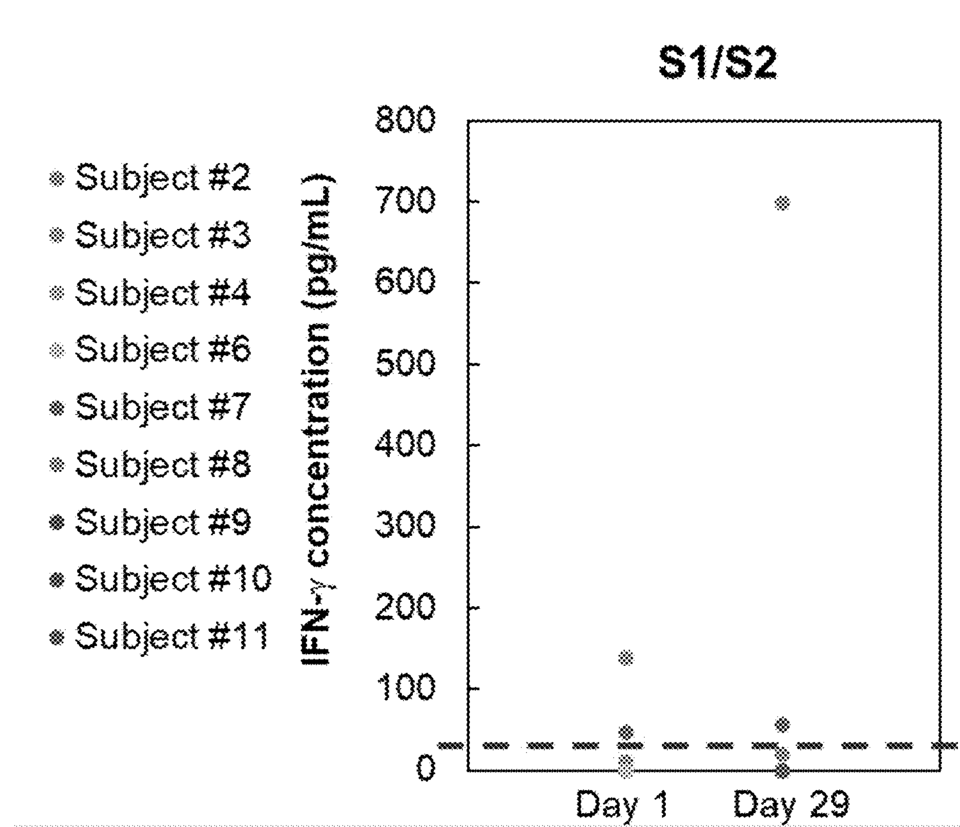
FIG. 28 shows the results of a QuantiFERON assay on blood samples drawn from nine immunized patients on days 1 and 29 of the vaccination regime. The dashed line near the bottom of the panel indicates the threshold of detection. The dashed-line boxes indicate the results from subject #8.

Example 5. Human volunteers received $5\times10^{10}$ viral particles of vaccine by subcutaneous injection on day 1 of the study, and again on day 22. Blood was drawn from each subject on days 1 and 29. These blood samples were assayed for immune reactivity to the SARS-CoV2 S protein by the methods described in co-pending U.S. 63/124,979 (filed 14 Dec. 2020). FIG. 28 shows the results of these assays. As can be seen, subject #8 shown a level of immune response to the S protein above the level of detection already on the first day of the experiment, indicating that this particular individual had already been previously infected with SARS-CoV2. The course of immunization produced a notable increase in immune response relative to baseline. This result constitutes in vivo evidence that the vaccines described herein can serve as vaccine boosts even to individuals whose immunity derives from some other source than prior immunization with the vaccines described herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The present disclosure, therefore, is not to be restricted except in the scope of the appended claims. Moreover, in interpreting both the specification and the claims, all terms should be interpreted in the broadest manner consistent with the context.

Example 6: The hAd5 [E1-, E2b-, E3-] Platform and Constructs

For studies here, the next generation hAd5 [E1-, E2b-, E3-] vector was used (FIG. 1c) to create viral vaccine candidate constructs. As shown in FIG. 8d-h, a variety of constructs were created:

FIG. 8(d): S WT: S protein comprising 1273 amino acids and all S domains: extracellular (1-1213), transmembrane (1214-1234), and cytoplasmic (1235-1273) (Unitprot PODTC2);

FIG. 8(e): S RBD-ETSD: S Receptor Binding Domain with an Enhanced T-cell Stimulation Domain (ETSD);

FIG. 8(f): S Fusion: S optimized to enhance surface expression and display of RBD;

FIG. 8(g): N-ETSD: The nucleocapsid (N) sequence with the ETSD; and

FIG. 8(h): Bivalent S-Fusion+N-ETSD;

S-WT+N-ETSD and S RBD-ETSD+N-ETSD constructs were also produced, but are not shown.

Figure 9:
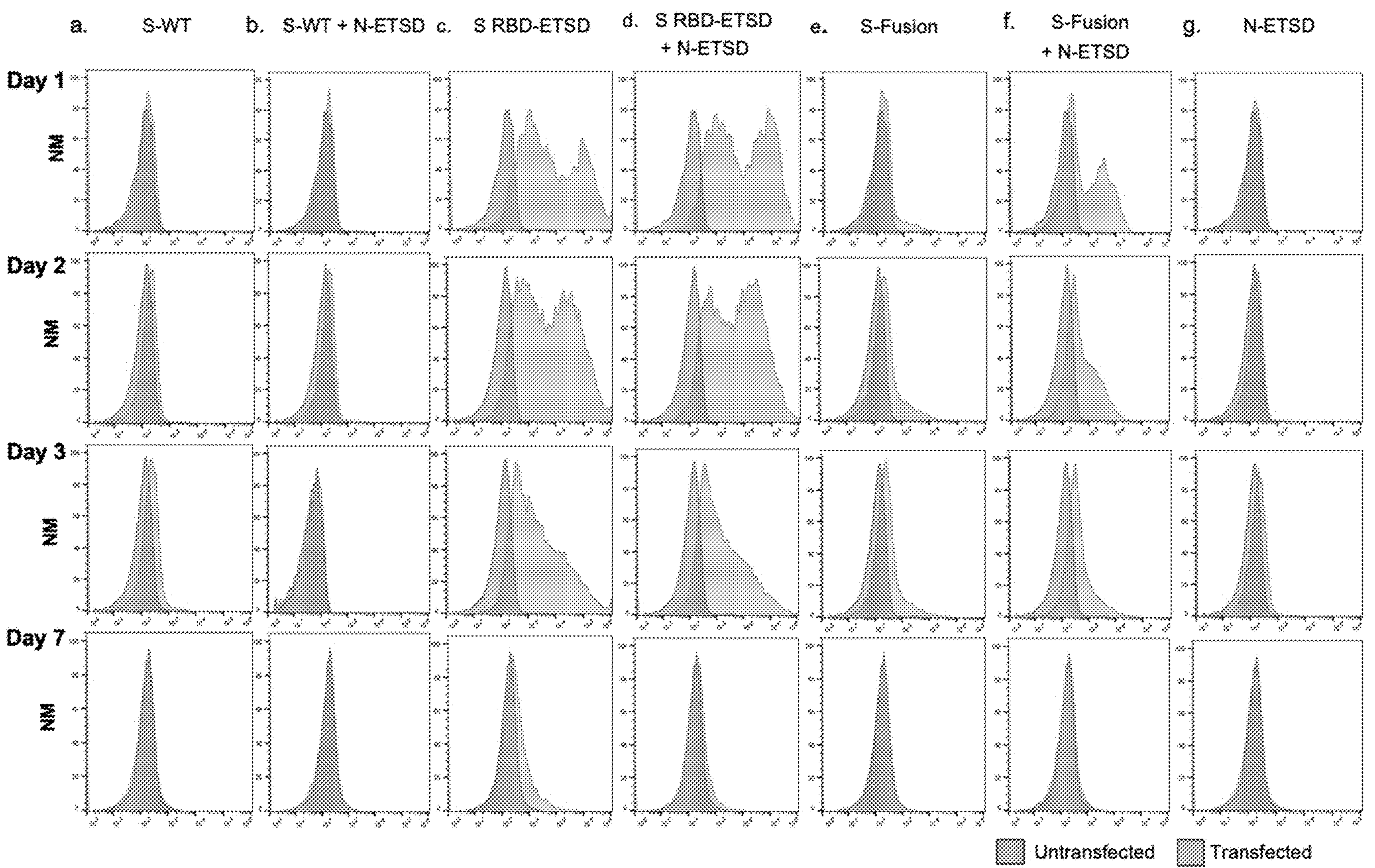

Example 7: Enhanced HEK 293T Cell-Surface Expression of RBD Following Transfection with Ad5 S— Fusion+N-ETSD As shown in FIG. 9, anti-RBD-specific antibodies did not detect RBD on the surface of HEK 293T cells transfected with hAd5 S-WT (FIG. 9a) or hAd5 S-WT+N-ETSD (FIG. 9b) constructs, while hAd5 S-Fusion alone was slightly higher (FIG. 9e). As expected, both constructs with RBD, hAd5 RBD-ETSD and RBD-ETSD+N-ETSD, showed high binding of anti-RBD antibody (FIGS. 9c and d). Notably, high cell-surface expression of RBD was detected after transfection with bivalent hAd5 S-Fusion+N-ETSD (FIG. 9f). These findings support our proposition that an hAd5 S-Fusion+N-ETSD construct, containing a high number and variety of antigens provided by both full-length, optimized S with proper folding and N leads to enhanced expression and cell surface display of RBD in a vaccine construct.

Figure 10:
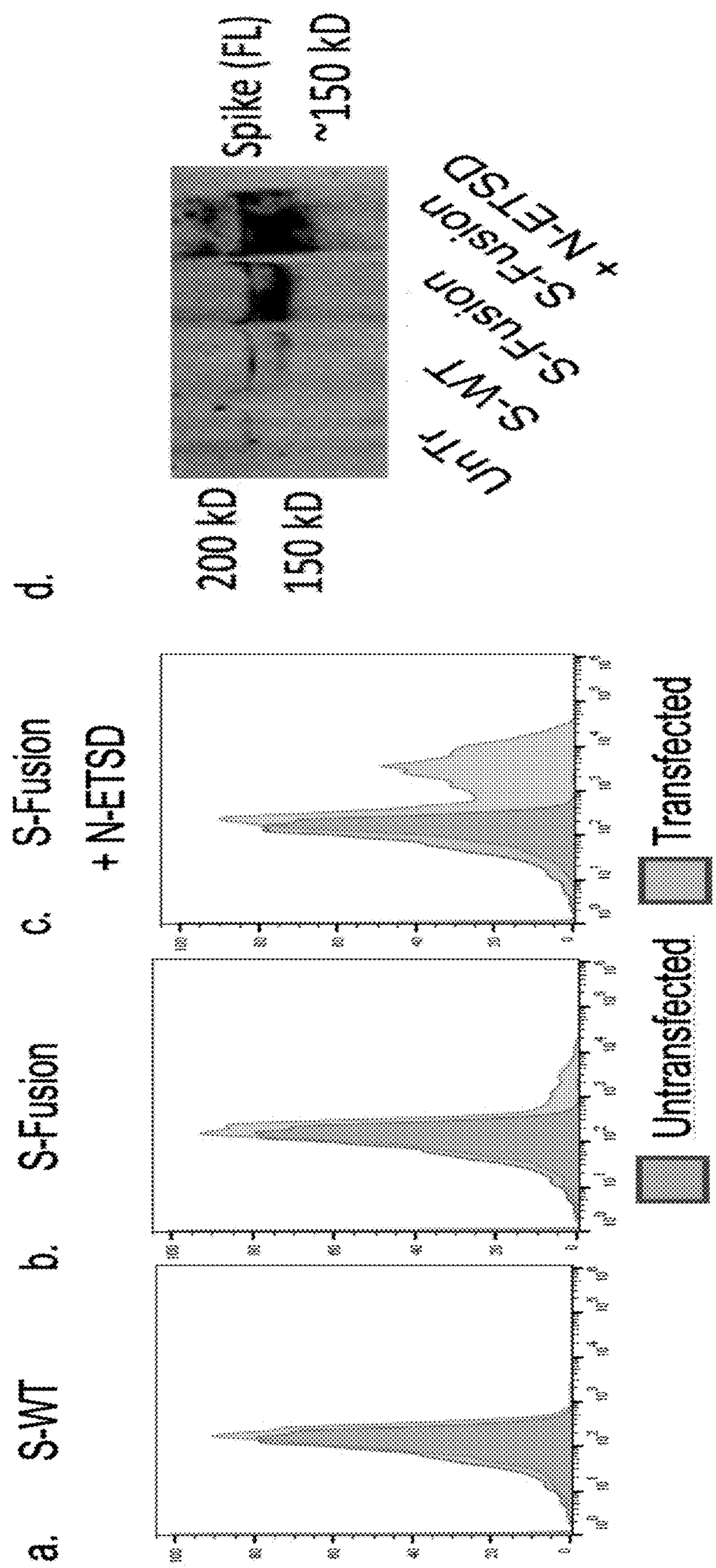
FIG. 10 exemplarily depicts immunoblot analysis of S expression. Cell surface RBD expression with (a) hAd5 S-WT, S-Fusion, and (c)S-Fusion+N-ETSD in HEK 293T cells shows high correlation with (d) expression of S in immunoblots of HEK 293T cell lysates probed using anti-full length (S2) antibody. Y-axis scale is normalized to mode (NM).

Example 8: Immunoblot Correlation of Enhanced S Expression with hAd5 S-Fusion+N-ETSD Immunoblot analysis of S expression correlated with enhanced S expression (FIG. 10), showing again that the bivalent hAd5 S-Fusion+N-ETSD construct enhances expression of S compared to S-Fusion alone.

Figure 11:
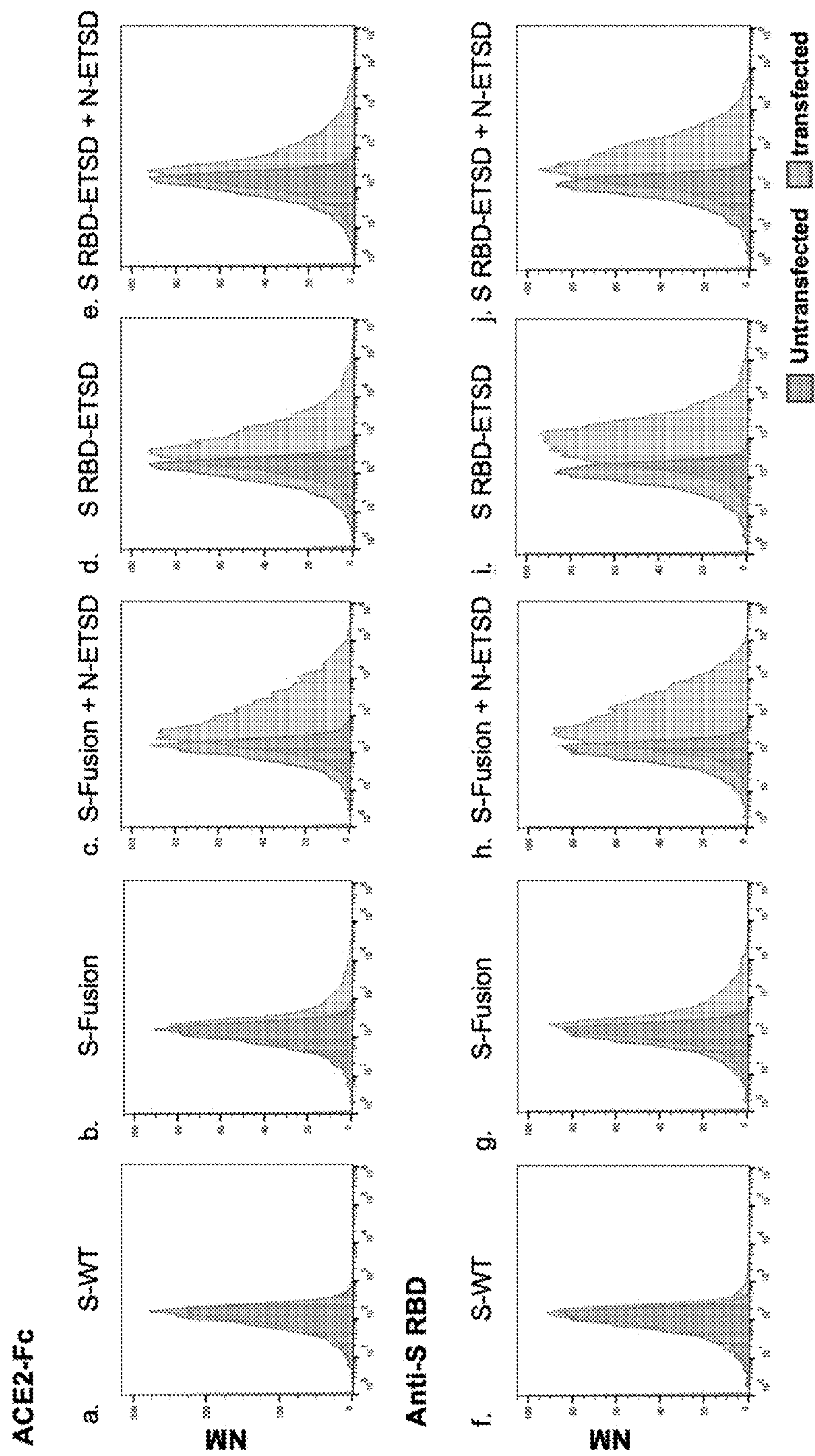
FIG. 11 exemplarily depicts binding of recombinant ACE2-Fc HEK293T cell-surface expressed RBD after transfection confirms native protein folding. Flow cytometric analysis of binding between recombinant ACE2-Fc, with which the spike RBD interacts in vivo to initiate infection, and cell-surface antigens expressed after transfection of HEK293T cells with (a) hAd5 S-WT, (b) hAd5 S-Fusion, (c) hAd5 S-Fusion+N-ETSD, (d) hAd5 S RBD-ETSD, or (e) hAd5 S RBD-ETSD+N-ETSD constructs reveals the highest binding is seen for both ACE-Fc and an anti-RBD specific antibody (f-j) after transfection with the bivalent S-Fusion+N-ETSD. Both S RBD-ETSD-containing constructs also showed binding. Y-axis scale is normalized to mode (NM).

Example 9: Confirmation of Native Folding of Enhanced Surface RBD Following hAd5 S-Fusion+N-ETSD Transfection Determination of the binding of recombinant ACE2-Fc was performed to confirm the native, physiologically-relevant folding of the S RBD after expression from the hAd5 S-Fusion+N-ETSD vaccine candidate. S RBD binds ACE2 during the course of SARS-CoV-2 infection and an effective neutralizing antibody prevents this interaction and thus infection. Such a neutralizing antibody is more likely to be effective if raised in response to S presented in the correct conformation. In addition to enhancement of cell surface expression, the optimized S allows for proper protein folding. It was found that compared to either hAd5 S-WT or hAd5 S-Fusion (FIGS. 11a and b, respectively), ACE2-Fc binding to S RBD expressed from the hAd5 S-Fusion+N-ETSD was clearly enhanced (FIG. 11c). Anti-RBD antibody binding studies (FIG. 1 if j) performed with the same experiment, confirmed the enhanced surface expression findings noted by ACE2-Fc binding. These findings of conformationally correct and enhanced S RBD expression, important for production of neutralizing antibodies, directed us to elect the hAd5 S-Fusion+N-ETSD vaccine candidate for clinical trials.

Figure 12:
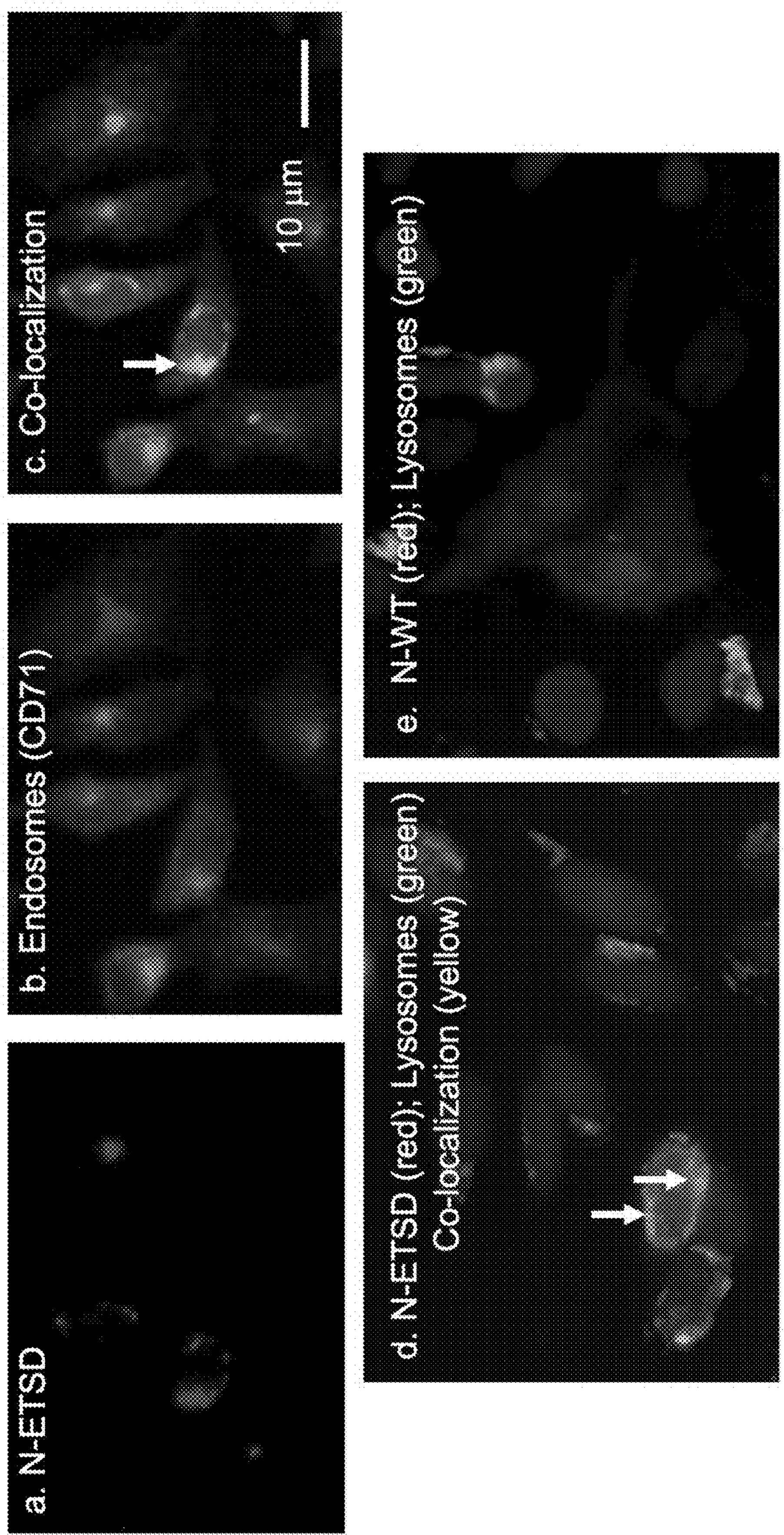
FIG. 12 exemplarily depicts N expressed from hAd5 N-ETSD is localized to the endosomal/lysosomal compartment. In HeLa cells infected with N-ETSD, (a) N (red) co-localizes with the endosomal marker CD71 (b) as indicated by the arrow in (c). In transfected HeLa cells, (d)N-ETSD also co-localizes with the lysosomal marker Lamp1 whereas (e) N wild type (N-WT) does not, showing instead diffuse cytoplasmic distribution.

Example 10: hAd5 N-ETSD Successfully Directs N to an Endosomal/Lysosomal Compartment The ETSD design successfully translocated N to the endosomal subcellular compartment. After infection of HeLa cells with N-ETSD, N co-localized with the endosomal marker 45 transferrin receptor (CD71), as shown in FIG. 12c, and also co-localized with the lysosomal marker Lamp1 (FIG. 12d), demonstrating that N-ETSD is translocated throughout the endosomal pathway to lysosomes, enabling processing for MHC II presentation. N-wild type (N-WT), compared to N-ETSD, shows diffuse cytoplasmic distribution and does not co-localize with the lysosomal marker (FIG. 12e). These findings confirm the role of the ETSD in directing N to an endosomal/lysosomal compartment that will result in increased MHC II presentation and CD4+activation by N.

Example 11: In Vivo hAd5 S-Fusion+N-ETSD Vaccine Immunogenicity Studies

Figure 13:
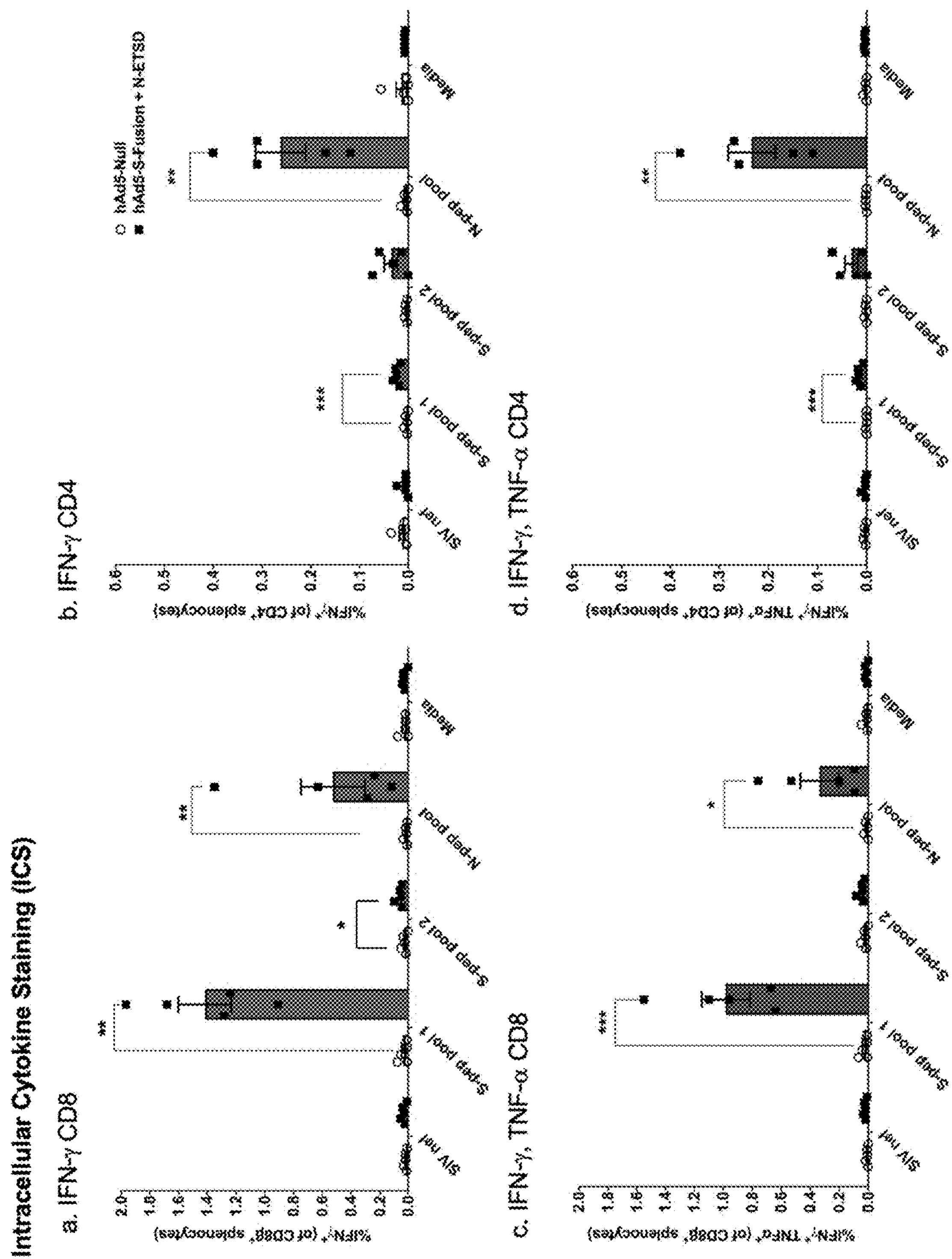
FIG. 13 exemplarily depicts ICS detection of cytokine-expressing splenocytes from hAd5 S-Fusion+N-ETSD inoculated Day 28 CD-1 mice in response to peptide pools. (a) The highest CD8β' splenocyte IFN-γresponse was in hAd5 S-Fusion+N-ETSD-inoculated mouse splenocytes exposed to S peptide pool 1 (S— pep pool 1); splenocytes from these mice also expressed IFN-γin response to the N peptide pool (N-pep pool). (b) CD4+splenocytes from hAd5 S-Fusion+N-ETSD-inoculated mice only expressed IFN-γin response to the N peptide pool. (c) IFN-γTNF-α responses of CD8β' splenocytes from hAd5 S-Fusion+N-ETSD-inoculated mice were very similar to those in (a); as were (d) CD4+splenocytes to the N peptide pool to those in (b). N=5 mice per group. All data sets graphed as the mean with SEM and all statistics performed using the Mann-Whitney test where *<0.05, <0.01, *<0.001, and ****<0.0001.

Based on the evidence that S-Fusion+N-ETSD resulted in enhanced expression of physiologically-relevant RBD and that N-ETSD successfully translocated to the endosomal/lysosomal compartment, the bivalent hAd5 S-Fusion+N-ETSD vaccine was chosen for inoculation of 7-week old female CD-1 mice. The unique properties of this construct would result in the generation of both CD8+ and CD4+ T-cell responses and neutralizing antibodies. As described in Methods, mice received an initial injection on Day 0 and a second injection on Day 21. Sera were collected on Day 0 and at the end of the study on Day 28 for antibody and neutralization analyses. Splenocytes were also collected on Day 28 for intracellular cytokine staining (ICS) and ELISpot analyses. All age- and gender-matched animals assigned to the study appeared normal with no site reactions and no loss of body weight throughout the dosing were seen, consistent with previous observations with the hAd5 [E1-, E2b-, E3-] platform Example 12: hAd5 S-Fusion+N-ETSD Generates Both CD8□+ and CD4+ T-Cell Responses CD8+activation by both S and N: CD80+splenocytes from hAd5 S-Fusion+N-ETSD vaccinated mice exposed to S peptide pool 1 (containing RBD and 51) show IFN-γ expression that is significantly higher compared to hAd5 null mice (FIG. 13*a*); splenocytes from these mice also expressed intracellular IFN-γ in response to the N peptide pool. Evaluation of simultaneous IFN-γ/TNF-α expression from CD8β+splenocytes (FIG. 13*c*) mirrored those for IFN-γ expression alone. These results indicate that both S and N activate CD8+ T cells.

CD4+activation by N: Although CD8+ cytotoxic T cells mediate killing of virus infected cells, CD4+ T cells are required for sustained cytotoxic T lymphocyte (CTL) activity. Thus, CD4+ T cells in the vaccinated animals was evaluated. In contrast to CD8β+splenocytes, only the N peptide pool stimulated CD4+splenocytes from hAd5 S-Fusion+N-ETSD-inoculated mice to express IFN-γ (FIG. 13*b*) or IFN-γ/TNF-α (FIG. 13*d*) at levels that were substantially higher than hAd5 Null control. The contribution by N of CD4+ T-cell responses is vital to an effective immune response to the candidate vaccine.

Example 13: hAd5 S-Fusion+N-ETSD Generates Antibody Responses to Both S and N Antigens The primary objective of coronavirus vaccines currently in development are neutralizing antibodies against spike, thus we examined antibody production in mice vaccinated with our bivalent vaccine. There was significant production of both anti-S(FIG. 14*a*) and anti-N(FIG. 14*c*) antibodies in the sera from CD-1 mice vaccinated with hAd5 S-Fusion+N-ETSD at Day 28 in the study. Compared to anti-S antibodies, anti-N antibodies were higher in sera, given the dilution factor for sera was 1:90 for anti-N antibody analysis and 1:30 for anti-S antibody analysis.

Figure 14:
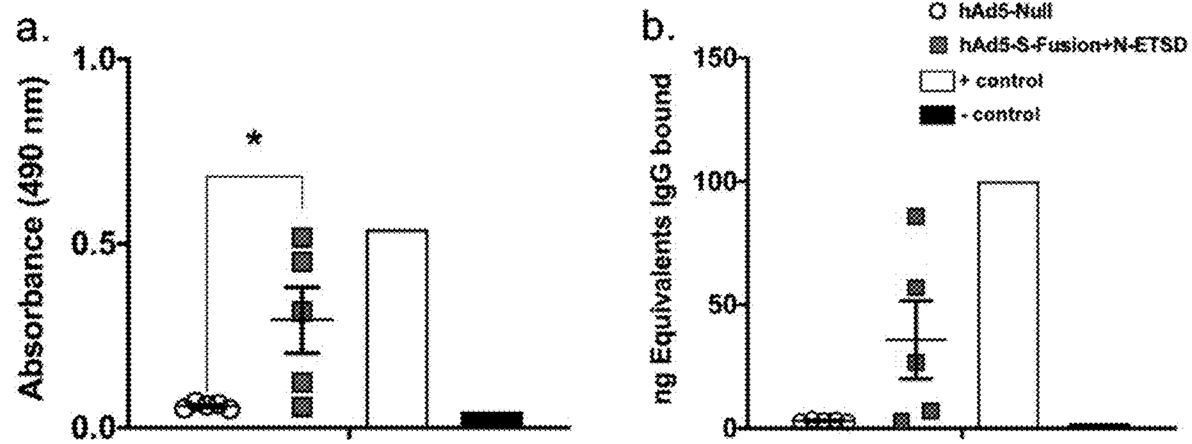
FIG. 14 exemplarily depicts anti-spike and anti-nucleocapsid antibody responses in sera from hAd5 S-Fusion+N-ETSD vaccinated mice. Based on absorbance, there was significant production of both (a) anti-S antibodies and (c) anti-nucleocapsid antibodies. (b, d) The ng equivalents are shown. Sera diluted 1:30 for anti-spike and 1:90 for anti-nucleocapsid antibodies. Data graphed as the mean and SEM. Statistical analysis was performed using an unpaired two-tailed Student's t-test where *<0.05, <0.01, *<0.001, and ****<0.0001.
Figure 14:
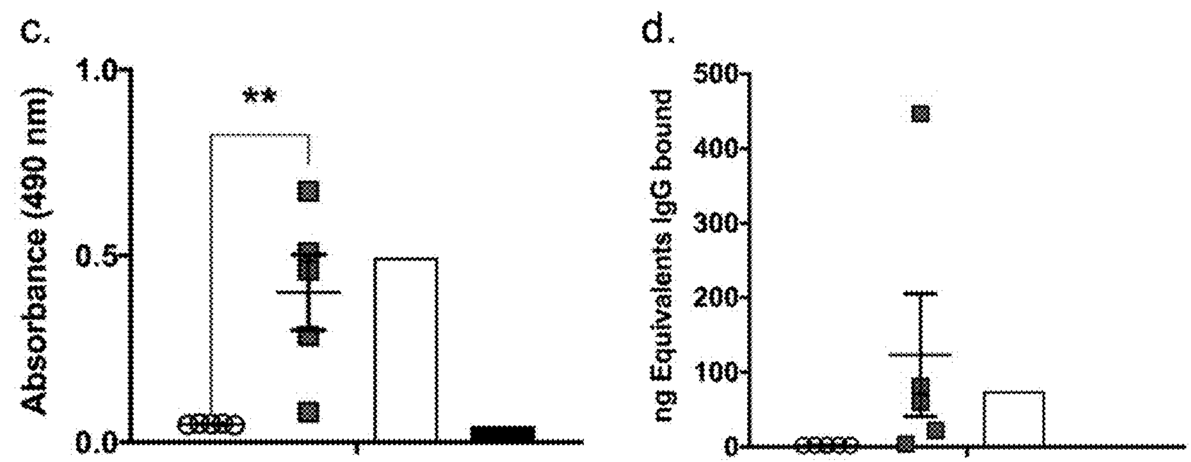

A standard curve of IgG was generated, then absorbance values were converted into mass equivalents for both anti-S and anti-N antibodies (FIGS. 14*b* and *d*). These values were used to calculate that hAd5 S-Fusion+NETSD vaccination generated a geometric mean value of 5.8 μg S-specific IgG and 42 μg N-specific IgG per mL of serum, therefore the relative μg amount of anti-N antibodies is higher than that for anti-S antibodies and reflects the strong contribution of N to anti-SARS-CoV-2 antibody production.

Figure 15:
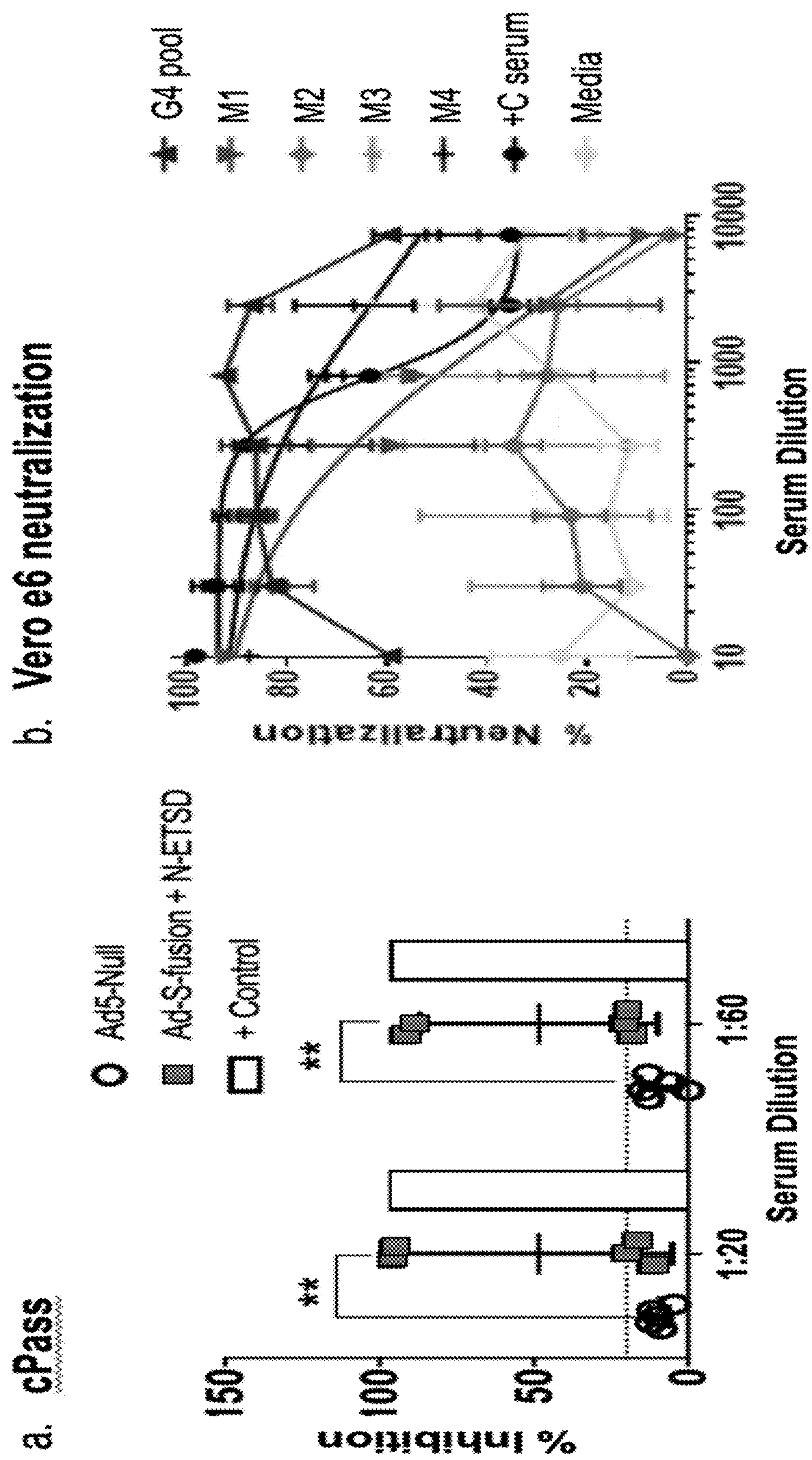
FIG. 15 exemplarily depicts cPass and Vero E6 cell SARS-CoV-2 confirm neutralization by antibodies. (a) In the cPass assay, inhibition of S RBD interaction with ACE2 was significant at both 1:20 and 1:60 dilutions of serum from hAd5 S-Fusion+N-ETSD vaccinated mice. (b) The results in the Vero E6 cell SARS-CoV-2 viral infection for mice that showed S-specific antibodies by ELISA also showed high neutralization for mice and very high neutralization for pooled sera (G4 pool, blue line) even compared to COVID-19 convalescent serum. G4 pool—mice with S-specific antibodies; M1, M2, M3, M4— mouse ID; +C— convalescent serum; and media—media only negative control.
Figure 16:
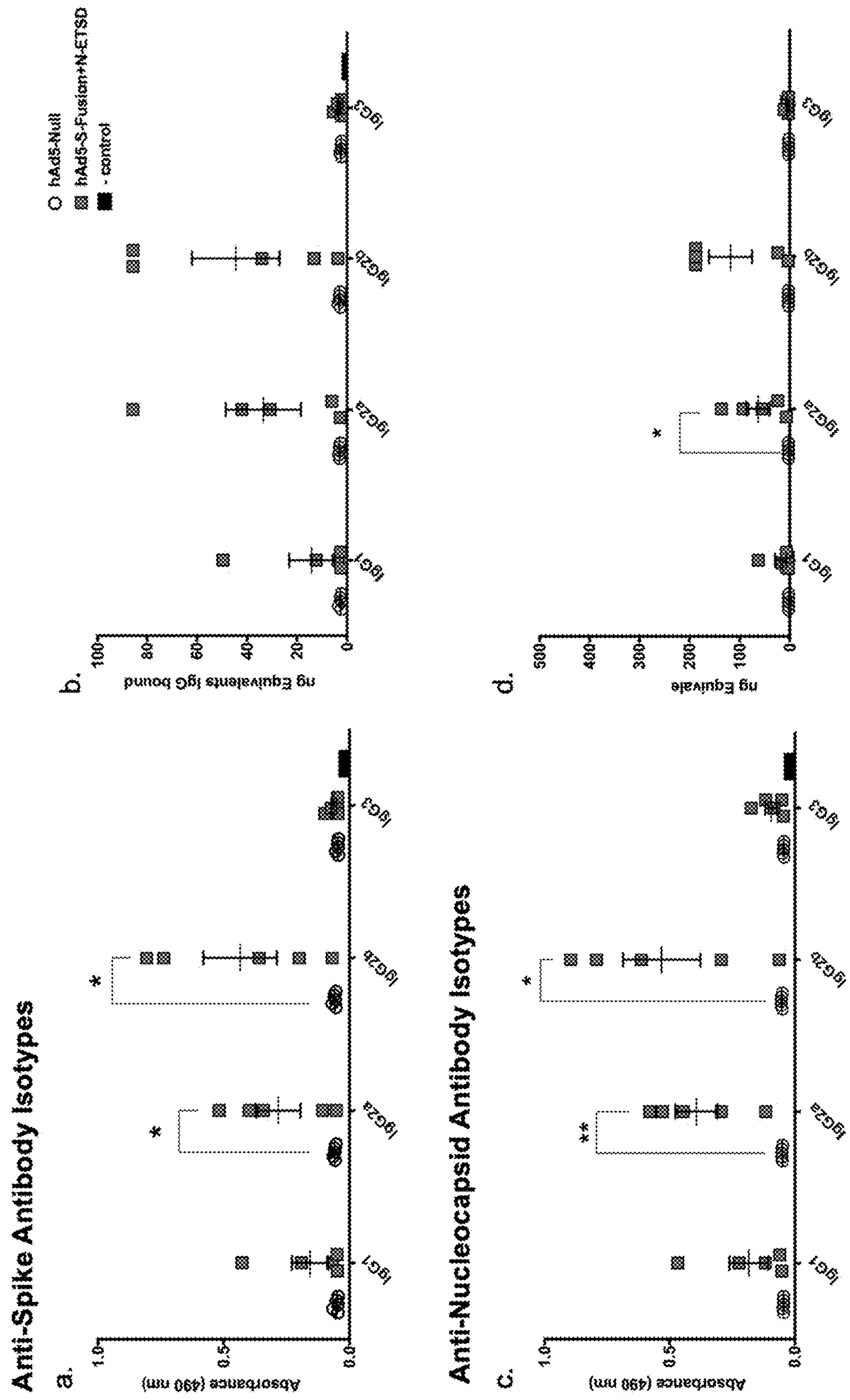
FIG. 16 exemplarily depicts isotypes for anti-spike and anti-nucleocapsid antibodies. (a, c) IgG2a and IgG2b isotype anti-spike and anti-nucleocapsid antibodies were significantly increased for hAd5 S-Fusion+N-ETSD mice compared to hAd5 Null mice. (b, d) The ng equivalents for antibody isotypes are shown. Data graphed as the mean and SEM. Statistical analysis was performed using an unpaired two-tailed Student's t-test where *<0.05, <0.01, *<0.001, and ****<0.0001.
Figure 17:
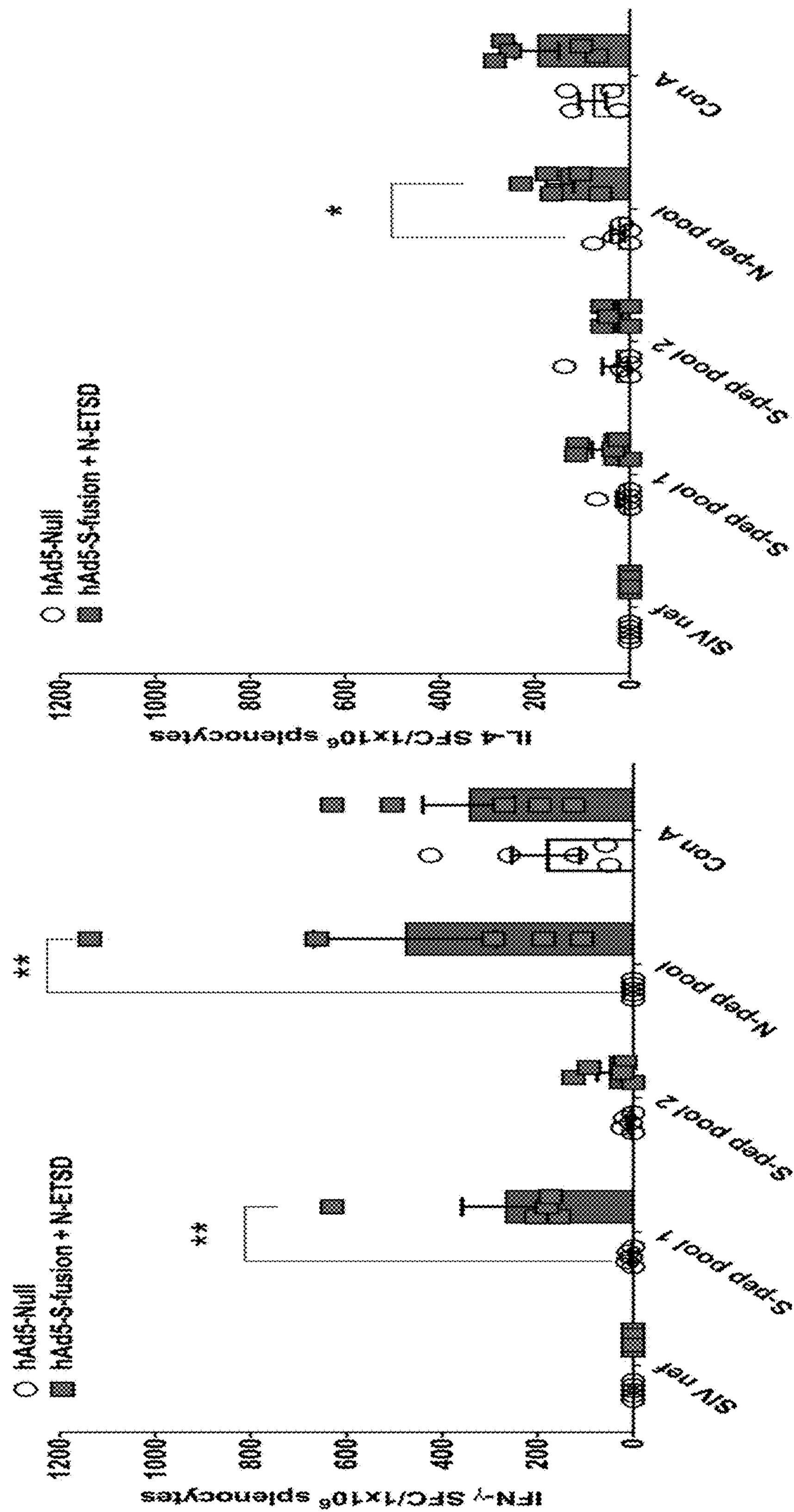
FIG. 17 exemplarily depicts ELISpot detection of secreted cytokines. (a) IFN-111 secretion by hAd5 S-Fusion+N-ETSD splenocytes was significantly higher than hAd5 Null in response to both S peptide pool 1 and the N peptide pool; but (b) IL-4 was only secreted with hAd5 S-Fusion+N-ETSD in response to the N peptide pool (one high outlier in hAd5 null removed). N=5 mice per group. All data sets graphed as the mean with SEM and all statistics performed using the Mann-Whitney test where *<0.05, <0.01, *<0.001, and ****<0.0001.

Example 14: hAd5 S-Fusion+N-ETSD Vaccine Generates Potent Neutralizing Antibodies as Assessed by Both cPass and Live Virus Neutralization Assays Neutralizing antibody activity was evaluated using a cell free assay (cPass) as well as live virus infection in vitro. As seen in FIG. 15*a*, the cPass assay showed inhibition of S RBD:ACE2 binding for all mice and ~100% inhibition for two mice at both dilutions of 1:20 and 1:60. The Vero E6 neutralization assay results are shown for the four mice that showed S-specific antibodies by ELISA. The high persistent neutralization seen even at the high dilution factors suggests the intriguing possibility that the bivalent, multi-antigen, multi-epitope generation by hAd5 S-Fusion+N-ETSD vaccine, could result in synergies of neutralizing immune responses (FIG. 15*b*); at epitopes in addition to those associated with RBD-ACE2 binding. As can be seen in FIG. 15*b*, the value for 50% neutralization (IC50) is present at 1:10,000 serum dilution for the G4 pool of sera from mice that showed S-specific antibodies, ten times higher than the convalescent serum with a dilution of 1:1,000. The potent neutralization, confirmed by two assays, supports the predicted efficacy of the hAd5 S-Fusion+ETSD vaccine candidate and its advancement to clinical trials Example 15: hAd5 S-Fusion+N-ETSD Generates Th1 Dominant Responses Both in Humoral and T-Cell Immunity Antibody Th1 dominance in response to N and S: IgG2a, IgG2b, and IgG3 represent Th1 dominance; while IgG1 represents Th2 dominance. For both anti-S(FIG. 16*a*) and anti-N(FIG. 16*c*) antibodies in sera from hAd5 S-Fusion+N-ETSD vaccinated mice, IgG2a and IgG2b isotypes were predominant and significantly higher compared to the hAd5 Null control. These data show the Th1 dominance of antibody production in response to the hAd5 S-Fusion+N-ETSD vaccine T-cell Th1 dominance in response to N and S: IFN-γ production correlates with CTL activity 47 (Th1 dominance), whereas, IL-4 causes delayed viral clearance 48 (Th2 dominance). A ratio of IFN-γ to IL-4 of 1 is balanced and a ratio greater than 1 is demonstrative of Th1 dominance. Thus, we examined IFN-γ and IL-4 production in animals immunized with the bivalent S plus N vaccine. As determined by ELISpot, IFN-γ secretion was significantly higher for hAd5 S-Fusion+N-ETSD than for hAd5 Null splenocytes in response to both S peptide pool 1 and the N peptide pool (FIG. 17*a*), but IL-4 was only secreted at significantly higher levels for hAd5 S-Fusion+N-ETSD in response to the N peptide pool (FIG. 17*b*).

Figure 18:
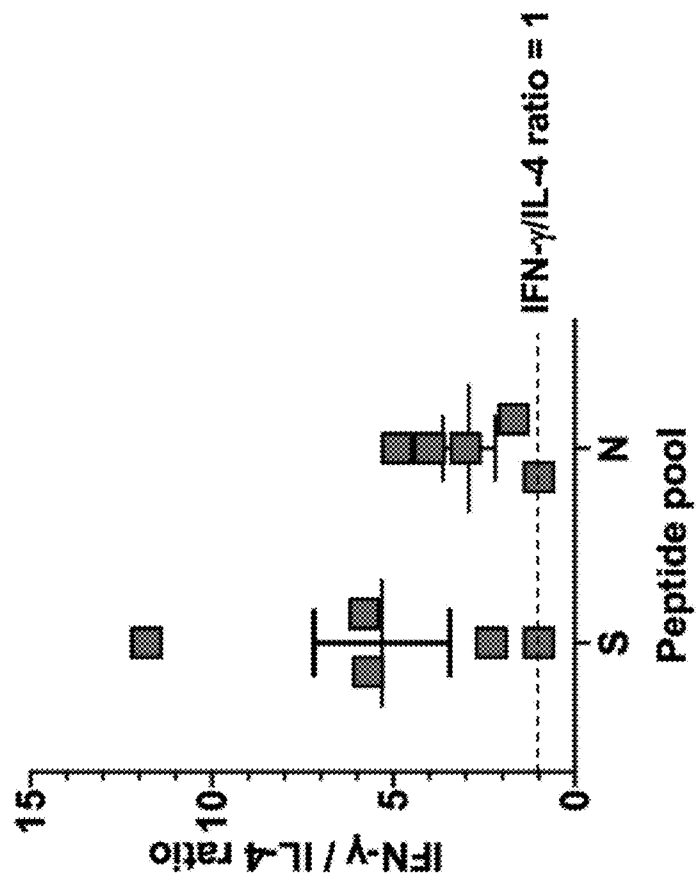
FIG. 18 exemplarily depicts ratios for T-cell and humoral responses reveal Th1 predominance. (a) The ratio of total Th1 (IFN-γ) to Th2 (IL-4) spot-forming units is shown for responses to the combined S pools and to the N pool. (b) The Th1/Th2 ratio for antibodies against S and N is shown. For both (a) and(b) the dashed line indicates a ratio of 1 or a balance of Th1 and Th2 (no predominance).
Figure 18:
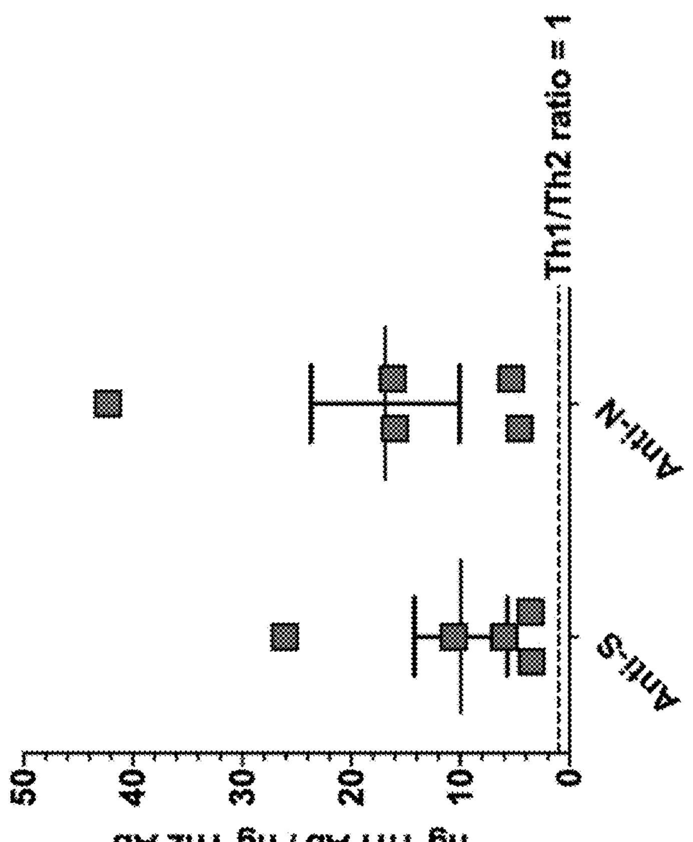

The Th1-type predominance is also seen when the ratio of IFN-□to IL-4 based on spot forming units in response to the combined S peptide pools and the N peptide pool, is considered (FIG. 18*a*).

Th1 predominance was seen again in humoral responses, where the ratio based on ng equivalence of Th1 related antibodies (IgG2a, IgG2b, and IgG3) to Th2 related antibodies (IgG1) for both anti-S and anti-N antibodies is greater than 1 in all mice (FIG. 18*b*).

This Th1 dominant profile of the hAd5 S-Fusion+N-ETSD vaccine candidate provides further justification for hAd5 S-Fusion+N-ETSD to be our lead candidate for clinical testing The hAd5 S-Fusion+N-ETSD vaccine was designed to overcome the risks of an S-only vaccine and elicit both T-cell immunity and neutralizing antibodies, leveraging the vital role T cells play in generating long-lasting antibody responses and in directly killing infected cells. Both CD4+ and CD8+ T cells are multifunctional, and induction of such multifunctional T cells by vaccines correlated with better protection against infection. We posit that enhanced CD4+ T-cell responses and Th1 predominance resulting from expression of an S antigen optimized for surface display and an N antigen optimized for endosomal/lysosomal subcellular compartment localization and thus MHC I and II presentation, led to increased dendritic cell presentation, cross-presentation, B cell activation, and ultimately high neutralization capability. Furthermore, the potent neutralization capability at high dilution seen for the pooled sera from hAd5 S-Fusion+N-ETSD vaccinated mice, combined with Th1 dominance of antibodies generated in response to both S and N antigens, supports the objective of this vaccine design.

Contemporaneous MHC I and MHC II presentation of an antigen by the antigen presenting cell activates CD4+ and CD8+ T cells simultaneously and is optimal for the generation of memory B and T cells. A key finding of our construct is that N-ETSD, which we show is directed to the endosomal/lysosomal compartment, elicits a CD4+response, a necessity for induction of memory T cells and helper cells for B cell antibody production. Others have also reported on the importance of lysosomal localization for eliciting the strongest T-cell IFN-γ and CTL responses, compared to natural N.50,51

The T-cell responses to the S and N antigens expressed by hAd5 S-Fusion+N-ETSD were polycytokine, including IFN-g and TNF-α, consistent with successful antimicrobial immunity in bacterial and viral infections. Post-vaccination polycytokine T-cell responses have been shown to correlate with vaccine efficacy, including those with a viral vector. Highly relevant here, polycytokine T-cell responses to SARS-CoV-2 N protein are consistent with recovered COVID-19 patients, suggesting that the bivalent hAd5 S-Fusion+N-ETSD vaccine will provide vaccine subjects with greater protection against SARS-CoV-2.

In contrast to N, the S protein, here expressed as S-Fusion with confirmed enhanced RBD cell-surface expression and conformational integrity as evidenced by high ACE2-Fc binding, generated predominantly CD8+ T cells. Our results confirmed our vaccine design goal, showing that S-Fusion induced elevated levels of antigen-specific T-cell responses against S compared to S-WT. To ensure MHC presentation to both MHC I (for CD8+ T-cell activation) and MHC II (for CD4+ T-cell activation), it is necessary to vaccinate with both S and N antigens optimized to produce this coordinated response.

The neutralization data with live SARS-CoV-2 virus demonstrated the potency of the antibody response generated following vaccination with hAd5 S-Fusion+N-ETSD, with evidence of high neutralization even at a high dilution factor. In addition, a striking synergistic effect of pooled sera was evident, with potent neutralization even greater than control convalescent serum at >1:1,000 dilution.

The hAd5 S-Fusion+N-ETSD construct described above is delivered by a next generation hAd5 [E1-, E2b-, E3-] platform wherein the E2b deletion (pol) alone enables prolonged transgene production and allows homologous vaccination (prime and the boost formulation is the same) in the presence of pre-existing adenoviral immunity.38 In addition to the generation of cellular and humoral immunity by the subcutaneous injection of hAd5 S-Fusion+N-ETSD, we are also exploring the potential of inducing IgA mucosal immunity by utilizing the same vaccine in an oral or sublingual formulation in clinical trials.

Example 16: Methods

The hAd5 [E1-, E2b-, E3-] platform and constructs For studies herein, the 2nd generation hAd5 [E1-, E2b-, E3-] vector was used (FIG. 1*c*) to create viral vaccine candidate constructs. hAd5 [E1-, E2b-, E3-] backbones containing SARS-CoV-2 antigen expressing inserts and virus particles were produced as previously described.37 In brief, high titer adenoviral stocks were generated by serial propagation in the E1- and E2b-expressing E.C7 packaging cell line, followed by CsCl2 purification, and dialysis into storage buffer (2.5% glycerol, 20 mM Tris pH 8, 25 mM NaCl) by ViraQuest Inc. (North Liberty, IA). Viral particle counts were determined by sodium dodecyl sulfate disruption and spectrophotometry at 260 and 280 nm and viral titers were determined using the Adeno-X™ Rapid Titer Kit (Takara Bio). The constructs created included:

S-WT: S protein comprising 1273 amino acids and all S domains: extracellular (1-1213), transmembrane (1214-1234), and cytoplasmic (1235-1273) (Unitprot PODTC2);

S RBD-ETSD: S Receptor Binding Domain (S RBD) with an ETSD;

N-ETSD: Nucleocapsid (N) with ETSD;

S-WT+N-ETSD: S-WT with an Enhanced T-cell Stimulation Domain (ETSD);

S-RBD-ETSD+N-ETSD;

S Fusion: S optimized to enhance surface expression and display of RBD; and Bivalent S-Fusion+N-ETSD;

Transfection of HEK 293T Cells with hAd5 Constructs

To determine surface expression of the RBD epitope by vaccine candidate constructs, we transfected HEK 293T cells with hAd5 construct DNA and quantified surface RBD by flow cytometric detection using anti-RBD antibodies. There were seven constructs tested: S-WT, S-WT+N-ETSD, S RBD-ETSD, S RBD-ETSD+N-ETSD, S-Fusion, S-Fusion+N-ETSD, and N-ETSD. HEK 293T cells ($2.5\times10^5$ cells/well in 24 well plates) were grown in DMEM (Gibco Cat #11995-065) with 10% FBS and 1X PSA (100 units/mL penicillin, 100 μg/mL streptomycin, 0.25 ug/mL Amphotericin B) at 37° C. Cells were transfected with 0.5 ug of hAd5 plasmid DNA using a JetPrime transfection reagent (Polyplus Catalog #89129-924) according to the manufacturer's instructions. Cells were harvested 1, 2, 3, and 7 days post transfection by gently pipetting cells into medium and labeled with an anti-RBD monoclonal antibody (clone D003 Sino Biological Catalog #40150-D003) and F(ab')2-Goat anti-Human IgG-Fc secondary antibody conjugated with R-phycoerythrin (ThermoFisher Catalog #H10104). Labeled cells were acquired using a Thermo-Fisher Attune NxT flow cytometer and analyzed using Flowjo Software.

Immunocytochemical Labeling of hAd5 Infected HeLa Cells

To determine subcellular localization of N after infection or transfection of HeLa cells with hAd5 N-wild type (WT) or hAd5 N-ETSD (each with a flag tag to allow labeling), 48 hours after infection or transfection cells were fixed with 4% paraformaldehyde (PFA) and permeabilized with 0.4% Triton X100, in PBS) for 15 min. at room temperature. To label N, cells were then incubated with an anti-flag monoclonal (Anti-Flag M2 produced in mouse, Sigma cat #F1804) antibody at 1:1000 in phosphate buffered saline with 3% BSA overnight at 4° C., followed by washes in PBS and a 1 hour incubation with a goat anti-Mouse IgG (H+L) Highly Cross-Adsorbed Secondary Antibody, Alexa Fluor Plus 555 (Life Technologies, Cat #A32727) at 1:500. For co-localization studies, cells were also incubated overnight at 4° C. with a sheep anti-Lamp1 Alexa Fluor 488-conjugated (lysosomal marker) antibody (R&D systems, Cat #IC7985G) at 1:10 or a rabbit anti-CD71 (transferrin receptor, endosomal marker) antibody (ThermoFisher Cat #PAS-83022) at 1:200. After removal of the primary antibody, two washes in PBS and three 3 washes in PBS with 3% BSA, cells were incubated with fluor-conjugated secondary antibodies when applicable at 1:500 (Goat anti-Rabbit IgG (H+L) Highly Cross-Adsorbed Secondary Antibody, Alexa Fluor 488, Life technologies, A-11034) for 1 hour at room temperature. After brief washing, cells were mounted with Vectashield Antifade mounting medium with DAPI (Fisher Scientific, Cat #NC9524612) and immediately imaged using a Keyence all-in-one Fluorescence microscope camera and Keyence software.

Immunoblot Analysis of S Antigen Expression

HEK 293T cells transfected with hAd5 S-WT, S-Fusion, or S-Fusion+N-ETSD constructs were cultured and transfected as described in the main manuscript and harvested 3 days after transfection in 150 mL RIPA lysis buffer with 1× final Protease Inhibitor cocktail (Roche). After protein assay, equivalent amounts of total protein were loaded into and run on a 4 to 12% gradient polyacrylamide gel (type) and transferred to nitrocellulose membranes using semi-dry transfer apparatus. Anti-Spike S2 (SinoBiological Cat #40590-T62) was used as the primary antibody and IRDye® 800CW Goat anti-Rabbit IgG (H+L) (Li-Cor, 925-32211) as the secondary antibody using the Ibind Flex platform. Antibody-specific signals were detected with an infrared Licor Odyssey instrument.

ACE2-IgG1Fc Binding to hAd5 Transfected HEK 293T Cells

HEK 293T cells were cultured at 37° C. under conditions described above for transfection with hAd5 S-WT, S-Fusion, S-Fusion+N-ETSD, S RBD-ETSD, or S RBD-ETSD+N-ETSD and were incubated for 2 days and harvested for ACE2-Fc binding analysis. Recombinant ACE2-IgG1Fc protein was produced using Maxcyte transfection in CHO-S cells that were cultured for 14 days. ACE2-IgG1Fc was then purified using a Mab Select SuRe affinity column on AKTA Explorer.

Purified ACE2-IgG1Fc was dialyzed into 10 mM HEPES, pH7.4, 150 mM NaCl and concentrated to 2.6 mg/mL. For binding studies, the ACE2-IgG1Fc was used at a concentration of 1 □g/mL for binding. Cells were incubated with ACE2-Fc for 20 minutes and, after a washing step, were then labeled with a PE conjugated F(ab')2-goat anti-human IgG Fc secondary antibody at a 1:100 dilution, incubated for 20 minutes, washed and acquired on flow cytometer. Histograms are based on normalized mode (NM) of cell count—count of cells positive for signal in PE channel.

Vaccination of CD-1 Mice with the hAd5 S-Fusion+N-ETSD Vaccine Candidate

CD-1 female mice (Charles River Laboratories) 7 weeks of age were used for immunological studies performed at the vivarium facilities of Omeros Inc. (Seattle, WA). After an initial blood draw, mice were injected with either hAd5 Null (a negative control) or vaccine candidate hAd5 S-Fusion+N-ETSD on Day 0 at a dose of 1×1010 viral particles (VP). There were 5 mice per group. Mice received a second vaccine dose on Day 21 and on Day 28, blood was collected via the submandibular vein from isoflurane-anesthetized mice for isolation of sera and then mice were euthanized for collection of spleen and other tissues.

Splenocyte Collection and Intracellular Cytokine Staining (ICS)

Spleens were removed from each mouse and placed in 5 mL of sterile medium of RPMI (Gibco Cat #22400105), HEPES (Hyclone Cat #SH30237.01), 1X Pen/Strep (Gibco Cat #15140122), and 10% FBS (Gibco Cat #16140-089). Splenocytes were isolated within 2 hours of collection. ICS for flow cytometric detection of CD8β+ and CD4+ T-cell-associated IFN-γ and IFN-γ/TNFα+production in response to stimulation by S and N peptide pools.

Stimulation assays were performed using 106 live splenocytes per well in 96-well U-bottom plates. Splenocytes in RPMI media supplemented with 10% FBS were stimulated by the addition of peptide pools at 2 μg/mL/peptide for 6 h at 37° C. in 5% CO2, with protein transport inhibitor, GolgiStop (BD) added two hours after initiation of incubation. Stimulated splenocytes were then stained for lymphocyte surface markers CD8□and CD4, fixed with CytoFix (BD), permeabilized, and stained for intracellular accumulation of IFN-γ and TNF-α. Fluorescent-conjugated antibodies against mouse CD8□antibody (clone H35-17.2, ThermoFisher), CD4 (clone RM4-5, BD), IFN-γ (clone XMG1.2, BD), and TNF-α (clone MP6-XT22, BD) and staining was performed in the presence of unlabeled anti-CD16/CD32 antibody (clone 2.4G2). Flow cytometry was performed using a Beckman-Coulter Cytoflex S flow cytometer and analyzed using Flowjo Software.

ELISpot Assay

ELISpot assays were used to detect cytokines secreted by splenocytes from inoculated mice. Fresh splenocytes were used on the same day, as were cryopreserved splenocytes containing lymphocytes. The cells (2-4×105 cells per well of a 96-well plate) were added to the ELISpot plate containing an immobilized primary antibodies to either IFN-γ or IL-4 (BD), and were exposed to various stimuli (e.g. control peptides, target peptide pools/proteins) comprising 2 μg/mL peptide pools or 10 μg/mL protein for 36-40 hours. After aspiration and washing to remove cells and media, extracellular cytokine was detected by a secondary antibody to cytokine conjugated to biotin (BD). A streptavidin/horseradish peroxidase conjugate was used detect the biotin-conjugated secondary antibody. The number of spots per well, or per 2-4×105 cells, was counted using an ELISpot plate reader.

ELISA for Detection of Antibodies

For antibody detection in sera from inoculated mice, ELISAs specific for spike and nucleocapsid antibodies, as well as for IgG subtype (IgG1, IgG2a, IgG2b, and IgG3) antibodies were used. A microtiter plate was coated overnight with 100 ng of either purified recombinant SARS-CoV-2 S-FTD (full-length S with fibritin trimerization domain, constructed and purified in-house by ImmunityBio), SARS-CoV-2 S RBD (Sino Biological, Beijing, China; Cat #401591-VO8B1-100) or purified recombinant SARS-CoV-2 nucleocapsid (N) protein (Sino Biological, Beijing, China; Cat #40588-VO8B) in 100 μL of coating buffer (0.05 M Carbonate Buffer, pH 9.6). The wells were washed three times with 250 μL PBS containing 1% Tween 20 (PBST) to remove unbound protein and the plate was blocked for 60 minutes at room temperature with 250 μL PBST. After blocking, the wells were washed with PBST, 100 μL of diluted serum samples were added to wells, and samples incubated for 60 minutes at room temperature. After incubation, the wells were washed with PBST and 100 μL of a 1/5000 dilution of anti-mouse IgG HRP (GE Health Care; Cat #NA9310V), or anti-mouse IgG1 HRP (Sigma; Cat #SAB3701171), or anti-mouse IgG2a HRP (Sigma; Cat #SAB3701178), or anti-mouse IgG2b HRP (Sigma; catalog#SAB3701185), or anti-mouse IgG3 HRP conjugated antibody (Sigma; Cat #SAB3701192) was added to wells. For positive controls, a 100 μL of a 1/5000 dilution of rabbit anti-N IgG Ab or 100 μL of a 1/25 dilution of mouse anti-S serum (from mice immunized with purified S antigen in adjuvant) were added to appropriate wells. After incubation at room temperature for 1 hour, the wells were washed with PBS-T and incubated with 200 μL o-phenylenediamine-dihydrochloride (OPD substrate (Thermo Scientific Cat #A34006) until appropriate color development. The color reaction was stopped with addition of 50 μL 10% phosphoric acid solution (Fisher Cat #A260-500) in water and the absorbance at 490 nm was determined using a microplate reader (SoftMax® Pro, Molecular Devices).

Calculation of Relative μg Amounts of Antibodies

A standard curve of IgG was generated and absorbance values were converted into mass equivalents for both anti-S and anti-N antibodies. Using these values, we were able to calculate that hAd5 S-Fusion+N-ETSD vaccination generated a geometric mean value of 5.8 S-specific IgG and 42 μg N-specific IgG per milliliter of serum.

cPassTM Neutralizing Antibody Detection

The GenScript cPassTM (https://www.genscript.com/cpass-sars-cov-2-neutralization-antibody-detection-Kit.html) for detection of neutralizing antibodies was used according to the manufacturer's instructions.44 The kit detects circulating neutralizing antibodies against SARS-CoV-2 that block the interaction between the S RBD with the ACE2 cell surface receptor. It is suitable for all antibody isotypes and appropriate for use with in animal models without modification.

Vero E6 Cell Neutralization Assay

All aspects of the assay utilizing virus were performed in a BSL3 containment facility according to the ISMMS Conventional Biocontainment Facility SOPs for SARS-CoV-2 cell culture studies. Vero e6 kidney epithelial cells from *Cercopithecus aethiops* (ATCC CRL-1586) were plated at 20,000 cells/well in a 96-well format and 24 hours later, cells were incubated with antibodies or heat inactivated sera previously serially diluted in 3-fold steps in DMEM containing 2% FBS, 1% NEAAs, and 1% Pen-Strep; the diluted samples were mixed 1:1 with SARS-CoV-2 in DMEM containing 2% FBS, 1% NEAAs, and 1% Pen-Strep at 10,000 TCID 50/mL for 1 hr. at 37° C., 5% CO2. This incubation did not include cells to allow for neutralizing activity to occur prior to infection. The samples for testing included sera from the four mice that showed >20% inhibition of ACE2 binding in cPass, pooled sera from those four mice, sera from a COVID-19 convalescent patient, and media only. For detection of neutralization, 120 μL of the virus/sample mixture was transferred to the Vero E6 cells and incubated for 48 hours before fixation with 4% PFA. Each well received 60 μL of virus or an infectious dose of 600 TCID50. Control wells including 6 wells on each plate for no virus and virus-only controls were used. The percent neutralization was calculated as 100-((sample of interest-[average of "no virus"])/[average of "virus only"])*100) with a stain for CoV-2 Np imaged on a Celigo Imaging Cytometer (Nexcelom Bioscience).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosures herein, and does not pose a limitation on the scope of the invention otherwise claimed. No language in the specification should be construed as indicating any non-claimed element essential to the practice of the claimed invention.

Many more modifications besides those already described are possible without departing from the concepts disclosed herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of inducing immunity against a severe acute respiratory syndrome (SARS) coronavirus 2 (SARS-CoV2) in mucosal tissue of a patient, the method comprising administering a vaccine composition to the patient by delivery to nasal mucosa, wherein the vaccine composition comprises a replication defective adenovirus, and wherein the adenovirus comprises an E1 gene region deletion and an E2b gene region deletion, a nucleic acid portion that encodes a SARS-CoV2 S protein, and a nucleic acid portion that encodes a chimeric protein comprising a SARS-CoV2 N protein and an endosomal targeting sequence.

2. The method of claim 1, further comprising administering to the patient an anti-SARSCoV2 vaccine by injection, wherein the anti-SARS-CoV2 vaccine injection comprises a nucleotide encoding SARS-CoV2 spike (S) and/or nucleocapsid (N) protein, and wherein injection includes intramuscular (IM) injection, (IV) intravenous injection, and/or subcutaneous injection.

3. The method of claim 2, wherein the vaccine composition of claim 1 is administered after the anti-SARS-CoV2 vaccine injection.

4. The method of claim 2, wherein the anti-SARS-CoV2 vaccine injection comprises a lipid nanoparticle encasing the nucleotide encoding SARS-CoV2 S and/or N protein.

5. The method of claim 2, wherein the intranasal vaccine composition is administered as a booster immunization at least one week after the anti-SARS-CoV2 vaccine injection.

6. The method of claim 5, wherein the intranasal vaccine composition is administered at least two weeks after the anti-SARS-CoV2 vaccine injection.

7. The method of claim 1, wherein the adenovirus further comprises an E3 gene region deletion and/or an E4 gene region deletion.

8. The method of claim 1, further comprising analyzing a sample of saliva from the patient for antibodies targeting the coronavirus and/or for a protein specific to the coronavirus.

9. The method of claim 8, further comprising administering a second dose of the intranasal vaccine composition to the patient.

10. The method of claim 1, wherein the intranasal vaccine composition comprises SEQ ID NO:11.

11. The method of claim 1, wherein the intranasal vaccine composition comprises SEQ ID NO:13.

* * * * *

SEQUENCE LISTING

```
<160> NUMBER OF SEQ ID NOS: 13

<210> SEQ ID NO 1
<211> LENGTH: 473
<212> TYPE: PRT
<213> ORGANISM: Artificial Sequence
<220> FEATURE:
<223> OTHER INFORMATION: SARS-COV2 Nucleocapsid protein

<400> SEQUENCE: 1

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110
```

```
Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala Gly Pro Gly Pro Gly Asn Leu Val Pro Met Val Ala Thr
            420                 425                 430

Val Gly Pro Gly Pro Gly Met Leu Ile Pro Ile Ala Val Gly Gly Ala
        435                 440                 445

Leu Ala Gly Leu Val Leu Ile Val Leu Ile Ala Tyr Leu Ile Gly Lys
    450                 455                 460

Lys His Cys Ser Tyr Gln Asp Ile Leu
465                 470
```

<210> SEQ ID NO 2
<211> LENGTH: 516
<212> TYPE: PRT
<213> ORGANISM: Artificial Sequence
<220> FEATURE:
<223> OTHER INFORMATION: SARS-CoV2 Nucleocapsid protein tagged with ETSD signal

```
<400> SEQUENCE: 2

Met Leu Leu Leu Pro Phe Gln Leu Leu Ala Val Leu Phe Pro Gly Gly
1               5                   10                  15

Asn Ser Glu Asp Tyr Lys Asp Asp Asp Asp Lys Gly Gly Gly Ser Gly
            20                  25                  30

Gly Gly Ser Gly Gly Gly Ser Gly Gly Gly Ser Met Ser Asp Asn Gly
        35                  40                  45

Pro Gln Asn Gln Arg Asn Ala Pro Arg Ile Thr Phe Gly Gly Pro Ser
    50                  55                  60

Asp Ser Thr Gly Ser Asn Gln Asn Gly Glu Arg Ser Gly Ala Arg Ser
65                  70                  75                  80

Lys Gln Arg Arg Pro Gln Gly Leu Pro Asn Asn Thr Ala Ser Trp Phe
                85                  90                  95

Thr Ala Leu Thr Gln His Gly Lys Glu Asp Leu Lys Phe Pro Arg Gly
            100                 105                 110

Gln Gly Val Pro Ile Asn Thr Asn Ser Ser Pro Asp Asp Gln Ile Gly
        115                 120                 125

Tyr Tyr Arg Arg Ala Thr Arg Arg Ile Arg Gly Gly Asp Gly Lys Met
    130                 135                 140

Lys Asp Leu Ser Pro Arg Trp Tyr Phe Tyr Tyr Leu Gly Thr Gly Pro
145                 150                 155                 160

Glu Ala Gly Leu Pro Tyr Gly Ala Asn Lys Asp Gly Ile Ile Trp Val
                165                 170                 175

Ala Thr Glu Gly Ala Leu Asn Thr Pro Lys Asp His Ile Gly Thr Arg
            180                 185                 190

Asn Pro Ala Asn Asn Ala Ala Ile Val Leu Gln Leu Pro Gln Gly Thr
        195                 200                 205

Thr Leu Pro Lys Gly Phe Tyr Ala Glu Gly Ser Arg Gly Gly Ser Gln
    210                 215                 220

Ala Ser Ser Arg Ser Ser Ser Arg Ser Arg Asn Ser Ser Arg Asn Ser
225                 230                 235                 240

Thr Pro Gly Ser Ser Arg Gly Thr Ser Pro Ala Arg Met Ala Gly Asn
                245                 250                 255

Gly Gly Asp Ala Ala Leu Ala Leu Leu Leu Leu Asp Arg Leu Asn Gln
            260                 265                 270

Leu Glu Ser Lys Met Ser Gly Lys Gly Gln Gln Gln Gln Gly Gln Thr
        275                 280                 285

Val Thr Lys Lys Ser Ala Ala Glu Ala Ser Lys Lys Pro Arg Gln Lys
    290                 295                 300

Arg Thr Ala Thr Lys Ala Tyr Asn Val Thr Gln Ala Phe Gly Arg Arg
305                 310                 315                 320

Gly Pro Glu Gln Thr Gln Gly Asn Phe Gly Asp Gln Glu Leu Ile Arg
                325                 330                 335

Gln Gly Thr Asp Tyr Lys His Trp Pro Gln Ile Ala Gln Phe Ala Pro
            340                 345                 350

Ser Ala Ser Ala Phe Phe Gly Met Ser Arg Ile Gly Met Glu Val Thr
        355                 360                 365

Pro Ser Gly Thr Trp Leu Thr Tyr Thr Gly Ala Ile Lys Leu Asp Asp
    370                 375                 380

Lys Asp Pro Asn Phe Lys Asp Gln Val Ile Leu Leu Asn Lys His Ile
385                 390                 395                 400

Asp Ala Tyr Lys Thr Phe Pro Pro Thr Glu Pro Lys Lys Asp Lys Lys
                405                 410                 415
```

```
Lys Lys Ala Asp Glu Thr Gln Ala Leu Pro Gln Arg Gln Lys Lys Gln
            420                 425                 430

Gln Thr Val Thr Leu Leu Pro Ala Ala Asp Leu Asp Asp Phe Ser Lys
        435                 440                 445

Gln Leu Gln Gln Ser Met Ser Ser Ala Asp Ser Thr Gln Ala Gly Pro
    450                 455                 460

Gly Pro Gly Asn Leu Val Pro Met Val Ala Thr Val Gly Pro Gly Pro
465                 470                 475                 480

Gly Met Leu Ile Pro Ile Ala Val Gly Gly Ala Leu Ala Gly Leu Val
                485                 490                 495

Leu Ile Val Leu Ile Ala Tyr Leu Ile Gly Lys Lys His Cys Ser Tyr
            500                 505                 510

Gln Asp Ile Leu
        515
```

<210> SEQ ID NO 3
<211> LENGTH: 1551
<212> TYPE: DNA
<213> ORGANISM: Artificial Sequence
<220> FEATURE:
<223> OTHER INFORMATION: N-ETSD cargo in AdV. Seq I.(2)

<400> SEQUENCE: 3

```
atgctgctgc tgcccttcca gttgctggct gtcctctttc ccggcggcaa ctccgaggat      60

tacaaggacg acgacgacaa gggtggaggc tctggaggtg gctctggtgg aggttccggt     120

ggcggatcta tgagcgacaa cggtccccag aatcaaagaa atgcgcccag aattacattc     180

ggcggccctt ctgatagcac tggctcaaat caaaacgggg agagaagcgg agccaggtcc     240

aaacagcgga gaccccaagg cctgcctaat aacaccgctt cctggttcac agctctgacg     300

caacacggca aggaggatct gaagtttcca cggggtcagg gcgtcccgat taacacgaac     360

tctagcccag atgaccaaat agggtactac agaagagcga caaggcggat cagaggaggc     420

gatggaaaaa tgaaggatct gtcccctagg tggtatttct attacctggg cacaggccct     480

gaagctgggt tgccttacgg cgcaaacaaa gatggaatta tatgggtggc caccgagggg     540

gcgttgaaca ccccaaagga tcacatcgga acgaggaatc ccgccaacaa tgctgctata     600

gtgctccaac tgccacaggg aacaaccctg cctaagggct tctacgccga ggggagccgc     660

ggtggcagcc aggccagctc cagaagttcc tcccgcagcc ggaacagctc tagaaacagc     720

actcccggca gctccagagg gacaagccca gccagaatgg ccggcaatgg cggcgacgct     780

gccctcgcac ttctgttgct tgatcggctc aatcaactcg aaagcaaaat gtccggcaag     840

ggacaacaac agcaaggaca gaccgttaca aaaaaaagcg ccgccgaggc tagcaagaag     900

cccagacaga agcgaaccgc aacaaaggcc tataatgtaa cacaagcctt tggaaggcgg     960

ggacccgaac agacccaggg aaattttggc gaccaggaac tgatccggca agggacagac    1020

tataaacatt ggccacagat agcgcaattt gctccctccg cctccgcctt ctttggcatg    1080

tcaagaatag gcatggaagt aactccttct ggaacctggc tgacgtacac tggggcaatc    1140

aagttggatg ataaggaccc taatttcaag gaccaagtta ttttgctcaa caagcatata    1200

gacgcctaca agactttccc gcctaccgaa cctaaaaagg ataagaagaa gaaagcagac    1260

gagacccagg ccctgcctca acggcaaaag aagcagcaaa ctgtgacact cctgcccgcc    1320

gctgacttgg atgatttttc aaaacagctc caacagagta tgagcagcgc cgatagcacc    1380

caagctggac cgggtccggg caacctggtg ccgatggtgg cgaccgtggg tccaggaccg    1440
```

ggtatgctga tccccatcgc cgtgggcggg gccctggccg gcctcgtgct gatcgtcctt 1500
atcgcctacc tcatcggcaa gaagcactgc tcatatcagg acatcctgtg a 1551

<210> SEQ ID NO 4
<211> LENGTH: 1282
<212> TYPE: PRT
<213> ORGANISM: Artificial Sequence
<220> FEATURE:
<223> OTHER INFORMATION: spike protein

<400> SEQUENCE: 4

```
Met Phe Val Phe Leu Val Leu Leu Pro Leu Val Ser Ser Tyr Pro Tyr
1               5                   10                  15

Asp Val Pro Asp Tyr Ala Gln Cys Val Asn Leu Thr Thr Arg Thr Gln
            20                  25                  30

Leu Pro Pro Ala Tyr Thr Asn Ser Phe Thr Arg Gly Val Tyr Tyr Pro
        35                  40                  45

Asp Lys Val Phe Arg Ser Ser Val Leu His Ser Thr Gln Asp Leu Phe
    50                  55                  60

Leu Pro Phe Phe Ser Asn Val Thr Trp Phe His Ala Ile His Val Ser
65                  70                  75                  80

Gly Thr Asn Gly Thr Lys Arg Phe Asp Asn Pro Val Leu Pro Phe Asn
                85                  90                  95

Asp Gly Val Tyr Phe Ala Ser Thr Glu Lys Ser Asn Ile Ile Arg Gly
            100                 105                 110

Trp Ile Phe Gly Thr Thr Leu Asp Ser Lys Thr Gln Ser Leu Leu Ile
        115                 120                 125

Val Asn Asn Ala Thr Asn Val Val Ile Lys Val Cys Glu Phe Gln Phe
    130                 135                 140

Cys Asn Asp Pro Phe Leu Gly Val Tyr Tyr His Lys Asn Asn Lys Ser
145                 150                 155                 160

Trp Met Glu Ser Glu Phe Arg Val Tyr Ser Ser Ala Asn Asn Cys Thr
                165                 170                 175

Phe Glu Tyr Val Ser Gln Pro Phe Leu Met Asp Leu Glu Gly Lys Gln
            180                 185                 190

Gly Asn Phe Lys Asn Leu Arg Glu Phe Val Phe Lys Asn Ile Asp Gly
        195                 200                 205

Tyr Phe Lys Ile Tyr Ser Lys His Thr Pro Ile Asn Leu Val Arg Asp
    210                 215                 220

Leu Pro Gln Gly Phe Ser Ala Leu Glu Pro Leu Val Asp Leu Pro Ile
225                 230                 235                 240

Gly Ile Asn Ile Thr Arg Phe Gln Thr Leu Leu Ala Leu His Arg Ser
                245                 250                 255

Tyr Leu Thr Pro Gly Asp Ser Ser Ser Gly Trp Thr Ala Gly Ala Ala
            260                 265                 270

Ala Tyr Tyr Val Gly Tyr Leu Gln Pro Arg Thr Phe Leu Leu Lys Tyr
        275                 280                 285

Asn Glu Asn Gly Thr Ile Thr Asp Ala Val Asp Cys Ala Leu Asp Pro
    290                 295                 300

Leu Ser Glu Thr Lys Cys Thr Leu Lys Ser Phe Thr Val Glu Lys Gly
305                 310                 315                 320

Ile Tyr Gln Thr Ser Asn Phe Arg Val Gln Pro Thr Glu Ser Ile Val
                325                 330                 335

Arg Phe Pro Asn Ile Thr Asn Leu Cys Pro Phe Gly Glu Val Phe Asn
```

```
            340                 345                 350

Ala Thr Arg Phe Ala Ser Val Tyr Ala Trp Asn Arg Lys Arg Ile Ser
        355                 360                 365

Asn Cys Val Ala Asp Tyr Ser Val Leu Tyr Asn Ser Ala Ser Phe Ser
    370                 375                 380

Thr Phe Lys Cys Tyr Gly Val Ser Pro Thr Lys Leu Asn Asp Leu Cys
385                 390                 395                 400

Phe Thr Asn Val Tyr Ala Asp Ser Phe Val Ile Arg Gly Asp Glu Val
                405                 410                 415

Arg Gln Ile Ala Pro Gly Gln Thr Gly Lys Ile Ala Asp Tyr Asn Tyr
            420                 425                 430

Lys Leu Pro Asp Asp Phe Thr Gly Cys Val Ile Ala Trp Asn Ser Asn
        435                 440                 445

Asn Leu Asp Ser Lys Val Gly Gly Asn Tyr Asn Tyr Leu Tyr Arg Leu
    450                 455                 460

Phe Arg Lys Ser Asn Leu Lys Pro Phe Glu Arg Asp Ile Ser Thr Glu
465                 470                 475                 480

Ile Tyr Gln Ala Gly Ser Thr Pro Cys Asn Gly Val Glu Gly Phe Asn
                485                 490                 495

Cys Tyr Phe Pro Leu Gln Ser Tyr Gly Phe Gln Pro Thr Asn Gly Val
            500                 505                 510

Gly Tyr Gln Pro Tyr Arg Val Val Val Leu Ser Phe Glu Leu Leu His
        515                 520                 525

Ala Pro Ala Thr Val Cys Gly Pro Lys Lys Ser Thr Asn Leu Val Lys
    530                 535                 540

Asn Lys Cys Val Asn Phe Asn Phe Asn Gly Leu Thr Gly Thr Gly Val
545                 550                 555                 560

Leu Thr Glu Ser Asn Lys Lys Phe Leu Pro Phe Gln Gln Phe Gly Arg
                565                 570                 575

Asp Ile Ala Asp Thr Thr Asp Ala Val Arg Asp Pro Gln Thr Leu Glu
            580                 585                 590

Ile Leu Asp Ile Thr Pro Cys Ser Phe Gly Gly Val Ser Val Ile Thr
        595                 600                 605

Pro Gly Thr Asn Thr Ser Asn Gln Val Ala Val Leu Tyr Gln Asp Val
    610                 615                 620

Asn Cys Thr Glu Val Pro Val Ala Ile His Ala Asp Gln Leu Thr Pro
625                 630                 635                 640

Thr Trp Arg Val Tyr Ser Thr Gly Ser Asn Val Phe Gln Thr Arg Ala
                645                 650                 655

Gly Cys Leu Ile Gly Ala Glu His Val Asn Asn Ser Tyr Glu Cys Asp
            660                 665                 670

Ile Pro Ile Gly Ala Gly Ile Cys Ala Ser Tyr Gln Thr Gln Thr Asn
        675                 680                 685

Ser Pro Arg Arg Ala Arg Ser Val Ala Ser Gln Ser Ile Ile Ala Tyr
    690                 695                 700

Thr Met Ser Leu Gly Ala Glu Asn Ser Val Ala Tyr Ser Asn Asn Ser
705                 710                 715                 720

Ile Ala Ile Pro Thr Asn Phe Thr Ile Ser Val Thr Thr Glu Ile Leu
                725                 730                 735

Pro Val Ser Met Thr Lys Thr Ser Val Asp Cys Thr Met Tyr Ile Cys
            740                 745                 750

Gly Asp Ser Thr Glu Cys Ser Asn Leu Leu Leu Gln Tyr Gly Ser Phe
        755                 760                 765
```

-continued

```
Cys Thr Gln Leu Asn Arg Ala Leu Thr Gly Ile Ala Val Glu Gln Asp
    770                 775                 780

Lys Asn Thr Gln Glu Val Phe Ala Gln Val Lys Gln Ile Tyr Lys Thr
785                 790                 795                 800

Pro Pro Ile Lys Asp Phe Gly Gly Phe Asn Phe Ser Gln Ile Leu Pro
                805                 810                 815

Asp Pro Ser Lys Pro Ser Lys Arg Ser Phe Ile Glu Asp Leu Leu Phe
            820                 825                 830

Asn Lys Val Thr Leu Ala Asp Ala Gly Phe Ile Lys Gln Tyr Gly Asp
        835                 840                 845

Cys Leu Gly Asp Ile Ala Ala Arg Asp Leu Ile Cys Ala Gln Lys Phe
    850                 855                 860

Asn Gly Leu Thr Val Leu Pro Pro Leu Leu Thr Asp Glu Met Ile Ala
865                 870                 875                 880

Gln Tyr Thr Ser Ala Leu Leu Ala Gly Thr Ile Thr Ser Gly Trp Thr
                885                 890                 895

Phe Gly Ala Gly Ala Ala Leu Gln Ile Pro Phe Ala Met Gln Met Ala
            900                 905                 910

Tyr Arg Phe Asn Gly Ile Gly Val Thr Gln Asn Val Leu Tyr Glu Asn
        915                 920                 925

Gln Lys Leu Ile Ala Asn Gln Phe Asn Ser Ala Ile Gly Lys Ile Gln
    930                 935                 940

Asp Ser Leu Ser Ser Thr Ala Ser Ala Leu Gly Lys Leu Gln Asp Val
945                 950                 955                 960

Val Asn Gln Asn Ala Gln Ala Leu Asn Thr Leu Val Lys Gln Leu Ser
                965                 970                 975

Ser Asn Phe Gly Ala Ile Ser Ser Val Leu Asn Asp Ile Leu Ser Arg
            980                 985                 990

Leu Asp Lys Val Glu Ala Glu Val  Gln Ile Asp Arg Leu  Ile Thr Gly
        995                 1000                 1005

Arg Leu  Gln Ser Leu Gln Thr  Tyr Val Thr Gln Gln  Leu Ile Arg
    1010                 1015                 1020

Ala Ala  Glu Ile Arg Ala Ser  Ala Asn Leu Ala Ala  Thr Lys Met
    1025                 1030                 1035

Ser Glu  Cys Val Leu Gly Gln  Ser Lys Arg Val Asp  Phe Cys Gly
    1040                 1045                 1050

Lys Gly  Tyr His Leu Met Ser  Phe Pro Gln Ser Ala  Pro His Gly
    1055                 1060                 1065

Val Val  Phe Leu His Val Thr  Tyr Val Pro Ala Gln  Glu Lys Asn
    1070                 1075                 1080

Phe Thr  Thr Ala Pro Ala Ile  Cys His Asp Gly Lys  Ala His Phe
    1085                 1090                 1095

Pro Arg  Glu Gly Val Phe Val  Ser Asn Gly Thr His  Trp Phe Val
    1100                 1105                 1110

Thr Gln  Arg Asn Phe Tyr Glu  Pro Gln Ile Ile Thr  Thr Asp Asn
    1115                 1120                 1125

Thr Phe  Val Ser Gly Asn Cys  Asp Val Val Ile Gly  Ile Val Asn
    1130                 1135                 1140

Asn Thr  Val Tyr Asp Pro Leu  Gln Pro Glu Leu Asp  Ser Phe Lys
    1145                 1150                 1155

Glu Glu  Leu Asp Lys Tyr Phe  Lys Asn His Thr Ser  Pro Asp Val
    1160                 1165                 1170
```

```
Asp Leu  Gly Asp Ile Ser Gly  Ile Asn Ala Ser Val  Val Asn Ile
    1175                 1180                 1185

Gln Lys  Glu Ile Asp Arg Leu  Asn Glu Val Ala Lys  Asn Leu Asn
    1190                 1195                 1200

Glu Ser  Leu Ile Asp Leu Gln  Glu Leu Gly Lys Tyr  Glu Gln Tyr
    1205                 1210                 1215

Ile Lys  Trp Pro Trp Tyr Ile  Trp Leu Gly Phe Ile  Ala Gly Leu
    1220                 1225                 1230

Ile Ala  Ile Val Met Val Thr  Ile Met Leu Cys Cys  Met Thr Ser
    1235                 1240                 1245

Cys Cys  Ser Cys Leu Lys Gly  Cys Cys Ser Cys Gly  Ser Cys Cys
    1250                 1255                 1260

Lys Phe  Asp Glu Asp Asp Ser  Glu Pro Val Leu Lys  Gly Val Lys
    1265                 1270                 1275

Leu His  Tyr Thr
    1280
```

<210> SEQ ID NO 5
<211> LENGTH: 3849
<212> TYPE: DNA
<213> ORGANISM: Artificial Sequence
<220> FEATURE:
<223> OTHER INFORMATION: S-HA cargo in AdV. Seq I.(2)

<400> SEQUENCE: 5

```
atgttcgttt ttctcgttct cctcccgctt gtgagcagct atccgtatga tgtgccggat     60

tatgcgcaat gtgtcaacct caccacaagg acacagctcc ctcccgcata tacgaatagc    120

tttaccagag gcgtatacta tcctgataag gtctttagga gctcagtact gcatagcact    180

caggatctct tcctgccgtt cttcagtaat gttacttggt ttcacgccat tcatgtttcc    240

gggaccaatg gcaccaaacg gttcgataat ccagtgcttc ccttcaacga tggggtgtac    300

tttgccagca ctgaaaaatc taatataatt cggggatgga ttttcggaac cacactcgat    360

tccaagactc agtccctctt gatcgttaac aacgctacta atgttgtcat taaggtgtgt    420

gagtttcagt tctgcaacga ccctttcctg ggtgtctact accataaaaa taacaagagc    480

tggatggagt ccgaatttcg cgtctactca agcgccaata attgcacttt tgagtatgtg    540

tcccagccct tttgatgga tctggaggga aagcagggca atttcaaaaa tctgagagaa     600

ttcgttttta agaatataga tggatacttc aaaatctaca gcaaacacac acccataaat    660

cttgtgcgcg atcttcccca gggcttcagc gcgttggaac cccttgttga cttgcccata    720

ggcatcaaca ttaccaggtt ccaaacgctg ctcgccctcc accgcagcta cttgacaccc    780

ggggattcca gctccggatg gaccgccggc gccgcagcgt attatgtggg gtacctgcaa    840

cccaggacat ttttgctcaa gtacaatgag aatgggacca tcacagatgc ggtagactgt    900

gcactggatc cactcagcga aactaaatgt accctgaaaa gctttaccgt ggagaaagga    960

atctaccaaa ccagcaactt cagggtccag cccactgaat ccatcgttag atttccaaat   1020

ataactaatt tgtgtccatt tggagaggtg ttcaatgcta caaggttcgc gtctgtatac   1080

gcttggaacc ggaagcgcat ctcaaattgc gtggctgatt atagcgttct ttacaacagc   1140

gcttcctttt ccacgttcaa gtgctatggt gtatccccga caaagctgaa tgacttgtgc   1200

ttcaccaatg tgtatgcgga ttctttcgtt attcgaggcg atgaagtcag acaaattgcg   1260

cctggccaga ccggaaagat tgccgactac aactataaac tgccggacga ctttactggt   1320

tgcgtgatcg cttggaacag caataatctt gatagtaaag ttggaggaaa ctacaattac   1380
```

```
ctctatagac tgttcagaaa gagcaacttg aagccattcg aacgggatat ctctacggag   1440
atctatcaag ctggcagcac cccctgcaat ggtgtggaag gctttaattg ttattttcct   1500
ttgcagagct atggcttcca acctaccaac ggagtgggct accagcccta cagagtggtg   1560
gtgctcagct ttgaactgct gcatgccccg gccacagttt gcgggcccaa aaaaagcacg   1620
aatctggtta agaacaaatg cgtcaacttc aattttaatg ggttgacagg tacaggcgta   1680
ctgaccgaat ccaacaaaaa gttcctgcct tttcagcagt tcgggagaga tatcgccgac   1740
actacagacg ccgtcaggga tccccaaaca ctcgaaattc tggacatcac accttgttcc   1800
ttcggcgggg tatctgtgat tactccgggc acaaatacca gtaaccaggt agcggtgctt   1860
taccaggatg tcaactgtac ggaagtacct gtcgctattc atgcggatca actcactcct   1920
acctggagag tttattccac tgggtccaac gtgtttcaga cccgagccgg ctgcttgatt   1980
ggcgcggaac atgttaacaa ctcctacgaa tgtgacatcc ctatcggagc tggcatctgt   2040
gcttcctatc aaacgcaaac gaacagccca cggcgggcca gatccgtagc ctctcaaagc   2100
atcatcgctt atactatgtc cttgggggct gaaaacagcg ttgcctattc caacaatagc   2160
atcgctatcc ctaccaactt taccatttcc gtgaccacag aaatactgcc ggtgagcatg   2220
acaaagactt ctgtggactg taccatgtat atatgcggcg atagcacaga gtgttctaat   2280
ttgctgctgc agtacggcag cttttgtacc caactcaaca gagcacttac agggattgcc   2340
gtcgagcagg ataaaaacac ccaggaggtt ttcgcccagg ttaagcagat ctacaagacc   2400
ccaccaatca aggatttcgg cggcttcaat tttcccaga tactgcccga tccttccaag   2460
ccatccaaaa ggagctttat agaggatctg ctgttcaaca aggtgactct ggccgacgct   2520
ggctttatca agcaatatgg cgattgcctg gggggatattg ccgctaggga ccttatctgc   2580
gctcaaaaat tcaacggtct taccgttctc ccgcccctgc tcaccgacga gatgatagcc   2640
cagtacacga gcgcactttt ggccggcacg ataaccagcg gctggacatt cggtgccggg   2700
gccgctcttc aaatcccctt tgccatgcag atggcctaca gatttaatgg gataggcgtg   2760
acacaaaatg tcttgtatga aaatcagaaa ctgattgcaa accagtttaa tagcgctatt   2820
ggcaagatcc aagatagcct ttcctccacc gcatccgctc tgggaaagtt gcaagacgtc   2880
gtgaatcaaa acgcccaagc tctgaatacc ctcgtgaagc agcttagctc caactttggc   2940
gcgatatcct ccgtgctgaa cgatatcctg tccagattgg acaaggtcga ggcagaagtc   3000
cagatcgata gattgataac cggcagactc cagtctctgc agacatatgt gactcagcag   3060
ttgataagag cggccgaaat acgagcgtct gcaaatctcg cagcaacgaa aatgtcagag   3120
tgtgtattgg ggcaaagtaa aagagtagat ttctgtggaa agggttacca tctgatgtca   3180
ttcccccagt ctgcaccaca tggagtagtt tttttgcatg tgacttatgt gcctgcccag   3240
gagaaaaatt tcaccactgc acctgcgatc tgtcatgacg gcaaggcaca tttccctaga   3300
gaaggcgtct tcgtatcaaa tggaacacac tggtttgtaa cccaaaggaa cttttacgag   3360
ccccaaatta taactaccga caacaccttc gtaagcggaa actgcgacgt cgttataggg   3420
atagtcaata atacggtcta tgaccctctt cagccggaac tggactcctt taaagaagaa   3480
ctggataagt acttcaagaa ccatacgtct ccggatgtgg atctcggaga tataagtgga   3540
atcaacgcaa gcgtagtaaa cattcagaag gagatagacc gactcaatga ggttgctaaa   3600
aacctgaacg aaagcttgat agacttgcag gagctgggta agtacgaaca gtacattaag   3660
tggccatggt atatctggtt gggcttcata gcaggactca tagctatcgt catggtgaca   3720
```

```
ataatgcttt gttgtatgac cagctgttgt tcttgtctga aaggctgctg cagctgtggc   3780

agctgttgta aatttgacga agatgattcc gagcctgtgc ttaagggcgt aaaactccac   3840

tatacatga                                                           3849


<210> SEQ ID NO 6
<211> LENGTH: 1298
<212> TYPE: PRT
<213> ORGANISM: Artificial Sequence
<220> FEATURE:
<223> OTHER INFORMATION: Spike fusion construct prt

<400> SEQUENCE: 6

Met Phe Val Phe Leu Val Leu Leu Pro Leu Val Ser Ser Tyr Pro Tyr
1               5                   10                  15

Asp Val Pro Asp Tyr Ala Gly Gly Gly Ser Gly Gly Gly Ser Gly Gly
            20                  25                  30

Gly Ser Gly Gly Gly Ser Gln Cys Val Asn Leu Thr Thr Arg Thr Gln
        35                  40                  45

Leu Pro Pro Ala Tyr Thr Asn Ser Phe Thr Arg Gly Val Tyr Tyr Pro
    50                  55                  60

Asp Lys Val Phe Arg Ser Ser Val Leu His Ser Thr Gln Asp Leu Phe
65                  70                  75                  80

Leu Pro Phe Phe Ser Asn Val Thr Trp Phe His Ala Ile His Val Ser
                85                  90                  95

Gly Thr Asn Gly Thr Lys Arg Phe Asp Asn Pro Val Leu Pro Phe Asn
            100                 105                 110

Asp Gly Val Tyr Phe Ala Ser Thr Glu Lys Ser Asn Ile Ile Arg Gly
        115                 120                 125

Trp Ile Phe Gly Thr Thr Leu Asp Ser Lys Thr Gln Ser Leu Leu Ile
    130                 135                 140

Val Asn Asn Ala Thr Asn Val Val Ile Lys Val Cys Glu Phe Gln Phe
145                 150                 155                 160

Cys Asn Asp Pro Phe Leu Gly Val Tyr Tyr His Lys Asn Asn Lys Ser
                165                 170                 175

Trp Met Glu Ser Glu Phe Arg Val Tyr Ser Ser Ala Asn Asn Cys Thr
            180                 185                 190

Phe Glu Tyr Val Ser Gln Pro Phe Leu Met Asp Leu Glu Gly Lys Gln
        195                 200                 205

Gly Asn Phe Lys Asn Leu Arg Glu Phe Val Phe Lys Asn Ile Asp Gly
    210                 215                 220

Tyr Phe Lys Ile Tyr Ser Lys His Thr Pro Ile Asn Leu Val Arg Asp
225                 230                 235                 240

Leu Pro Gln Gly Phe Ser Ala Leu Glu Pro Leu Val Asp Leu Pro Ile
                245                 250                 255

Gly Ile Asn Ile Thr Arg Phe Gln Thr Leu Leu Ala Leu His Arg Ser
            260                 265                 270

Tyr Leu Thr Pro Gly Asp Ser Ser Ser Gly Trp Thr Ala Gly Ala Ala
        275                 280                 285

Ala Tyr Tyr Val Gly Tyr Leu Gln Pro Arg Thr Phe Leu Leu Lys Tyr
    290                 295                 300

Asn Glu Asn Gly Thr Ile Thr Asp Ala Val Asp Cys Ala Leu Asp Pro
305                 310                 315                 320

Leu Ser Glu Thr Lys Cys Thr Leu Lys Ser Phe Thr Val Glu Lys Gly
                325                 330                 335
```

```
Ile Tyr Gln Thr Ser Asn Phe Arg Val Gln Pro Thr Glu Ser Ile Val
            340                 345                 350

Arg Phe Pro Asn Ile Thr Asn Leu Cys Pro Phe Gly Glu Val Phe Asn
        355                 360                 365

Ala Thr Arg Phe Ala Ser Val Tyr Ala Trp Asn Arg Lys Arg Ile Ser
    370                 375                 380

Asn Cys Val Ala Asp Tyr Ser Val Leu Tyr Asn Ser Ala Ser Phe Ser
385                 390                 395                 400

Thr Phe Lys Cys Tyr Gly Val Ser Pro Thr Lys Leu Asn Asp Leu Cys
                405                 410                 415

Phe Thr Asn Val Tyr Ala Asp Ser Phe Val Ile Arg Gly Asp Glu Val
            420                 425                 430

Arg Gln Ile Ala Pro Gly Gln Thr Gly Lys Ile Ala Asp Tyr Asn Tyr
        435                 440                 445

Lys Leu Pro Asp Asp Phe Thr Gly Cys Val Ile Ala Trp Asn Ser Asn
    450                 455                 460

Asn Leu Asp Ser Lys Val Gly Gly Asn Tyr Asn Tyr Leu Tyr Arg Leu
465                 470                 475                 480

Phe Arg Lys Ser Asn Leu Lys Pro Phe Glu Arg Asp Ile Ser Thr Glu
                485                 490                 495

Ile Tyr Gln Ala Gly Ser Thr Pro Cys Asn Gly Val Glu Gly Phe Asn
            500                 505                 510

Cys Tyr Phe Pro Leu Gln Ser Tyr Gly Phe Gln Pro Thr Asn Gly Val
        515                 520                 525

Gly Tyr Gln Pro Tyr Arg Val Val Val Leu Ser Phe Glu Leu Leu His
    530                 535                 540

Ala Pro Ala Thr Val Cys Gly Pro Lys Lys Ser Thr Asn Leu Val Lys
545                 550                 555                 560

Asn Lys Cys Val Asn Phe Asn Phe Asn Gly Leu Thr Gly Thr Gly Val
                565                 570                 575

Leu Thr Glu Ser Asn Lys Lys Phe Leu Pro Phe Gln Gln Phe Gly Arg
            580                 585                 590

Asp Ile Ala Asp Thr Thr Asp Ala Val Arg Asp Pro Gln Thr Leu Glu
        595                 600                 605

Ile Leu Asp Ile Thr Pro Cys Ser Phe Gly Gly Val Ser Val Ile Thr
    610                 615                 620

Pro Gly Thr Asn Thr Ser Asn Gln Val Ala Val Leu Tyr Gln Asp Val
625                 630                 635                 640

Asn Cys Thr Glu Val Pro Val Ala Ile His Ala Asp Gln Leu Thr Pro
                645                 650                 655

Thr Trp Arg Val Tyr Ser Thr Gly Ser Asn Val Phe Gln Thr Arg Ala
            660                 665                 670

Gly Cys Leu Ile Gly Ala Glu His Val Asn Asn Ser Tyr Glu Cys Asp
        675                 680                 685

Ile Pro Ile Gly Ala Gly Ile Cys Ala Ser Tyr Gln Thr Gln Thr Asn
    690                 695                 700

Ser Pro Arg Arg Ala Arg Ser Val Ala Ser Gln Ser Ile Ile Ala Tyr
705                 710                 715                 720

Thr Met Ser Leu Gly Ala Glu Asn Ser Val Ala Tyr Ser Asn Asn Ser
                725                 730                 735

Ile Ala Ile Pro Thr Asn Phe Thr Ile Ser Val Thr Thr Glu Ile Leu
            740                 745                 750

Pro Val Ser Met Thr Lys Thr Ser Val Asp Cys Thr Met Tyr Ile Cys
```

```
        755                 760                 765

Gly Asp Ser Thr Glu Cys Ser Asn Leu Leu Leu Gln Tyr Gly Ser Phe
    770                 775                 780

Cys Thr Gln Leu Asn Arg Ala Leu Thr Gly Ile Ala Val Glu Gln Asp
785                 790                 795                 800

Lys Asn Thr Gln Glu Val Phe Ala Gln Val Lys Gln Ile Tyr Lys Thr
                805                 810                 815

Pro Pro Ile Lys Asp Phe Gly Gly Phe Asn Phe Ser Gln Ile Leu Pro
            820                 825                 830

Asp Pro Ser Lys Pro Ser Lys Arg Ser Phe Ile Glu Asp Leu Leu Phe
        835                 840                 845

Asn Lys Val Thr Leu Ala Asp Ala Gly Phe Ile Lys Gln Tyr Gly Asp
    850                 855                 860

Cys Leu Gly Asp Ile Ala Ala Arg Asp Leu Ile Cys Ala Gln Lys Phe
865                 870                 875                 880

Asn Gly Leu Thr Val Leu Pro Pro Leu Leu Thr Asp Glu Met Ile Ala
                885                 890                 895

Gln Tyr Thr Ser Ala Leu Leu Ala Gly Thr Ile Thr Ser Gly Trp Thr
            900                 905                 910

Phe Gly Ala Gly Ala Ala Leu Gln Ile Pro Phe Ala Met Gln Met Ala
        915                 920                 925

Tyr Arg Phe Asn Gly Ile Gly Val Thr Gln Asn Val Leu Tyr Glu Asn
    930                 935                 940

Gln Lys Leu Ile Ala Asn Gln Phe Asn Ser Ala Ile Gly Lys Ile Gln
945                 950                 955                 960

Asp Ser Leu Ser Ser Thr Ala Ser Ala Leu Gly Lys Leu Gln Asp Val
                965                 970                 975

Val Asn Gln Asn Ala Gln Ala Leu Asn Thr Leu Val Lys Gln Leu Ser
            980                 985                 990

Ser Asn Phe Gly Ala Ile Ser Ser  Val Leu Asn Asp Ile  Leu Ser Arg
        995                 1000                1005

Leu Asp  Lys Val Glu Ala Glu  Val Gln Ile Asp Arg  Leu Ile Thr
    1010                1015                1020

Gly Arg  Leu Gln Ser Leu Gln  Thr Tyr Val Thr Gln  Gln Leu Ile
    1025                1030                1035

Arg Ala  Ala Glu Ile Arg Ala  Ser Ala Asn Leu Ala  Ala Thr Lys
    1040                1045                1050

Met Ser  Glu Cys Val Leu Gly  Gln Ser Lys Arg Val  Asp Phe Cys
    1055                1060                1065

Gly Lys  Gly Tyr His Leu Met  Ser Phe Pro Gln Ser  Ala Pro His
    1070                1075                1080

Gly Val  Val Phe Leu His Val  Thr Tyr Val Pro Ala  Gln Glu Lys
    1085                1090                1095

Asn Phe  Thr Thr Ala Pro Ala  Ile Cys His Asp Gly  Lys Ala His
    1100                1105                1110

Phe Pro  Arg Glu Gly Val Phe  Val Ser Asn Gly Thr  His Trp Phe
    1115                1120                1125

Val Thr  Gln Arg Asn Phe Tyr  Glu Pro Gln Ile Ile  Thr Thr Asp
    1130                1135                1140

Asn Thr  Phe Val Ser Gly Asn  Cys Asp Val Val Ile  Gly Ile Val
    1145                1150                1155

Asn Asn  Thr Val Tyr Asp Pro  Leu Gln Pro Glu Leu  Asp Ser Phe
    1160                1165                1170
```

```
Lys Glu  Glu Leu Asp Lys Tyr  Phe Lys Asn His Thr  Ser Pro Asp
    1175                 1180                 1185

Val Asp  Leu Gly Asp Ile Ser  Gly Ile Asn Ala Ser  Val Val Asn
    1190                 1195                 1200

Ile Gln  Lys Glu Ile Asp Arg  Leu Asn Glu Val Ala  Lys Asn Leu
    1205                 1210                 1215

Asn Glu  Ser Leu Ile Asp Leu  Gln Glu Leu Gly Lys  Tyr Glu Gln
    1220                 1225                 1230

Tyr Ile  Lys Trp Pro Trp Tyr  Ile Trp Leu Gly Phe  Ile Ala Gly
    1235                 1240                 1245

Leu Ile  Ala Ile Val Met Val  Thr Ile Met Leu Cys  Cys Met Thr
    1250                 1255                 1260

Ser Cys  Cys Ser Cys Leu Lys  Gly Cys Cys Ser Cys  Gly Ser Cys
    1265                 1270                 1275

Cys Lys  Phe Asp Glu Asp Asp  Ser Glu Pro Val Leu  Lys Gly Val
    1280                 1285                 1290

Lys Leu  His Tyr Thr
    1295
```

<210> SEQ ID NO 7
<211> LENGTH: 3897
<212> TYPE: DNA
<213> ORGANISM: Artificial Sequence
<220> FEATURE:
<223> OTHER INFORMATION: spike fusion construct dna

<400> SEQUENCE: 7

```
atgttcgttt ttctcgttct cctcccgctt gtgagcagct atccgtatga tgtgccggat     60

tatgcgggtg gaggctctgg aggtggctct ggtggaggtt ccggtggcgg atctcaatgt    120

gtcaacctca ccacaaggac acagctccct cccgcatata cgaatagctt taccagaggc    180

gtatactatc ctgataaggt ctttaggagc tcagtactgc atagcactca ggatctcttc    240

ctgccgttct tcagtaatgt tacttggttt cacgccattc atgtttccgg gaccaatggc    300

accaaacggt tcgataatcc agtgcttccc ttcaacgatg ggtgtactt  tgccagcact    360

gaaaaatcta atataattcg ggatggattt ttcggaacca cactcgattc caagactcag    420

tccctcttga tcgttaacaa cgctactaat gttgtcatta aggtgtgtga gtttcagttc    480

tgcaacgacc ctttcctggg tgtctactac cataaaaata acaagagctg gatggagtcc    540

gaatttcgcg tctactcaag cgccaataat tgcacttttg agtatgtgtc ccagcccttt    600

ttgatggatc tggagggaaa gcagggcaat ttcaaaaatc tgagagaatt cgtttttaag    660

aatatagatg gatacttcaa aatctacagc aaacacacac ccataaatct tgtgcgcgat    720

cttccccagg gcttcagcgc gttggaaccc cttgttgact tgcccatagg catcaacatt    780

accaggttcc aaacgctgct cgccctccac cgcagctact tgacacccgg ggattccagc    840

tccggatgga ccgccggcgc cgcagcgtat tatgtggggt acctgcaacc caggacattt    900

ttgctcaagt acaatgagaa tgggaccatc acagatgcgg tagactgtgc actggatcca    960

ctcagcgaaa ctaaatgtac cctgaaaagc tttaccgtgg agaaaggaat ctaccaaacc   1020

agcaacttca gggtccagcc cactgaatcc atcgttagat ttccaaatat aactaatttg   1080

tgtccatttg gagaggtgtt caatgctaca aggttcgcgt ctgtatacgc ttggaaccgg   1140

aagcgcatct caaattgcgt ggctgattat agcgttcttt acaacagcgc ttccttttcc   1200

acgttcaagt gctatggtgt atccccgaca aagctgaatg acttgtgctt caccaatgtg   1260
```

```
tatgcggatt ctttcgttat tcgaggcgat gaagtcagac aaattgcgcc tggccagacc   1320
ggaaagattg ccgactacaa ctataaactg ccggacgact ttactggttg cgtgatcgct   1380
tggaacagca ataatcttga tagtaaagtt ggaggaaact acaattacct ctatagactg   1440
ttcagaaaga gcaacttgaa gccattcgaa cgggatatct ctacggagat ctatcaagct   1500
ggcagcaccc cctgcaatgg tgtggaaggc tttaattgtt attttccttt gcagagctat   1560
ggcttccaac ctaccaacgg agtgggctac cagccctaca gagtggtggt gctcagcttt   1620
gaactgctgc atgccccggc cacagtttgc gggcccaaaa aaagcacgaa tctggttaag   1680
aacaaatgcg tcaacttcaa ttttaatggg ttgacaggta caggcgtact gaccgaatcc   1740
aacaaaaagt tcctgccttt tcagcagttc gggagagata tcgccgacac tacagacgcc   1800
gtcagggatc cccaaacact cgaaattctg gacatcacac cttgttcctt cggcggggta   1860
tctgtgatta ctccgggcac aaataccagt aaccaggtag cggtgcttta ccaggatgtc   1920
aactgtacgg aagtacctgt cgctattcat gcggatcaac tcactcctac ctggagagtt   1980
tattccactg ggtccaacgt gtttcagacc cgagccggct gcttgattgg cgcggaacat   2040
gttaacaact cctacgaatg tgacatccct atcggagctg gcatctgtgc ttcctatcaa   2100
acgcaaacga acagcccacg gcgggccaga tccgtagcct ctcaaagcat catcgcttat   2160
actatgtcct tgggggctga aaacagcgtt gcctattcca acaatagcat cgctatccct   2220
accaacttta ccatttccgt gaccacagaa atactgccgg tgagcatgac aaagacttct   2280
gtggactgta ccatgtatat atgcggcgat agcacagagt gttctaattt gctgctgcag   2340
tacggcagct tttgtaccca actcaacaga gcacttacag ggattgccgt cgagcaggat   2400
aaaaacaccc aggaggtttt cgcccaggtt aagcagatct acaagacccc accaatcaag   2460
gatttcggcg gcttcaattt ttcccagata ctgcccgatc cttccaagcc atccaaaagg   2520
agctttatag aggatctgct gttcaacaag gtgactctgg ccgacgctgg ctttatcaag   2580
caatatggcg attgcctggg ggatattgcc gctagggacc ttatctgcgc tcaaaaattc   2640
aacggtctta ccgttctccc gcccctgctc accgacgaga tgatagccca gtacacgagc   2700
gcacttttgg ccggcacgat aaccagcggc tggacattcg gtgccggggc cgctcttcaa   2760
atcccctttg ccatgcagat ggcctacaga tttaatggga taggcgtgac acaaaatgtc   2820
ttgtatgaaa atcagaaact gattgcaaac cagtttaata gcgctattgg caagatccaa   2880
gatagccttt cctccaccgc atccgctctg ggaaagttgc aagacgtcgt gaatcaaaac   2940
gcccaagctc tgaataccct cgtgaagcag cttagctcca actttggcgc gatatcctcc   3000
gtgctgaacg atatcctgtc cagattggac aaggtcgagg cagaagtcca gatcgataga   3060
ttgataaccg gcagactcca gtctctgcag acatatgtga ctcagcagtt gataagagcg   3120
gccgaaatac gagcgtctgc aaatctcgca gcaacgaaaa tgtcagagtg tgtattgggg   3180
caaagtaaaa gagtagattt ctgtggaaag ggttaccatc tgatgtcatt cccccagtct   3240
gcaccacatg gagtagtttt tttgcatgtg acttatgtgc ctgcccagga gaaaaatttc   3300
accactgcac ctgcgatctg tcatgacggc aaggcacatt tccctagaga aggcgtcttc   3360
gtatcaaatg gaacacactg gtttgtaacc caaaggaact tttacgagcc ccaaattata   3420
actaccgaca acaccttcgt aagcggaaac tgcgacgtcg ttatagggat agtcaataat   3480
acggtctatg accctcttca gccggaactg gactccttta aagaagaact ggataagtac   3540
ttcaagaacc atacgtctcc ggatgtggat ctcggagata taagtggaat caacgcaagc   3600
```

```
gtagtaaaca ttcagaagga gatagaccga ctcaatgagg ttgctaaaaa cctgaacgaa   3660

agcttgatag acttgcagga gctgggtaag tacgaacagt acattaagtg gccatggtat   3720

atctggttgg gcttcatagc aggactcata gctatcgtca tggtgacaat aatgctttgt   3780

tgtatgacca gctgttgttc ttgtctgaaa ggctgctgca gctgtggcag ctgttgtaaa   3840

tttgacgaag atgattccga gcctgtgctt aagggcgtaa aactccacta tacatga      3897
```

```
<210> SEQ ID NO 8
<211> LENGTH: 805
<212> TYPE: PRT
<213> ORGANISM: Artificial Sequence
<220> FEATURE:
<223> OTHER INFORMATION: Human ACE2 protein

<400> SEQUENCE: 8

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320
```

```
Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735
```

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 9
<211> LENGTH: 594
<212> TYPE: PRT
<213> ORGANISM: Artificial Sequence
<220> FEATURE:
<223> OTHER INFORMATION: Soluble ACE2 mutant constructs
<220> FEATURE:
<221> NAME/KEY: MISC_FEATURE
<222> LOCATION: (4)..(4)
<223> OTHER INFORMATION: Can be Gln or Leu
<220> FEATURE:
<221> NAME/KEY: MISC_FEATURE
<222> LOCATION: (7)..(7)
<223> OTHER INFORMATION: Can be Thr, Phe, Trp, or Tyr
<220> FEATURE:
<221> NAME/KEY: MISC_FEATURE
<222> LOCATION: (10)..(10)
<223> OTHER INFORMATION: Can be Asp, Glu, Leu
<220> FEATURE:
<221> NAME/KEY: MISC_FEATURE
<222> LOCATION: (14)..(14)
<223> OTHER INFORMATION: Can be His, Glu, Phe, Lys, Met, Trp, Tyr, or Ala
<220> FEATURE:
<221> NAME/KEY: MISC_FEATURE
<222> LOCATION: (18)..(18)
<223> OTHER INFORMATION: Can be Asp, Glu, Met, or Phe
<220> FEATURE:
<221> NAME/KEY: MISC_FEATURE
<222> LOCATION: (335)..(335)
<223> OTHER INFORMATION: Can be Asp or Leu

<400> SEQUENCE: 9

Ile Glu Glu Xaa Ala Lys Xaa Phe Leu Xaa Lys Phe Asn Xaa Glu Ala
1               5                   10                  15

Glu Xaa Leu Phe Tyr Gln Ser Ser Leu Ala Ser Trp Asn Tyr Asn Thr
            20                  25                  30

Asn Ile Thr Glu Glu Asn Val Gln Asn Met Asn Asn Ala Gly Asp Lys
        35                  40                  45

Trp Ser Ala Phe Leu Lys Glu Gln Ser Thr Leu Ala Gln Met Tyr Pro
    50                  55                  60

Leu Gln Glu Ile Gln Asn Leu Thr Val Lys Leu Gln Leu Gln Ala Leu
65                  70                  75                  80

Gln Gln Asn Gly Ser Ser Val Leu Ser Glu Asp Lys Ser Lys Arg Leu
                85                  90                  95

Asn Thr Ile Leu Asn Thr Met Ser Thr Ile Tyr Ser Thr Gly Lys Val
            100                 105                 110

Cys Asn Pro Asp Asn Pro Gln Glu Cys Leu Leu Leu Glu Pro Gly Leu
        115                 120                 125

Asn Glu Ile Met Ala Asn Ser Leu Asp Tyr Asn Glu Arg Leu Trp Ala
    130                 135                 140

Trp Glu Ser Trp Arg Ser Glu Val Gly Lys Gln Leu Arg Pro Leu Tyr
145                 150                 155                 160

```
Glu Glu Tyr Val Val Leu Lys Asn Glu Met Ala Arg Ala Asn His Tyr
                165                 170                 175

Glu Asp Tyr Gly Asp Tyr Trp Arg Gly Asp Tyr Glu Val Asn Gly Val
            180                 185                 190

Asp Gly Tyr Asp Tyr Ser Arg Gly Gln Leu Ile Glu Asp Val Glu His
        195                 200                 205

Thr Phe Glu Glu Ile Lys Pro Leu Tyr Glu His Leu His Ala Tyr Val
    210                 215                 220

Arg Ala Lys Leu Met Asn Ala Tyr Pro Ser Tyr Ile Ser Pro Ile Gly
225                 230                 235                 240

Cys Leu Pro Ala His Leu Leu Gly Asp Met Trp Gly Arg Phe Trp Thr
                245                 250                 255

Asn Leu Tyr Ser Leu Thr Val Pro Phe Gly Gln Lys Pro Asn Ile Asp
            260                 265                 270

Val Thr Asp Ala Met Val Asp Gln Ala Trp Asp Ala Gln Arg Ile Phe
        275                 280                 285

Lys Glu Ala Glu Lys Phe Phe Val Ser Val Gly Leu Pro Asn Met Thr
    290                 295                 300

Gln Gly Phe Trp Glu Asn Ser Met Leu Thr Asp Pro Gly Asn Val Gln
305                 310                 315                 320

Lys Ala Val Cys His Pro Thr Ala Trp Asp Leu Gly Lys Gly Xaa Phe
                325                 330                 335

Arg Ile Leu Met Cys Thr Lys Val Thr Met Asp Asp Phe Leu Thr Ala
            340                 345                 350

His His Glu Met Gly His Ile Gln Tyr Asp Met Ala Tyr Ala Ala Gln
        355                 360                 365

Pro Phe Leu Leu Arg Asn Gly Ala Asn Glu Gly Phe His Glu Ala Val
    370                 375                 380

Gly Glu Ile Met Ser Leu Ser Ala Ala Thr Pro Lys His Leu Lys Ser
385                 390                 395                 400

Ile Gly Leu Leu Ser Pro Asp Phe Gln Glu Asp Asn Glu Thr Glu Ile
                405                 410                 415

Asn Phe Leu Leu Lys Gln Ala Leu Thr Ile Val Gly Thr Leu Pro Phe
            420                 425                 430

Thr Tyr Met Leu Glu Lys Trp Arg Trp Met Val Phe Lys Gly Glu Ile
        435                 440                 445

Pro Lys Asp Gln Trp Met Lys Lys Trp Trp Glu Met Lys Arg Glu Ile
    450                 455                 460

Val Gly Val Val Glu Pro Val Pro His Asp Glu Thr Tyr Cys Asp Pro
465                 470                 475                 480

Ala Ser Leu Phe His Val Ser Asn Asp Tyr Ser Phe Ile Arg Tyr Tyr
                485                 490                 495

Thr Arg Thr Leu Tyr Gln Phe Gln Phe Gln Glu Ala Leu Cys Gln Ala
            500                 505                 510

Ala Lys His Glu Gly Pro Leu His Lys Cys Asp Ile Ser Asn Ser Thr
        515                 520                 525

Glu Ala Gly Gln Lys Leu Phe Asn Met Leu Arg Leu Gly Lys Ser Glu
    530                 535                 540

Pro Trp Thr Leu Ala Leu Glu Asn Val Val Gly Ala Lys Asn Met Asn
545                 550                 555                 560

Val Arg Pro Leu Leu Asn Tyr Phe Glu Pro Leu Phe Thr Trp Leu Lys
                565                 570                 575
```

```
Asp Gln Asn Lys Asn Ser Phe Val Gly Trp Ser Thr Asp Trp Ser Pro
            580                 585                 590

Tyr Ala


<210> SEQ ID NO 10
<211> LENGTH: 1298
<212> TYPE: PRT
<213> ORGANISM: Artificial Sequence
<220> FEATURE:
<223> OTHER INFORMATION: SARS-CoV2 spike mutant (p35)

<400> SEQUENCE: 10

Met Phe Val Phe Leu Val Leu Leu Pro Leu Val Ser Ser Tyr Pro Tyr
1               5                   10                  15

Asp Val Pro Asp Tyr Ala Gly Gly Gly Ser Gly Gly Gly Ser Gly Gly
            20                  25                  30

Gly Ser Gly Gly Gly Ser Gln Cys Val Asn Leu Thr Thr Arg Thr Gln
        35                  40                  45

Leu Pro Pro Ala Tyr Thr Asn Ser Phe Thr Arg Gly Val Tyr Tyr Pro
    50                  55                  60

Asp Lys Val Phe Arg Ser Ser Val Leu His Ser Thr Gln Asp Leu Phe
65                  70                  75                  80

Leu Pro Phe Phe Ser Asn Val Thr Trp Phe His Ala Ile His Val Ser
                85                  90                  95

Gly Thr Asn Gly Thr Lys Arg Phe Asp Asn Pro Val Leu Pro Phe Asn
            100                 105                 110

Asp Gly Val Tyr Phe Ala Ser Thr Glu Lys Ser Asn Ile Ile Arg Gly
        115                 120                 125

Trp Ile Phe Gly Thr Thr Leu Asp Ser Lys Thr Gln Ser Leu Leu Ile
    130                 135                 140

Val Asn Asn Ala Thr Asn Val Val Ile Lys Val Cys Glu Phe Gln Phe
145                 150                 155                 160

Cys Asn Asp Pro Phe Leu Gly Val Tyr Tyr His Lys Asn Asn Lys Ser
                165                 170                 175

Trp Met Glu Ser Glu Phe Arg Val Tyr Ser Ser Ala Asn Asn Cys Thr
            180                 185                 190

Phe Glu Tyr Val Ser Gln Pro Phe Leu Met Asp Leu Glu Gly Lys Gln
        195                 200                 205

Gly Asn Phe Lys Asn Leu Arg Glu Phe Val Phe Lys Asn Ile Asp Gly
    210                 215                 220

Tyr Phe Lys Ile Tyr Ser Lys His Thr Pro Ile Asn Leu Val Arg Asp
225                 230                 235                 240

Leu Pro Gln Gly Phe Ser Ala Leu Glu Pro Leu Val Asp Leu Pro Ile
                245                 250                 255

Gly Ile Asn Ile Thr Arg Phe Gln Thr Leu Leu Ala Leu His Arg Ser
            260                 265                 270

Tyr Leu Thr Pro Gly Asp Ser Ser Ser Gly Trp Thr Ala Gly Ala Ala
        275                 280                 285

Ala Tyr Tyr Val Gly Tyr Leu Gln Pro Arg Thr Phe Leu Leu Lys Tyr
    290                 295                 300

Asn Glu Asn Gly Thr Ile Thr Asp Ala Val Asp Cys Ala Leu Asp Pro
305                 310                 315                 320

Leu Ser Glu Thr Lys Cys Thr Leu Lys Ser Phe Thr Val Glu Lys Gly
                325                 330                 335

Ile Tyr Gln Thr Ser Asn Phe Arg Val Gln Pro Thr Glu Ser Ile Val
```

```
            340                 345                 350

Arg Phe Pro Asn Ile Thr Asn Leu Cys Pro Phe Gly Glu Val Phe Asn
        355                 360                 365

Ala Thr Arg Phe Ala Ser Val Tyr Ala Trp Asn Arg Lys Arg Ile Ser
    370                 375                 380

Asn Cys Val Ala Asp Tyr Ser Val Leu Tyr Asn Ser Ala Ser Phe Ser
385                 390                 395                 400

Thr Phe Lys Cys Tyr Gly Val Ser Pro Thr Lys Leu Asn Asp Leu Cys
                405                 410                 415

Phe Thr Asn Val Tyr Ala Asp Ser Phe Val Ile Arg Gly Asp Glu Val
            420                 425                 430

Arg Gln Ile Ala Pro Gly Gln Thr Gly Lys Ile Ala Asp Tyr Asn Tyr
        435                 440                 445

Lys Leu Pro Asp Asp Phe Thr Gly Cys Val Ile Ala Trp Asn Ser Asn
    450                 455                 460

Asn Leu Asp Ser Lys Val Gly Gly Asn Tyr Asn Tyr Leu Tyr Arg Leu
465                 470                 475                 480

Phe Arg Lys Ser Asn Leu Lys Pro Phe Glu Arg Asp Ile Ser Thr Glu
                485                 490                 495

Ile Tyr Gln Ala Gly Ser Thr Pro Cys Asn Gly Val Glu Gly Phe Asn
            500                 505                 510

Cys Tyr Phe Pro Leu Gln Ser Tyr Gly Phe Gln Pro Thr Asn Gly Val
        515                 520                 525

Gly Tyr Gln Pro Tyr Arg Val Val Val Leu Ser Phe Glu Leu Leu His
    530                 535                 540

Ala Pro Ala Thr Val Cys Gly Pro Lys Lys Ser Thr Asn Leu Val Lys
545                 550                 555                 560

Asn Lys Cys Val Asn Phe Asn Phe Asn Gly Leu Thr Gly Thr Gly Val
                565                 570                 575

Leu Thr Glu Ser Asn Lys Lys Phe Leu Pro Phe Gln Gln Phe Gly Arg
            580                 585                 590

Asp Ile Ala Asp Thr Thr Asp Ala Val Arg Asp Pro Gln Thr Leu Glu
        595                 600                 605

Ile Leu Asp Ile Thr Pro Cys Ser Phe Gly Gly Val Ser Val Ile Thr
    610                 615                 620

Pro Gly Thr Asn Thr Ser Asn Gln Val Ala Val Leu Tyr Gln Asp Val
625                 630                 635                 640

Asn Cys Thr Glu Val Pro Val Ala Ile His Ala Asp Gln Leu Thr Pro
                645                 650                 655

Thr Trp Arg Val Tyr Ser Thr Gly Ser Asn Val Phe Gln Thr Arg Ala
            660                 665                 670

Gly Cys Leu Ile Gly Ala Glu His Val Asn Asn Ser Tyr Glu Cys Asp
        675                 680                 685

Ile Pro Ile Gly Ala Gly Ile Cys Ala Ser Tyr Gln Thr Gln Thr Asn
    690                 695                 700

Ser Pro Ser Ala Ala Gly Ser Val Ala Ser Gln Ser Ile Ile Ala Tyr
705                 710                 715                 720

Thr Met Ser Leu Gly Ala Glu Asn Ser Val Ala Tyr Ser Asn Asn Ser
                725                 730                 735

Ile Ala Ile Pro Thr Asn Phe Thr Ile Ser Val Thr Thr Glu Ile Leu
            740                 745                 750

Pro Val Ser Met Thr Lys Thr Ser Val Asp Cys Thr Met Tyr Ile Cys
        755                 760                 765
```

```
Gly Asp Ser Thr Glu Cys Ser Asn Leu Leu Leu Gln Tyr Gly Ser Phe
    770                 775                 780

Cys Thr Gln Leu Asn Arg Ala Leu Thr Gly Ile Ala Val Glu Gln Asp
785                 790                 795                 800

Lys Asn Thr Gln Glu Val Phe Ala Gln Val Lys Gln Ile Tyr Lys Thr
                805                 810                 815

Pro Pro Ile Lys Asp Phe Gly Gly Phe Asn Phe Ser Gln Ile Leu Pro
            820                 825                 830

Asp Pro Ser Lys Pro Ser Lys Arg Ser Phe Ile Glu Asp Leu Leu Phe
        835                 840                 845

Asn Lys Val Thr Leu Ala Asp Ala Gly Phe Ile Lys Gln Tyr Gly Asp
    850                 855                 860

Cys Leu Gly Asp Ile Ala Ala Arg Asp Leu Ile Cys Ala Gln Lys Phe
865                 870                 875                 880

Asn Gly Leu Thr Val Leu Pro Pro Leu Leu Thr Asp Glu Met Ile Ala
                885                 890                 895

Gln Tyr Thr Ser Ala Leu Leu Ala Gly Thr Ile Thr Ser Gly Trp Thr
            900                 905                 910

Phe Gly Ala Gly Ala Ala Leu Gln Ile Pro Phe Ala Met Gln Met Ala
        915                 920                 925

Tyr Arg Phe Asn Gly Ile Gly Val Thr Gln Asn Val Leu Tyr Glu Asn
    930                 935                 940

Gln Lys Leu Ile Ala Asn Gln Phe Asn Ser Ala Ile Gly Lys Ile Gln
945                 950                 955                 960

Asp Ser Leu Ser Ser Thr Ala Ser Ala Leu Gly Lys Leu Gln Asp Val
                965                 970                 975

Val Asn Gln Asn Ala Gln Ala Leu Asn Thr Leu Val Lys Gln Leu Ser
            980                 985                 990

Ser Asn Phe Gly Ala Ile Ser Ser  Val Leu Asn Asp Ile  Leu Ser Arg
        995                 1000                 1005

Leu Asp  Lys Val Glu Ala Glu  Val Gln Ile Asp Arg  Leu Ile Thr
    1010                 1015                 1020

Gly Arg  Leu Gln Ser Leu Gln  Thr Tyr Val Thr Gln  Gln Leu Ile
    1025                 1030                 1035

Arg Ala  Ala Glu Ile Arg Ala  Ser Ala Asn Leu Ala  Ala Thr Lys
    1040                 1045                 1050

Met Ser  Glu Cys Val Leu Gly  Gln Ser Lys Arg Val  Asp Phe Cys
    1055                 1060                 1065

Gly Lys  Gly Tyr His Leu Met  Ser Phe Pro Gln Ser  Ala Pro His
    1070                 1075                 1080

Gly Val  Val Phe Leu His Val  Thr Tyr Val Pro Ala  Gln Glu Lys
    1085                 1090                 1095

Asn Phe  Thr Thr Ala Pro Ala  Ile Cys His Asp Gly  Lys Ala His
    1100                 1105                 1110

Phe Pro  Arg Glu Gly Val Phe  Val Ser Asn Gly Thr  His Trp Phe
    1115                 1120                 1125

Val Thr  Gln Arg Asn Phe Tyr  Glu Pro Gln Ile Ile  Thr Thr Asp
    1130                 1135                 1140

Asn Thr  Phe Val Ser Gly Asn  Cys Asp Val Val Ile  Gly Ile Val
    1145                 1150                 1155

Asn Asn  Thr Val Tyr Asp Pro  Leu Gln Pro Glu Leu  Asp Ser Phe
    1160                 1165                 1170
```

```
Lys Glu  Glu Leu Asp Lys Tyr  Phe Lys Asn His Thr  Ser Pro Asp
    1175                 1180                 1185

Val Asp  Leu Gly Asp Ile Ser  Gly Ile Asn Ala Ser  Val Val Asn
    1190                 1195                 1200

Ile Gln  Lys Glu Ile Asp Arg  Leu Asn Glu Val Ala  Lys Asn Leu
    1205                 1210                 1215

Asn Glu  Ser Leu Ile Asp Leu  Gln Glu Leu Gly Lys  Tyr Glu Gln
    1220                 1225                 1230

Tyr Ile  Lys Trp Pro Trp Tyr  Ile Trp Leu Gly Phe  Ile Ala Gly
    1235                 1240                 1245

Leu Ile  Ala Ile Val Met Val  Thr Ile Met Leu Cys  Cys Met Thr
    1250                 1255                 1260

Ser Cys  Cys Ser Cys Leu Lys  Gly Cys Cys Ser Cys  Gly Ser Cys
    1265                 1270                 1275

Cys Lys  Phe Asp Glu Asp Asp  Ser Glu Pro Val Leu  Lys Gly Val
    1280                 1285                 1290

Lys Leu  His Tyr Thr
    1295
```

<210> SEQ ID NO 11
<211> LENGTH: 40866
<212> TYPE: DNA
<213> ORGANISM: Artificial Sequence
<220> FEATURE:
<223> OTHER INFORMATION: p35 vector sequence

<400> SEQUENCE: 11

```
tattattgat gatgttaatt aacatgcatg gatcctacgt ctcgaccgat gcccttgaga     60

gccttcaacc cagtcagctc cttccggtgg gcgcggggca tgactatcgt cgccgcactt    120

atgactgtct tctttatcat gcaactcgta ggacaggtgc cggcagcgct ctgggtcatt    180

ttcggcgagg accgctttcg ctggagcgcg acgatgatcg gcctgtcgct tgcggtattc    240

ggaatcttgc acgccctcgc tcaagccttc gtcactggtc ccgccaccaa acgtttcggc    300

gagaagcagg ccattatcgc cggcatggcg gccgacgcgc tgggctacgt cttgctggcg    360

ttcgcgacgc gaggctggat ggccttcccc attatgattc ttctcgcttc cggcggcatc    420

gggatgcccg cgttgcaggc catgctgtcc aggcaggtag atgacgacca tcagggacag    480

cttcaaggat cgctcgcggc tcttaccagc ctaacttcga tcattggacc gctgatcgtc    540

acggcgattt atgccgcctc ggcgagcaca tggaacgggt tggcatggat tgtaggcgcc    600

gccctatacc ttgtctgcct ccccgcgttg cgtcgcggtg catggagccg ggccacctcg    660

acctgaatgg aagccggcgg cacctcgcta acggattcac cactccaaga attggagcca    720

atcaattctt gcggagaact gtgaatgcgc aaaccaaccc ttggcagaac atatccatcg    780

cgtccgccat ctccagcagc cgcacgcggc gcatctcggg cagcgttggg tcctggccac    840

gggtgcgcat gatcgtgctc ctgtcgttga ggacccggct aggctggcgg ggttgcctta    900

ctggttagca gaatgaatca ccgatacgcg agcgaacgtg aagcgactgc tgctgcaaaa    960

cgtctgcgac ctgagcaaca acatgaatgg tcttcggttt ccgtgtttcg taaagtctgg   1020

aaacgcggaa gtcagcgccc tgcaccatta tgttccggat ctgcatcgca ggatgctgct   1080

ggctaccctg tggaacacct acatctgtat taacgaagcg ctggcattga ccctgagtga   1140

tttttctctg gtcccgccgc atccataccg ccagttgttt accctcacaa cgttccagta   1200

accgggcatg ttcatcatca gtaacccgta tcgtgagcat cctctctcgt ttcatcggta   1260
```

-continued

```
tcattacccc catgaacaga aatccccctt acacggaggc atcagtgacc aaacaggaaa   1320
aaaccgccct taacatggcc cgctttatca gaagccagac attaacgctt ctggagaaac   1380
tcaacgagct ggacgcggat gaacaggcag acatctgtga atcgcttcac gaccacgctg   1440
atgagcttta ccgcagctgc ctcgcgcgtt tcggtgatga cggtgaaaac ctctgacaca   1500
tgcagctccc ggagacggtc acagcttgtc tgtaagcgga tgccgggagc agacaagccc   1560
gtcagggcgc gtcagcgggt gttggcgggt gtcggggcgc agccatgacc cagtcacgta   1620
gcgatagcgg agtgtatact ggcttaacta tgcggcatca gagcagattg tactgagagt   1680
gcaccatatg cggtgtgaaa taccgcacag atgcgtaagg agaaaatacc gcatcaggcg   1740
ctcttccgct tcctcgctca ctgactcgct gcgctcggtc gttcggctgc ggcgagcggt   1800
atcagctcac tcaaaggcgg taatacggtt atccacagaa tcaggggata acgcaggaaa   1860
gaacatgtga gcaaaaggcc agcaaaaggc caggaaccgt aaaaaggccg cgttgctggc   1920
gtttttccat aggctccgcc cccctgacga gcatcacaaa aatcgacgct caagtcagag   1980
gtggcgaaac ccgacaggac tataaagata ccaggcgttt ccccctggaa gctccctcgt   2040
gcgctctcct gttccgaccc tgccgcttac cggatacctg tccgcctttc tcccttcggg   2100
aagcgtggcg ctttctcata gctcacgctg taggtatctc agttcggtgt aggtcgttcg   2160
ctccaagctg ggctgtgtgc acgaaccccc cgttcagccc gaccgctgcg ccttatccgg   2220
taactatcgt cttgagtcca acccggtaag acacgactta tcgccactgg cagcagccac   2280
tggtaacagg attagcagag cgaggtatgt aggcggtgct acagagttct tgaagtggtg   2340
gcctaactac ggctacacta gaaggacagt atttggtatc tgcgctctgc tgaagccagt   2400
taccttcgga aaaagagttg gtagctcttg atccggcaaa caaaccaccg ctggtagcgg   2460
tggttttttt gtttgcaagc agcagattac gcgcagaaaa aaaggatctc aagaagatcc   2520
tttgatcttt tctacggggt ctgacgctca gtggaacgaa aactcacgtt aagggatttt   2580
ggtcatgaga ttatcaaaaa ggatcttcac ctagatcctt ttaaattaaa aatgaagttt   2640
taaatcaatc taaagtatat atgagtaaac ttggtctgac agttaccaat gcttaatcag   2700
tgaggcacct atctcagcga tctgtctatt tcgttcatcc atagttgcct gactccccgt   2760
cgtgtagata actacgatac gggagggctt accatctggc cccagtgctg caatgatacc   2820
gcgagaccca cgctcaccgg ctccagattt atcagcaata aaccagccag ccggaagggc   2880
cgagcgcaga agtggtcctg caactttatc cgcctccatc cagtctatta attgttgccg   2940
ggaagctaga gtaagtagtt cgccagttaa tagtttgcgc aacgttgttg ccattgctgc   3000
agccatgaga ttatcaaaaa ggatcttcac ctagatcctt ttcacgtaga aagccagtcc   3060
gcagaaacgg tgctgacccc ggatgaatgt cagctactgg gctatctgga caagggaaaa   3120
cgcaagcgca aagagaaagc aggtagcttg cagtgggctt acatggcgat agctagactg   3180
ggcggtttta tggacagcaa gcgaaccgga attgccagct ggggcgccct ctggtaaggt   3240
tgggaagccc tgcaaagtaa actggatggc tttcttgccg ccaaggatct gatggcgcag   3300
gggatcaagc tctgatcaag agacaggatg aggatcgttt cgcatgattg aacaagatgg   3360
attgcacgca ggttctccgg ccgcttgggt ggagaggcta ttcggctatg actgggcaca   3420
acagacaatc ggctgctctg atgccgccgt gttccggctg tcagcgcagg ggcgcccggt   3480
tctttttgtc aagaccgacc tgtccggtgc cctgaatgaa ctgcaagacg aggcagcgcg   3540
gctatcgtgg ctggccacga cgggcgttcc ttgcgcagct gtgctcgacg ttgtcactga   3600
agcgggaagg gactggctgc tattgggcga agtgccgggg caggatctcc tgtcatctca   3660
```

```
ccttgctcct gccgagaaag tatccatcat ggctgatgca atgcggcggc tgcatacgct   3720
tgatccggct acctgcccat tcgaccacca agcgaaacat cgcatcgagc gagcacgtac   3780
tcggatggaa gccggtcttg tcgatcagga tgatctggac gaagagcatc aggggctcgc   3840
gccagccgaa ctgttcgcca ggctcaaggc gagcatgccc gacggcgagg atctcgtcgt   3900
gacccatggc gatgcctgct tgccgaatat catggtggaa aatggccgct tttctggatt   3960
catcgactgt ggccggctgg gtgtggcgga ccgctatcag gacatagcgt tggctacccg   4020
tgatattgct gaagagcttg gcggcgaatg ggctgaccgc ttcctcgtgc tttacggtat   4080
cgccgctccc gattcgcagc gcatcgcctt ctatcgcctt cttgacgagt tcttctgaat   4140
tttgttaaaa tttttgttaa atcagctcat tttttaacca ataggccgaa atcggcaaaa   4200
tcccttataa atcaaaagaa tagaccgaga tagggttgag tgttgttcca gtttggaaca   4260
agagtccact attaaagaac gtggactcca acgtcaaagg gcgaaaaacc gtctatcagg   4320
gcgatggccc actacgtgaa ccatcaccct aatcaagttt tttggggtcg aggtgccgta   4380
aagcactaaa tcggaaccct aaagggagcc cccgatttag agcttgacgg ggaaagccgg   4440
cgaacgtggc gagaaaggaa gggaagaaag cgaaaggagc gggcgctagg gcgctggcaa   4500
gtgtagcggt cacgctgcgc gtaaccacca cacccgccgc gcttaatgcg ccgctacagg   4560
gcgcgtccat tcgccattca ggatcgaatt aattcttaat taacatcatc aataatatac   4620
cttattttgg attgaagcca atatgataat gagggggtgg agtttgtgac gtggcgcggg   4680
gcgtgggaac ggggcgggtg acgtagtagt gtggcggaag tgtgatgttg caagtgtggc   4740
ggaacacatg taagcgacgg atgtggcaaa agtgacgttt ttggtgtgcg ccggtgtaca   4800
caggaagtga caattttcgc gcggttttag gcggatgttg tagtaaattt gggcgtaacc   4860
gagtaagatt tggccatttt cgcgggaaaa ctgaataaga ggaagtgaaa tctgaataat   4920
tttgtgttac tcatagcgcg taatactgta atagtaatca attacggggt cattagttca   4980
tagcccatat atggagttcc gcgttacata acttacggta aatggcccgc ctggctgacc   5040
gcccaacgac ccccgcccat tgacgtcaat aatgacgtat gttcccatag taacgccaat   5100
agggactttc cattgacgtc aatgggtgga gtatttacgg taaactgccc acttggcagt   5160
acatcaagtg tatcatatgc caagtacgcc ccctattgac gtcaatgacg gtaaatggcc   5220
cgcctggcat tatgcccagt acatgacctt atgggacttt cctacttggc agtacatcta   5280
cgtattagtc atcgctatta ccatggtgat gcggttttgg cagtacatca atgggcgtgg   5340
atagcggttt gactcacggg gatttccaag tctccacccc attgacgtca atgggagttt   5400
gttttggcac caaaatcaac gggactttcc aaaatgtcgt aacaactccg ccccattgac   5460
gcaaatgggc ggtaggcgtg tacggtggga ggtctatata agcagagctg gtttagtgaa   5520
ccgtcagatc cgctagagat ctggtaccgt cgacgcggcc gctcgagcct aagcttatgt   5580
tcgtttttct cgttctcctc ccgcttgtga gcagctatcc gtatgatgtg ccggattatg   5640
cgggtggagg ctctggaggt ggctctggtg gaggttccgg tggcggatct caatgtgtca   5700
acctcaccac aaggacacag ctccctcccg catatacgaa tagctttacc agaggcgtat   5760
actatcctga taaggtcttt aggagctcag tactgcatag cactcaggat ctcttcctgc   5820
cgttcttcag taatgttact tggtttcacg ccattcatgt ttccgggacc aatggcacca   5880
aacggttcga taatccagtg cttcccttca acgatggggt gtactttgcc agcactgaaa   5940
aatctaatat aattcgggga tggattttcg gaaccacact cgattccaag actcagtccc   6000
```

-continued

```
tcttgatcgt taacaacgct actaatgttg tcattaaggt gtgtgagttt cagttctgca   6060
acgacccttt cctgggtgtc tactaccata aaaataacaa gagctggatg gagtccgaat   6120
ttcgcgtcta ctcaagcgcc aataattgca cttttgagta tgtgtcccag cccttttga    6180
tggatctgga gggaaagcag ggcaatttca aaaatctgag agaattcgtt tttaagaata   6240
tagatggata cttcaaaatc tacagcaaac acacacccat aaatcttgtg cgcgatcttc   6300
cccagggctt cagcgcgttg gaacccttg ttgacttgcc cataggcatc aacattacca    6360
ggttccaaac gctgctcgcc ctccaccgca gctacttgac acccggggat tccagctccg   6420
gatggaccgc cggcgccgca gcgtattatg tggggtacct gcaacccagg acatttttgc   6480
tcaagtacaa tgagaatggg accatcacag atgcggtaga ctgtgcactg gatccactca   6540
gcgaaactaa atgtaccctg aaaagcttta ccgtggagaa aggaatctac caaaccagca   6600
acttcagggt ccagcccact gaatccatcg ttagatttcc aaatataact aatttgtgtc   6660
catttggaga ggtgttcaat gctacaaggt tcgcgtctgt atacgcttgg aaccggaagc   6720
gcatctcaaa ttgcgtggct gattatagcg ttctttacaa cagcgcttcc ttttccacgt   6780
tcaagtgcta tggtgtatcc ccgacaaagc tgaatgactt gtgcttcacc aatgtgtatg   6840
cggattcttt cgttattcga ggcgatgaag tcagacaaat tgcgcctggc cagaccggaa   6900
agattgccga ctacaactat aaactgccgg acgactttac tggttgcgtg atcgcttgga   6960
acagcaataa tcttgatagt aaagttggag gaaactacaa ttacctctat agactgttca   7020
gaaagagcaa cttgaagcca ttcgaacggg atatctctac ggagatctat caagctggca   7080
gcacccctg caatggtgtg gaaggcttta attgttattt tcctttgcag agctatggct    7140
tccaacctac caacggagtg ggctaccagc cctacagagt ggtggtgctc agctttgaac   7200
tgctgcatgc cccggccaca gtttgcgggc ccaaaaaaag cacgaatctg gttaagaaca   7260
aatgcgtcaa cttcaatttt aatgggttga caggtacagg cgtactgacc gaatccaaca   7320
aaaagttcct gccttttcag cagttcggga gagatatcgc cgacactaca gacgccgtca   7380
gggatcccca aacactcgaa attctggaca tcacaccttg ttccttcggc ggggtatctg   7440
tgattactcc gggcacaaat accagtaacc aggtagcggt gctttaccag gatgtcaact   7500
gtacggaagt acctgtcgct attcatgcgg atcaactcac tcctacctgg agagtttatt   7560
ccactgggtc caacgtgttt cagacccgag ccggctgctt gattggcgcg gaacatgtta   7620
acaactccta cgaatgtgac atccctatcg gagctggcat ctgtgcttcc tatcaaacgc   7680
aaacgaacag cccatctgct gctggttccg tagcctctca aagcatcatc gcttatacta   7740
tgtccttggg ggctgaaaac agcgttgcct attccaacaa tagcatcgct atccctacca   7800
actttaccat ttccgtgacc acagaaatac tgccggtgag catgacaaag acttctgtgg   7860
actgtaccat gtatatatgc ggcgatagca cagagtgttc taatttgctg ctgcagtacg   7920
gcagcttttg tacccaactc aacagagcac ttacagggat tgccgtcgag caggataaaa   7980
acacccagga ggttttcgcc caggttaagc agatctacaa gaccccacca atcaaggatt   8040
tcggcggctt caatttttcc cagatactgc ccgatccttc caagccatcc aaaaggagct   8100
ttatagagga tctgctgttc aacaaggtga ctctggccga cgctggcttt atcaagcaat   8160
atggcgattg cctgggggat attgccgcta gggaccttat ctgcgctcaa aaattcaacg   8220
gtcttaccgt tctcccgccc ctgctcaccg acgagatgat agcccagtac acgagcgcac   8280
ttttggccgg cacgataacc agcggctgga cattcggtgc cggggccgct cttcaaatcc   8340
cctttgccat gcagatggcc tacagattta atgggatagg cgtgacacaa aatgtcttgt   8400
```

```
atgaaaatca gaaactgatt gcaaaccagt ttaatagcgc tattggcaag atccaagata   8460
gcctttcctc caccgcatcc gctctgggaa agttgcaaga cgtcgtgaat caaaacgccc   8520
aagctctgaa taccctcgtg aagcagctta gctccaactt tggcgcgata tcctccgtgc   8580
tgaacgatat cctgtccaga ttggacaagg tcgaggcaga agtccagatc gatagattga   8640
taaccggcag actccagtct ctgcagacat atgtgactca gcagttgata agagcggccg   8700
aaatacgagc gtctgcaaat ctcgcagcaa cgaaaatgtc agagtgtgta ttggggcaaa   8760
gtaaaagagt agatttctgt ggaaagggtt accatctgat gtcattcccc cagtctgcac   8820
cacatggagt agttttttg catgtgactt atgtgcctgc ccaggagaaa aatttcacca   8880
ctgcacctgc gatctgtcat gacggcaagg cacatttccc tagagaaggc gtcttcgtat   8940
caaatggaac acactggttt gtaacccaaa ggaactttta cgagccccaa attataacta   9000
ccgacaacac cttcgtaagc ggaaactgcg acgtcgttat agggatagtc aataatacgg   9060
tctatgaccc tcttcagccg gaactggact cctttaaaga agaactggat aagtacttca   9120
agaaccatac gtctccggat gtggatctcg gagatataag tggaatcaac gcaagcgtag   9180
taaacattca gaaggagata gaccgactca atgaggttgc taaaaacctg aacgaaagct   9240
tgatagactt gcaggagctg ggtaagtacg aacagtacat taagtggcca tggtatatct   9300
ggttgggctt catagcagga ctcatagcta tcgtcatggt gacaataatg ctttgttgta   9360
tgaccagctg ttgttcttgt ctgaaaggct gctgcagctg tggcagctgt tgtaaatttg   9420
acgaagatga ttccgagcct gtgcttaagg gcgtaaaact ccactataca tgagatatcc   9480
gatccaccgg atctagataa ctgatcataa tcagccatac cacatttgta gaggttttac   9540
ttgctttaaa aaacctccca cacctccccc tgaacctgaa acataaaatg aatgcaattg   9600
ttgttgttaa cttgtttatt gcagcttata atggttacaa ataaagcaat agcatcacaa   9660
atttcacaaa taaagcattt ttttcactgc attctagttg tggtttgtcc aaactcatca   9720
atgtatctta ggtttagtga accgtcagat ccgctagcgt tacataactt acggtaaatg   9780
gcccgcctgg ctgaccgccc aacgaccccc gcccattgac gtcaataatg acgtatgttc   9840
ccatagtaac gccaataggg actttccatt gacgtcaatg ggtggagtat ttacggtaaa   9900
ctgcccactt ggcagtacat caagtgtatc atatgccaag tacgccccct attgacgtca   9960
atgacggtaa atggcccgcc tggcattatg cccagtacat gaccttatgg gactttccta  10020
cttggcagta catctacgta ttagtcatcg ctattaccat ggtgatgcgg ttttggcagt  10080
acatcaatgg gcgtggatag cggtttgact cacggggatt tccaagtctc caccccattg  10140
acgtcaatgg gagtttgttt tggcaccaaa atcaacggga ctttccaaaa tgtcgtaaca  10200
actccgcccc attgacgcaa atgggcggta ggcgtgtacg gtgggaggtc tatataagca  10260
gagctggttt agtgaaccgt cagatccgct agagatctgg taccgtcgac gcggccgctc  10320
gagcctaagc ttatgctgct gctgcccttc cagttgctgg ctgtcctctt tcccggcggc  10380
aactccgagg attacaagga cgacgacgac aagggtggag gctctggagg tggctctggt  10440
ggaggttccg gtggcggatc tatgagcgac aacggtcccc agaatcaaag aaatgcgccc  10500
agaattacat tcggcggccc ttctgatagc actggctcaa atcaaaacgg ggagagaagc  10560
ggagccaggt ccaaacagcg gagaccccaa ggcctgccta ataacaccgc ttcctggttc  10620
acagctctga cgcaacacgg caaggaggat ctgaagtttc cacggggtca gggcgtcccg  10680
attaacacga actctagccc agatgaccaa atagggtact acagaagagc gacaaggcgg  10740
```

-continued

```
atcagaggag gcgatggaaa aatgaaggat ctgtccccta ggtggtattt ctattacctg  10800
ggcacaggcc ctgaagctgg gttgccttac ggcgcaaaca aagatggaat tatatgggtg  10860
gccaccgagg gggcgttgaa caccccaaag gatcacatcg gaacgaggaa tcccgccaac  10920
aatgctgcta tagtgctcca actgccacag ggaacaaccc tgcctaaggg cttctacgcc  10980
gaggggagcc gcggtggcag ccaggccagc tccagaagtt cctcccgcag ccggaacagc  11040
tctagaaaca gcactcccgg cagctccaga gggacaagcc cagccagaat ggccggcaat  11100
ggcggcgacg ctgccctcgc acttctgttg cttgatcggc tcaatcaact cgaaagcaaa  11160
atgtccggca agggacaaca acagcaagga cagaccgtta caaaaaaaag cgccgccgag  11220
gctagcaaga agcccagaca gaagcgaacc gcaacaaagg cctataatgt aacacaagcc  11280
tttggaaggc ggggacccga acagacccag ggaaattttg gcgaccagga actgatccgg  11340
caagggacag actataaaca ttggccacag atagcgcaat ttgctccctc cgcctccgcc  11400
ttctttggca tgtcaagaat aggcatggaa gtaactcctt ctggaacctg gctgacgtac  11460
actggggcaa tcaagttgga tgataaggac cctaatttca aggaccaagt tattttgctc  11520
aacaagcata tagacgccta caagactttc ccgcctaccg aacctaaaaa ggataagaag  11580
aagaaagcag acgagaccca ggccctgcct caacggcaaa agaagcagca aactgtgaca  11640
ctcctgcccg ccgctgactt ggatgatttt tcaaaacagc tccaacagag tatgagcagc  11700
gccgatagca cccaagctgg accgggtccg ggcaacctgg tgccgatggt ggcgaccgtg  11760
ggtccaggac cgggtatgct gatccccatc gccgtgggcg gggccctggc cggcctcgtg  11820
ctgatcgtcc ttatcgccta cctcatcggc aagaagcact gctcatatca ggacatcctg  11880
tgagatatcc gatccaccgg atctagataa ctgatcataa tcagccatac cacatttgta  11940
gaggttttac ttgctttaaa aaacctccca cacctccccc tgaacctgaa acataaaatg  12000
aatgcaattg ttgttgttaa cttgtttatt gcagcttata atggttacaa ataaagcaat  12060
agcatcacaa atttcacaaa taaagcattt ttttcactgc attctagttg tggtttgtcc  12120
aaactcatca atgtatctta acgcggatct gggcgtggtt aagggtggga aagaatatat  12180
aaggtggggg tcttatgtag ttttgtatct gttttgcagc agccgccgcc gccatgagca  12240
ccaactcgtt tgatggaagc attgtgagct catatttgac aacgcgcatg cccccatggg  12300
ccggggtgcg tcagaatgtg atgggctcca gcattgatgg tcgccccgtc ctgcccgcaa  12360
actctactac cttgacctac gagaccgtgt ctggaacgcc gttggagact gcagcctccg  12420
ccgccgcttc agccgctgca gccaccgccc gcgggattgt gactgacttt gctttcctga  12480
gcccgcttgc aagcagtgca gcttcccgtt catccgcccg cgatgacaag ttgacggctc  12540
ttttggcaca attggattct ttgacccggg aacttaatgt cgtttctcag cagctgttgg  12600
atctgcgcca gcaggtttct gccctgaagg cttcctcccc tcccaatgcg gtttaaaaca  12660
taaataaaaa accagactct gtttggattt ggatcaagca agtgtcttgc tgtctttatt  12720
taggggtttt gcgcgcgcgg taggcccggg accagcggtc tcggtcgttg agggtcctgt  12780
gtattttttc caggacgtgg taaaggtgac tctggatgtt cagatacatg ggcataagcc  12840
cgtctctggg gtggaggtag caccactgca gagcttcatg ctgcggggtg gtgttgtaga  12900
tgatccagtc gtagcaggag cgctgggcgt ggtgcctaaa aatgtctttc agtagcaagc  12960
tgattgccag gggcaggccc ttggtgtaag tgtttacaaa gcggttaagc tgggatgggt  13020
gcatacgtgg ggatatgaga tgcatcttgg actgtatttt taggttggct atgttcccag  13080
ccatatccct ccggggattc atgttgtgca gaaccaccag cacagtgtat ccggtgcact  13140
```

```
tgggaaattt gtcatgtagc ttagaaggaa atgcgtggaa gaacttggag acgcccttgt  13200
gacctccaag attttccatg cattcgtcca taatgatggc aatgggccca cgggcggcgg  13260
cctgggcgaa gatatttctg ggatcactaa cgtcatagtt gtgttccagg atgagatcgt  13320
cataggccat ttttacaaag cgcgggcgga gggtgccaga ctgcggtata atggttccat  13380
ccggcccagg ggcgtagtta ccctcacaga tttgcatttc ccacgctttg agttcagatg  13440
gggggatcat gtctacctgc ggggcgatga agaaaacggt ttccggggta ggggagatca  13500
gctgggaaga aagcaggttc ctgagcagct gcgacttacc gcagccggtg ggcccgtaaa  13560
tcacacctat taccggctgc aactggtagt taagagagct gcagctgccg tcatccctga  13620
gcaggggggc cacttcgtta agcatgtccc tgactcgcat gttttccctg accaaatccg  13680
ccagaaggcg ctcgccgccc agcgatagca gttcttgcaa ggaagcaaag tttttcaacg  13740
gtttgagacc gtccgccgta ggcatgcttt tgagcgtttg accaagcagt tccaggcggt  13800
cccacagctc ggtcacctgc tctacggcat ctcgatccag catatctcct cgtttcgcgg  13860
gttggggcgg ctttcgctgt acggcagtag tcggtgctcg tccagacggg ccagggtcat  13920
gtctttccac gggcgcaggg tcctcgtcag cgtagtctgg gtcacggtga aggggtgcgc  13980
tccgggctgc gcgctggcca gggtgcgctt gaggctggtc ctgctggtgc tgaagcgctg  14040
ccggtcttcg ccctgcgcgt cggccaggta gcatttgacc atggtgtcat agtccagccc  14100
ctccgcggcg tggcccttgg cgcgcagctt gcccttggag gaggcgccgc acgaggggca  14160
gtgcagactt ttgagggcgt agagcttggg cgcgagaaat accgattccg gggagtaggc  14220
atccgcgccg caggccccgc agacggtctc gcattccacg agccaggtga gctctggccg  14280
ttcggggtca aaaaccaggt ttcccccatg ctttttgatg cgtttcttac ctctggtttc  14340
catgagccgg tgtccacgct cggtgacgaa aaggctgtcc gtgtccccgt atacagactt  14400
gagaggcctg tcctcgagcg gtgttccgcg gtcctcctcg tatagaaact cggaccactc  14460
tgagacaaag gctcgcgtcc aggccagcac gaaggaggct aagtgggagg ggtagcggtc  14520
gttgtccact agggggtcca ctcgctccag ggtgtgaaga cacatgtcgc cctcttcggc  14580
atcaaggaag gtgattggtt tgtaggtgta ggccacgtga ccgggtgttc ctgaaggggg  14640
gctataaaag gggtgggggg cgcgttcgtc ctcactctct tccgcatcgc tgtctgcgag  14700
ggccagctgt tggggtgagt actccctctg aaaagcgggc atgacttctg cgctaagatt  14760
gtcagtttcc aaaaacgagg aggatttgat attcacctgg cccgcggtga tgcctttgag  14820
ggtggccgca tccatctggt cagaaaagac aatctttttg ttgtcaagct tggtggcaaa  14880
cgacccgtag agggcgttgg acagcaactt ggcgatggag cgcagggttt ggtttttgtc  14940
gcgatcggcg cgctccttgg ccgcgatgtt tagctgcacg tattcgcgcg caacgcaccg  15000
ccattcggga aagacggtgg tgcgctcgtc gggcaccagg tgcacgcgcc aaccgcggtt  15060
gtgcagggtg acaaggtcaa cgctggtggc tacctctccg cgtaggcgct cgttggtcca  15120
gcagaggcgg ccgcccttgc gcgagcagaa tggcggtagg gggtctagct gcgtctcgtc  15180
cggggggtct gcgtccacgg taaagacccc gggcagcagg cgcgcgtcga agtagtctat  15240
cttgcatcct tgcaagtcta gcgcctgctg ccatgcgcgg gcggcaagcg cgcgctcgta  15300
tgggttgagt gggggacccc atggcatggg gtgggtgagc gcggaggcgt acatgccgca  15360
aatgtcgtaa acgtagaggg gctctctgag tattccaaga tatgtagggt agcatcttcc  15420
accgcggatg ctggcgcgca cgtaatcgta tagttcgtgc gagggagcga ggaggtcggg  15480
```

```
accgaggttg ctacgggcgg gctgctctgc tcggaagact atctgcctga agatggcatg  15540
tgagttggat gatatggttg gacgctggaa gacgttgaag ctggcgtctg tgagacctac  15600
cgcgtcacgc acgaaggagg cgtaggagtc gcgcagcttg ttgaccagct cggcggtgac  15660
ctgcacgtct agggcgcagt agtccagggt ttccttgatg atgtcatact tatcctgtcc  15720
ctttttttc cacagctcgc ggttgaggac aaactcttcg cggtctttcc agtactcttg  15780
gatcggaaac ccgtcggcct ccgaacggta agagcctagc atgtagaact ggttgacggc  15840
ctggtaggcg cagcatccct tttctacggg tagcgcgtat gcctgcgcgg ccttccggca  15900
tgaccagcat gaagggcacg agctgcttcc caaaggcccc catccaagta taggtctcta  15960
catcgtaggt gacaaagaga cgctcggtgc gaggatgcga gccgatcggg aagaactgga  16020
tctcccgcca ccaattggag gagtggctat tgatgtggtg aaagtagaag tccctgcgac  16080
gggccgaaca ctcgtgctgg cttttgtaaa aacgtgcgca gtactggcag cggtgcacgg  16140
gctgtacatc ctgcacgagg ttgacctgac gaccgcgcac aaggaagcag agtgggaatt  16200
tgagcccctc gcctggcggg tttggctggt ggtcttctac ttcggctgct tgtccttgac  16260
cgtctggctg ctcgagggga gttacggtgg atcggaccac cacgccgcgc gagcccaaag  16320
tccagatgtc cgcgcgcggc ggtcggagct tgatgacaac atcgcgcaga tgggagctgt  16380
ccatggtctg gagctcccgc ggcgtcaggt caggcgggag ctcctgcagg tttacctcgc  16440
atagacgggt cagggcgcgg gctagatcca ggtgatacct aatttccagg ggctggttgg  16500
tggcggcgtc gatggcttgc aagaggccgc atccccgcgg cgcgactacg gtaccgcgcg  16560
gcgggcggtg ggccgcgggg gtgtccttgg atgatgcatc taaaagcggt gacgcgggcg  16620
agcccccgga ggtagggggg gctccggacc cgccgggaga gggggcaggg gcacgtcggc  16680
gccgcgcgcg ggcaggagct ggtgctgcgc gcgtaggttg ctggcgaacg cgacgacgcg  16740
gcggttgatc tcctgaatct ggcgcctctg cgtgaagacg acgggcccgg tgagcttgaa  16800
cctgaaagag agttcgacag aatcaatttc ggtgtcgttg acggcggcct ggcgcaaaat  16860
ctcctgcacg tctcctgagt tgtcttgata ggcgatctcg gccatgaact gctcgatctc  16920
ttcctcctgg agatctccgc gtccggctcg ctccacggtg gcggcgaggt cgttggaaat  16980
gcgggccatg agctgcgaga aggcgttgag gcctccctcg ttccagacgc ggctgtagac  17040
cacgcccccct tcggcatcgc gggcgcgcat gaccacctgc gcgagattga gctccacgtg  17100
ccgggcgaag acggcgtagt ttcgcaggcg ctgaaagagg tagttgaggg tggtggcggt  17160
gtgttctgcc acgaagaagt acataaccca gcgtcgcaac gtggattcgt tgataattgt  17220
tgtgtaggta ctccgccgcc gagggacctg agcgagtccg catcgaccgg atcggaaaac  17280
ctctcgagaa aggcgtctaa ccagtcacag tcgcaaggta ggctgagcac cgtggcgggc  17340
ggcagcgggc ggcggtcggg gttgtttctg gcggaggtgc tgctgatgat gtaattaaag  17400
taggcggtct tgagacggcg gatggtcgac agaagcacca tgtccttggg tccggcctgc  17460
tgaatgcgca ggcggtcggc catgccccag gcttcgtttt gacatcggcg caggtctttg  17520
tagtagtctt gcatgagcct ttctaccggc acttcttctt ctccttcctc ttgtcctgca  17580
tctcttgcat ctatcgctgc ggcggcggcg gagtttggcc gtaggtggcg ccctcttcct  17640
cccatgcgtg tgaccccgaa gcccctcatc ggctgaagca gggctaggtc ggcgacaacg  17700
cgctcggcta atatggcctg ctgcacctgc gtgagggtag actggaagtc atccatgtcc  17760
acaaagcggt ggtatgcgcc cgtgttgatg gtgtaagtgc agttggccat aacggaccag  17820
ttaacggtct ggtgacccgg ctgcgagagc tcggtgtacc tgagacgcga gtaagccctc  17880
```

```
gagtcaaata cgtagtcgtt gcaagtccgc accaggtact ggtatcccac caaaaagtgc  17940
ggcggcggct ggcggtagag gggccagcgt agggtggccg gggctccggg ggcgagatct  18000
tccaacataa ggcgatgata tccgtagatg tacctggaca tccaggtgat gccggcggcg  18060
gtggtggagg cgcgcggaaa gtcgcggacg cggttccaga tgttgcgcag cggcaaaaag  18120
tgctccatgg tcgggacgct ctggccggtc aggcgcgcgc aatcgttgac gctctagcgt  18180
gcaaaaggag agcctgtaag cgggcactct tccgtggtct ggtggataaa ttcgcaaggg  18240
tatcatggcg gacgaccggg gttcgagccc cgtatccggc cgtccgccgt gatccatgcg  18300
gttaccgccc gcgtgtcgaa cccaggtgtg cgacgtcaga caacggggga gtgctccttt  18360
tggcttcctt ccaggcgcgg cggctgctgc gctagctttt ttggccactg gccgcgcgca  18420
gcgtaagcgg ttaggctgga aagcgaaagc attaagtggc tcgctccctg tagccggagg  18480
gttattttcc aagggttgag tcgcgggacc cccggttcga gtctcggacc ggccggactg  18540
cggcgaacgg gggtttgcct ccccgtcatg caagaccccg cttgcaaatt cctccggaaa  18600
cagggacgag cccctttttt gcttttccca gatgcatccg gtgctgcggc agatgcgccc  18660
ccctcctcag cagcggcaag agcaagagca gcggcagaca tgcagggcac cctcccctcc  18720
tcctaccgcg tcaggagggg cgacatccgc ggttgacgcg gcagcagatg gtgattacga  18780
acccccgcgg cgccgggccc ggcactacct ggacttggag gagggcgagg gcctggcgcg  18840
gctaggagcg ccctctcctg agcggcaccc aagggtgcag ctgaagcgtg atacgcgtga  18900
ggcgtacgtg ccgcggcaga acctgtttcg cgaccgcgag ggagaggagc ccgaggagat  18960
gcgggatcga aagttccacg cagggcgcga gctgcggcat ggcctgaatc gcgagcggtt  19020
gctgcgcgag gaggactttg agcccgacgc gcgaaccggg attagtcccg cgcgcgcaca  19080
cgtggcggcc gccgacctgg taaccgcata cgagcagacg gtgaaccagg agattaactt  19140
tcaaaaaagc tttaacaacc acgtgcgtac gcttgtggcg cgcgaggagg tggctatagg  19200
actgatgcat ctgtgggact ttgtaagcgc gctggagcaa aacccaaata gcaagccgct  19260
catggcgcag ctgttcctta tagtgcagca cagcagggac aacgaggcat tcagggatgc  19320
gctgctaaac atagtagagc ccgagggccg ctggctgctc gatttgataa acatcctgca  19380
gagcatagtg gtgcaggagc gcagcttgag cctggctgac aaggtggccg ccatcaacta  19440
ttccatgctt agcctgggca agttttacgc ccgcaagata taccataccc cttacgttcc  19500
catagacaag gaggtaaaga tcgaggggtt ctacatgcgc atggcgctga aggtgcttac  19560
cttgagcgac gacctgggcg tttatcgcaa cgagcgcatc cacaaggccg tgagcgtgag  19620
ccggcggcgc gagctcagcg accgcgagct gatgcacagc ctgcaaaggg ccctggctgg  19680
cacgggcagc ggcgatagag aggccgagtc ctactttgac gcgggcgctg acctgcgctg  19740
ggccccaagc cgacgcgccc tggaggcagc tggggccgga cctgggctgg cggtggcacc  19800
cgcgcgcgct ggcaacgtcg gcggcgtgga ggaatatgac gaggacgatg agtacgagcc  19860
agaggacggc gagtactaag cggtgatgtt tctgatcaga tgatgcaaga cgcaacggac  19920
ccggcggtgc gggcggcgct gcagagccag ccgtccggcc ttaactccac ggacgactgg  19980
cgccaggtca tggaccgcat catgtcgctg actgcgcgca atcctgacgc gttccggcag  20040
cagccgcagg ccaaccggct ctccgcaatt ctggaagcgg tggtcccggc gcgcgcaaac  20100
cccacgcacg agaaggtgct ggcgatcgta aacgcgctgg ccgaaaacag ggccatccgg  20160
cccgacgagg ccggcctggt ctacgacgcg ctgcttcagc gcgtggctcg ttacaacagc  20220
```

```
ggcaacgtgc agaccaacct ggaccggctg gtgggggatg tgcgcgaggc cgtggcgcag  20280
cgtgagcgcg cgcagcagca gggcaacctg ggctccatgg ttgcactaaa cgccttcctg  20340
agtacacagc ccgccaacgt gccgcgggga caggaggact acaccaactt tgtgagcgca  20400
ctgcggctaa tggtgactga gacaccgcaa agtgaggtgt accagtctgg gccagactat  20460
tttttccaga ccagtagaca aggcctgcag accgtaaacc tgagccaggc tttcaaaaac  20520
ttgcaggggc tgtggggggt gcgggctccc acaggcgacc gcgcgaccgt gtctagcttg  20580
ctgacgccca actcgcgcct gttgctgctg ctaatagcgc ccttcacgga cagtggcagc  20640
gtgtcccggg acacatacct aggtcacttg ctgacactgt accgcgaggc cataggtcag  20700
gcgcatgtgg acgagcatac tttccaggag attacaagtg tcagccgcgc gctggggcag  20760
gaggacacgg gcagcctgga ggcaacccta aactacctgc tgaccaaccg gcggcagaag  20820
atcccctcgt tgcacagttt aaacagcgag gaggagcgca ttttgcgcta cgtgcagcag  20880
agcgtgagcc ttaacctgat gcgcgacggg gtaacgccca gcgtggcgct ggacatgacc  20940
gcgcgcaaca tggaaccggg catgtatgcc tcaaaccggc cgtttatcaa ccgcctaatg  21000
gactacttgc atcgcgcggc cgccgtgaac cccgagtatt tcaccaatgc catcttgaac  21060
ccgcactggc taccgccccc tggtttctac accgggggat tcgaggtgcc cgagggtaac  21120
gatggattcc tctgggacga catagacgac agcgtgtttt ccccgcaacc gcagaccctg  21180
ctagagttgc aacagcgcga gcaggcagag gcggcgctgc gaaaggaaag cttccgcagg  21240
ccaagcagct tgtccgatct aggcgctgcg gccccgcggt cagatgctag tagcccattt  21300
ccaagcttga tagggtctct taccagcact cgcaccaccc gcccgcgcct gctgggcgag  21360
gaggagtacc taaacaactc gctgctgcag ccgcagcgcg aaaaaaacct gcctccggca  21420
tttcccaaca acgggataga gagcctagtg gacaagatga gtagatggaa gacgtacgcg  21480
caggagcaca gggacgtgcc aggcccgcgc ccgcccaccc gtcgtcaaag gcacgaccgt  21540
cagcggggtc tggtgtggga ggacgatgac tcggcagacg acagcagcgt cctggatttg  21600
ggagggagtg gcaacccgtt tgcgcacctt cgccccaggc tggggagaat gttttaaaaa  21660
aaaaaaagca tgatgcaaaa taaaaaactc accaaggcca tggcaccgag cgttggtttt  21720
cttgtattcc ccttagtatg cggcgcgcgg cgatgtatga ggaaggtcct cctccctcct  21780
acgagagtgt ggtgagcgcg gcgccagtgg cggcggcgct gggttctccc ttcgatgctc  21840
ccctggaccc gccgtttgtg cctccgcggt acctgcggcc taccgggggg agaaacagca  21900
tccgttactc tgagttggca cccctattcg acaccacccg tgtgtacctg gtggacaaca  21960
agtcaacgga tgtggcatcc ctgaactacc agaacgacca cagcaacttt ctgaccacgg  22020
tcattcaaaa caatgactac agcccggggg aggcaagcac acagaccatc aatcttgacg  22080
accggtcgca ctggggcggc gacctgaaaa ccatcctgca taccaacatg ccaaatgtga  22140
acgagttcat gtttaccaat aagtttaagg cgcgggtgat ggtgtcgcgc ttgcctacta  22200
aggacaatca ggtggagctg aaatacgagt gggtggagtt cacgctgccc gagggcaact  22260
actccgagac catgaccata gaccttatga acaacgcgat cgtggagcac tacttgaaag  22320
tgggcagaca gaacggggtt ctggaaagcg acatcggggt aaagtttgac acccgcaact  22380
tcagactggg gtttgacccc gtcactggtc ttgtcatgcc tggggtatat acaaacgaag  22440
ccttccatcc agacatcatt ttgctgccag gatgcggggt ggacttcacc cacagccgcc  22500
tgagcaactt gttgggcatc cgcaagcggc aacccttcca ggagggcttt aggatcacct  22560
acgatgatct ggagggtggt aacattcccg cactgttgga tgtggacgcc taccaggcga  22620
```

```
gcttgaaaga tgacaccgaa cagggcgggg gtggcgcagg cggcagcaac agcagtggca  22680
gcggcgcgga agagaactcc aacgcggcag ccgcggcaat gcagccggtg gaggacatga  22740
acgatcatgc cattcgcggc gacacctttg ccacacgggc tgaggagaag cgcgctgagg  22800
ccgaagcagc ggccgaagct gccgccccccg ctgcgcaacc cgaggtcgag aagcctcaga  22860
agaaaccggt gatcaaaccc ctgacagagg acagcaagaa acgcagttac aacctaataa  22920
gcaatgacag caccttcacc cagtaccgca gctggtacct tgcatacaac tacggcgacc  22980
ctcagaccgg aatccgctca tggaccctgc tttgcactcc tgacgtaacc tgcggctcgg  23040
agcaggtcta ctggtcgttg ccagacatga tgcaagaccc cgtgaccttc cgctccacgc  23100
gccagatcag caactttccg gtggtgggcg ccgagctgtt gcccgtgcac tccaagagct  23160
tctacaacga ccaggccgtc tactcccaac tcatccgcca gtttacctct ctgacccacg  23220
tgttcaatcg ctttcccgag aaccagattt tggcgcgccc gccagccccc accatcacca  23280
ccgtcagtga aaacgttcct gctctcacag atcacgggac gctaccgctg cgcaacagca  23340
tcggaggagt ccagcgagtg accattactg acgccagacg ccgcacctgc ccctacgttt  23400
acaaggccct gggcatagtc tcgccgcgcg tcctatcgag ccgcactttt tgagcaagca  23460
tgtccatcct tatatcgccc agcaataaca caggctgggg cctgcgcttc ccaagcaaga  23520
tgtttggcgg ggccaagaag cgctccgacc aacacccagt gcgcgtgcgc gggcactacc  23580
gcgcgccctg gggcgcgcac aaacgcggcc gcactgggcg caccaccgtc gatgacgcca  23640
tcgacgcggt ggtggaggag gcgcgcaact acacgcccac gccgccacca gtgtccacag  23700
tggacgcggc cattcagacc gtggtgcgcg gagcccggcg ctatgctaaa atgaagagac  23760
ggcggaggcg cgtagcacgt cgccaccgcc gccgacccgg cactgccgcc caacgcgcgg  23820
cggcggccct gcttaaccgc gcacgtcgca ccggccgacg ggcggccatg cgggccgctc  23880
gaaggctggc cgcgggtatt gtcactgtgc cccccaggtc caggcgacga gcggccgccg  23940
cagcagccgc ggccattagt gctatgactc agggtcgcag gggcaacgtg tattgggtgc  24000
gcgactcggt tagcggcctg cgcgtgcccg tgcgcacccg ccccccgcgc aactagattg  24060
caagaaaaaa ctacttagac tcgtactgtt gtatgtatcc agcggcggcg gcgcgcaacg  24120
aagctatgtc caagcgcaaa atcaaagaag agatgctcca ggtcatcgcg ccggagatct  24180
atggcccccc gaagaaggaa gagcaggatt acaagccccg aaagctaaag cgggtcaaaa  24240
agaaaaagaa agatgatgat gatgaacttg acgacgaggt ggaactgctg cacgctaccg  24300
cgcccaggcg acgggtacag tggaaaggtc gacgcgtaaa acgtgttttg cgacccggca  24360
ccaccgtagt ctttacgccc ggtgagcgct ccacccgcac ctacaagcgc gtgtatgatg  24420
aggtgtacgg cgacgaggac ctgcttgagc aggccaacga gcgcctcggg gagtttgcct  24480
acggaaagcg gcataaggac atgctggcgt tgccgctgga cgagggcaac ccaacaccta  24540
gcctaaagcc cgtaacactg cagcaggtgc tgcccgcgct tgcaccgtcc gaagaaaagc  24600
gcggcctaaa gcgcgagtct ggtgacttgg cacccaccgt gcagctgatg gtacccaagc  24660
gccagcgact ggaagatgtc ttggaaaaaa tgaccgtgga acctgggctg gagcccgagg  24720
tccgcgtgcg gccaatcaag caggtggcgc cgggactggg cgtgcagacc gtggacgttc  24780
agatacccac taccagtagc accagtattg ccaccgccac agagggcatg gagacacaaa  24840
cgtccccggt tgcctcagcg gtggcggatg ccgcggtgca ggcggtcgct gcggccgcgt  24900
ccaagacctc tacggaggtg caaacggacc cgtggatgtt tcgcgtttca gccccccggc  24960
```

```
gcccgcgccg ttcgaggaag tacggcgccg ccagcgcgct actgcccgaa tatgccctac  25020
atccttccat tgcgcctacc cccggctatc gtggctacac ctaccgcccc agaagacgag  25080
caactacccg acgccgaacc accactggaa cccgccgccg ccgtcgccgt cgccagcccg  25140
tgctggcccc gatttccgtg cgcagggtgg ctcgcgaagg aggcaggacc ctggtgctgc  25200
caacagcgcg ctaccacccc agcatcgttt aaaagccggt ctttgtggtt cttgcagata  25260
tggccctcac ctgccgcctc cgtttcccgg tgccgggatt ccgaggaaga atgcaccgta  25320
ggaggggcat ggccggccac ggcctgacgg gcggcatgcg tcgtgcgcac caccggcggc  25380
ggcgcgcgtc gcaccgtcgc atgcgcggcg gtatcctgcc cctccttatt ccactgatcg  25440
ccgcggcgat tggcgccgtg cccggaattg catccgtggc cttgcaggcg cagagacact  25500
gattaaaaac aagttgcatg tggaaaaatc aaaataaaaa gtctggactc tcacgctcgc  25560
ttggtcctgt aactattttg tagaatggaa gacatcaact ttgcgtctct ggccccgcga  25620
cacggctcgc gcccgttcat gggaaactgg caagatatcg gcaccagcaa tatgagcggt  25680
ggcgccttca gctggggctc gctgtggagc ggcattaaaa atttcggttc caccgttaag  25740
aactatggca gcaaggcctg gaacagcagc acaggccaga tgctgaggga taagttgaaa  25800
gagcaaaatt tccaacaaaa ggtggtagat ggcctggcct ctggcattag cggggtggtg  25860
gacctggcca accaggcagt gcaaaataag attaacagta agcttgatcc ccgccctccc  25920
gtagaggagc ctccaccggc cgtggagaca gtgtctccag aggggcgtgg cgaaaagcgt  25980
ccgcgccccg acagggaaga aactctggtg acgcaaatag acgagcctcc ctcgtacgag  26040
gaggcactaa agcaaggcct gcccaccacc cgtcccatcg cgcccatggc taccggagtg  26100
ctgggccagc acacacccgt aacgctggac ctgcctcccc ccgccgacac ccagcagaaa  26160
cctgtgctgc caggcccgac cgccgttgtt gtaacccgtc ctagccgcgc gtccctgcgc  26220
cgcgccgcca gcggtccgcg atcgttgcgg cccgtagcca gtggcaactg gcaaagcaca  26280
ctgaacagca tcgtgggtct gggggtgcaa tccctgaagc gccgacgatg cttctgatag  26340
ctaacgtgtc gtatgtgtgt catgtatgcg tccatgtcgc cgccagagga gctgctgagc  26400
cgccgcgcgc ccgctttcca agatggctac cccttcgatg atgccgcagt ggtcttacat  26460
gcacatctcg ggccaggacg cctcggagta cctgagcccc gggctggtgc agtttgcccg  26520
cgccaccgag acgtacttca gcctgaataa caagtttaga aaccccacgg tggcgcctac  26580
gcacgacgtg accacagacc ggtcccagcg tttgacgctg cggttcatcc ctgtggaccg  26640
tgaggatact gcgtactcgt acaaggcgcg gttcacccta gctgtgggtg ataaccgtgt  26700
gctggacatg gcttccacgt actttgacat ccgcggcgtg ctggacaggg gccctacttt  26760
taagccctac tctggcactg cctacaacgc cctggctccc aagggtgccc caaatccttg  26820
cgaatgggat gaagctgcta ctgctcttga aataaaccta gaagaagagg acgatgacaa  26880
cgaagacgaa gtagacgagc aagctgagca gcaaaaaact cacgtatttg ggcaggcgcc  26940
ttattctggt ataaatatta caaaggaggg tattcaaata ggtgtcgaag gtcaaacacc  27000
taaatatgcc gataaaacat ttcaacctga acctcaaata ggagaatctc agtggtacga  27060
aacagaaatt aatcatgcag ctgggagagt cctaaaaaag actaccccaa tgaaaccatg  27120
ttacggttca tatgcaaaac ccacaaatga aaatggaggg caaggcattc ttgtaaagca  27180
acaaaatgga aagctagaaa gtcaagtgga aatgcaattt ttctcaacta ctgaggcagc  27240
cgcaggcaat ggtgataact tgactcctaa agtggtattg tacagtgaag atgtagatat  27300
agaaacccca gacactcata tttcttacat gcccactatt aaggaaggta actcacgaga  27360
```

```
actaatgggc caacaatcta tgcccaacag gcctaattac attgctttta gggacaattt  27420
tattggtcta atgtattaca acagcacggg taatatgggt gttctggcgg gccaagcatc  27480
gcagttgaat gctgttgtag atttgcaaga cagaaacaca gagctttcat accagctttt  27540
gcttgattcc attggtgata gaaccaggta cttttctatg tggaatcagg ctgttgacag  27600
ctatgatcca gatgttagaa ttattgaaaa tcatggaact gaagatgaac ttccaaatta  27660
ctgctttcca ctgggaggtg tgattaatac agagactctt accaaggtaa aacctaaaac  27720
aggtcaggaa aatggatggg aaaaagatgc tacagaattt tcagataaaa atgaaataag  27780
agttggaaat aattttgcca tggaaatcaa tctaaatgcc aacctgtgga gaaatttcct  27840
gtactccaac atagcgctgt atttgcccga caagctaaag tacagtcctt ccaacgtaaa  27900
aatttctgat aacccaaaca cctacgacta catgaacaag cgagtggtgg ctcccgggct  27960
agtggactgc tacattaacc ttggagcacg ctggtccctt gactatatgg acaacgtcaa  28020
cccatttaac caccaccgca atgctggcct gcgctaccgc tcaatgttgc tgggcaatgg  28080
tcgctatgtg cccttccaca tccaggtgcc tcagaagttc tttgccatta aaaacctcct  28140
tctcctgccg ggctcataca cctacgagtg gaacttcagg aaggatgtta acatggttct  28200
gcagagctcc ctaggaaatg acctaagggt tgacggagcc agcattaagt ttgatagcat  28260
ttgcctttac gccaccttct tccccatggc ccacaacacc gcctccacgc ttgaggccat  28320
gcttagaaac gacaccaacg accagtcctt taacgactat ctctccgccg ccaacatgct  28380
ctaccctata cccgccaacg ctaccaacgt gcccatatcc atcccctccc gcaactgggc  28440
ggctttccgc ggctgggcct tcacgcgcct taagactaag gaaaccccat cactgggctc  28500
gggctacgac ccttattaca cctactctgg ctctataccc tacctagatg gaacctttta  28560
cctcaaccac acctttaaga aggtggccat tacctttgac tcttctgtca gctggcctgg  28620
caatgaccgc ctgcttaccc ccaacgagtt tgaaattaag cgctcagttg acggggaggg  28680
ttacaacgtt gcccagtgta acatgaccaa agactggttc ctggtacaaa tgctagctaa  28740
ctataacatt ggctaccagg gcttctatat cccagagagc tacaaggacc gcatgtactc  28800
cttctttaga aacttccagc ccatgagccg tcaggtggtg gatgatacta aatacaagga  28860
ctaccaacag gtgggcatcc tacaccaaca caacaactct ggatttgttg gctaccttgc  28920
ccccaccatg cgcgaaggac aggcctaccc tgctaacttc ccctatccgc ttataggcaa  28980
gaccgcagtt gacagcatta cccagaaaaa gtttctttgc gatcgcaccc tttggcgcat  29040
cccattctcc agtaacttta tgtccatggg cgcactcaca gacctgggcc aaaaccttct  29100
ctacgccaac tccgcccacg cgctagacat gacttttgag gtggatccca tggacgagcc  29160
caccccttctt tatgttttgt ttgaagtctt tgacgtggtc cgtgtgcacc agccgcaccg  29220
cggcgtcatc gaaaccgtgt acctgcgcac gcccttctcg gccggcaacg ccacaacata  29280
aagaagcaag caacatcaac aacagctgcc gccatgggct ccagtgagca ggaactgaaa  29340
gccattgtca aagatcttgg ttgtgggcca tattttttgg gcacctatga caagcgcttt  29400
ccaggctttg tttctccaca caagctcgcc tgcgccatag tcaatacggc cggtcgcgag  29460
actgggggcg tacactggat ggcctttgcc tggaacccgc actcaaaaac atgctacctc  29520
tttgagccct ttggcttttc tgaccagcga ctcaagcagg tttaccagtt tgagtacgag  29580
tcactcctgc gccgtagcgc cattgcttct tcccccgacc gctgtataac gctggaaaag  29640
tccacccaaa gcgtacaggg gcccaactcg gccgcctgtg gactattctg ctgcatgttt  29700
```

```
ctccacgcct ttgccaactg gccccaaact cccatggatc acaaccccac catgaacctt  29760
attaccgggg tacccaactc catgctcaac agtccccagg tacagcccac cctgcgtcgc  29820
aaccaggaac agctctacag cttcctggag cgccactcgc cctacttccg cagccacagt  29880
gcgcagatta ggagcgccac ttctttttgt cacttgaaaa acatgtaaaa ataatgtact  29940
agagacactt tcaataaagg caaatgcttt tatttgtaca ctctcgggtg attatttacc  30000
cccacccttg ccgtctgcgc cgtttaaaaa tcaaaggggt tctgccgcgc atcgctatgc  30060
gccactggca gggacacgtt gcgatactgg tgtttagtgc tccacttaaa ctcaggcaca  30120
accatccgcg gcagctcggt gaagttttca ctccacaggc tgcgcaccat caccaacgcg  30180
tttagcaggt cgggcgccga tatcttgaag tcgcagttgg ggcctccgcc ctgcgcgcgc  30240
gagttgcgat acacagggtt gcagcactgg aacactatca gcgccgggtg gtgcacgctg  30300
gccagcacgc tcttgtcgga gatcagatcc gcgtccaggt cctccgcgtt gctcagggcg  30360
aacggagtca actttggtag ctgccttccc aaaaagggcg cgtgcccagg ctttgagttg  30420
cactcgcacc gtagtggcat caaaaggtga ccgtgcccgg tctgggcgtt aggatacagc  30480
gcctgcataa aagccttgat ctgcttaaaa gccacctgag cctttgcgcc ttcagagaag  30540
aacatgccgc aagacttgcc ggaaaactga ttggccggac aggccgcgtc gtgcacgcag  30600
caccttgcgt cggtgttgga gatctgcacc acatttcggc cccaccggtt cttcacgatc  30660
ttggccttgc tagactgctc cttcagcgcg cgctgcccgt tttcgctcgt cacatccatt  30720
tcaatcacgt gctccttatt tatcataatg cttccgtgta gacacttaag ctcgccttcg  30780
atctcagcgc agcggtgcag ccacaacgcg cagcccgtgg gctcgtgatg cttgtaggtc  30840
acctctgcaa acgactgcag gtacgcctgc aggaatcgcc ccatcatcgt cacaaaggtc  30900
ttgttgctgg tgaaggtcag ctgcaacccg cggtgctcct cgttcagcca ggtcttgcat  30960
acggccgcca gagcttccac ttggtcaggc agtagtttga agttcgcctt tagatcgtta  31020
tccacgtggt acttgtccat cagcgcgcgc gcagcctcca tgcccttctc ccacgcagac  31080
acgatcggca cactcagcgg gttcatcacc gtaatttcac tttccgcttc gctgggctct  31140
tcctcttcct cttgcgtccg cataccacgc gccactgggt cgtcttcatt cagccgccgc  31200
actgtgcgct tacctccttt gccatgcttg attagcaccg gtgggttgct gaaacccacc  31260
atttgtagcg ccacatcttc tctttcttcc tcgctgtcca cgattacctc tggtgatggc  31320
gggcgctcgg gcttgggaga agggcgcttc tttttcttct tgggcgcaat ggccaaatcc  31380
gccgccgagg tcgatggccg cgggctgggt gtgcgcggca ccagcgcgtc ttgtgatgag  31440
tcttcctcgt cctcggactc gatacgccgc ctcatccgct tttttggggg cgcccgggga  31500
ggcggcggcg acggggacgg ggacgacacg tcctccatgg ttgggggacg tcgcgccgca  31560
ccgcgtccgc gctcgggggt ggtttcgcgc tgctcctctt cccgactggc catttccttc  31620
tcctataggc agaaaaagat catggagtca gtcgagaaga aggacagcct aaccgccccc  31680
tctgagttcg ccaccaccgc ctccaccgat gccgccaacg cgcctaccac cttccccgtc  31740
gaggcacccc cgcttgagga ggaggaagtg attatcgagc aggacccagg ttttgtaagc  31800
gaagacgacg aggaccgctc agtaccaaca gaggataaaa agcaagacca ggacaacgca  31860
gaggcaaacg aggaacaagt cgggcggggg gacgaaaggc atggcgacta cctagatgtg  31920
ggagacgacg tgctgttgaa gcatctgcag cgccagtgcg ccattatctg cgacgcgttg  31980
caagagcgca gcgatgtgcc cctcgccata gcggatgtca gccttgccta cgaacgccac  32040
ctattctcac cgcgcgtacc ccccaaacgc caagaaaacg gcacatgcga gcccaacccg  32100
```

cgcctcaact tctaccccgt atttgccgtg ccagaggtgc ttgccaccta tcacatcttt 32160
ttccaaaact gcaagatacc cctatcctgc cgtgccaacc gcagccgagc ggacaagcag 32220
ctggccttgc ggcagggcgc tgtcatacct gatatcgcct cgctcaacga agtgccaaaa 32280
atctttgagg gtcttggacg cgacgagaag cgcgcggcaa acgctctgca acaggaaaac 32340
agcgaaaatg aaagtcactc tggagtgttg gtggaactcg agggtgacaa cgcgcgccta 32400
gccgtactaa aacgcagcat cgaggtcacc cactttgcct acccggcact taacctaccc 32460
cccaaggtca tgagcacagt catgagtgag ctgatcgtgc gccgtgcgca gcccctggag 32520
agggatgcaa atttgcaaga acaaacagag gagggcctac ccgcagttgg cgacgagcag 32580
ctagcgcgct ggcttcaaac gcgcgagcct gccgacttgg aggagcgacg caaactaatg 32640
atggccgcag tgctcgttac cgtggagctt gagtgcatgc agcggttctt tgctgacccg 32700
gagatgcagc gcaagctaga ggaaacattg cactacacct ttcgacaggg ctacgtacgc 32760
caggcctgca agatctccaa cgtggagctc tgcaacctgg tctcctacct tggaattttg 32820
cacgaaaacc gccttgggca aaacgtgctt cattccacgc tcaagggcga ggcgcgccgc 32880
gactacgtcc gcgactgcgt ttacttattt ctatgctaca cctggcagac ggccatgggc 32940
gtttggcagc agtgcttgga ggagtgcaac ctcaaggagc tgcagaaact gctaaagcaa 33000
aacttgaagg acctatggac ggccttcaac gagcgctccg tggccgcgca cctggcggac 33060
atcattttcc ccgaacgcct gcttaaaacc ctgcaacagg gtctgccaga cttcaccagt 33120
caaagcatgt tgcagaactt taggaacttt atcctagagc gctcaggaat cttgcccgcc 33180
acctgctgtg cacttcctag cgactttgtg cccattaagt accgcgaatg ccctccgccg 33240
ctttggggcc actgctacct tctgcagcta gccaactacc ttgcctacca ctctgacata 33300
atggaagacg tgagcggtga cggtctactg gagtgtcact gtcgctgcaa cctatgcacc 33360
ccgcaccgct ccctggtttg caattcgcag ctgcttaacg aaagtcaaat tatcggtacc 33420
tttgagctgc agggtccctc gcctgacgaa aagtccgcgg ctccggggtt gaaactcact 33480
ccggggctgt ggacgtcggc ttaccttcgc aaatttgtac ctgaggacta ccacgcccac 33540
gagattaggt tctacgaaga ccaatcccgc ccgcctaatg cggagcttac cgcctgcgtc 33600
attacccagg gccacattct tggccaattg caagccatca acaaagcccg ccaagagttt 33660
ctgctacgaa agggacgggg ggtttacttg gacccccagt ccggcgagga gctcaaccca 33720
atcccccggc cgccgcagcc ctatcagcag cagccgcggg cccttgcttc ccaggatggc 33780
acccaaaaag aagctgcagc tgccgccgcc acccacggac gaggaggaat actgggacag 33840
tcaggcagag gaggttttgg acgaggagga ggaggacatg atggaagact gggagagcct 33900
agacgaggaa gcttccgagg tcgaagaggt gtcagacgaa acaccgtcac cctcggtcgc 33960
attcccctcg ccggcgcccc agaaatcggc aaccggttcc agcatggcta caacctccgc 34020
tcctcaggcg ccgccggcac tgcccgttcg ccgacccaac cgtagatggg acaccactgg 34080
aaccagggcc ggtaagtcca agcagccgcc gccgttagcc caagagcaac aacagcgcca 34140
aggctaccgc tcatggcgcg ggcacaagaa cgccatagtt gcttgcttgc aagactgtgg 34200
gggcaacatc tccttcgccc gccgctttct tctctaccat cacggcgtgg ccttcccccg 34260
taacatcctg cattactacc gtcatctcta cagcccatac tgcaccggcg gcagcggcag 34320
caacagcagc ggccacacag aagcaaaggc gaccggatag caagactctg acaaagccca 34380
agaaatccac agcggcggca gcagcaggag gaggagcgct gcgtctggcg cccaacgaac 34440

```
ccgtatcgac ccgcgagctt agaaacagga tttttcccac tctgtatgct atatttcaac  34500
agagcagggg ccaagaacaa gagctgaaaa taaaaaacag gtctctgcga tccctcaccc  34560
gcagctgcct gtatcacaaa agcgaagatc agcttcggcg cacgctggaa gacgcggagg  34620
ctctcttcag taaatactgc gcgctgactc ttaaggacta gtttcgcgcc ctttctcaaa  34680
tttaagcgcg aaaactacgt catctccagc ggccacaccc ggcgccagca cctgttgtca  34740
gcgccattat gagcaaggaa attcccacgc cctacatgtg gagttaccag ccacaaatgg  34800
gacttgcggc tggagctgcc caagactact caacccgaat aaactacatg agcgcgggac  34860
cccacatgat atcccgggtc aacggaatac gcgcccaccg aaaccgaatt ctcctggaac  34920
aggcggctat taccaccaca cctcgtaata accttaatcc ccgtagttgg cccgctgccc  34980
tggtgtacca ggaaagtccc gctcccacca ctgtggtact tcccagagac gcccaggccg  35040
aagttcagat gactaactca ggggcgcagc ttgcgggcgg ctttcgtcac agggtgcggt  35100
cgcccgggca gggtataact cacctgacaa tcagagggcg aggtattcag ctcaacgacg  35160
agtcggtgag ctcctcgctt ggtctccgtc cggacgggac atttcagatc ggcggcgccg  35220
gccgctcttc attcacgcct cgtcaggcaa tcctaactct gcagacctcg tcctctgagc  35280
cgcgctctgg aggcattgga actctgcaat ttattgagga gtttgtgcca tcggtctact  35340
ttaacccctt ctcgggacct cccggccact atccggatca atttattcct aactttgacg  35400
cggtaaagga ctcggcggac ggctacgact gaatgttaag tggagaggca gagcaactgc  35460
gcctgaaaca cctggtccac tgtcgccgcc acaagtgctt tgcccgcgac tccggtgagt  35520
tttgctactt tgaattgccc gaggatcata tcgagggccc ggcgcacggc gtccggctta  35580
ccgcccaggg agagcttgcc cgtagcctga ttcgggagtt tacccagcgc cccctgctag  35640
ttgagcggga caggggaccc tgtgttctca ctgtgatttg caactgtcct aaccctggat  35700
tacatcaaga tcctctagtt aatgtcaggt cgcctaagtc gattaactag agtacccggg  35760
gatcttattc cctttaacta ataaaaaaaa ataataaagc atcacttact taaaatcagt  35820
tagcaaattt ctgtccagtt tattcagcag cacctccttg ccctcctccc agctctggta  35880
ttgcagcttc ctcctggctg caaactttct ccacaatcta aatggaatgt cagtttcctc  35940
ctgttcctgt ccatccgcac ccactatctt catgttgttg cagatgaagc gcgcaagacc  36000
gtctgaagat accttcaacc ccgtgtatcc atatgacacg gaaaccggtc ctccaactgt  36060
gccttttctt actcctccct ttgtatcccc caatgggttt caagagagtc cccctggggt  36120
actctctttg cgcctatccg aacctctagt tacctccaat ggcatgcttg cgctcaaaat  36180
gggcaacggc ctctctctgg acgaggccgg caaccttacc tcccaaaatg taaccactgt  36240
gagcccacct ctcaaaaaaa ccaagtcaaa cataaacctg gaaatatctg cacccctcac  36300
agttacctca gaagccctaa ctgtggctgc cgccgcacct ctaatggtcg cgggcaacac  36360
actcaccatg caatcacagg ccccgctaac cgtgcacgac tccaaactta gcattgccac  36420
ccaaggaccc ctcacagtgt cagaaggaaa gctagccctg caaacatcag gcccccctcac  36480
caccaccgat agcagtaccc ttactatcac tgcctcaccc cctctaacta ctgccactgg  36540
tagcttgggc attgacttga aagagcccat ttatacacaa aatggaaaac taggactaaa  36600
gtacggggct cctttgcatg taacagacga cctaaacact ttgaccgtag caactggtcc  36660
aggtgtgact attaataata cttccttgca aactaaagtt actggagcct tgggttttga  36720
ttcacaaggc aatatgcaac ttaatgtagc aggaggacta aggattgatt ctcaaaacag  36780
acgccttata cttgatgtta gttatccgtt tgatgctcaa aaccaactaa atctaagact  36840
```

```
aggacagggc cctcttttta taaactcagc ccacaacttg gatattaact acaacaaagg  36900
cctttacttg tttacagctt caaacaattc caaaaagctt gaggttaacc taagcactgc  36960
caaggggttg atgtttgacg ctacagccat agccattaat gcaggagatg ggcttgaatt  37020
tggttcacct aatgcaccaa acacaaatcc cctcaaaaca aaaattggcc atggcctaga  37080
atttgattca aacaaggcta tggttcctaa actaggaact ggccttagtt ttgacagcac  37140
aggtgccatt acagtaggaa acaaaaataa tgataagcta actttgtgga ccacaccagc  37200
tccatctcct aactgtagac taaatgcaga gaaagatgct aaactcactt tggtcttaac  37260
aaaatgtggc agtcaaatac ttgctacagt ttcagttttg gctgttaaag gcagtttggc  37320
tccaatatct ggaacagttc aaagtgctca tcttattata agatttgacg aaaatggagt  37380
gctactaaac aattccttcc tggacccaga atattggaac tttagaaatg gagatcttac  37440
tgaaggcaca gcctatacaa acgctgttgg atttatgcct aacctatcag cttatccaaa  37500
atctcacggt aaaactgcca aaagtaacat tgtcagtcaa gtttacttaa acggagacaa  37560
aactaaacct gtaacactaa ccattacact aaacggtaca caggaaacag gagacacaac  37620
tccaagtgca tactctatgt cattttcatg ggactggtct ggccacaact acattaatga  37680
aatatttgcc acatcctctt acactttttc atacattgcc caagaataaa gaatcgtttg  37740
tgttatgttt caacgtgttt atttttcaat tgcagaaaat ttcaagtcat ttttcattca  37800
gtagtatagc cccaccacca catagcttat acagatcacc gtaccttaat caaactcaca  37860
gaaccctagt attcaacctg ccacctccct cccaacacac agagtacaca gtcctttctc  37920
cccggctggc cttaaaaagc atcatatcat gggtaacaga catattctta ggtgttatat  37980
tccacacggt ttcctgtcga gccaaacgct catcagtgat attaataaac tccccgggca  38040
gctcacttaa gttcatgtcg ctgtccagct gctgagccac aggctgctgt ccaacttgcg  38100
gttgcttaac gggcggcgaa ggagaagtcc acgcctacat gggggtagag tcataatcgt  38160
gcatcaggat agggcggtgg tgctgcagca gcgcgcgaat aaactgctgc cgccgccgct  38220
ccgtcctgca ggaatacaac atggcagtgg tctcctcagc gatgattcgc accgcccgca  38280
gcataaggcg ccttgtcctc cgggcacagc agcgcaccct gatctcactt aaatcagcac  38340
agtaactgca gcacagcacc acaatattgt tcaaaatccc acagtgcaag gcgctgtatc  38400
caaagctcat ggcggggacc acagaaccca cgtggccatc ataccacaag cgcaggtaga  38460
ttaagtggcg acccctcata aacacgctgg acataaacat tacctctttt ggcatgttgt  38520
aattcaccac ctcccggtac catataaacc tctgattaaa catggcgcca tccaccacca  38580
tcctaaacca gctggccaaa acctgcccgc cggctataca ctgcagggaa ccgggactgg  38640
aacaatgaca gtggagagcc caggactcgt aaccatggat catcatgctc gtcatgatat  38700
caatgttggc acaacacagg cacacgtgca tacacttcct caggattaca agctcctccc  38760
gcgttagaac catatcccag ggaacaaccc attcctgaat cagcgtaaat cccacactgc  38820
agggaagacc tcgcacgtaa ctcacgttgt gcattgtcaa agtgttacat tcgggcagca  38880
gcggatgatc ctccagtatg gtagcgcggg tttctgtctc aaaaggaggt agacgatccc  38940
tactgtacgg agtgcgccga gacaaccgag atcgtgttgg tcgtagtgtc atgccaaatg  39000
gaacgccgga cgtagtcata tttcctgaag caaaaccagg tgcgggcgtg acaaacagat  39060
ctgcgtctcc ggtctcgccg cttagatcgc tctgtgtagt agttgtagta tatccactct  39120
ctcaaagcat ccaggcgccc cctggcttcg ggttctatgt aaactccttc atgcgccgct  39180
```

```
gccctgataa catccaccac cgcagaataa gccacaccca gccaacctac acattcgttc  39240

tgcgagtcac acacgggagg agcgggaaga gctggaagaa ccatgttttt tttttattc  39300

caaaagatta tccaaaacct caaaatgaag atctattaag tgaacgcgct cccctccggt  39360

ggcgtggtca aactctacag ccaaagaaca gataatggca tttgtaagat gttgcacaat  39420

ggcttccaaa aggcaaacgg ccctcacgtc caagtggacg taaaggctaa acccttcagg  39480

gtgaatctcc tctataaaca ttccagcacc ttcaaccatg cccaaataat tctcatctcg  39540

ccaccttctc aatatatctc taagcaaatc ccgaatatta agtccggcca ttgtaaaaat  39600

ctgctccaga gcgccctcca ccttcagcct caagcagcga atcatgattg caaaaattca  39660

ggttcctcac agacctgtat aagattcaaa agcggaacat taacaaaaat accgcgatcc  39720

cgtaggtccc ttcgcagggc cagctgaaca taatcgtgca ggtctgcacg gaccagcgcg  39780

gccacttccc cgccaggaac catgacaaaa gaacccacac tgattatgac acgcatactc  39840

ggagctatgc taaccagcgt agccccgatg taagcttgtt gcatgggcgg cgatataaaa  39900

tgcaaggtgc tgctcaaaaa atcaggcaaa gcctcgcgca aaaaagaaag cacatcgtag  39960

tcatgctcat gcagataaag gcaggtaagc tccggaacca ccacagaaaa agacaccatt  40020

tttctctcaa acatgtctgc gggtttctgc ataaacacaa aataaaataa caaaaaaaca  40080

tttaaacatt agaagcctgt cttacaacag gaaaaacaac ccttataagc ataagacgga  40140

ctacggccat gccggcgtga ccgtaaaaaa actggtcacc gtgattaaaa agcaccaccg  40200

acagctcctc ggtcatgtcc ggagtcataa tgtaagactc ggtaaacaca tcaggttgat  40260

tcacatcggt cagtgctaaa aagcgaccga aatagcccgg gggaatacat acccgcaggc  40320

gtagagacaa cattacagcc cccataggag gtataacaaa attaatagga gagaaaaaca  40380

cataaacacc tgaaaaaccc tcctgcctag gcaaaatagc accctcccgc tccagaacaa  40440

catacagcgc ttccacagcg gcagccataa cagtcagcct taccagtaaa aaagaaaacc  40500

tattaaaaaa acaccactcg acacggcacc agctcaatca gtcacagtgt aaaaaagggc  40560

caagtgcaga gcgagtatat ataggactaa aaaatgacgt aacggttaaa gtccacaaaa  40620

aacacccaga aaaccgcacg cgaacctacg cccagaaacg aaagccaaaa aacccacaac  40680

ttcctcaaat cgtcacttcc gttttcccac gttacgtcac ttcccatttt aagaaaacta  40740

caattcccaa cacatacaag ttactccgcc ctaaaaccta cgtcacccgc cccgttccca  40800

cgccccgcgc cacgtcacaa actccacccc ctcattatca tattggcttc aatccaaaat  40860

aaggta                                                            40866
```

<210> SEQ ID NO 12
<211> LENGTH: 1285
<212> TYPE: PRT
<213> ORGANISM: Artificial Sequence
<220> FEATURE:
<223> OTHER INFORMATION: SARS-CoV2 spike mutant (p68)

<400> SEQUENCE: 12

```
Met Leu Leu Leu Pro Phe Gln Leu Leu Ala Val Leu Phe Pro Gly Gly
1               5                   10                  15

Asn Ser Glu Tyr Pro Tyr Asp Val Pro Asp Tyr Ala Gly Gly Gly Ser
            20                  25                  30

Gly Gly Gly Ser Gly Gly Gly Ser Gly Gly Gly Ser Gln Cys Val Asn
        35                  40                  45

Leu Thr Thr Arg Thr Gln Leu Pro Pro Ala Tyr Thr Asn Ser Phe Thr
    50                  55                  60
```

```
Arg Gly Val Tyr Tyr Pro Asp Lys Val Phe Arg Ser Ser Val Leu His
65                  70                  75                  80

Ser Thr Gln Asp Leu Phe Leu Pro Phe Phe Ser Asn Val Thr Trp Phe
                85                  90                  95

His Ala Ile His Val Ser Gly Thr Asn Gly Thr Lys Arg Phe Asp Asn
            100                 105                 110

Pro Val Leu Pro Phe Asn Asp Gly Val Tyr Phe Ala Ser Thr Glu Lys
        115                 120                 125

Ser Asn Ile Ile Arg Gly Trp Ile Phe Gly Thr Thr Leu Asp Ser Lys
    130                 135                 140

Thr Gln Ser Leu Leu Ile Val Asn Asn Ala Thr Asn Val Val Ile Lys
145                 150                 155                 160

Val Cys Glu Phe Gln Phe Cys Asn Asp Pro Phe Leu Gly Val Tyr Tyr
                165                 170                 175

His Lys Asn Asn Lys Ser Trp Met Glu Ser Glu Phe Arg Val Tyr Ser
            180                 185                 190

Ser Ala Asn Asn Cys Thr Phe Glu Tyr Val Ser Gln Pro Phe Leu Met
        195                 200                 205

Asp Leu Glu Gly Lys Gln Gly Asn Phe Lys Asn Leu Arg Glu Phe Val
    210                 215                 220

Phe Lys Asn Ile Asp Gly Tyr Phe Lys Ile Tyr Ser Lys His Thr Pro
225                 230                 235                 240

Ile Asn Leu Val Arg Asp Leu Pro Gln Gly Phe Ser Ala Leu Glu Pro
                245                 250                 255

Leu Val Asp Leu Pro Ile Gly Ile Asn Ile Thr Arg Phe Gln Thr Leu
            260                 265                 270

Leu Ala Leu His Arg Ser Tyr Leu Thr Pro Gly Asp Ser Ser Ser Gly
        275                 280                 285

Trp Thr Ala Gly Ala Ala Ala Tyr Tyr Val Gly Tyr Leu Gln Pro Arg
    290                 295                 300

Thr Phe Leu Leu Lys Tyr Asn Glu Asn Gly Thr Ile Thr Asp Ala Val
305                 310                 315                 320

Asp Cys Ala Leu Asp Pro Leu Ser Glu Thr Lys Cys Thr Leu Lys Ser
                325                 330                 335

Phe Thr Val Glu Lys Gly Ile Tyr Gln Thr Ser Asn Phe Arg Val Gln
            340                 345                 350

Pro Thr Glu Ser Ile Val Arg Phe Pro Asn Ile Thr Asn Leu Cys Pro
        355                 360                 365

Phe Gly Glu Val Phe Asn Ala Thr Arg Phe Ala Ser Val Tyr Ala Trp
    370                 375                 380

Asn Arg Lys Arg Ile Ser Asn Cys Val Ala Asp Tyr Ser Val Leu Tyr
385                 390                 395                 400

Asn Ser Ala Ser Phe Ser Thr Phe Lys Cys Tyr Gly Val Ser Pro Thr
                405                 410                 415

Lys Leu Asn Asp Leu Cys Phe Thr Asn Val Tyr Ala Asp Ser Phe Val
            420                 425                 430

Ile Arg Gly Asp Glu Val Arg Gln Ile Ala Pro Gly Gln Thr Gly Lys
        435                 440                 445

Ile Ala Asp Tyr Asn Tyr Lys Leu Pro Asp Asp Phe Thr Gly Cys Val
    450                 455                 460

Ile Ala Trp Asn Ser Asn Asn Leu Asp Ser Lys Val Gly Gly Asn Tyr
465                 470                 475                 480
```

```
Asn Tyr Leu Tyr Arg Leu Phe Arg Lys Ser Asn Leu Lys Pro Phe Glu
                485                 490                 495

Arg Asp Ile Ser Thr Glu Ile Tyr Gln Ala Gly Ser Thr Pro Cys Asn
            500                 505                 510

Gly Val Glu Gly Phe Asn Cys Tyr Phe Pro Leu Gln Ser Tyr Gly Phe
        515                 520                 525

Gln Pro Thr Asn Gly Val Gly Tyr Gln Pro Tyr Arg Val Val Val Leu
    530                 535                 540

Ser Phe Glu Leu Leu His Ala Pro Ala Thr Val Cys Gly Pro Lys Lys
545                 550                 555                 560

Ser Thr Asn Leu Val Lys Asn Lys Cys Val Asn Phe Asn Phe Asn Gly
                565                 570                 575

Leu Thr Gly Thr Gly Val Leu Thr Glu Ser Asn Lys Lys Phe Leu Pro
            580                 585                 590

Phe Gln Gln Phe Gly Arg Asp Ile Ala Asp Thr Thr Asp Ala Val Arg
        595                 600                 605

Asp Pro Gln Thr Leu Glu Ile Leu Asp Ile Thr Pro Cys Ser Phe Gly
    610                 615                 620

Gly Val Ser Val Ile Thr Pro Gly Thr Asn Thr Ser Asn Gln Val Ala
625                 630                 635                 640

Val Leu Tyr Gln Asp Val Asn Cys Thr Glu Val Pro Val Ala Ile His
                645                 650                 655

Ala Asp Gln Leu Thr Pro Thr Trp Arg Val Tyr Ser Thr Gly Ser Asn
            660                 665                 670

Val Phe Gln Thr Arg Ala Gly Cys Leu Ile Gly Ala Glu His Val Asn
        675                 680                 685

Asn Ser Tyr Glu Cys Asp Ile Pro Ile Gly Ala Gly Ile Cys Ala Ser
    690                 695                 700

Tyr Gln Thr Gln Thr Asn Ser Pro Ser Ala Ala Gly Ser Val Ala Ser
705                 710                 715                 720

Gln Ser Ile Ile Ala Tyr Thr Met Ser Leu Gly Ala Glu Asn Ser Val
                725                 730                 735

Ala Tyr Ser Asn Asn Ser Ile Ala Ile Pro Thr Asn Phe Thr Ile Ser
            740                 745                 750

Val Thr Thr Glu Ile Leu Pro Val Ser Met Thr Lys Thr Ser Val Asp
        755                 760                 765

Cys Thr Met Tyr Ile Cys Gly Asp Ser Thr Glu Cys Ser Asn Leu Leu
    770                 775                 780

Leu Gln Tyr Gly Ser Phe Cys Thr Gln Leu Asn Arg Ala Leu Thr Gly
785                 790                 795                 800

Ile Ala Val Glu Gln Asp Lys Asn Thr Gln Glu Val Phe Ala Gln Val
                805                 810                 815

Lys Gln Ile Tyr Lys Thr Pro Pro Ile Lys Asp Phe Gly Gly Phe Asn
            820                 825                 830

Phe Ser Gln Ile Leu Pro Asp Pro Ser Lys Pro Ser Lys Arg Ser Phe
        835                 840                 845

Ile Glu Asp Leu Leu Phe Asn Lys Val Thr Leu Ala Asp Ala Gly Phe
    850                 855                 860

Ile Lys Gln Tyr Gly Asp Cys Leu Gly Asp Ile Ala Ala Arg Asp Leu
865                 870                 875                 880

Ile Cys Ala Gln Lys Phe Asn Gly Leu Thr Val Leu Pro Pro Leu Leu
                885                 890                 895

Thr Asp Glu Met Ile Ala Gln Tyr Thr Ser Ala Leu Leu Ala Gly Thr
```

```
            900                 905                 910

Ile Thr Ser Gly Trp Thr Phe Gly Ala Gly Ala Ala Leu Gln Ile Pro
        915                 920                 925

Phe Ala Met Gln Met Ala Tyr Arg Phe Asn Gly Ile Gly Val Thr Gln
    930                 935                 940

Asn Val Leu Tyr Glu Asn Gln Lys Leu Ile Ala Asn Gln Phe Asn Ser
945                 950                 955                 960

Ala Ile Gly Lys Ile Gln Asp Ser Leu Ser Ser Thr Ala Ser Ala Leu
                965                 970                 975

Gly Lys Leu Gln Asp Val Val Asn Gln Asn Ala Gln Ala Leu Asn Thr
            980                 985                 990

Leu Val Lys Gln Leu Ser Ser Asn  Phe Gly Ala Ile Ser  Ser Val Leu
        995                 1000                1005

Asn Asp  Ile Leu Ser Arg Leu  Asp Lys Val Glu Ala  Glu Val Gln
    1010                1015                1020

Ile Asp  Arg Leu Ile Thr Gly  Arg Leu Gln Ser Leu  Gln Thr Tyr
    1025                1030                1035

Val Thr  Gln Gln Leu Ile Arg  Ala Ala Glu Ile Arg  Ala Ser Ala
    1040                1045                1050

Asn Leu  Ala Ala Thr Lys Met  Ser Glu Cys Val Leu  Gly Gln Ser
    1055                1060                1065

Lys Arg  Val Asp Phe Cys Gly  Lys Gly Tyr His Leu  Met Ser Phe
    1070                1075                1080

Pro Gln  Ser Ala Pro His Gly  Val Val Phe Leu His  Val Thr Tyr
    1085                1090                1095

Val Pro  Ala Gln Glu Lys Asn  Phe Thr Thr Ala Pro  Ala Ile Cys
    1100                1105                1110

His Asp  Gly Lys Ala His Phe  Pro Arg Glu Gly Val  Phe Val Ser
    1115                1120                1125

Asn Gly  Thr His Trp Phe Val  Thr Gln Arg Asn Phe  Tyr Glu Pro
    1130                1135                1140

Gln Ile  Ile Thr Thr Asp Asn  Thr Phe Val Ser Gly  Asn Cys Asp
    1145                1150                1155

Val Val  Ile Gly Ile Val Asn  Asn Thr Val Tyr Asp  Pro Leu Gln
    1160                1165                1170

Pro Glu  Leu Asp Ser Phe Lys  Glu Glu Leu Asp Lys  Tyr Phe Lys
    1175                1180                1185

Asn His  Thr Ser Pro Asp Val  Asp Leu Gly Asp Ile  Ser Gly Ile
    1190                1195                1200

Asn Ala  Ser Val Val Asn Ile  Gln Lys Glu Ile Asp  Arg Leu Asn
    1205                1210                1215

Glu Val  Ala Lys Asn Leu Asn  Glu Ser Leu Ile Asp  Leu Gln Glu
    1220                1225                1230

Leu Gly  Lys Tyr Glu Gln Tyr  Ile Lys Trp Pro Trp  Tyr Ile Trp
    1235                1240                1245

Leu Gly  Phe Ile Ala Gly Leu  Ile Ala Ile Val Met  Val Thr Ile
    1250                1255                1260

Met Leu  Cys Cys Met Thr Ser  Cys Cys Ser Cys Leu  Lys Lys His
    1265                1270                1275

Cys Ser  Tyr Gln Asp Ile Leu
    1280                1285
```

<210> SEQ ID NO 13

<211> LENGTH: 40827
<212> TYPE: DNA
<213> ORGANISM: Artificial Sequence
<220> FEATURE:
<223> OTHER INFORMATION: p68 vector sequence

<400> SEQUENCE: 13
tattattgat gatgttaatt aacatgcatg gatcctacgt ctcgaccgat gcccttgaga 60
gccttcaacc cagtcagctc cttccggtgg gcgcggggca tgactatcgt cgccgcactt 120
atgactgtct tctttatcat gcaactcgta ggacaggtgc cggcagcgct ctgggtcatt 180
ttcggcgagg accgctttcg ctggagcgcg acgatgatcg gcctgtcgct tgcggtattc 240
ggaatcttgc acgccctcgc tcaagccttc gtcactggtc ccgccaccaa acgtttcggc 300
gagaagcagg ccattatcgc cggcatggcg gccgacgcgc tgggctacgt cttgctggcg 360
ttcgcgacgc gaggctggat ggccttcccc attatgattc ttctcgcttc cggcggcatc 420
gggatgcccg cgttgcaggc catgctgtcc aggcaggtag atgacgacca tcagggacag 480
cttcaaggat cgctcgcggc tcttaccagc ctaacttcga tcattggacc gctgatcgtc 540
acggcgattt atgccgcctc ggcgagcaca tggaacgggt tggcatggat tgtaggcgcc 600
gccctatacc ttgtctgcct ccccgcgttg cgtcgcggtg catggagccg ggccacctcg 660
acctgaatgg aagccggcgg cacctcgcta acggattcac cactccaaga attggagcca 720
atcaattctt gcggagaact gtgaatgcgc aaaccaaccc ttggcagaac atatccatcg 780
cgtccgccat ctccagcagc cgcacgcggc gcatctcggg cagcgttggg tcctggccac 840
gggtgcgcat gatcgtgctc ctgtcgttga ggacccggct aggctggcgg ggttgcctta 900
ctggttagca gaatgaatca ccgatacgcg agcgaacgtg aagcgactgc tgctgcaaaa 960
cgtctgcgac ctgagcaaca acatgaatgg tcttcggttt ccgtgtttcg taaagtctgg 1020
aaacgcggaa gtcagcgccc tgcaccatta tgttccggat ctgcatcgca ggatgctgct 1080
ggctaccctg tggaacacct acatctgtat taacgaagcg ctggcattga ccctgagtga 1140
tttttctctg gtcccgccgc atccataccg ccagttgttt accctcacaa cgttccagta 1200
accgggcatg ttcatcatca gtaacccgta tcgtgagcat cctctctcgt ttcatcggta 1260
tcattacccc catgaacaga aatccccctt acacggaggc atcagtgacc aaacaggaaa 1320
aaaccgccct taacatggcc cgctttatca gaagccagac attaacgctt ctggagaaac 1380
tcaacgagct ggacgcggat gaacaggcag acatctgtga atcgcttcac gaccacgctg 1440
atgagcttta ccgcagctgc ctcgcgcgtt tcggtgatga cggtgaaaac ctctgacaca 1500
tgcagctccc ggagacggtc acagcttgtc tgtaagcgga tgccgggagc agacaagccc 1560
gtcagggcgc gtcagcgggt gttggcgggt gtcggggcgc agccatgacc cagtcacgta 1620
gcgatagcgg agtgtatact ggcttaacta tgcggcatca gagcagattg tactgagagt 1680
gcaccatatg cggtgtgaaa taccgcacag atgcgtaagg agaaaatacc gcatcaggcg 1740
ctcttccgct tcctcgctca ctgactcgct gcgctcggtc gttcggctgc ggcgagcggt 1800
atcagctcac tcaaaggcgg taatacggtt atccacagaa tcaggggata acgcaggaaa 1860
gaacatgtga gcaaaaggcc agcaaaaggc caggaaccgt aaaaaggccg cgttgctggc 1920
gtttttccat aggctccgcc cccctgacga gcatcacaaa aatcgacgct caagtcagag 1980
gtggcgaaac ccgacaggac tataaagata ccaggcgttt ccccctggaa gctccctcgt 2040
gcgctctcct gttccgaccc tgccgcttac cggatacctg tccgcctttc tcccttcggg 2100
aagcgtggcg ctttctcata gctcacgctg taggtatctc agttcggtgt aggtcgttcg 2160

```
ctccaagctg ggctgtgtgc acgaaccccc cgttcagccc gaccgctgcg ccttatccgg   2220
taactatcgt cttgagtcca acccggtaag acacgactta tcgccactgg cagcagccac   2280
tggtaacagg attagcagag cgaggtatgt aggcggtgct acagagttct tgaagtggtg   2340
gcctaactac ggctacacta gaaggacagt atttggtatc tgcgctctgc tgaagccagt   2400
taccttcgga aaaagagttg gtagctcttg atccggcaaa caaaccaccg ctggtagcgg   2460
tggttttttt gtttgcaagc agcagattac gcgcagaaaa aaaggatctc aagaagatcc   2520
tttgatcttt tctacggggt ctgacgctca gtggaacgaa aactcacgtt aagggatttt   2580
ggtcatgaga ttatcaaaaa ggatcttcac ctagatcctt ttaaattaaa aatgaagttt   2640
taaatcaatc taaagtatat atgagtaaac ttggtctgac agttaccaat gcttaatcag   2700
tgaggcacct atctcagcga tctgtctatt tcgttcatcc atagttgcct gactccccgt   2760
cgtgtagata actacgatac gggagggctt accatctggc cccagtgctg caatgatacc   2820
gcgagaccca cgctcaccgg ctccagattt atcagcaata aaccagccag ccggaagggc   2880
cgagcgcaga agtggtcctg caactttatc cgcctccatc cagtctatta attgttgccg   2940
ggaagctaga gtaagtagtt cgccagttaa tagtttgcgc aacgttgttg ccattgctgc   3000
agccatgaga ttatcaaaaa ggatcttcac ctagatcctt ttcacgtaga aagccagtcc   3060
gcagaaacgg tgctgacccc ggatgaatgt cagctactgg gctatctgga caagggaaaa   3120
cgcaagcgca aagagaaagc aggtagcttg cagtgggctt acatggcgat agctagactg   3180
ggcggtttta tggacagcaa gcgaaccgga attgccagct ggggcgccct ctggtaaggt   3240
tgggaagccc tgcaaagtaa actggatggc tttcttgccg ccaaggatct gatggcgcag   3300
gggatcaagc tctgatcaag agacaggatg aggatcgttt cgcatgattg aacaagatgg   3360
attgcacgca ggttctccgg ccgcttgggt ggagaggcta ttcggctatg actgggcaca   3420
acagacaatc ggctgctctg atgccgccgt gttccggctg tcagcgcagg ggcgcccggt   3480
tctttttgtc aagaccgacc tgtccggtgc cctgaatgaa ctgcaagacg aggcagcgcg   3540
gctatcgtgg ctggccacga cgggcgttcc ttgcgcagct gtgctcgacg ttgtcactga   3600
agcgggaagg gactggctgc tattgggcga agtgccgggg caggatctcc tgtcatctca   3660
ccttgctcct gccgagaaag tatccatcat ggctgatgca atgcggcggc tgcatacgct   3720
tgatccggct acctgcccat tcgaccacca agcgaaacat cgcatcgagc gagcacgtac   3780
tcggatggaa gccggtcttg tcgatcagga tgatctggac gaagagcatc aggggctcgc   3840
gccagccgaa ctgttcgcca ggctcaaggc gagcatgccc gacggcgagg atctcgtcgt   3900
gacccatggc gatgcctgct tgccgaatat catggtggaa aatggccgct tttctggatt   3960
catcgactgt ggccggctgg gtgtggcgga ccgctatcag gacatagcgt tggctacccg   4020
tgatattgct gaagagcttg gcggcgaatg ggctgaccgc ttcctcgtgc tttacggtat   4080
cgccgctccc gattcgcagc gcatcgcctt ctatcgcctt cttgacgagt tcttctgaat   4140
tttgttaaaa tttttgttaa atcagctcat tttttaacca ataggccgaa atcggcaaaa   4200
tcccttataa atcaaaagaa tagaccgaga tagggttgag tgttgttcca gtttggaaca   4260
agagtccact attaaagaac gtggactcca acgtcaaagg gcgaaaaacc gtctatcagg   4320
gcgatggccc actacgtgaa ccatcaccct aatcaagttt tttggggtcg aggtgccgta   4380
aagcactaaa tcggaaccct aaagggagcc cccgatttag agcttgacgg ggaaagccgg   4440
cgaacgtggc gagaaaggaa gggaagaaag cgaaaggagc gggcgctagg gcgctggcaa   4500
```

```
gtgtagcggt cacgctgcgc gtaaccacca cacccgccgc gcttaatgcg ccgctacagg   4560
gcgcgtccat tcgccattca ggatcgaatt aattcttaat taacatcatc aataatatac   4620
cttattttgg attgaagcca atatgataat gagggggtgg agtttgtgac gtggcgcggg   4680
gcgtgggaac ggggcgggtg acgtagtagt gtggcggaag tgtgatgttg caagtgtggc   4740
ggaacacatg taagcgacgg atgtggcaaa agtgacgttt ttggtgtgcg ccggtgtaca   4800
caggaagtga caattttcgc gcggttttag gcggatgttg tagtaaattt gggcgtaacc   4860
gagtaagatt tggccatttt cgcgggaaaa ctgaataaga ggaagtgaaa tctgaataat   4920
tttgtgttac tcatagcgcg taatactgta atagtaatca attacggggt cattagttca   4980
tagcccatat atggagttcc gcgttacata acttacggta aatggcccgc ctggctgacc   5040
gcccaacgac ccccgcccat tgacgtcaat aatgacgtat gttcccatag taacgccaat   5100
agggactttc cattgacgtc aatgggtgga gtatttacgg taaactgccc acttggcagt   5160
acatcaagtg tatcatatgc caagtacgcc ccctattgac gtcaatgacg gtaaatggcc   5220
cgcctggcat tatgcccagt acatgacctt atgggacttt cctacttggc agtacatcta   5280
cgtattagtc atcgctatta ccatggtgat gcggttttgg cagtacatca atgggcgtgg   5340
atagcggttt gactcacggg gatttccaag tctccacccc attgacgtca atgggagttt   5400
gttttggcac caaaatcaac gggactttcc aaaatgtcgt aacaactccg ccccattgac   5460
gcaaatgggc ggtaggcgtg tacggtggga ggtctatata agcagagctg gtttagtgaa   5520
ccgtcagatc cgctagagat ctggtaccgt cgacgcggcc gctcgagcct aagcttatgc   5580
ttctgcttcc tttccaattg ctggctgttc tctttcctgg aggtaactct gaatatccgt   5640
atgatgtgcc ggattatgcg ggtggaggct ctggaggtgg ctctggtgga ggttccggtg   5700
gcggatctca atgtgtcaac ctcaccacaa ggacacagct ccctcccgca tatacgaata   5760
gctttaccag aggcgtatac tatcctgata aggtctttag gagctcagta ctgcatagca   5820
ctcaggatct cttcctgccg ttcttcagta atgttacttg gtttcacgcc attcatgttt   5880
ccgggaccaa tggcaccaaa cggttcgata atccagtgct tcccttcaac gatggggtgt   5940
actttgccag cactgaaaaa tctaatataa ttcggggatg gattttcgga accacactcg   6000
attccaagac tcagtccctc ttgatcgtta acaacgctac taatgttgtc attaaggtgt   6060
gtgagtttca gttctgcaac gaccctttcc tgggtgtcta ctaccataaa aataacaaga   6120
gctggatgga gtccgaattt cgcgtctact caagcgccaa taattgcact tttgagtatg   6180
tgtcccagcc ctttttgatg gatctggagg gaaagcaggg caatttcaaa aatctgagag   6240
aattcgtttt taagaatata gatggatact tcaaaatcta cagcaaacac acacccataa   6300
atcttgtgcg cgatcttccc cagggcttca gcgcgttgga accccttgtt gacttgccca   6360
taggcatcaa cattaccagg ttccaaacgc tgctcgccct ccaccgcagc tacttgacac   6420
ccggggattc cagctccgga tggaccgccg gcgccgcagc gtattatgtg ggtacctgc   6480
aacccaggac atttttgctc aagtacaatg agaatgggac catcacagat gcggtagact   6540
gtgcactgga tccactcagc gaaactaaat gtaccctgaa aagctttacc gtggagaaag   6600
gaatctacca aaccagcaac ttcagggtcc agcccactga atccatcgtt agatttccaa   6660
atataactaa tttgtgtcca tttggagagg tgttcaatgc tacaaggttc gcgtctgtat   6720
acgcttggaa ccggaagcgc atctcaaatt gcgtggctga ttatagcgtt ctttacaaca   6780
gcgcttcctt ttccacgttc aagtgctatg gtgtatcccc gacaaagctg aatgacttgt   6840
gcttcaccaa tgtgtatgcg gattctttcg ttattcgagg cgatgaagtc agacaaattg   6900
```

```
cgcctggcca gaccggaaag attgccgact acaactataa actgccggac gactttactg   6960
gttgcgtgat cgcttggaac agcaataatc ttgatagtaa agttggagga aactacaatt   7020
acctctatag actgttcaga aagagcaact tgaagccatt cgaacgggat atctctacgg   7080
agatctatca agctggcagc accccctgca atggtgtgga aggctttaat tgttattttc   7140
ctttgcagag ctatggcttc caacctacca acggagtggg ctaccagccc tacagagtgg   7200
tggtgctcag ctttgaactg ctgcatgccc cggccacagt ttgcgggccc aaaaaaagca   7260
cgaatctggt taagaacaaa tgcgtcaact tcaattttaa tgggttgaca ggtacaggcg   7320
tactgaccga atccaacaaa aagttcctgc cttttcagca gttcgggaga gatatcgccg   7380
acactacaga cgccgtcagg gatccccaaa cactcgaaat tctggacatc acaccttgtt   7440
ccttcggcgg ggtatctgtg attactccgg gcacaaatac cagtaaccag gtagcggtgc   7500
tttaccagga tgtcaactgt acggaagtac ctgtcgctat tcatgcggat caactcactc   7560
ctacctggag agtttattcc actgggtcca acgtgtttca gacccgagcc ggctgcttga   7620
ttggcgcgga acatgttaac aactcctacg aatgtgacat ccctatcgga gctggcatct   7680
gtgcttccta tcaaacgcaa acgaacagcc catctgctgc tggttccgta gcctctcaaa   7740
gcatcatcgc ttatactatg tccttggggg ctgaaaacag cgttgcctat tccaacaata   7800
gcatcgctat ccctaccaac tttaccattt ccgtgaccac agaaatactg ccggtgagca   7860
tgacaaagac ttctgtggac tgtaccatgt atatatgcgg cgatagcaca gagtgttcta   7920
atttgctgct gcagtacggc agcttttgta cccaactcaa cagagcactt acagggattg   7980
ccgtcgagca ggataaaaac acccaggagg ttttcgccca ggttaagcag atctacaaga   8040
ccccaccaat caaggatttc ggcggcttca atttttccca gatactgccc gatccttcca   8100
agccatccaa aaggagcttt atagaggatc tgctgttcaa caaggtgact ctggccgacg   8160
ctggctttat caagcaatat ggcgattgcc tgggggatat tgccgctagg gaccttatct   8220
gcgctcaaaa attcaacggt cttaccgttc tcccgcccct gctcaccgac gagatgatag   8280
cccagtacac gagcgcactt ttggccggca cgataaccag cggctggaca ttcggtgccg   8340
gggccgctct tcaaatcccc tttgccatgc agatggccta cagatttaat gggataggcg   8400
tgacacaaaa tgtcttgtat gaaaatcaga aactgattgc aaaccagttt aatagcgcta   8460
ttggcaagat ccaagatagc ctttcctcca ccgcatccgc tctgggaaag ttgcaagacg   8520
tcgtgaatca aaacgcccaa gctctgaata ccctcgtgaa gcagcttagc tccaactttg   8580
gcgcgatatc ctccgtgctg aacgatatcc tgtccagatt ggacaaggtc gaggcagaag   8640
tccagatcga tagattgata accggcagac tccagtctct gcagacatat gtgactcagc   8700
agttgataag agcggccgaa atacgagcgt ctgcaaatct cgcagcaacg aaaatgtcag   8760
agtgtgtatt ggggcaaagt aaaagagtag atttctgtgg aaagggttac catctgatgt   8820
cattccccca gtctgcacca catggagtag ttttttttgca tgtgacttat gtgcctgccc   8880
aggagaaaaa tttcaccact gcacctgcga tctgtcatga cggcaaggca catttcccta   8940
gagaaggcgt cttcgtatca aatggaacac actggtttgt aacccaaagg aacttttacg   9000
agccccaaat tataactacc gacaacacct tcgtaagcgg aaactgcgac gtcgttatag   9060
ggatagtcaa taatacggtc tatgaccctc ttcagccgga actggactcc tttaaagaag   9120
aactggataa gtacttcaag aaccatacgt ctccggatgt ggatctcgga gatataagtg   9180
gaatcaacgc aagcgtagta aacattcaga aggagataga ccgactcaat gaggttgcta   9240
```

-continued

```
aaaacctgaa cgaaagcttg atagacttgc aggagctggg taagtacgaa cagtacatta    9300
agtggccatg gtatatctgg ttgggcttca tagcaggact catagctatc gtcatggtga    9360
caataatgct ttgttgtatg accagctgtt gttcttgtct gaagaagcac tgctcatatc    9420
aggacatcct gtgagatatc cgatccaccg gatctagata actgatcata atcagccata    9480
ccacatttgt agaggtttta cttgctttaa aaaacctccc acacctcccc ctgaacctga    9540
aacataaaat gaatgcaatt gttgttgtta acttgtttat tgcagcttat aatggttaca    9600
aataaagcaa tagcatcaca aatttcacaa ataaagcatt tttttcactg cattctagtt    9660
gtggtttgtc caaactcatc aatgtatctt aggtttagtg aaccgtcaga tccgctagcg    9720
ttacataact tacggtaaat ggcccgcctg gctgaccgcc caacgacccc cgcccattga    9780
cgtcaataat gacgtatgtt cccatagtaa cgccaatagg gactttccat tgacgtcaat    9840
gggtggagta tttacggtaa actgcccact tggcagtaca tcaagtgtat catatgccaa    9900
gtacgccccc tattgacgtc aatgacggta aatggcccgc ctggcattat gcccagtaca    9960
tgaccttatg ggactttcct acttggcagt acatctacgt attagtcatc gctattacca   10020
tggtgatgcg gttttggcag tacatcaatg ggcgtggata gcggtttgac tcacggggat   10080
ttccaagtct ccaccccatt gacgtcaatg ggagtttgtt ttggcaccaa aatcaacggg   10140
actttccaaa atgtcgtaac aactccgccc cattgacgca aatgggcggt aggcgtgtac   10200
ggtgggaggt ctatataagc agagctggtt tagtgaaccg tcagatccgc tagagatctg   10260
gtaccgtcga cgcggccgct cgagcctaag cttatgctgc tgctgccctt ccagttgctg   10320
gctgtcctct ttcccggcgg caactccgag gattacaagg acgacgacga caagggtgga   10380
ggctctggag gtggctctgg tggaggttcc ggtggcggat ctatgagcga caacggtccc   10440
cagaatcaaa gaaatgcgcc cagaattaca ttcggcggcc cttctgatag cactggctca   10500
aatcaaaacg gggagagaag cggagccagg tccaaacagc ggagacccca aggcctgcct   10560
aataacaccg cttcctggtt cacagctctg acgcaacacg gcaaggagga tctgaagttt   10620
ccacggggtc agggcgtccc gattaacacg aactctagcc cagatgacca aatagggtac   10680
tacagaagag cgacaaggcg gatcagagga ggcgatggaa aaatgaagga tctgtcccct   10740
aggtggtatt tctattacct gggcacaggc cctgaagctg ggttgcctta cggcgcaaac   10800
aaagatggaa ttatatgggt ggccaccgag ggggcgttga acaccccaaa ggatcacatc   10860
ggaacgagga atcccgccaa caatgctgct atagtgctcc aactgccaca gggaacaacc   10920
ctgcctaagg gcttctacgc cgaggggagc cgcggtggca gccaggccag ctccagaagt   10980
tcctcccgca gccggaacag ctctagaaac agcactcccg gcagctccag agggacaagc   11040
ccagccagaa tggccggcaa tggcggcgac gctgccctcg cacttctgtt gcttgatcgg   11100
ctcaatcaac tcgaaagcaa aatgtccggc aagggacaac aacagcaagg acagaccgtt   11160
acaaaaaaaa gcgccgccga ggctagcaag aagcccagac agaagcgaac cgcaacaaag   11220
gcctataatg taacacaagc ctttggaagg cggggacccg aacagaccca gggaaatttt   11280
ggcgaccagg aactgatccg gcaagggaca gactataaac attggccaca gatagcgcaa   11340
tttgctccct ccgcctccgc cttctttggc atgtcaagaa taggcatgga agtaactcct   11400
tctggaacct ggctgacgta cactggggca atcaagttgg atgataagga ccctaatttc   11460
aaggaccaag ttattttgct caacaagcat atagacgcct acaagacttt cccgcctacc   11520
gaacctaaaa aggataagaa gaagaaagca gacgagaccc aggccctgcc tcaacggcaa   11580
aagaagcagc aaactgtgac actcctgccc gccgctgact tggatgattt ttcaaaacag   11640
```

```
ctccaacaga gtatgagcag cgccgatagc acccaagctg gaccgggtcc gggcaacctg  11700
gtgccgatgg tggcgaccgt gggtccagga ccgggtatgc tgatccccat cgccgtgggc  11760
ggggccctgg ccggcctcgt gctgatcgtc cttatcgcct acctcatcgg caagaagcac  11820
tgctcatatc aggacatcct gtgagatatc cgatccaccg gatctagata actgatcata  11880
atcagccata ccacatttgt agaggtttta cttgctttaa aaaacctccc acacctcccc  11940
ctgaacctga aacataaaat gaatgcaatt gttgttgtta acttgtttat tgcagcttat  12000
aatggttaca aataaagcaa tagcatcaca aatttcacaa ataaagcatt tttttcactg  12060
cattctagtt gtggtttgtc caaactcatc aatgtatctt aacgcggatc tgggcgtggt  12120
taagggtggg aaagaatata taaggtgggg gtcttatgta gttttgtatc tgttttgcag  12180
cagccgccgc cgccatgagc accaactcgt ttgatggaag cattgtgagc tcatatttga  12240
caacgcgcat gcccccatgg gccggggtgc gtcagaatgt gatgggctcc agcattgatg  12300
gtcgccccgt cctgcccgca aactctacta ccttgaccta cgagaccgtg tctggaacgc  12360
cgttggagac tgcagcctcc gccgccgctt cagccgctgc agccaccgcc cgcgggattg  12420
tgactgactt tgctttcctg agcccgcttg caagcagtgc agcttcccgt tcatccgccc  12480
gcgatgacaa gttgacggct cttttggcac aattggattc tttgacccgg gaacttaatg  12540
tcgtttctca gcagctgttg gatctgcgcc agcaggtttc tgccctgaag gcttcctccc  12600
ctcccaatgc ggtttaaaac ataaataaaa aaccagactc tgtttggatt tggatcaagc  12660
aagtgtcttg ctgtctttat ttaggggttt tgcgcgcgcg gtaggcccgg gaccagcggt  12720
ctcggtcgtt gagggtcctg tgtatttttt ccaggacgtg gtaaaggtga ctctggatgt  12780
tcagatacat gggcataagc ccgtctctgg ggtggaggta gcaccactgc agagcttcat  12840
gctgcggggt ggtgttgtag atgatccagt cgtagcagga gcgctgggcg tggtgcctaa  12900
aaatgtcttt cagtagcaag ctgattgcca ggggcaggcc cttggtgtaa gtgtttacaa  12960
agcggttaag ctgggatggg tgcatacgtg gggatatgag atgcatcttg gactgtattt  13020
ttaggttggc tatgttccca gccatatccc tccggggatt catgttgtgc agaaccacca  13080
gcacagtgta tccggtgcac ttgggaaatt tgtcatgtag cttagaagga aatgcgtgga  13140
agaacttgga gacgcccttg tgacctccaa gattttccat gcattcgtcc ataatgatgg  13200
caatgggccc acgggcggcg gcctgggcga agatatttct gggatcacta acgtcatagt  13260
tgtgttccag gatgagatcg tcataggcca tttttacaaa gcgcgggcgg agggtgccag  13320
actgcggtat aatggttcca tccggcccag gggcgtagtt accctcacag atttgcattt  13380
cccacgcttt gagttcagat gggggggatca tgtctacctg cggggcgatg aagaaaacgg  13440
tttccggggt aggggagatc agctgggaag aaagcaggtt cctgagcagc tgcgacttac  13500
cgcagccggt gggcccgtaa atcacaccta ttaccggctg caactggtag ttaagagagc  13560
tgcagctgcc gtcatccctg agcagggggg ccacttcgtt aagcatgtcc ctgactcgca  13620
tgttttccct gaccaaatcc gccagaaggc gctcgccgcc cagcgatagc agttcttgca  13680
aggaagcaaa gtttttcaac ggtttgagac cgtccgccgt aggcatgctt ttgagcgttt  13740
gaccaagcag ttccaggcgg tcccacagct cggtcacctg ctctacggca tctcgatcca  13800
gcatatctcc tcgtttcgcg ggttggggcg gctttcgctg tacggcagta gtcggtgctc  13860
gtccagacgg gccagggtca tgtctttcca cgggcgcagg gtcctcgtca gcgtagtctg  13920
ggtcacggtg aaggggtgcg ctccgggctg cgcgctggcc agggtgcgct tgaggctggt  13980
```

-continued

```
cctgctggtg ctgaagcgct gccggtcttc gccctgcgcg tcggccaggt agcatttgac  14040
catggtgtca tagtccagcc cctccgcggc gtggcccttg gcgcgcagct tgcccttgga  14100
ggaggcgccg cacgaggggc agtgcagact tttgagggcg tagagcttgg gcgcgagaaa  14160
taccgattcc ggggagtagg catccgcgcc gcaggccccg cagacggtct cgcattccac  14220
gagccaggtg agctctggcc gttcggggtc aaaaaccagg tttcccccat gctttttgat  14280
gcgtttctta cctctggttt ccatgagccg gtgtccacgc tcggtgacga aaaggctgtc  14340
cgtgtccccg tatacagact tgagaggcct gtcctcgagc ggtgttccgc ggtcctcctc  14400
gtatagaaac tcggaccact ctgagacaaa ggctcgcgtc caggccagca cgaaggaggc  14460
taagtgggag gggtagcggt cgttgtccac taggggggtcc actcgctcca gggtgtgaag  14520
acacatgtcg ccctcttcgg catcaaggaa ggtgattggt ttgtaggtgt aggccacgtg  14580
accgggtgtt cctgaagggg ggctataaaa gggggtgggg gcgcgttcgt cctcactctc  14640
ttccgcatcg ctgtctgcga gggccagctg ttggggtgag tactccctct gaaaagcggg  14700
catgacttct gcgctaagat tgtcagtttc caaaaacgag gaggatttga tattcacctg  14760
gcccgcggtg atgcctttga gggtggccgc atccatctgg tcagaaaaga caatcttttt  14820
gttgtcaagc ttggtggcaa acgacccgta gagggcgttg gacagcaact tggcgatgga  14880
gcgcagggtt tggtttttgt cgcgatcggc gcgctccttg gccgcgatgt ttagctgcac  14940
gtattcgcgc gcaacgcacc gccattcggg aaagacggtg gtgcgctcgt cgggcaccag  15000
gtgcacgcgc caaccgcggt tgtgcagggt gacaaggtca acgctggtgg ctacctctcc  15060
gcgtaggcgc tcgttggtcc agcagaggcg gccgcccttg cgcgagcaga atggcggtag  15120
ggggtctagc tgcgtctcgt ccgggggggtc tgcgtccacg gtaaagaccc cgggcagcag  15180
gcgcgcgtcg aagtagtcta tcttgcatcc ttgcaagtct agcgcctgct gccatgcgcg  15240
ggcggcaagc gcgcgctcgt atgggttgag tgggggaccc catggcatgg ggtgggtgag  15300
cgcggaggcg tacatgccgc aaatgtcgta aacgtagagg ggctctctga gtattccaag  15360
atatgtaggg tagcatcttc caccgcggat gctggcgcgc acgtaatcgt atagttcgtg  15420
cgagggagcg aggaggtcgg gaccgaggtt gctacgggcg ggctgctctg ctcggaagac  15480
tatctgcctg aagatggcat gtgagttgga tgatatggtt ggacgctgga agacgttgaa  15540
gctggcgtct gtgagaccta ccgcgtcacg cacgaaggag gcgtaggagt cgcgcagctt  15600
gttgaccagc tcggcggtga cctgcacgtc tagggcgcag tagtccaggg tttccttgat  15660
gatgtcatac ttatcctgtc cctttttttt ccacagctcg cggttgagga caaactcttc  15720
gcggtctttc cagtactctt ggatcggaaa cccgtcggcc tccgaacggt aagagcctag  15780
catgtagaac tggttgacgg cctggtaggc gcagcatccc ttttctacgg gtagcgcgta  15840
tgcctgcgcg gccttccggc atgaccagca tgaagggcac gagctgcttc ccaaaggccc  15900
ccatccaagt ataggtctct acatcgtagg tgacaaagag acgctcggtg cgaggatgcg  15960
agccgatcgg gaagaactgg atctcccgcc accaattgga ggagtggcta ttgatgtggt  16020
gaaagtagaa gtccctgcga cgggccgaac actcgtgctg gcttttgtaa aaacgtgcgc  16080
agtactggca gcggtgcacg ggctgtacat cctgcacgag gttgacctga cgaccgcgca  16140
caaggaagca gagtgggaat ttgagcccct cgcctggcgg gtttggctgg tggtcttcta  16200
cttcggctgc ttgtccttga ccgtctggct gctcgagggg agttacggtg gatcggacca  16260
ccacgccgcg cgagcccaaa gtccagatgt ccgcgcgcgg cggtcggagc ttgatgacaa  16320
catcgcgcag atgggagctg tccatggtct ggagctcccg cggcgtcagg tcaggcggga  16380
```

```
gctcctgcag gtttacctcg catagacggg tcagggcgcg ggctagatcc aggtgatacc  16440
taatttccag ggctggttg gtggcggcgt cgatggcttg caagaggccg catccccgcg  16500
gcgcgactac ggtaccgcgc ggcgggcggt gggccgcggg ggtgtccttg gatgatgcat  16560
ctaaaagcgg tgacgcgggc gagcccccgg aggtaggggg ggctccggac ccgccgggag  16620
agggggcagg ggcacgtcgg cgccgcgcgc gggcaggagc tggtgctgcg cgcgtaggtt  16680
gctggcgaac gcgacgacgc ggcggttgat ctcctgaatc tggcgcctct gcgtgaagac  16740
gacgggcccg gtgagcttga acctgaaaga gagttcgaca gaatcaattt cggtgtcgtt  16800
gacggcggcc tggcgcaaaa tctcctgcac gtctcctgag ttgtcttgat aggcgatctc  16860
ggccatgaac tgctcgatct cttcctcctg gagatctccg cgtccggctc gctccacggt  16920
ggcggcgagg tcgttggaaa tgcgggccat gagctgcgag aaggcgttga ggcctccctc  16980
gttccagacg cggctgtaga ccacgccccc ttcggcatcg cgggcgcgca tgaccacctg  17040
cgcgagattg agctccacgt gccgggcgaa gacggcgtag tttcgcaggc gctgaaagag  17100
gtagttgagg gtggtggcgg tgtgttctgc cacgaagaag tacataaccc agcgtcgcaa  17160
cgtggattcg ttgataattg ttgtgtaggt actccgccgc cgagggacct gagcgagtcc  17220
gcatcgaccg gatcggaaaa cctctcgaga aaggcgtcta accagtcaca gtcgcaaggt  17280
aggctgagca ccgtggcggg cggcagcggg cggcggtcgg ggttgtttct ggcggaggtg  17340
ctgctgatga tgtaattaaa gtaggcggtc ttgagacggc ggatggtcga cagaagcacc  17400
atgtccttgg gtccggcctg ctgaatgcgc aggcggtcgg ccatgcccca ggcttcgttt  17460
tgacatcggc gcaggtcttt gtagtagtct tgcatgagcc tttctaccgg cacttcttct  17520
tctccttcct cttgtcctgc atctcttgca tctatcgctg cggcggcggc ggagtttggc  17580
cgtaggtggc gccctcttcc tcccatgcgt gtgaccccga agcccctcat cggctgaagc  17640
agggctaggt cggcgacaac gcgctcggct aatatggcct gctgcacctg cgtgagggta  17700
gactggaagt catccatgtc cacaaagcgg tggtatgcgc ccgtgttgat ggtgtaagtg  17760
cagttggcca taacggacca gttaacggtc tggtgacccg gctgcgagag ctcggtgtac  17820
ctgagacgcg agtaagccct cgagtcaaat acgtagtcgt tgcaagtccg caccaggtac  17880
tggtatccca ccaaaaagtg cggcggcggc tggcggtaga ggggccagcg tagggtggcc  17940
ggggctccgg gggcgagatc ttccaacata aggcgatgat atccgtagat gtacctggac  18000
atccaggtga tgccggcggc ggtggtggag gcgcgcggaa agtcgcggac gcggttccag  18060
atgttgcgca gcggcaaaaa gtgctccatg gtcgggacgc tctggccggt caggcgcgcg  18120
caatcgttga cgctctagcg tgcaaaagga gagcctgtaa gcgggcactc ttccgtggtc  18180
tggtggataa attcgcaagg gtatcatggc ggacgaccgg ggttcgagcc ccgtatccgg  18240
ccgtccgccg tgatccatgc ggttaccgcc cgcgtgtcga acccaggtgt gcgacgtcag  18300
acaacggggg agtgctcctt ttggcttcct tccaggcgcg gcggctgctg cgctagcttt  18360
tttggccact ggccgcgcgc agcgtaagcg gttaggctgg aaagcgaaag cattaagtgg  18420
ctcgctccct gtagccggag ggttattttc caagggttga gtcgcgggac ccccggttcg  18480
agtctcggac cggccggact gcggcgaacg gggtttgcc tccccgtcat gcaagacccc  18540
gcttgcaaat tcctccggaa acagggacga gcccctttt tgcttttccc agatgcatcc  18600
ggtgctgcgg cagatgcgcc cccctcctca gcagcggcaa gagcaagagc agcggcagac  18660
atgcagggca ccctcccctc ctcctaccgc gtcaggaggg gcgacatccg cggttgacgc  18720
```

```
ggcagcagat ggtgattacg aacccccgcg gcgccgggcc cggcactacc tggacttgga  18780
ggagggcgag ggcctggcgc ggctaggagc gccctctcct gagcggcacc caagggtgca  18840
gctgaagcgt gatacgcgtg aggcgtacgt gccgcggcag aacctgtttc gcgaccgcga  18900
gggagaggag cccgaggaga tgcgggatcg aaagttccac gcagggcgcg agctgcggca  18960
tggcctgaat cgcgagcggt tgctgcgcga ggaggacttt gagcccgacg cgcgaaccgg  19020
gattagtccc gcgcgcgcac acgtggcggc cgccgacctg gtaaccgcat acgagcagac  19080
ggtgaaccag gagattaact ttcaaaaaag ctttaacaac cacgtgcgta cgcttgtggc  19140
gcgcgaggag gtggctatag gactgatgca tctgtgggac tttgtaagcg cgctggagca  19200
aaacccaaat agcaagccgc tcatggcgca gctgttcctt atagtgcagc acagcaggga  19260
caacgaggca ttcagggatg cgctgctaaa catagtagag cccgagggcc gctggctgct  19320
cgatttgata aacatcctgc agagcatagt ggtgcaggag cgcagcttga gcctggctga  19380
caaggtggcc gccatcaact attccatgct tagcctgggc aagttttacg cccgcaagat  19440
ataccatacc ccttacgttc ccatagacaa ggaggtaaag atcgaggggt tctacatgcg  19500
catggcgctg aaggtgctta ccttgagcga cgacctgggc gtttatcgca acgagcgcat  19560
ccacaaggcc gtgagcgtga gccggcggcg cgagctcagc gaccgcgagc tgatgcacag  19620
cctgcaaagg gccctggctg gcacgggcag cggcgataga gaggccgagt cctactttga  19680
cgcgggcgct gacctgcgct gggccccaag ccgacgcgcc ctggaggcag ctggggccgg  19740
acctgggctg gcggtggcac ccgcgcgcgc tggcaacgtc ggcggcgtgg aggaatatga  19800
cgaggacgat gagtacgagc cagaggacgg cgagtactaa gcggtgatgt ttctgatcag  19860
atgatgcaag acgcaacgga cccggcggtg cgggcggcgc tgcagagcca gccgtccggc  19920
cttaactcca cggacgactg gcgccaggtc atggaccgca tcatgtcgct gactgcgcgc  19980
aatcctgacg cgttccggca gcagccgcag gccaaccggc tctccgcaat tctggaagcg  20040
gtggtcccgg cgcgcgcaaa ccccacgcac gagaaggtgc tggcgatcgt aaacgcgctg  20100
gccgaaaaca gggccatccg gcccgacgag gccggcctgg tctacgacgc gctgcttcag  20160
cgcgtggctc gttacaacag cggcaacgtg cagaccaacc tggaccggct ggtgggggat  20220
gtgcgcgagg ccgtggcgca gcgtgagcgc gcgcagcagc agggcaacct gggctccatg  20280
gttgcactaa acgccttcct gagtacacag cccgccaacg tgccgcgggg acaggaggac  20340
tacaccaact ttgtgagcgc actgcggcta atggtgactg agacaccgca aagtgaggtg  20400
taccagtctg ggccagacta ttttttccag accagtagac aaggcctgca gaccgtaaac  20460
ctgagccagg ctttcaaaaa cttgcagggg ctgtgggggg tgcgggctcc cacaggcgac  20520
cgcgcgaccg tgtctagctt gctgacgccc aactcgcgcc tgttgctgct gctaatagcg  20580
cccttcacgg acagtggcag cgtgtcccgg gacacatacc taggtcactt gctgacactg  20640
taccgcgagg ccataggtca ggcgcatgtg gacgagcata ctttccagga gattacaagt  20700
gtcagccgcg cgctggggca ggaggacacg ggcagcctgg aggcaaccct aaactacctg  20760
ctgaccaacc ggcggcagaa gatcccctcg ttgcacagtt taaacagcga ggaggagcgc  20820
attttgcgct acgtgcagca gagcgtgagc cttaacctga tgcgcgacgg ggtaacgccc  20880
agcgtggcgc tggacatgac cgcgcgcaac atggaaccgg gcatgtatgc ctcaaaccgg  20940
ccgtttatca accgcctaat ggactacttg catcgcgcgg ccgccgtgaa ccccgagtat  21000
ttcaccaatg ccatcttgaa cccgcactgg ctaccgcccc ctggtttcta caccggggga  21060
ttcgaggtgc ccgagggtaa cgatggattc ctctgggacg acatagacga cagcgtgttt  21120
```

```
tccccgcaac cgcagaccct gctagagttg caacagcgcg agcaggcaga ggcggcgctg  21180
cgaaaggaaa gcttccgcag gccaagcagc ttgtccgatc taggcgctgc ggccccgcgg  21240
tcagatgcta gtagcccatt tccaagcttg atagggtctc ttaccagcac tcgcaccacc  21300
cgcccgcgcc tgctgggcga ggaggagtac ctaaacaact cgctgctgca gccgcagcgc  21360
gaaaaaaacc tgcctccggc atttcccaac aacgggatag agagcctagt ggacaagatg  21420
agtagatgga agacgtacgc gcaggagcac agggacgtgc caggcccgcg cccgcccacc  21480
cgtcgtcaaa ggcacgaccg tcagcggggt ctggtgtggg aggacgatga ctcggcagac  21540
gacagcagcg tcctggattt gggagggagt ggcaacccgt ttgcgcacct tcgccccagg  21600
ctggggagaa tgttttaaaa aaaaaaaagc atgatgcaaa ataaaaaact caccaaggcc  21660
atggcaccga gcgttggttt tcttgtattc cccttagtat gcggcgcgcg gcgatgtatg  21720
aggaaggtcc tcctccctcc tacgagagtg tggtgagcgc ggcgccagtg gcggcggcgc  21780
tgggttctcc cttcgatgct cccctggacc cgccgtttgt gcctccgcgg tacctgcggc  21840
ctaccggggg gagaaacagc atccgttact ctgagttggc acccctattc gacaccaccc  21900
gtgtgtacct ggtggacaac aagtcaacgg atgtggcatc cctgaactac cagaacgacc  21960
acagcaactt tctgaccacg gtcattcaaa acaatgacta cagcccgggg gaggcaagca  22020
cacagaccat caatcttgac gaccggtcgc actggggcgg cgacctgaaa accatcctgc  22080
ataccaacat gccaaatgtg aacgagttca tgtttaccaa taagtttaag gcgcgggtga  22140
tggtgtcgcg cttgcctact aaggacaatc aggtggagct gaaatacgag tgggtggagt  22200
tcacgctgcc cgagggcaac tactccgaga ccatgaccat agaccttatg aacaacgcga  22260
tcgtggagca ctacttgaaa gtgggcagac agaacggggt tctggaaagc gacatcgggg  22320
taaagtttga cacccgcaac ttcagactgg ggtttgaccc cgtcactggt cttgtcatgc  22380
ctggggtata tacaaacgaa gccttccatc cagacatcat tttgctgcca ggatgcgggg  22440
tggacttcac ccacagccgc ctgagcaact tgttgggcat ccgcaagcgg caacccttcc  22500
aggagggctt taggatcacc tacgatgatc tggagggtgg taacattccc gcactgttgg  22560
atgtggacgc ctaccaggcg agcttgaaag atgacaccga acagggcggg ggtggcgcag  22620
gcggcagcaa cagcagtggc agcggcgcgg aagagaactc caacgcggca gccgcggcaa  22680
tgcagccggt ggaggacatg aacgatcatg ccattcgcgg cgacaccttt gccacacggg  22740
ctgaggagaa gcgcgctgag gccgaagcag cggccgaagc tgccgccccc gctgcgcaac  22800
ccgaggtcga gaagcctcag aagaaaccgg tgatcaaacc cctgacagag gacagcaaga  22860
aacgcagtta caacctaata agcaatgaca gcaccttcac ccagtaccgc agctggtacc  22920
ttgcatacaa ctacggcgac cctcagaccg gaatccgctc atggaccctg ctttgcactc  22980
ctgacgtaac ctgcggctcg gagcaggtct actggtcgtt gccagacatg atgcaagacc  23040
ccgtgacctt ccgctccacg cgccagatca gcaactttcc ggtggtgggc gccgagctgt  23100
tgcccgtgca ctccaagagc ttctacaacg accaggccgt ctactcccaa ctcatccgcc  23160
agtttacctc tctgacccac gtgttcaatc gctttcccga gaaccagatt ttggcgcgcc  23220
cgccagcccc caccatcacc accgtcagtg aaaacgttcc tgctctcaca gatcacggga  23280
cgctaccgct gcgcaacagc atcggaggag tccagcgagt gaccattact gacgccagac  23340
gccgcacctg cccctacgtt tacaaggccc tgggcatagt ctcgccgcgc gtcctatcga  23400
gccgcacttt ttgagcaagc atgtccatcc ttatatcgcc cagcaataac acaggctggg  23460
```

-continued

```
gcctgcgctt cccaagcaag atgtttggcg gggccaagaa gcgctccgac caacacccag  23520
tgcgcgtgcg cgggcactac cgcgcgccct ggggcgcgca caaacgcggc cgcactgggc  23580
gcaccaccgt cgatgacgcc atcgacgcgg tggtggagga ggcgcgcaac tacacgccca  23640
cgccgccacc agtgtccaca gtggacgcgg ccattcagac cgtggtgcgc ggagcccggc  23700
gctatgctaa aatgaagaga cggcggaggc gcgtagcacg tcgccaccgc cgccgacccg  23760
gcactgccgc ccaacgcgcg gcggcggccc tgcttaaccg cgcacgtcgc accggccgac  23820
gggcggccat gcgggccgct cgaaggctgg ccgcgggtat tgtcactgtg ccccccaggt  23880
ccaggcgacg agcggccgcc gcagcagccg cggccattag tgctatgact cagggtcgca  23940
ggggcaacgt gtattgggtg cgcgactcgg ttagcggcct gcgcgtgccc gtgcgcaccc  24000
gccccccgcg caactagatt gcaagaaaaa actacttaga ctcgtactgt tgtatgtatc  24060
cagcggcggc ggcgcgcaac gaagctatgt ccaagcgcaa aatcaaagaa gagatgctcc  24120
aggtcatcgc gccggagatc tatggccccc cgaagaagga agagcaggat tacaagcccc  24180
gaaagctaaa gcgggtcaaa aagaaaaaga aagatgatga tgatgaactt gacgacgagg  24240
tggaactgct gcacgctacc gcgcccaggc gacgggtaca gtggaaaggt cgacgcgtaa  24300
aacgtgtttt gcgacccggc accaccgtag tctttacgcc cggtgagcgc tccacccgca  24360
cctacaagcg cgtgtatgat gaggtgtacg gcgacgagga cctgcttgag caggccaacg  24420
agcgcctcgg ggagtttgcc tacggaaagc ggcataagga catgctggcg ttgccgctgg  24480
acgagggcaa cccaacacct agcctaaagc ccgtaacact gcagcaggtg ctgcccgcgc  24540
ttgcaccgtc cgaagaaaag cgcggcctaa agcgcgagtc tggtgacttg gcacccaccg  24600
tgcagctgat ggtacccaag cgccagcgac tggaagatgt cttggaaaaa atgaccgtgg  24660
aacctgggct ggagcccgag gtccgcgtgc ggccaatcaa gcaggtggcg ccgggactgg  24720
gcgtgcagac cgtggacgtt cagataccca ctaccagtag caccagtatt gccaccgcca  24780
cagagggcat ggagacacaa acgtccccgg ttgcctcagc ggtggcggat gccgcggtgc  24840
aggcggtcgc tgcggccgcg tccaagacct ctacggaggt gcaaacggac ccgtggatgt  24900
ttcgcgtttc agcccccegg cgcccgcgcc gttcgaggaa gtacggcgcc gccagcgcgc  24960
tactgcccga atatgcccta catccttcca ttgcgcctac ccccggctat cgtggctaca  25020
cctaccgccc cagaagacga gcaactaccc gacgccgaac caccactgga acccgccgcc  25080
gccgtcgccg tcgccagccc gtgctggccc cgatttccgt gcgcagggtg gctcgcgaag  25140
gaggcaggac cctggtgctg ccaacagcgc gctaccaccc cagcatcgtt taaaagccgg  25200
tctttgtggt tcttgcagat atggccctca cctgccgcct ccgtttcccg gtgccgggat  25260
tccgaggaag aatgcaccgt aggaggggca tggccggcca cggcctgacg ggcggcatgc  25320
gtcgtgcgca ccaccggcgg cggcgcgcgt cgcaccgtcg catgcgcggc ggtatcctgc  25380
ccctccttat tccactgatc gccgcggcga ttggcgccgt gcccggaatt gcatccgtgg  25440
ccttgcaggc gcagagacac tgattaaaaa caagttgcat gtggaaaaat caaaataaaa  25500
agtctggact ctcacgctcg cttggtcctg taactatttt gtagaatgga agacatcaac  25560
tttgcgtctc tggccccgcg acacggctcg cgcccgttca tgggaaactg gcaagatatc  25620
ggcaccagca atatgagcgg tggcgccttc agctggggct cgctgtggag cggcattaaa  25680
aatttcggtt ccaccgttaa gaactatggc agcaaggcct ggaacagcag cacaggccag  25740
atgctgaggg ataagttgaa agagcaaaat ttccaacaaa aggtggtaga tggcctggcc  25800
tctggcatta gcggggtggt ggacctggcc aaccaggcag tgcaaaataa gattaacagt  25860
```

```
aagcttgatc cccgccctcc cgtagaggag cctccaccgg ccgtggagac agtgtctcca  25920
gaggggcgtg gcgaaaagcg tccgcgcccc gacagggaag aaactctggt gacgcaaata  25980
gacgagcctc cctcgtacga ggaggcacta aagcaaggcc tgcccaccac ccgtcccatc  26040
gcgcccatgg ctaccggagt gctgggccag cacacacccg taacgctgga cctgcctccc  26100
cccgccgaca cccagcagaa acctgtgctg ccaggcccga ccgccgttgt tgtaacccgt  26160
cctagccgcg cgtccctgcg ccgcgccgcc agcggtccgc gatcgttgcg gcccgtagcc  26220
agtggcaact ggcaaagcac actgaacagc atcgtgggtc tgggggtgca atccctgaag  26280
cgccgacgat gcttctgata gctaacgtgt cgtatgtgtg tcatgtatgc gtccatgtcg  26340
ccgccagagg agctgctgag ccgccgcgcg cccgctttcc aagatggcta ccccttcgat  26400
gatgccgcag tggtcttaca tgcacatctc gggccaggac gcctcggagt acctgagccc  26460
cgggctggtg cagtttgccc gcgccaccga gacgtacttc agcctgaata acaagtttag  26520
aaaccccacg gtggcgccta cgcacgacgt gaccacagac cggtcccagc gtttgacgct  26580
gcggttcatc cctgtggacc gtgaggatac tgcgtactcg tacaaggcgc ggttcaccct  26640
agctgtgggt gataaccgtg tgctggacat ggcttccacg tactttgaca tccgcggcgt  26700
gctggacagg ggccctactt ttaagcccta ctctggcact gcctacaacg ccctggctcc  26760
caagggtgcc ccaaatcctt gcgaatggga tgaagctgct actgctcttg aaataaacct  26820
agaagaagag gacgatgaca acgaagacga agtagacgag caagctgagc agcaaaaaac  26880
tcacgtattt gggcaggcgc cttattctgg tataaatatt acaaaggagg gtattcaaat  26940
aggtgtcgaa ggtcaaacac ctaaatatgc cgataaaaca tttcaacctg aacctcaaat  27000
aggagaatct cagtggtacg aaacagaaat taatcatgca gctgggagag tcctaaaaaa  27060
gactacccca atgaaaccat gttacggttc atatgcaaaa cccacaaatg aaaatggagg  27120
gcaaggcatt cttgtaaagc aacaaaatgg aaagctagaa agtcaagtgg aaatgcaatt  27180
tttctcaact actgaggcag ccgcaggcaa tggtgataac ttgactccta aagtggtatt  27240
gtacagtgaa gatgtagata tagaaacccc agacactcat atttcttaca tgcccactat  27300
taaggaaggt aactcacgag aactaatggg ccaacaatct atgcccaaca ggcctaatta  27360
cattgctttt agggacaatt ttattggtct aatgtattac aacagcacgg gtaatatggg  27420
tgttctggcg ggccaagcat cgcagttgaa tgctgttgta gatttgcaag acagaaacac  27480
agagctttca taccagcttt tgcttgattc cattggtgat agaaccaggt acttttctat  27540
gtggaatcag gctgttgaca gctatgatcc agatgttaga attattgaaa atcatggaac  27600
tgaagatgaa cttccaaatt actgctttcc actgggaggt gtgattaata cagagactct  27660
taccaaggta aaacctaaaa caggtcagga aaatggatgg gaaaaagatg ctacagaatt  27720
ttcagataaa aatgaaataa gagttggaaa taattttgcc atggaaatca atctaaatgc  27780
caacctgtgg agaaatttcc tgtactccaa catagcgctg tatttgcccg acaagctaaa  27840
gtacagtcct tccaacgtaa aaatttctga taacccaaac acctacgact acatgaacaa  27900
gcgagtggtg gctcccgggc tagtggactg ctacattaac cttggagcac gctggtccct  27960
tgactatatg gacaacgtca acccatttaa ccaccaccgc aatgctggcc tgcgctaccg  28020
ctcaatgttg ctgggcaatg gtcgctatgt gcccttccac atccaggtgc ctcagaagtt  28080
ctttgccatt aaaaacctcc ttctcctgcc gggctcatac acctacgagt ggaacttcag  28140
gaaggatgtt aacatggttc tgcagagctc cctaggaaat gacctaaggg ttgacggagc  28200
```

```
cagcattaag tttgatagca tttgccttta cgccaccttc ttccccatgg cccacaacac  28260
cgcctccacg cttgaggcca tgcttagaaa cgacaccaac gaccagtcct ttaacgacta  28320
tctctccgcc gccaacatgc tctaccctat acccgccaac gctaccaacg tgcccatatc  28380
catcccctcc cgcaactggg cggctttccg cggctgggcc ttcacgcgcc ttaagactaa  28440
ggaaacccca tcactgggct cgggctacga cccttattac acctactctg gctctatacc  28500
ctacctagat ggaacctttt acctcaacca cacctttaag aaggtggcca ttacctttga  28560
ctcttctgtc agctggcctg gcaatgaccg cctgcttacc cccaacgagt ttgaaattaa  28620
gcgctcagtt gacggggagg gttacaacgt tgcccagtgt aacatgacca aagactggtt  28680
cctggtacaa atgctagcta actataacat tggctaccag ggcttctata tcccagagag  28740
ctacaaggac cgcatgtact ccttctttag aaacttccag cccatgagcc gtcaggtggt  28800
ggatgatact aaatacaagg actaccaaca ggtgggcatc ctacaccaac acaacaactc  28860
tggatttgtt ggctaccttg cccccaccat gcgcgaagga caggcctacc ctgctaactt  28920
cccctatccg cttataggca agaccgcagt tgacagcatt acccagaaaa agtttctttg  28980
cgatcgcacc ctttggcgca tcccattctc cagtaacttt atgtccatgg gcgcactcac  29040
agacctgggc caaaaccttc tctacgccaa ctccgcccac gcgctagaca tgacttttga  29100
ggtggatccc atggacgagc ccacccttct ttatgttttg tttgaagtct ttgacgtggt  29160
ccgtgtgcac cagccgcacc gcggcgtcat cgaaaccgtg tacctgcgca cgcccttctc  29220
ggccggcaac gccacaacat aaagaagcaa gcaacatcaa caacagctgc cgccatgggc  29280
tccagtgagc aggaactgaa agccattgtc aaagatcttg gttgtgggcc atatttttttg  29340
ggcacctatg acaagcgctt tccaggcttt gtttctccac acaagctcgc ctgcgccata  29400
gtcaatacgg ccggtcgcga gactgggggc gtacactgga tggcctttgc ctggaacccg  29460
cactcaaaaa catgctacct ctttgagccc tttggctttt ctgaccagcg actcaagcag  29520
gtttaccagt ttgagtacga gtcactcctg cgccgtagcg ccattgcttc ttcccccgac  29580
cgctgtataa cgctggaaaa gtccacccaa agcgtacagg ggcccaactc ggccgcctgt  29640
ggactattct gctgcatgtt tctccacgcc tttgccaact ggccccaaac tcccatggat  29700
cacaacccca ccatgaacct tattaccggg gtacccaact ccatgctcaa cagtccccag  29760
gtacagccca ccctgcgtcg caaccaggaa cagctctaca gcttcctgga gcgccactcg  29820
ccctacttcc gcagccacag tgcgcagatt aggagcgcca cttctttttg tcacttgaaa  29880
aacatgtaaa aataatgtac tagagacact ttcaataaag gcaaatgctt ttatttgtac  29940
actctcgggt gattatttac cccccaccctt gccgtctgcg ccgtttaaaa atcaaagggg  30000
ttctgccgcg catcgctatg cgccactggc agggacacgt tgcgatactg gtgtttagtg  30060
ctccacttaa actcaggcac aaccatccgc ggcagctcgg tgaagttttc actccacagg  30120
ctgcgcacca tcaccaacgc gtttagcagg tcgggcgccg atatcttgaa gtcgcagttg  30180
gggcctccgc cctgcgcgcg cgagttgcga tacacagggt tgcagcactg gaacactatc  30240
agcgccgggt ggtgcacgct ggccagcacg ctcttgtcgg agatcagatc cgcgtccagg  30300
tcctccgcgt tgctcagggc gaacggagtc aactttggta gctgccttcc caaaaagggc  30360
gcgtgcccag gctttgagtt gcactcgcac cgtagtggca tcaaaaggtg accgtgcccg  30420
gtctgggcgt taggatacag cgcctgcata aaagccttga tctgcttaaa agccacctga  30480
gcctttgcgc cttcagagaa gaacatgccg caagacttgc cggaaaactg attggccgga  30540
caggccgcgt cgtgcacgca gcaccttgcg tcggtgttgg agatctgcac cacatttcgg  30600
```

```
ccccaccggt tcttcacgat cttggccttg ctagactgct ccttcagcgc gcgctgcccg  30660
ttttcgctcg tcacatccat ttcaatcacg tgctccttat ttatcataat gcttccgtgt  30720
agacacttaa gctcgccttc gatctcagcg cagcggtgca gccacaacgc gcagcccgtg  30780
ggctcgtgat gcttgtaggt cacctctgca aacgactgca ggtacgcctg caggaatcgc  30840
cccatcatcg tcacaaaggt cttgttgctg gtgaaggtca gctgcaaccc gcggtgctcc  30900
tcgttcagcc aggtcttgca tacggccgcc agagcttcca cttggtcagg cagtagtttg  30960
aagttcgcct ttagatcgtt atccacgtgg tacttgtcca tcagcgcgcg cgcagcctcc  31020
atgcccttct cccacgcaga cacgatcggc acactcagcg ggttcatcac cgtaatttca  31080
ctttccgctt cgctgggctc ttcctcttcc tcttgcgtcc gcataccacg cgccactggg  31140
tcgtcttcat tcagccgccg cactgtgcgc ttacctcctt tgccatgctt gattagcacc  31200
ggtgggttgc tgaaacccac catttgtagc gccacatctt ctctttcttc ctcgctgtcc  31260
acgattacct ctggtgatgg cgggcgctcg ggcttgggag aagggcgctt ctttttcttc  31320
ttgggcgcaa tggccaaatc cgccgccgag gtcgatggcc gcgggctggg tgtgcgcggc  31380
accagcgcgt cttgtgatga gtcttcctcg tcctcggact cgatacgccg cctcatccgc  31440
ttttttgggg gcgcccgggg aggcggcggc gacggggacg gggacgacac gtcctccatg  31500
gttgggggac gtcgcgccgc accgcgtccg cgctcggggg tggtttcgcg ctgctcctct  31560
tcccgactgg ccatttcctt ctcctatagg cagaaaaaga tcatggagtc agtcgagaag  31620
aaggacagcc taaccgcccc ctctgagttc gccaccaccg cctccaccga tgccgccaac  31680
gcgcctacca ccttccccgt cgaggcaccc ccgcttgagg aggaggaagt gattatcgag  31740
caggacccag gttttgtaag cgaagacgac gaggaccgct cagtaccaac agaggataaa  31800
aagcaagacc aggacaacgc agaggcaaac gaggaacaag tcgggcgggg ggacgaaagg  31860
catggcgact acctagatgt gggagacgac gtgctgttga agcatctgca gcgccagtgc  31920
gccattatct gcgacgcgtt gcaagagcgc agcgatgtgc ccctcgccat agcggatgtc  31980
agccttgcct acgaacgcca cctattctca ccgcgcgtac cccccaaacg ccaagaaaac  32040
ggcacatgcg agcccaaccc gcgcctcaac ttctaccccg tatttgccgt gccagaggtg  32100
cttgccacct atcacatctt tttccaaaac tgcaagatac ccctatcctg ccgtgccaac  32160
cgcagccgag cggacaagca gctggccttg cggcagggcg ctgtcatacc tgatatcgcc  32220
tcgctcaacg aagtgccaaa aatctttgag ggtcttggac gcgacgagaa gcgcgcggca  32280
aacgctctgc aacaggaaaa cagcgaaaat gaaagtcact ctggagtgtt ggtggaactc  32340
gagggtgaca acgcgcgcct agccgtacta aaacgcagca tcgaggtcac ccactttgcc  32400
tacccggcac ttaacctacc ccccaaggtc atgagcacag tcatgagtga gctgatcgtg  32460
cgccgtgcgc agcccctgga gagggatgca aatttgcaag aacaaacaga ggagggccta  32520
cccgcagttg gcgacgagca gctagcgcgc tggcttcaaa cgcgcgagcc tgccgacttg  32580
gaggagcgac gcaaactaat gatggccgca gtgctcgtta ccgtggagct tgagtgcatg  32640
cagcggttct ttgctgaccc ggagatgcag cgcaagctag aggaaacatt gcactacacc  32700
tttcgacagg gctacgtacg ccaggcctgc aagatctcca acgtggagct ctgcaacctg  32760
gtctcctacc ttggaatttt gcacgaaaac cgccttgggc aaaacgtgct tcattccacg  32820
ctcaagggcg aggcgcgccg cgactacgtc cgcgactgcg tttacttatt tctatgctac  32880
acctggcaga cggccatggg cgtttggcag cagtgcttgg aggagtgcaa cctcaaggag  32940
```

```
ctgcagaaac tgctaaagca aaacttgaag gacctatgga cggccttcaa cgagcgctcc  33000
gtggccgcgc acctggcgga catcattttc cccgaacgcc tgcttaaaac cctgcaacag  33060
ggtctgccag acttcaccag tcaaagcatg ttgcagaact ttaggaactt tatcctagag  33120
cgctcaggaa tcttgcccgc cacctgctgt gcacttccta gcgactttgt gcccattaag  33180
taccgcgaat gccctccgcc gctttggggc cactgctacc ttctgcagct agccaactac  33240
cttgcctacc actctgacat aatggaagac gtgagcggtg acggtctact ggagtgtcac  33300
tgtcgctgca acctatgcac cccgcaccgc tccctggttt gcaattcgca gctgcttaac  33360
gaaagtcaaa ttatcggtac ctttgagctg cagggtccct cgcctgacga aaagtccgcg  33420
gctccggggt tgaaactcac tccggggctg tggacgtcgg cttaccttcg caaatttgta  33480
cctgaggact accacgccca cgagattagg ttctacgaag accaatcccg cccgcctaat  33540
gcggagctta ccgcctgcgt cattacccag ggccacattc ttggccaatt gcaagccatc  33600
aacaaagccc gccaagagtt tctgctacga aagggacggg gggtttactt ggacccccag  33660
tccggcgagg agctcaaccc aatcccccg ccgccgcagc cctatcagca gcagccgcgg  33720
gcccttgctt cccaggatgg cacccaaaaa gaagctgcag ctgccgccgc cacccacgga  33780
cgaggaggaa tactgggaca gtcaggcaga ggaggttttg gacgaggagg aggaggacat  33840
gatggaagac tgggagagcc tagacgagga agcttccgag gtcgaagagg tgtcagacga  33900
aacaccgtca ccctcggtcg cattcccctc gccggcgccc cagaaatcgg caaccggttc  33960
cagcatggct acaacctccg ctcctcaggc gccgccggca ctgcccgttc gccgacccaa  34020
ccgtagatgg gacaccactg gaaccagggc cggtaagtcc aagcagccgc cgccgttagc  34080
ccaagagcaa caacagcgcc aaggctaccg ctcatggcgc gggcacaaga acgccatagt  34140
tgcttgcttg caagactgtg gggcaacat ctccttcgcc cgccgctttc ttctctacca  34200
tcacggcgtg gccttccccc gtaacatcct gcattactac cgtcatctct acagcccata  34260
ctgcaccggc ggcagcggca gcaacagcag cggccacaca gaagcaaagg cgaccggata  34320
gcaagactct gacaaagccc aagaaatcca cagcggcggc agcagcagga ggaggagcgc  34380
tgcgtctggc gcccaacgaa cccgtatcga cccgcgagct tagaaacagg atttttccca  34440
ctctgtatgc tatatttcaa cagagcaggg gccaagaaca agagctgaaa ataaaaaaca  34500
ggtctctgcg atccctcacc cgcagctgcc tgtatcacaa aagcgaagat cagcttcggc  34560
gcacgctgga agacgcggag gctctcttca gtaaatactg cgcgctgact cttaaggact  34620
agtttcgcgc cctttctcaa atttaagcgc gaaaactacg tcatctccag cggccacacc  34680
cggcgccagc acctgttgtc agcgccatta tgagcaagga aattcccacg ccctacatgt  34740
ggagttacca gccacaaatg ggacttgcgg ctggagctgc ccaagactac tcaacccgaa  34800
taaactacat gagcgcggga ccccacatga tatcccgggt caacggaata cgcgcccacc  34860
gaaaccgaat tctcctggaa caggcggcta ttaccaccac acctcgtaat aaccttaatc  34920
cccgtagttg gcccgctgcc ctggtgtacc aggaaagtcc cgctcccacc actgtggtac  34980
ttcccagaga cgcccaggcc gaagttcaga tgactaactc aggggcgcag cttgcgggcg  35040
gctttcgtca cagggtgcgg tcgcccgggc agggtataac tcacctgaca atcagagggc  35100
gaggtattca gctcaacgac gagtcggtga gctcctcgct tggtctccgt ccggacggga  35160
catttcagat cggcggcgcc ggccgctctt cattcacgcc tcgtcaggca atcctaactc  35220
tgcagacctc gtcctctgag ccgcgctctg gaggcattgg aactctgcaa tttattgagg  35280
agtttgtgcc atcggtctac tttaacccct tctcgggacc tcccggccac tatccggatc  35340
```

```
aatttattcc taactttgac gcggtaaagg actcggcgga cggctacgac tgaatgttaa  35400
gtggagaggc agagcaactg cgcctgaaac acctggtcca ctgtcgccgc cacaagtgct  35460
ttgcccgcga ctccggtgag ttttgctact ttgaattgcc cgaggatcat atcgagggcc  35520
cggcgcacgg cgtccggctt accgcccagg gagagcttgc ccgtagcctg attcgggagt  35580
ttacccagcg ccccctgcta gttgagcggg acaggggacc ctgtgttctc actgtgattt  35640
gcaactgtcc taaccctgga ttacatcaag atcctctagt taatgtcagg tcgcctaagt  35700
cgattaacta gagtacccgg ggatcttatt ccctttaact aataaaaaaa aataataaag  35760
catcacttac ttaaaatcag ttagcaaatt tctgtccagt ttattcagca gcacctcctt  35820
gccctcctcc cagctctggt attgcagctt cctcctggct gcaaactttc tccacaatct  35880
aaatggaatg tcagtttcct cctgttcctg tccatccgca cccactatct tcatgttgtt  35940
gcagatgaag cgcgcaagac cgtctgaaga taccttcaac cccgtgtatc catatgacac  36000
ggaaaccggt cctccaactg tgccttttct tactcctccc tttgtatccc ccaatgggtt  36060
tcaagagagt ccccctgggg tactctcttt gcgcctatcc gaacctctag ttacctccaa  36120
tggcatgctt gcgctcaaaa tgggcaacgg cctctctctg gacgaggccg gcaaccttac  36180
ctcccaaaat gtaaccactg tgagcccacc tctcaaaaaa accaagtcaa acataaacct  36240
ggaaatatct gcacccctca cagttacctc agaagcccta actgtggctg ccgccgcacc  36300
tctaatggtc gcgggcaaca cactcaccat gcaatcacag gccccgctaa ccgtgcacga  36360
ctccaaactt agcattgcca cccaaggacc cctcacagtg tcagaaggaa agctagccct  36420
gcaaacatca ggcccctca ccaccaccga tagcagtacc cttactatca ctgcctcacc  36480
ccctctaact actgccactg gtagcttggg cattgacttg aaagagccca tttatacaca  36540
aaatggaaaa ctaggactaa agtacggggc tcctttgcat gtaacagacg acctaaacac  36600
tttgaccgta gcaactggtc caggtgtgac tattaataat acttccttgc aaactaaagt  36660
tactggagcc ttgggttttg attcacaagg caatatgcaa cttaatgtag caggaggact  36720
aaggattgat tctcaaaaca gacgccttat acttgatgtt agttatccgt ttgatgctca  36780
aaaccaacta aatctaagac taggacaggg ccctctttt ataaactcag cccacaactt  36840
ggatattaac tacaacaaag gcctttactt gtttacagct tcaaacaatt ccaaaaagct  36900
tgaggttaac ctaagcactg ccaaggggtt gatgtttgac gctacagcca tagccattaa  36960
tgcaggagat gggcttgaat ttggttcacc taatgcacca aacacaaatc ccctcaaaac  37020
aaaaattggc catggcctag aatttgattc aaacaaggct atggttccta aactaggaac  37080
tggccttagt tttgacagca caggtgccat tacagtagga aacaaaaata atgataagct  37140
aactttgtgg accacaccag ctccatctcc taactgtaga ctaaatgcag agaaagatgc  37200
taaactcact ttggtcttaa caaaatgtgg cagtcaaata cttgctacag tttcagtttt  37260
ggctgttaaa ggcagtttgg ctccaatatc tggaacagtt caaagtgctc atcttattat  37320
aagatttgac gaaaatggag tgctactaaa caattccttc ctggacccag aatattggaa  37380
ctttagaaat ggagatctta ctgaaggcac agcctataca aacgctgttg gatttatgcc  37440
taacctatca gcttatccaa aatctcacgg taaaactgcc aaaagtaaca ttgtcagtca  37500
agtttactta aacggagaca aaactaaacc tgtaacacta accattacac taaacggtac  37560
acaggaaaca ggagacacaa ctccaagtgc atactctatg tcattttcat gggactggtc  37620
tggccacaac tacattaatg aaatatttgc cacatcctct tacacttttt catacattgc  37680
```

```
ccaagaataa agaatcgttt gtgttatgtt tcaacgtgtt tatttttcaa ttgcagaaaa  37740

tttcaagtca tttttcattc agtagtatag ccccaccacc acatagctta tacagatcac  37800

cgtaccttaa tcaaactcac agaaccctag tattcaacct gccacctccc tcccaacaca  37860

cagagtacac agtcctttct ccccggctgg ccttaaaaag catcatatca tgggtaacag  37920

acatattctt aggtgttata ttccacacgg tttcctgtcg agccaaacgc tcatcagtga  37980

tattaataaa ctccccgggc agctcactta agttcatgtc gctgtccagc tgctgagcca  38040

caggctgctg tccaacttgc ggttgcttaa cgggcggcga aggagaagtc cacgcctaca  38100

tgggggtaga gtcataatcg tgcatcagga tagggcggtg gtgctgcagc agcgcgcgaa  38160

taaactgctg ccgccgccgc tccgtcctgc aggaatacaa catggcagtg gtctcctcag  38220

cgatgattcg caccgcccgc agcataaggc gccttgtcct ccgggcacag cagcgcaccc  38280

tgatctcact taaatcagca cagtaactgc agcacagcac cacaatattg ttcaaaatcc  38340

cacagtgcaa ggcgctgtat ccaaagctca tggcggggac cacagaaccc acgtggccat  38400

cataccacaa gcgcaggtag attaagtggc gacccctcat aaacacgctg gacataaaca  38460

ttacctcttt tggcatgttg taattcacca cctcccggta ccatataaac ctctgattaa  38520

acatggcgcc atccaccacc atcctaaacc agctggccaa aacctgcccg ccggctatac  38580

actgcaggga accgggactg gaacaatgac agtggagagc ccaggactcg taaccatgga  38640

tcatcatgct cgtcatgata tcaatgttgg cacaacacag gcacacgtgc atacacttcc  38700

tcaggattac aagctcctcc cgcgttagaa ccatatccca gggaacaacc cattcctgaa  38760

tcagcgtaaa tcccacactg cagggaagac ctcgcacgta actcacgttg tgcattgtca  38820

aagtgttaca ttcgggcagc agcggatgat cctccagtat ggtagcgcgg gtttctgtct  38880

caaaaggagg tagacgatcc ctactgtacg gagtgcgccg agacaaccga gatcgtgttg  38940

gtcgtagtgt catgccaaat ggaacgccgg acgtagtcat atttcctgaa gcaaaaccag  39000

gtgcgggcgt gacaaacaga tctgcgtctc cggtctcgcc gcttagatcg ctctgtgtag  39060

tagttgtagt atatccactc tctcaaagca tccaggcgcc ccctggcttc gggttctatg  39120

taaactcctt catgcgccgc tgccctgata acatccacca ccgcagaata agccacaccc  39180

agccaaccta cacattcgtt ctgcgagtca cacacgggag gagcgggaag agctggaaga  39240

accatgtttt ttttttttatt ccaaaagatt atccaaaacc tcaaaatgaa gatctattaa  39300

gtgaacgcgc tcccctccgg tggcgtggtc aaactctaca gccaaagaac agataatggc  39360

atttgtaaga tgttgcacaa tggcttccaa aaggcaaacg gccctcacgt ccaagtggac  39420

gtaaaggcta aacccttcag ggtgaatctc ctctataaac attccagcac cttcaaccat  39480

gcccaaataa ttctcatctc gccaccttct caatatatct ctaagcaaat cccgaatatt  39540

aagtccggcc attgtaaaaa tctgctccag agcgccctcc accttcagcc tcaagcagcg  39600

aatcatgatt gcaaaaattc aggttcctca cagacctgta taagattcaa aagcggaaca  39660

ttaacaaaaa taccgcgatc ccgtaggtcc cttcgcaggg ccagctgaac ataatcgtgc  39720

aggtctgcac ggaccagcgc ggccacttcc ccgccaggaa ccatgacaaa agaacccaca  39780

ctgattatga cacgcatact cggagctatg ctaaccagcg tagccccgat gtaagcttgt  39840

tgcatgggcg gcgatataaa atgcaaggtg ctgctcaaaa aatcaggcaa agcctcgcgc  39900

aaaaaagaaa gcacatcgta gtcatgctca tgcagataaa ggcaggtaag ctccggaacc  39960

accacagaaa aagacaccat ttttctctca aacatgtctg cgggtttctg cataaacaca  40020

aaataaaata acaaaaaaac atttaaacat tagaagcctg tcttacaaca ggaaaaacaa  40080
```

-continued

```
ccccttataag cataagacgg actacggcca tgccggcgtg accgtaaaaa aactggtcac  40140
cgtgattaaa aagcaccacc gacagctcct cggtcatgtc cggagtcata atgtaagact  40200
cggtaaacac atcaggttga ttcacatcgg tcagtgctaa aaagcgaccg aaatagcccg  40260
ggggaataca tacccgcagg cgtagagaca acattacagc cccccatagga ggtataacaa  40320
aattaatagg agagaaaaac acataaacac ctgaaaaacc ctcctgccta ggcaaaatag  40380
caccctcccg ctccagaaca acatacagcg cttccacagc ggcagccata acagtcagcc  40440
ttaccagtaa aaaagaaaac ctattaaaaa aacaccactc gacacggcac cagctcaatc  40500
agtcacagtg taaaaaaggg ccaagtgcag agcgagtata tataggacta aaaaatgacg  40560
taacggttaa agtccacaaa aaacacccag aaaaccgcac gcgaacctac gcccagaaac  40620
gaaagccaaa aaacccacaa cttcctcaaa tcgtcacttc cgttttccca cgttacgtca  40680
cttcccattt taagaaaact acaattccca acacatacaa gttactccgc cctaaaacct  40740
acgtcacccg ccccgttccc acgccccgcg ccacgtcaca aactccaccc cctcattatc  40800
atattggctt caatccaaaa taaggta                                      40827
```